US011332485B2

(12) United States Patent
Burns et al.

(10) Patent No.: US 11,332,485 B2
(45) Date of Patent: May 17, 2022

(54) PENICILLIN-BINDING PROTEIN INHIBITORS

(71) Applicant: VenatoRx Pharmaceuticals, Inc., Malvern, PA (US)

(72) Inventors: Christopher J. Burns, Malvern, PA (US); Denis Daigle, Street, MD (US); Guo-Hua Chu, Exton, PA (US); Jodie Hamrick, New Holland, PA (US); Matthew Lucas, Cambridge, MA (US); Steven A. Boyd, Chester Springs, PA (US); Allison L. Zulli, Chesterbrook, PA (US); Eugen F. Mesaros, Wallingford, PA (US); Stephen M. Condon, Glenmoore, PA (US); Robert E. Lee Trout, Collegeville, PA (US); Cullen L. Myers, Exton, PA (US)

(73) Assignee: VENATORX PHARMACEUTICALS, INC., Malvern, PA (US)

( * ) Notice: Subject to any disclaimer, the term of this patent is extended or adjusted under 35 U.S.C. 154(b) by 0 days.

(21) Appl. No.: 16/616,294

(22) PCT Filed: May 25, 2018

(86) PCT No.: PCT/US2018/034722
§ 371 (c)(1),
(2) Date: Nov. 22, 2019

(87) PCT Pub. No.: WO2018/218190
PCT Pub. Date: Nov. 29, 2018

(65) Prior Publication Data
US 2020/0157123 A1 May 21, 2020

Related U.S. Application Data

(60) Provisional application No. 62/511,613, filed on May 26, 2017.

(51) Int. Cl.
| | | |
|---|---|---|
| C07F 5/02 | (2006.01) | |
| A61P 31/04 | (2006.01) | |
| A61K 9/20 | (2006.01) | |
| A61K 9/48 | (2006.01) | |

(52) U.S. Cl.
CPC .......... *C07F 5/027* (2013.01); *A61K 9/205* (2013.01); *A61K 9/2009* (2013.01); *A61K 9/2013* (2013.01); *A61K 9/2018* (2013.01); *A61K 9/2059* (2013.01); *A61K 9/4858* (2013.01); *A61P 31/04* (2018.01)

(58) Field of Classification Search
CPC .......... C07F 5/027; C07F 5/025; A61P 31/04; A61K 9/2009; A61K 9/2013; A61K 9/2018; A61K 9/205; A61K 9/2059; A61K 9/4858
See application file for complete search history.

(56) References Cited

U.S. PATENT DOCUMENTS

| | | |
|---|---|---|
| 4,427,690 A | 1/1984 | Cole et al. |
| 7,271,186 B1 | 9/2007 | Shoichet et al. |
| 7,714,159 B2 | 5/2010 | Pickersgill et al. |
| 8,283,467 B2 | 10/2012 | Ammoscato et al. |
| 8,680,136 B2 | 3/2014 | Hirst et al. |
| 9,101,638 B2 | 8/2015 | Reddy et al. |
| 9,511,142 B2 | 12/2016 | Burns et al. |
| 9,642,869 B2 | 5/2017 | Reddy et al. |
| 9,802,966 B2 | 10/2017 | Burns et al. |
| 9,963,467 B2 | 5/2018 | Reddy et al. |
| 10,206,937 B2 | 2/2019 | Reddy et al. |
| 10,479,805 B2 | 11/2019 | Wu et al. |
| 2009/0156518 A1 | 6/2009 | Zhang |
| 2010/0056478 A1 | 3/2010 | Desarbre et al. |
| 2010/0120715 A1 | 5/2010 | Burns et al. |
| 2010/0286092 A1 | 11/2010 | Burns et al. |
| 2010/0292185 A1 | 11/2010 | Burns et al. |
| 2010/0317621 A1 | 12/2010 | Burns et al. |
| 2011/0294777 A1 | 12/2011 | Blizzard et al. |
| 2012/0040932 A1 | 2/2012 | Hirst et al. |
| 2014/0094457 A1 | 4/2014 | Gardner et al. |
| 2014/0170186 A1 | 6/2014 | Nabel et al. |

(Continued)

FOREIGN PATENT DOCUMENTS

| | | |
|---|---|---|
| CN | 1965838 A | 5/2007 |
| CN | 105801610 A | 7/2016 |

(Continued)

OTHER PUBLICATIONS

Kenneth D. Hardy et al., The Chemistry of Some 2-Aminothiazol-4-ylacetic Acid Derivatives and the Synthesis of Derived Penicillins, J. Chem. Soc Perkin Trans. l 1984, 1227-1235 (Year: 1984).*
Burns et al. CAPLUS AN 2014-1130723 (1 pg.) (2014).
Eidam et al. Design, synthesis, crystal structures, and antimicrobial activity of sulfonamide boronic acids as β-lactamase inhibitors. J. Med. Chem. 53(21):7852-7863 (2010).
Ishikura et al. Synthesis and structure-activity relationships of 7 beta-[(Z)-2-(2- aminothiazol-4-yl)-3-(substituted)-2-propenoyl-amino]-3-desacetoxymethylcephalosporins. J. Antibiotics 47:453-465 (1994).
Martin et al. Rational design and synthesis of a highly effective transition state analog inhibitor of the RTEM-1 β-lactamase. Tetrahedron Lett. 36:8399-8402 (1995).

(Continued)

*Primary Examiner* — Sarah Pihonak
*Assistant Examiner* — Jason Deck
(74) *Attorney, Agent, or Firm* — Wilson Sonsini Goodrich & Rosati

(57) ABSTRACT

Described herein are certain boron-containing compounds, compositions, preparations and their use as modulators of the transpeptidase function of bacterial penicillin-binding proteins and as antibacterial agents. In some embodiments, the compounds described herein inhibit penicillin-binding proteins. In certain embodiments, the compounds described herein are useful in the treatment of bacterial infections.

16 Claims, No Drawings

(56) References Cited

U.S. PATENT DOCUMENTS

| | | |
|---|---|---|
| 2014/0171390 A1 | 6/2014 | Burns et al. |
| 2014/0194385 A1 | 7/2014 | Reddy et al. |
| 2014/0194386 A1 | 7/2014 | Burns et al. |
| 2014/0227225 A1 | 8/2014 | Aube et al. |
| 2015/0094472 A1 | 4/2015 | Hecker et al. |
| 2015/0291630 A1 | 10/2015 | Burns et al. |
| 2015/0361107 A1 | 12/2015 | Trout |
| 2015/0361108 A1 | 12/2015 | Burns et al. |
| 2017/0073360 A1 | 3/2017 | Burns et al. |
| 2017/0281639 A1 | 10/2017 | Kawasaki et al. |
| 2017/0342092 A1 | 11/2017 | Burns et al. |
| 2018/0002351 A1 | 1/2018 | Hecker et al. |
| 2018/0273552 A1 | 9/2018 | Burns et al. |
| 2019/0292187 A1 | 9/2019 | Gutierrez et al. |
| 2020/0055877 A1 | 2/2020 | Burns et al. |
| 2020/0102331 A1 | 4/2020 | Burns et al. |
| 2020/0181174 A1 | 6/2020 | Amann et al. |
| 2020/0317698 A1 | 10/2020 | Burns et al. |
| 2020/0361962 A1 | 11/2020 | Burns et al. |
| 2021/0198288 A1 | 7/2021 | Burns et al. |

FOREIGN PATENT DOCUMENTS

| | | |
|---|---|---|
| KR | 20130064004 A | 6/2013 |
| RU | 2012107163 A | 9/2013 |
| WO | WO-2005004799 A2 | 1/2005 |
| WO | WO-2009064413 A1 | 5/2009 |
| WO | WO-2009064414 A1 | 5/2009 |
| WO | WO-2010056827 A1 | 5/2010 |
| WO | WO-2010065110 A2 | 6/2010 |
| WO | WO-2010130708 A1 | 11/2010 |
| WO | WO-2012021455 A1 | 2/2012 |
| WO | WO-2013014497 A1 | 1/2013 |
| WO | WO-2013053372 A1 | 4/2013 |
| WO | WO-2013092979 A1 | 6/2013 |
| WO | WO-2013122888 A2 | 8/2013 |
| WO | WO-2014086664 A1 | 6/2014 |
| WO | WO-2014089365 A1 | 6/2014 |
| WO | WO-2014107535 A1 | 7/2014 |
| WO | WO-2014107536 A1 | 7/2014 |
| WO | WO-2014110442 A1 | 7/2014 |
| WO | WO-2014151958 A1 | 9/2014 |
| WO | WO-2015157618 A1 | 10/2015 |
| WO | WO-2015171398 A1 | 11/2015 |
| WO | WO-2015171430 A1 | 11/2015 |
| WO | WO-2015179308 A1 | 11/2015 |
| WO | WO-2015191907 A1 | 12/2015 |
| WO | WO-2016003929 A1 | 1/2016 |
| WO | WO-2016100043 A1 | 6/2016 |
| WO | WO-2017001655 A1 | 1/2017 |
| WO | WO-2017044828 A1 | 3/2017 |
| WO | WO-2017100537 A1 | 6/2017 |
| WO | WO-2018027062 A1 | 2/2018 |
| WO | WO-2018165048 A1 | 9/2018 |
| WO | WO-2018218154 A1 | 11/2018 |
| WO | WO-2018218190 A1 | 11/2018 |
| WO | WO-2019165374 A1 | 8/2019 |
| WO | WO-2019185016 A1 | 10/2019 |
| WO | WO-2019223791 A1 | 11/2019 |
| WO | WO-2019226931 A1 | 11/2019 |
| WO | WO-2020056048 A1 | 3/2020 |
| WO | WO-2020112542 A1 | 6/2020 |
| WO | WO-2020205932 A1 | 10/2020 |
| WO | WO-2020231750 A1 | 11/2020 |

OTHER PUBLICATIONS

Matteson. Boronic esters in asymmetric synthesis. J Org Chem 78:10009-10023 (2013).
Matteson et al. Synthesis of 1-amino-2-phenylethane-1-boronic acid derivatives. Organometallics 3:614-18 (1984).
Morandi et al. Structure-based optimization of cephalothin-analogue boronic acids as β-lactamase inhibitors. Bioorg. Med. Chem. 16(3):1195-1205 (2008) (Epub: Nov. 7, 2007).
Ness et al. Structure-based design guides the improved efficacy of deacylation transition state analogue inhibitors of TEM-1 β-lactamase. Biochemistry 39(18):5312-5321 (2000).
PCT/US2018/034660 International Search Report and Written Opinion dated Sep. 14, 2018.
PCT/US2018/034722 International Search Report and Written Opinion dated Sep. 14, 2018.
PCT/US2019/033813 International Search Report and Written Opinion dated Sep. 10, 2019.
Powers et al. Structure-based approach for binding site identification on AmpC β-lactamase. J. Med. Chem. 45(15):3222-3234 (2002).
Powers et al. Structures of ceftazidime and its transition-state analogue in complex with AmpC β-lactamase: implications for resistance mutations and inhibitor design. Biochemistry 40(31):9207-9214 (2001).
Pub Chem Substance Record for SID 197433672. https://pubchem.ncbi.nim.nih/substance/197433672. Created Aug. 18, 2014. Retrieved Jan. 10, 2017 (5 pgs).
Reddy et al. Caplus 2014:1118372 (2014) (2 pgs.).
Watkins et al. Novel β-lactamase inhibitors: a therapeutic hope against the scourge of multi-drug resistance. © Dec. 24, 2013. Accessed Jul. 7, 2018. (18 pgs) (2013).
Weston et al. Structure-based enhancement of boronic acid-based inhibitors of AmpC β-lactamase. J. Med. Chem. 41(23):4577-4586 (1998).
Winkler et al. Design and exploration of novel boronic acid inhibitors reveals important interactions with a clavulanic acid-resistant sulfhydryl-variable (SHV) β-lactamase. J Med Chem 56:1084-1097 (2013) (Publication Date (Web): Dec. 19, 2012).
Zhou et al. Trigonelline: A Plant Alkaloid With Therapeutic Potential for Diabetes and Central Nervous System Disease. Curr Med Chem 19(21):3523-3531 (2012).
Cho et al. A practical synthesis of enantiopure 4,4,4-trifluoro-allo-threonine from an easily available fluorinated building block. Tetrahedron Lett. 56:127-131 (2015).
Deng et al. Dynamic pharmacophore model optimization: identification of novel HIV-1 integrase inhibitors. J Med Chem 49:1684-1692 (2006).
Germs: Understand and protect against bacteria, viruses and infection, PreventBacterialInfection, 2020. Available at https://www.mayoclinic.org/diseases-conditions/infectious-diseases/in-depth/germs/art-20045289#:-:text=Warding%20off%20germs%20and%20infection&text=You%20can%20prevent%20infections%20through ,vaccinations%2C%20and%20taking%20appropriate%20medications (Mar. 5, 2020).
King et al. Molecular Mechanism of Avibactam-Mediated β-Lactamase Inhibition. ACS Infect Dis 1(4): 175-84 (2015).
Krajnc et al., Bicyclic boronate VNRX-5133 inhibits metallo- and serine-beta-lactamases. Journal of Medicinal Chemistry 62(18):8544-8556 (2019).
PCT/US2020/026114 International Search Report and Written Opinion dated Jul. 23, 2020.
PCT/US2020/026114 Invitation to Pay Additional Fees dated May 22, 2020.
PCT/US2020/031927 International Search Report and Written Opinion dated Aug. 3, 2020.
PCT/US2020/051163 Invitation to Pay Additional Fees dated Nov. 24, 2020.
PCT/US2020/052439 International Search Report and Written Opinion dated Dec. 31, 2020.
Sharma et al. Synthesis of bioactive substituted pyrazolylbenzothiazinones. Research on Chemical Intermediates 41:6141-6143 (2014).
U.S. Appl. No. 16/491,116 Office Action dated Dec. 14, 2020.
U.S. Appl. No. 16/491,116 Office Action dated Mar. 25, 2021.
U.S. Appl. No. 16/514,904 Office Action dated Aug. 18, 2020.
U.S. Appl. No. 16/798,032 Office Action dated Sep. 21, 2020.
U.S. Appl. No. 16/864,634 Office Action dated Apr. 1, 2021.
Contreras-Martel et al. Structure-guided design of cell wall biosynthesis inhibitors that overcome β-lactam resistance in Staphylococcus aureus (MRSA). ACS Chem Biol 6(7):943-951 (2011).

(56) References Cited

OTHER PUBLICATIONS

Inglis et al. Synthesis and evaluation of 3-(dihydroxyboryl)benzoic acids as D,D-carboxypeptidase R39 inhibitors. J Med Chem 52:6097-6106 (2009).

Woon et al. Structure guided development of potent reversibly binding penicillin binding protein inhibitors. ACS Med Chem Lett 2(1):219-223 (2011).

\* cited by examiner

PENICILLIN-BINDING PROTEIN INHIBITORS

CROSS-REFERENCE TO RELATED APPLICATIONS

This application is a U.S. National Stage entry of International Application No. PCT/US2018/034722, filed May 25, 2018, which claims the benefit of U.S. Provisional Application Ser. No. 62/511,613 filed May 26, 2017, which are hereby incorporated by reference in their entirety.

STATEMENT AS TO FEDERALLY SPONSORED RESEARCH

This invention was made with the support of the United States government under SBIR Grant number 5R43AI094827 by the National Institutes of Health (NIH), and Federal Award 6 IDSEP16030-01-02, subaward 4500002377, awarded by the Health and Human Services Office of the Assistant Secretary for Preparedness and Response (HHS/ASPR) under the CARB-X Pass Through Entity. The government has certain rights in the invention.

BACKGROUND OF THE INVENTION

Antibiotics are the most effective drugs for curing bacteria-related infectious diseases clinically. They are incredibly valuable therapeutic options that are currently losing efficacy due to the evolution and spread of drug resistance genes, leading to multidrug resistance bacterial organisms. Among the different classes of antibiotics, the penicillin-binding protein-targeting beta-lactams (e.g. penicillins, cephalosporins, and carbapenems) are the most widely used antibiotic class because they have a strong bactericidal effect and low associated toxicity.

Penicillin Binding Proteins (PBPs) are a family of essential bacterial enzymes involved in the synthesis of peptidoglycan, the major structural polymer found in the bacterial cell wall. Beta-lactam antibiotics bind with high affinity to PBPs and inhibit their transpeptidase function, resulting in disruption of peptidoglycan cell wall synthesis and rapid cell lysis of actively dividing bacteria. As there are no close mammalian homologues to PBPs, and beta-lactams are well-regarded for their safety and efficacy, PBPs represent an ideal target for antibacterials.

SUMMARY OF THE INVENTION

Described herein are compounds that inhibit the activity of penicillin-binding proteins, the bacterial enzyme class targeted by the beta lactam antibiotics and do provide significant antibacterial activity in vitro.

Also provided herein are compounds of Formula (Va) or (Vb), or a pharmaceutically acceptable salt, solvate, stereoisomer, tautomer, N-oxide, dimer, or trimer thereof:

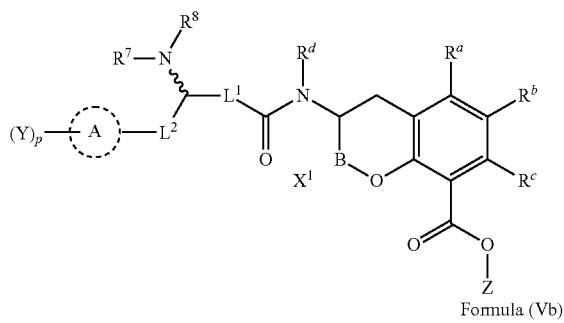

Formula (Va)

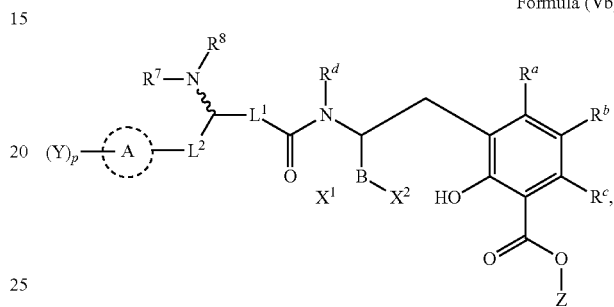

Formula (Vb)

wherein:
$L^1$ is —$(CR^1R^2)_n$—;
$L^2$ is —$(CR^1R^2)_m$—;
Ring A is cycloalkyl, heterocycloalkyl, aryl, or heteroaryl;
each $R^1$ and $R^2$ are independently hydrogen, halogen, optionally substituted alkyl, —OH, —$OR^{34}$, —$SR^{35}$, —$NR^{32}R^{33}$, —$NR^{32}C(=O)R^{34}$, —$C(=O)NR^{32}R^{33}$, —$NR^{32}S(=O)_2R^{34}$, —$C(=O)OH$, —$C(=O)OR^{34}$, optionally substituted cycloalkyl, optionally substituted heterocycloalkyl, optionally substituted aryl, or optionally substituted heteroaryl; or
$R^1$ and $R^2$ are taken together with the carbon to which they are attached to form an optionally substituted cycloalkyl;
$R^7$ and $R^8$ are independently hydrogen, optionally substituted alkyl, optionally substituted cycloalkyl, optionally substituted heterocycloalkyl, optionally substituted aryl, optionally substituted heteroaryl, —$S(=O)_2R^{44c}$, —$S(=O)_2NR^{42c}R^{43c}$, —$(CR^{40c}R^{41c})_vC(=O)OH$, —$(CR^{40c}R^{41c})_vC(=O)OR^{44c}$, —$(CR^{40c}R^{41c})_vC(=O)NR^{42c}R^{43c}$, or —$C(=O)R^{44c}$; or
$R^7$ and $R^8$ are taken together with the nitrogen to which they are attached to form an optionally substituted heterocycloalkyl;
each $R^{20}$ and $R^{21}$ are independently hydrogen, halogen, or optionally substituted alkyl;
$R^{22}$ and $R^{23}$ are independently hydrogen or optionally substituted alkyl; or
$R^{22}$ and $R^{23}$ are taken together with the nitrogen to which they are attached to form an optionally substituted heterocycloalkyl;
$R^{24}$ is optionally substituted alkyl, optionally substituted cycloalkyl, optionally substituted heterocycloalkyl, optionally substituted aryl, or optionally substituted heteroaryl;
$R^{25}$ is hydrogen, optionally substituted alkyl, optionally substituted cycloalkyl, optionally substituted heterocycloalkyl, optionally substituted aryl, optionally substituted heteroaryl;

each $R^{30}$, $R^{31}$, $R^{40c}$, $R^{41c}$, $R^{50}$, and $R^{51}$ are independently hydrogen, halogen, optionally substituted alkyl, optionally substituted cycloalkyl, optionally substituted heterocycloalkyl, optionally substituted aryl, optionally substituted heteroaryl, —OH, —OR$^{24}$, —SR$^{25}$, —NR$^{22}$R$^{23}$, —NR$^{22}$C(=O)R$^{24}$, —C(=O)NR$^{22}$R$^{23}$, —NR$^{22}$S(=O)$_2$R$^{24}$, —C(=O)OH, or —C(=O)OR$^{24}$; or $R^{30}$ and $R^{31}$, $R^{40c}$ and $R^{41c}$, or $R^{50}$ and $R^{51}$ are taken together with the carbon atom to which they are attached form an optionally substituted cycloalkyl; or two $R^{30}$, two $R^{40c}$, or two $R^{50}$ on adjacent carbons are taken together to form an alkenyl; or two $R^{30}$ and two $R^{31}$, two $R^{40c}$ and two $R^{41c}$, or two $R^{50}$ and two $R^{51}$ on adjacent carbons are taken together to form an alkynyl;

$R^{32}$, $R^{33}$, $R^{42c}$, $R^{43c}$, $R^{52}$, or $R^{53}$ are independently hydrogen, optionally substituted alkyl, optionally substituted cycloalkyl, optionally substituted heterocycloalkyl, optionally substituted aryl, optionally substituted heteroaryl, (poly-ethylene-glycol)-ethyl, optionally substituted saccharide, —CN, —OH, —S(=O)$_2$R$^{24}$, —S(=O)$_2$NR$^{22}$R$^{23}$, or —C(=O)R$^{24}$; or $R^{32}$ and $R^{33}$, $R^{42c}$ and $R^{43c}$, or $R^{52}$ and $R^{53}$ are taken together with the nitrogen to which they are attached to form an optionally substituted heterocycloalkyl;

$R^{34}$, $R^{44c}$, or $R^{54}$ are independently optionally substituted alkyl, optionally substituted cycloalkyl, optionally substituted heterocycloalkyl, optionally substituted aryl, or optionally substituted heteroaryl;

$R^{35}$ and $R^{55}$ are independently hydrogen, optionally substituted alkyl, optionally substituted cycloalkyl, optionally substituted heterocycloalkyl, optionally substituted aryl, optionally substituted heteroaryl;

$R^{36}$ and $R^{56}$ are independently hydrogen, —OH, —OR$^{24}$, —CN, —NO$_2$, —NR$^{22}$R$^{23}$, or optionally substituted alkyl;

Z is hydrogen, $R^{61}$, —(R$^{60}$)$_q$OR$^{61}$, —(R$^{60}$)$_q$O(R$^{60}$)$_q$OR$^{61}$, —R$^{60}$OC(=O)R$^{61}$, —R$^{60}$OC(=O)OR$^{61}$, —R$^{60}$OC(=O)NHR$^{61}$, —R$^{60}$OC(=O)N(R$^{61}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each $R^{60}$ is independently —CH$_2$—, —CH(CH$_3$)—, —C(CH$_3$)$_2$—, or optionally substituted 1,1'-cyclopropylene;

each $R^{61}$ is independently optionally substituted alkyl, optionally substituted cycloalkyl, optionally substituted heterocycloalkyl, optionally substituted aryl, or optionally substituted heteroaryl; or two $R^{61}$ are taken together with the nitrogen to which they are attached to form an optionally substituted heterocycloalkyl;

$R^a$, $R^b$, and $R^c$ are independently hydrogen, halogen, cyano, optionally substituted alkyl, optionally substituted cycloalkyl, optionally substituted heterocycloalkyl, optionally substituted aryl, optionally substituted heteroaryl, —OH, —OR$^{54}$, —O(CR$^{50}$R$^{51}$)$_w$NR$^{52}$R$^{53}$, —O(CR$^{50}$R$^{51}$)$_w$OH, —O(CR$^{50}$R$^{51}$)$_w$OR$^{54}$, —O(CR$^{50}$R$^{51}$)$_v$C(=O)OH, —O(CR$^{50}$R$^{51}$)$_v$C(=O)OR$^{54}$, —O(CR$^{50}$R$^{51}$)$_v$C(=O)NR$^{52}$R$^{53}$, —NR$^{52}$R$^{53}$, —NR$^{52}$(CR$^{50}$R$^{51}$)$_w$NR$^{52}$R$^{53}$, —NR$^{52}$(CR$^{50}$R$^{51}$)$_v$C(=O)OH, —NR$^{52}$(CR$^{50}$R$^{51}$)$_v$C(=O)OR$^{54}$, —NR$^{52}$(CR$^{50}$R$^{51}$)$_v$C(=O)NR$^{52}$R$^{53}$, —NR$^{52}$S(=O)$_{1,2}$R$^{54}$, —S(=O)$_{1,2}$R$^{54}$, —SR$^{55}$, —S(CR$^{50}$R$^{51}$)$_v$NR$^{52}$C(=NR$^{56}$)NR$^{52}$R$^{53}$, —S(CR$^{50}$R$^{51}$)$_v$NR$^{52}$CR$^{50}$(=NR$^{56}$), —S(CR$^{50}$R$^{51}$)$_v$C(=NR$^{56}$)NR$^{52}$R$^{53}$, —S(CR$^{50}$R$^{51}$)$_w$OH, —S(CR$^{50}$R$^{51}$)$_w$OR$^{54}$, —S(CR$^{50}$R$^{51}$)$_w$NR$^{52}$R$^{53}$, —S(CR$^{50}$R$^{51}$)$_v$C(=O)OH, —S(CR$^{50}$R$^{51}$)$_v$C(=O)OR$^{54}$, —S(CR$^{50}$R$^{51}$)$_v$C(=O)NR$^{52}$R$^{53}$, —C(=O)H, —C(=O)R$^{54}$, —C(=O)OH, —C(=O)OR$^{54}$, —C(=O)NR$^{52}$R$^{53}$, —(CR$^{50}$R$^{51}$)$_v$N(R$^{52}$)(CR$^{50}$R$^{51}$)$_v$C(=O)OH, —(CR$^{50}$R$^{51}$)$_v$OH, —(CR$^{50}$R$^{51}$)$_v$OR$^{54}$, —(CR$^{50}$R$^{51}$)$_v$C(=O)OH, —(CR$^{50}$R$^{51}$)$_v$C(=O)OR$^{54}$, —(CR$^{50}$R$^{51}$)$_v$C(=O)NR$^{52}$R$^{53}$, —(CR$^{50}$R$^{51}$)$_v$OC(=O)R$^{54}$, —(CR$^{50}$R$^{51}$)$_v$SR$^{55}$, —(CR$^{50}$R$^{51}$)$_v$NR$^{52}$C(=NR$^{56}$), —(CR$^{50}$R$^{51}$)$_v$NR$^{52}$R$^{53}$, —(CR$^{50}$R$^{51}$)$_v$C(=NR$^{56}$)NR$^{52}$R$^{53}$, —(CR$^{50}$R$^{51}$)$_v$C(=O)NR$^{52}$R$^{53}$, —(CR$^{50}$R$^{51}$)$_v$heterocycloalkyl, or —(CR$^{50}$R$^{51}$)$_v$heteroaryl;

$R^d$ is hydrogen, —CN, —OH, —S(=O)$_2$R$^{24}$, —S(=O)$_2$NR$^{22}$R$^{23}$, —(CR$^{20}$R$^{21}$)$_v$C(=O)OH, —C(=O)R$^{24}$, optionally substituted alkyl, optionally substituted cycloalkyl, optionally substituted heterocycloalkyl, optionally substituted aryl, optionally substituted heteroaryl, (poly-ethylene-glycol)-ethyl, an optionally substituted saccharide;

$R^X$ is optionally substituted alkyl or optionally substituted cycloalkyl;

$X^1$ and $X^2$ are independently —OH, —OR$^X$, or F; or $X^1$ and $X^2$ are taken together with the boron atom to which they are attached to form a cyclic boronate ester;

each Y is halogen, optionally substituted alkyl, optionally substituted cycloalkyl, optionally substituted heterocycloalkyl, optionally substituted aryl, optionally substituted heteroaryl, -heteroaryl-NR$^{32}$R$^{33}$, -heterocycloalkyl-NR$^{32}$R$^{33}$, -heteroaryl-N(R$^{32}$)C(=NR$^{32}$)NR$^{32}$R$^{33}$, -heterocycloalkyl-N(R$^{32}$)C(=NR$^{32}$)NR$^{32}$R$^{33}$, —OH, —OR$^{34}$, —O(CR$^{30}$R$^{31}$)$_w$OH, —O(CR$^{30}$R$^{31}$)$_w$OR$^{34}$, —O(CR$^{30}$R$^{31}$)$_w$NR$^{32}$R$^{33}$, —O(CR$^{30}$R$^{31}$)$_w$NR$^{32}$C(=O)R$^{34}$, —O(CR$^{30}$R$^{31}$)$_w$NR$^{32}$C(=O)OR$^{34}$, —O(CR$^{30}$R$^{31}$)$_w$NR$^{32}$C(=O)NR$^{32}$R$^{33}$, —O(CR$^{30}$R$^{31}$)$_w$C(=O)NR$^{32}$R$^{33}$, —O(CR$^{30}$R$^{31}$)$_w$NR$^{32}$S(=O)$_{0,1,2}$R$^{34}$, —O(CR$^{30}$R$^{31}$)$_w$NR$^{32}$S(=O)$_{0,1,2}$NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —O(CR$^{30}$R$^{31}$)$_v$C(=NR$^{36}$)NR$^{32}$R$^{33}$, —O(CR$^{30}$R$^{31}$)$_w$N(R$^{32}$)C(=NR$^{36}$)R$^{34}$, —O(CR$^{30}$R$^{31}$)$_v$C(=NR$^{36}$)NR$^{32}$C(=NR$^{36}$)NR$^{32}$R$^{33}$, —O(CR$^{30}$R$^{31}$)$_w$N(R$^{32}$)C(=NR$^{36}$)NR$^{32}$R$^{33}$, —O(CR$^{30}$R$^{31}$)$_w$S(=O)$_{0,1,2}$NR$^{32}$R$^{33}$, —O(CR$^{30}$R$^{31}$)$_w$S(=O)$_{0,1,2}$NR$^{32}$R$^{33}$, —OC(=O)R$^{34}$, —OC(=O)(CR$^{30}$R$^{31}$)$_w$NR$^{32}$R$^{33}$, —OC(=O)NR$^{32}$R$^{33}$, —OC(=O)OR$^{34}$, —OC(=O)NR$^{32}$(CR$^{30}$R$^{31}$)$_w$NR$^{32}$R$^{33}$, —O-heteroaryl, —O-heterocycloalkyl, —O(CR$^{30}$R$^{31}$)$_v$heteroaryl, —O(CR$^{30}$R$^{31}$)$_v$heterocycloalkyl, —O(CR$^{30}$R$^{31}$)$_w$NR$^{32}$-heteroaryl, —O(CR$^{30}$R$^{31}$)$_w$NR$^{32}$-heterocycloalkyl, —O(CR$^{30}$R$^{31}$)$_w$O-heterocycloalkyl, —NR$^{32}$R$^{33}$, —NR$^{32}$(CR$^{30}$R$^{31}$)$_w$R$^{32}$R$^{33}$, —NR$^{32}$(CR$^{30}$R$^{31}$)$_w$OH, —NR$^{32}$(CR$^{30}$R$^{31}$)$_w$OR$^{34}$, —NR$^{32}$C(=O)R$^{34}$, —NR$^{32}$C(=O)OR$^{34}$, —N(R$^{32}$)C(=O)(CR$^{30}$R$^{31}$)$_v$NR$^{32}$R$^{33}$, —NR$^{32}$C(=O)NR$^{32}$R$^{33}$, —NR$^{32}$C(=O)NR$^{32}$(CR$^{30}$R$^{31}$)$_w$NR$^{32}$R$^{33}$, —NR$^{32}$(CR$^{30}$R$^{31}$)$_w$S(=O)$_{0,1,2}$R$^{34}$, —NR$^{32}$(CR$^{30}$R$^{31}$)$_w$S(=O)$_{0,1,2}$NR$^{32}$R$^{33}$, —NR$^{32}$(CR$^{30}$R$^{31}$)$_w$NR$^{32}$R$^{33}$S(=O)$_{0,1,2}$R$^{34}$, —NR$^{32}$(CR$^{30}$R$^{31}$)$_w$NR$^{32}$S(=O)$_{0,1,2}$NR$^{32}$R$^{33}$, —NR$^{32}$C(=NR$^{36}$)NR$^{32}$R$^{33}$, —N(R$^{32}$)C(=NR$^{36}$)R$^{34}$, —NR$^{32}$(CR$^{30}$R$^{31}$)$_w$N(R$^{32}$)C(=NR$^{36}$)R$^{34}$, —NR$^{32}$(CR$^{30}$R$^{31}$)$_v$C(=NR$^{36}$)NR$^{32}$R$^{33}$, —NR$^{32}$(CR$^{30}$R$^{31}$)$_w$N(R$^{32}$)C(=NR$^{36}$)NR$^{32}$R$^{33}$, —NR$^{32}$(CR$^{30}$R$^{31}$)$_w$NR$^{32}$C(=O)NR$^{32}$R$^{33}$, —NR$^{32}$(CR$^{30}$R$^{31}$)$_w$NR$^{32}$C(=O)OR$^{34}$, —NR$^{32}$S(=O)$_{0,1,2}$R$^{34}$, —NR$^{32}$(CR$^{30}$R$^{31}$)$_v$CO$_2$H, —NR$^{32}$(CR$^{30}$R$^{31}$)$_v$CO$_2$R$^{34}$, —NR$^{32}$(CR$^{30}$R$^{31}$)$_v$C(=O)NR$^{32}$R$^{33}$, —N(R$^{32}$)-heteroaryl-NR$^{32}$R$^{33}$, —N(R$^{32}$)-heterocycloalkyl-NR$^{32}$R$^{33}$, —NR$^{32}$(CR$^{30}$R$^{31}$)$_v$heteroaryl, —NR$^{32}$(CR$^{30}$R$^{31}$)$_v$heterocycloalkyl, —NR$^{32}$(CR$^{30}$R$^{31}$)$_w$NR$^{32}$-heteroaryl, —NR$^{32}$(CR$^{30}$R$^{31}$)$_w$NR$^{32}$-heterocycloalkyl, —CN, —(CR$^{30}$R$^{31}$)$_v$CN, —(CR$^{30}$R$^{31}$)$_v$NR$^{32}$R$^{33}$, —(CR$^{30}$R$^{31}$)$_v$OH, —(CR$^{30}$R$^{31}$)$_v$OR$^{34}$, —(CR$^{30}$R$^{31}$)$_v$OC(=O)R$^{34}$, —(CR$^{30}$R$^{31}$)$_v$OC(=O)NR$^{32}$R$^{33}$, —(CR$^{30}$R$^{31}$)$_v$O(CR$^{30}$R$^{31}$)$_w$OR$^{34}$, —(CR$^{30}$R$^{31}$)$_v$O(CR$^{30}$R$^{31}$)$_w$OH, —(CR$^{30}$R$^{31}$)$_v$O(CR$^{30}$R$^{31}$)$_w$NR$^{32}$R$^{33}$, —(CR$^{30}$R$^{31}$)$_v$NR$^{32}$(CR$^{30}$R$^{31}$)$_w$OH, —(CR$^{30}$R$^{31}$)$_v$NR$^{32}$(CR$^{30}$R$^{31}$)$_w$OR$^{34}$, —(CR$^{30}$R$^{31}$)$_v$C(=O)NR$^{32}$R$^{33}$, —(CR$^{30}$R$^{31}$)$_v$C(=O)NR$^{32}$(CR$^{30}$R$^{31}$)$_w$NR$^{32}$R$^{33}$, —(CR$^{30}$R$^{31}$)$_v$C(=O)NR$^{32}$(CR$^{30}$R$^{31}$)$_w$OR$^{34}$, —(CR$^{30}$R$^{31}$)$_v$N(R$^{32}$)C(=O)R$^{34}$, —(CR$^{30}$R$^{31}$)$_v$N(R$^{32}$)C(=O)OR$^{34}$, —(CR$^{30}$R$^{31}$)$_v$N(R$^{32}$)C(=O)NR$^{32}$R$^{33}$, —(CR$^{30}$R$^{31}$)$_v$N(R$^{32}$)C(=O)(CR$^{30}$R$^{31}$)$_v$NR$^{32}$R$^{33}$, —(CR$^{30}$R$^{31}$)$_v$N(R$^{32}$)S(=O)$_{0,1,2}$R$^{34}$, —(CR$^{30}$R$^{31}$)$_v$N(R$^{32}$)S(=O)$_{0,1,2}$NR$^{32}$R$^{33}$, —(CR$^{30}$R$^{31}$)$_v$S(=O)$_{0,1,2}$NR$^{32}$R$^{33}$, —(CR$^{30}$R$^{31}$)$_v$NR$^{32}$(CR$^{30}$R$^{31}$)$_w$NR$^{32}$R$^{33}$, —(CR$^{30}$R$^{31}$)$_v$N(R$^{32}$)CH(=NR$^{36}$), —(CR$^{30}$R$^{31}$)$_v$N(R$^{32}$)C(=NR$^{36}$)R$^{34}$, —(CR$^{30}$R$^{31}$)$_v$C(=NR$^{36}$)NR$^{32}$R$^{33}$, —(CR$^{30}$R$^{31}$)$_v$N(R$^{32}$)C(=NR$^{36}$)NR$^{32}$R$^{33}$, —(CR$^{30}$R$^{31}$)$_v$C(=NR$^{36}$)NR$^{32}$C(=NR$^{36}$)NR$^{32}$R$^{33}$, —(CR$^{30}$R$^{31}$)$_v$heteroaryl-NR$^{32}$R$^{33}$, —(CR$^{30}$R$^{31}$)$_v$heterocycloalkyl-NR$^{32}$R$^{33}$, —(CR$^{30}$R$^{31}$)$_v$heteroaryl-N(R$^{32}$)C(=NR$^{36}$)NR$^{32}$R$^{33}$, —(CR$^{30}$R$^{31}$)$_v$heterocycloalkyl-N(R$^{32}$)C(=NR$^{36}$)NR$^{32}$R$^{33}$, —(CR$^{30}$R$^{31}$)$_v$heteroaryl, —(CR$^{30}$R$^{31}$)$_v$heterocycloalkyl, —C(=O)OH, —C(=O)OR$^{34}$, —C(=O)NR$^{32}$R$^{33}$, —C(=O)NR$^{32}$(CR$^{30}$R$^{31}$)$_w$NR$^{32}$R$^{33}$, —C(=O)NR$^{32}$(CR$^{30}$R$^{31}$)$_w$OH, —C(=O)NR$^{32}$(CR$^{30}$R$^{31}$)$_w$OR$^{34}$, —C(=NR$^{36}$)NR$^{32}$R$^{33}$, —C(=NR$^{36}$)NR$^{32}$C(=O)R$^{34}$, —S(=O)$_{1,2}$R$^{34}$, —SR$^{35}$, —S(=O)$_{0,1,2}$(CR$^{30}$R$^{31}$)$_w$NR$^{32}$R$^{33}$, —S(=O)$_{0,1,2}$(CR$^{30}$R$^{31}$)$_w$OH, —S(=O)$_{0,1,2}$(CR$^{30}$R$^{31}$)$_w$OR$^{34}$, —S(=O)$_{0,1,2}$NR$^{32}$R$^{33}$, —S(=O)$_{0,1,2}$NR$^{32}$(CR$^{30}$R$^{31}$)$_w$NR$^{32}$R$^{33}$, —S(=O)$_{0,1,2}$(CR$^{30}$R$^{31}$)$_w$N(R$^{32}$)C(=NR$^{36}$)R$^{34}$, —S(=O)$_{0,1,2}$(CR$^{30}$R$^{31}$)$_v$C(=NR$^{36}$)NR$^{32}$R$^{33}$, —S(=O)$_{0,1,2}$(CR$^{30}$R$^{31}$)$_w$N(R$^{32}$)C(=NR$^{36}$)NR$^{32}$R$^{33}$, —S(=O)$_{0,1,2}$(CR$^{30}$R$^{31}$)$_v$C(=NR$^{36}$)NR$^{32}$C(=NR$^{36}$)NR$^{32}$R$^{33}$, —Si(R$^{34}$)$_3$, —NR$^{32}$R$^{33}$R$^{34+}$Q$^-$, —(CR$^{30}$R$^{31}$)$_v$NR$^{32}$R$^{33}$R$^{34+}$Q$^-$, —NR$^{32}$(CR$^{30}$R$^{31}$)$_w$NR$^{32}$R$^{33}$R$^{34+}$Q$^-$, —NR$^{32}$R$^{34+}$(CR$^{30}$R$^{31}$)$_w$NR$^{32}$R$^{33}$R$^{34+}$Q$^-_2$, —(CR$^{30}$R$^{31}$)$_v$(T)$^+$Q$^-$, or —O(CR$^{30}$R$^{31}$)$_w$NR$^{32}$R$^{33}$R$^{34+}$Q$^-$;

or two Ys taken together with the atoms to which they are attached form an optionally substituted cycloalkyl or an optionally substituted heterocycloalkyl;

T is pyridin-1-yl, pyrimidin-1-yl, or thiazol-3-yl;
Q is a pharmaceutically acceptable counterion;
n is 0-3;
m is 0-3;
p is 0-3;
each q is independently 2-6;
each v is independently 1-5; and
each w is independently 2-5;
provided that the compound is not 3-(2-amino-2-phenylacetamido)-2-hydroxy-3,4-dihydro-2H-benzo[e][1,2]oxaborinine-8-carboxylic acid/3-(2-(2-amino-2-phenylacetamido)-2-boronoethyl)-2-hydroxybenzoic acid.

Also provided herein are compounds of Formula (VIa) or (VIb), or a pharmaceutically acceptable salt, solvate, stereoisomer, tautomer, N-oxide, dimer, or trimer thereof:

Formula (VIa)

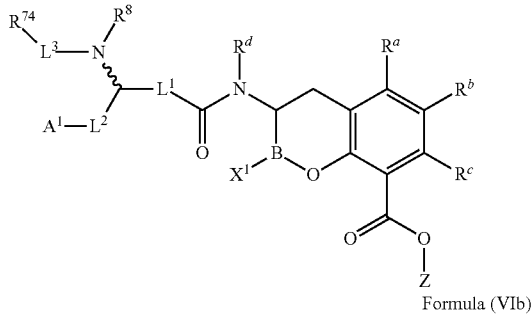

Formula (VIb)

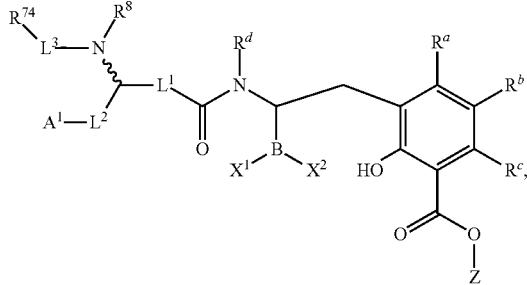

wherein:
L$^1$ is —(CR$^1$R$^2$)$_n$—;
L$^2$ is —(CR$^1$R$^2$)$_m$—;
L$^3$ is —C(=O)—, —S(=O)—, or —S(=O)$_2$—;
A$^1$ is hydrogen,

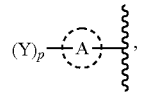

or Y;
Ring A is cycloalkyl, heterocycloalkyl, aryl, or heteroaryl;
each R$^1$ and R$^2$ are independently hydrogen, halogen, optionally substituted alkyl, —OH, —OR$^{34}$, —SR$^{35}$, —NR$^{32}$R$^{33}$, —NR$^{32}$C(=O)R$^{34}$, —C(=O)NR$^{32}$R$^{33}$, —NR$^{32}$S(=O)$_2$R$^{34}$, —C(=O)OH, —C(=O)OR$^{34}$, optionally substituted cycloalkyl, optionally substituted heterocycloalkyl, optionally substituted aryl, or optionally substituted heteroaryl; or
R$^1$ and R$^2$ are taken together with the carbon to which they are attached to form an optionally substituted cycloalkyl;
R$^8$ is hydrogen, optionally substituted alkyl, optionally substituted cycloalkyl, optionally substituted heterocycloalkyl, optionally substituted aryl, or optionally substituted heteroaryl;
each R$^{20}$ and R$^{21}$ are independently hydrogen, halogen, or optionally substituted alkyl;
R$^{22}$ and R$^{23}$ are independently hydrogen or optionally substituted alkyl; or
R$^{22}$ and R$^{23}$ are taken together with the nitrogen to which they are attached to form an optionally substituted heterocycloalkyl;
R$^{24}$ is optionally substituted alkyl, optionally substituted cycloalkyl, optionally substituted heterocycloalkyl, optionally substituted aryl, or optionally substituted heteroaryl;

$R^{25}$ is hydrogen, optionally substituted alkyl, optionally substituted cycloalkyl, optionally substituted heterocycloalkyl, optionally substituted aryl, optionally substituted heteroaryl;

each $R^{30}$, $R^{31}$, $R^{50}$, and $R^{51}$ are independently hydrogen, halogen, optionally substituted alkyl, optionally substituted cycloalkyl, optionally substituted heterocycloalkyl, optionally substituted aryl, optionally substituted heteroaryl, —OH, —OR$^{24}$, —SR$^{25}$, —NR$^{22}$R$^{23}$, —NR$^{22}$C(=O)R$^{24}$, —C(=O)NR$^{22}$R$^{23}$, —NR$^{22}$S(=O)$_2$R$^{24}$, —C(=O)OH, or —C(=O)OR$^{24}$; or $R^{30}$ and $R^{31}$, or $R^{50}$ and $R^{51}$ are taken together with the carbon atom to which they are attached form an optionally substituted cycloalkyl; or two $R^{30}$ or two $R^{50}$ on adjacent carbons are taken together to form an alkenyl; or two $R^{30}$ and two $R^{31}$, or two $R^{50}$ and two $R^{51}$ on adjacent carbons are taken together to form an alkynyl;

$R^{32}$, $R^{33}$, $R^{52}$, $R^{53}$, $R^{82}$, and $R^{83}$ are independently hydrogen, optionally substituted alkyl, optionally substituted cycloalkyl, optionally substituted heterocycloalkyl, optionally substituted aryl, optionally substituted heteroaryl, (poly-ethylene-glycol)-ethyl, optionally substituted saccharide, —CN, —OH, —S(=O)$_2$R$^{24}$, —S(=O)$_2$NR$^{22}$R$^{23}$, or —C(=O)R$^{24}$; or $R^{32}$ and $R^{33}$, or $R^{52}$ and $R^{53}$, or $R^{82}$ and $R^{83}$ are taken together with the nitrogen to which they are attached to form an optionally substituted heterocycloalkyl;

$R^{34}$, $R^{54}$, and $R^{84}$ are independently optionally substituted alkyl, optionally substituted cycloalkyl, optionally substituted heterocycloalkyl, optionally substituted aryl, or optionally substituted heteroaryl;

$R^{35}$ and $R^{55}$ are independently hydrogen, optionally substituted alkyl, optionally substituted cycloalkyl, optionally substituted heterocycloalkyl, optionally substituted aryl, optionally substituted heteroaryl;

$R^{36}$ and $R^{56}$ are independently hydrogen, —OH, —OR$^{24}$, —CN, —NO$_2$, —NR$^{22}$R$^{23}$, or optionally substituted alkyl;

Z is hydrogen, $R^{61}$, —(R$^{60}$)$_q$OR$^{61}$, —(R$^{60}$)$_q$O(R$^{60}$)$_q$OR$^{61}$, —R$^{60}$OC(=O)R$^{61}$, —R$^{60}$OC(=O)OR$^{61}$, —R$^{60}$OC(=O)NHR$^{61}$, —R$^{60}$OC(=O)N(R$^{61}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each $R^{60}$ is independently —CH$_2$—, —CH(CH$_3$)—, —C(CH$_3$)$_2$—, or optionally substituted 1,1'-cyclopropylene;

each $R^{61}$ is independently optionally substituted alkyl, optionally substituted cycloalkyl, optionally substituted heterocycloalkyl, optionally substituted aryl, or optionally substituted heteroaryl; or two $R^{61}$ are taken together with the nitrogen to which they are attached to form an optionally substituted heterocycloalkyl;

$R^{74}$ is optionally substituted alkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, —OH, —OR$^{84}$, —NR$^{82}$R$^{83}$, —C(=O)OH, or —C(=O)OR$^{84}$;

$R^a$, $R^b$, and $R^c$ are independently hydrogen, halogen, cyano, optionally substituted alkyl, optionally substituted cycloalkyl, optionally substituted heterocycloalkyl, optionally substituted aryl, optionally substituted heteroaryl, —OH, —OR$^{54}$, —O(CR$^{50}$R$^{51}$)$_w$NR$^{52}$R$^{53}$, —O(CR$^{50}$R$^{51}$)$_w$OH, —O(CR$^{50}$R$^{51}$)$_w$OR$^{54}$, —O(CR$^{50}$R$^{51}$)$_v$C(=O)OH, —O(CR$^{50}$R$^{51}$)$_v$C(=O)OR$^{54}$, —O(CR$^{50}$R$^{51}$)$_v$C(=O)NR$^{52}$R$^{53}$, —NR$^{52}$R$^{53}$, —NR$^{52}$(CR$^{50}$R$^{51}$)$_w$NR$^{52}$R$^{53}$, —NR$^{52}$(CR$^{50}$R$^{51}$)$_v$C(=O)OH, —NR$^{52}$(CR$^{50}$R$^{51}$)$_v$C(=O)OR$^{54}$, —NR$^{52}$(CR$^{50}$R$^{51}$)$_v$C(=O)NR$^{52}$R$^{53}$, —NR$^{52}$S(=O)$_{1,2}$R$^{54}$, —S(=O)$_{1,2}$R$^{54}$, —SR$^{55}$, —S(CR$^{50}$R$^{51}$)$_v$NR$^{52}$C(=NR$^{56}$)NR$^{52}$R$^{53}$, —S(CR$^{50}$R$^{51}$)$_v$NR$^{52}$CR$^{50}$(=NR$^{56}$), —S(CR$^{50}$R$^{51}$)C(=NR$^{56}$)NR$^{52}$R$^{53}$, —S(CR$^{50}$R$^{51}$)$_w$OH, —S(CR$^{50}$R$^{51}$)$_w$OR$^{54}$, —S(CR$^{50}$R$^{51}$)$_w$NR$^{52}$R$^{53}$, —S(CR$^{50}$R$^{51}$)$_v$C(=O)OH, —S(CR$^{50}$R$^{51}$)$_v$C(=O)OR$^{54}$, —S(CR$^{50}$R$^{51}$)$_v$C(=O)NR$^{52}$R$^{53}$, —C(=O)H, —C(=O)R$^{54}$, —C(=O)OH, —C(=O)OR$^{54}$, —C(=O)NR$^{52}$R$^{53}$, —(CR$^{50}$R$^{51}$)$_v$N(R$^{52}$)(CR$^{50}$R$^{51}$)$_v$C(=O)OH, —(CR$^{50}$R$^{51}$)$_v$OH, —(CR$^{50}$R$^{51}$)$_v$OR$^{54}$, —(CR$^{50}$R$^{51}$)$_v$C(=O)OH, —(CR$^{50}$R$^{51}$)$_v$C(=O)OR$^{54}$, —(CR$^{50}$R$^{51}$)$_v$C(=O)NR$^{52}$R$^{53}$, —(CR$^{50}$R$^{51}$)$_v$OC(=O)R$^{51}$, —(CR$^{50}$R$^{51}$)$_v$SR$^{55}$, —(CR$^{50}$R$^{51}$)$_v$NR$^{52}$C(=NR$^{56}$), —(CR$^{50}$R$^{51}$)$_v$NR$^{52}$R$^{53}$, —(CR$^{50}$R$^{51}$)$_v$C(=NR$^{56}$)NR$^{52}$R$^{53}$, —(CR$^{50}$R$^{51}$)$_v$C(=O)NR$^{52}$R$^{53}$, —(CR$^{50}$R$^{51}$)$_v$heterocycloalkyl, or —(CR$^{50}$R$^{51}$)$_v$heteroaryl;

$R^d$ is hydrogen, —CN, —OH, —S(=O)$_2$R$^{24}$, —S(=O)$_2$NR$^{22}$R$^{23}$, —(CR$^{20}$R$^{21}$)$_v$C(=O)OH, —C(=O)R$^{24}$, optionally substituted alkyl, optionally substituted cycloalkyl, optionally substituted heterocycloalkyl, optionally substituted aryl, optionally substituted heteroaryl, (poly-ethylene-glycol)-ethyl, an optionally substituted saccharide;

$R^X$ is optionally substituted alkyl or optionally substituted cycloalkyl;

$X^1$ and $X^2$ are independently —OH, —OR$^X$, or F; or $X^1$ and $X^2$ are taken together with the boron atom to which they are attached to form a cyclic boronate ester;

each Y is independently halogen, optionally substituted alkyl, optionally substituted cycloalkyl, optionally substituted heterocycloalkyl, optionally substituted aryl, optionally substituted heteroaryl, -heteroaryl-NR$^{32}$R$^{33}$, -heterocycloalkyl-NR$^{32}$R$^{33}$, -heteroaryl-N(R$^{32}$)C(=NR$^{32}$)NR$^{32}$R$^{33}$, -heterocycloalkyl-N(R$^{32}$)C(=NR$^{32}$)NR$^{32}$R$^{33}$, —OH, —OR$^{34}$, —O(CR$^{30}$R$^{31}$)$_w$OH, —O(CR$^{30}$R$^{31}$)$_w$OR$^{34}$, —O(CR$^{30}$R$^{31}$)$_w$NR$^{32}$R$^{33}$, —O(CR$^{30}$R$^{31}$)$_w$NR$^{32}$C(=O)R$^{34}$, —O(CR$^{30}$R$^{31}$)$_w$NR$^{32}$C(=O)OR$^{34}$, —O(CR$^{30}$R$^{31}$)$_w$NR$^{32}$C(=O)NR$^{32}$R$^{33}$, —O(CR$^{30}$R$^{31}$)$_v$C(=O)NR$^{32}$R$^{33}$, —O(CR$^{30}$R$^{31}$)$_w$NR$^{32}$S(=O)$_{0,1,2}$R$^{34}$, —O(CR$^{30}$R$^{31}$)$_w$NR$^{32}$S(=O)$_{0,1,2}$NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —O(CR$^{30}$R$^{31}$)$_v$C(=NR$^{36}$)NR$^{32}$R$^{33}$, —O(CR$^{30}$R$^{31}$)$_w$N(R$^{32}$)C(=NR$^{36}$)R$^{34}$, —O(CR$^{30}$R$^{31}$)$_v$C(=NR$^{36}$)NR$^{32}$C(=NR$^{36}$)NR$^{32}$R$^{33}$, —O(CR$^{30}$R$^{31}$)$_w$N(R$^{32}$)C(=NR$^{36}$)NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —OC(=O)R$^{34}$, —OC(=O)(CR$^{30}$R$^{31}$)$_v$NR$^{32}$R$^{33}$, —OC(=O)NR$^{32}$R$^{33}$, —OC(=O)OR$^{34}$, —OC(=O)NR$^{32}$(CR$^{30}$R$^{31}$)$_w$NR$^{32}$R$^{33}$, —O-heteroaryl, —O-heterocycloalkyl, —O(CR$^{30}$R$^{31}$)$_v$heteroaryl, —O(CR$^{30}$R$^{31}$)$_v$heterocycloalkyl, —O(CR$^{30}$R$^{31}$)$_w$NR$^{32}$-heteroaryl, —O(CR$^{30}$R$^{31}$)$_w$NR$^{32}$-heterocycloalkyl, —O(CR$^{30}$R$^{31}$)$_w$O-heterocycloalkyl, —NR$^{32}$R$^{33}$, —NR$^{32}$(CR$^{30}$R$^{31}$)$_w$NR$^{32}$R$^{33}$, —NR$^{32}$(CR$^{30}$R$^{31}$)$_w$OH, —NR$^{32}$(CR$^{30}$R$^{31}$)$_w$OR$^{34}$, —NR$^{32}$C(=O)R$^{34}$, —NR$^{32}$C(=O)OR$^{34}$, —N(R$^{32}$)C(=O)(CR$^{30}$R$^{31}$)$_v$NR$^{32}$R$^{33}$, —NR$^{32}$C(=O)NR$^{32}$R$^{33}$, —NR$^{32}$C(=O)NR$^{32}$(CR$^{30}$R$^{31}$)$_w$NR$^{32}$R$^{33}$, —NR$^{32}$(CR$^{30}$R$^{31}$)$_w$S(=O)$_{0,1,2}$R$^{34}$, —NR$^{32}$(CR$^{30}$R$^{31}$)$_v$S(=O)$_{0,1,2}$NR$^{32}$R$^{33}$, —NR$^{32}$(CR$^{30}$R$^{31}$)$_w$NR$^{32}$R$^{33}$S(=O)$_{0,1,2}$R$^{34}$, —NR$^{32}$(CR$^{30}$R$^{31}$)$_w$NR$^{32}$S(=O)$_{0,1,2}$NR$^{32}$R$^{33}$, —NR$^{32}$C(=NR$^{36}$)NR$^{32}$R$^{33}$, —N(R$^{32}$)C(=NR$^{36}$)R$^{34}$, —NR$^{32}$(CR$^{30}$R$^{31}$)$_w$N(R$^{32}$)C(=NR$^{36}$)R$^{34}$, —NR$^{32}$(CR$^{30}$R$^{31}$)$_v$C(=NR$^{36}$)NR$^{32}$R$^{33}$, —NR$^{32}$(CR$^{30}$R$^{31}$)$_w$N(R$^{32}$)C(=NR$^{36}$)NR$^{32}$R$^{33}$, —NR$^{32}$(CR$^{30}$R$^{31}$)$_w$NR$^{32}$C(=O)NR$^{32}$R$^{33}$, —NR$^{32}$(CR$^{30}$R$^{31}$)$_w$NR$^{32}$C(=O)OR$^{34}$, —NR$^{32}$S(=O)$_{0,1,2}$R$^{34}$, —NR$^{32}$(CR$^{30}$R$^{31}$)$_v$CO$_2$H, —NR$^{32}$(CR$^{30}$R$^{31}$)$_v$CO$_2$R$^{34}$, —NR$^{32}$(CR$^{30}$R$^{31}$)$_v$C(=O)NR$^{32}$R$^{33}$, —N(R$^{32}$)-heteroaryl-NR$^{32}$R$^{33}$, —N(R$^{32}$)-heterocycloalkyl- NR$^{32}$R$^{33}$, —NR$^{32}$(CR$^{30}$R$^{31}$)$_v$heteroaryl, —NR$^{32}$(CR$^{30}$R$^{31}$)$_v$heterocycloalkyl, —NR$^{32}$(CR$^{30}$R$^{31}$)$_w$NR$^{32}$-heteroaryl, —NR$^{32}$(CR$^{30}$R$^{31}$)$_w$NR$^{32}$-heterocycloalkyl, —CN, —(CR$^{30}$R$^{31}$)$_v$CN, —(CR$^{30}$R$^{31}$)$_v$NR$^{32}$R$^{33}$, —(CR$^{30}$R$^{31}$)$_v$OH, —(CR$^{30}$R$^{31}$)$_v$OR$^{34}$, —(CR$^{30}$R$^{31}$)$_v$OC(=O)R$^{34}$, —(CR$^{30}$R$^{31}$)$_v$OC(=O)NR$^{32}$R$^{33}$, —(CR$^{30}$R$^{31}$)$_v$O(CR$^{30}$R$^{31}$)$_w$OR$^{34}$, —(CR$^{30}$R$^{31}$)$_v$O(CR$^{30}$R$^{31}$)$_w$OH, —(CR$^{30}$R$^{31}$)$_v$O(CR$^{30}$R$^{31}$)$_w$NR$^{32}$R$^{33}$, —(CR$^{30}$R$^{31}$)$_v$NR$^{32}$(CR$^{30}$R$^{31}$)$_w$OH, —(CR$^{30}$R$^{31}$)$_v$NR$^{32}$(CR$^{30}$R$^{31}$)$_w$OR$^{34}$, —(CR$^{30}$R$^{31}$)$_v$C(=O)NR$^{32}$R$^{33}$, —(CR$^{30}$R$^{31}$)$_v$C(=O)NR$^{32}$(CR$^{30}$R$^{31}$)$_w$NR$^{32}$R$^{33}$, —(CR$^{30}$R$^{31}$)$_v$C(=O)NR$^{32}$(CR$^{30}$R$^{31}$)$_w$OR$^{34}$, —(CR$^{30}$R$^{31}$)$_v$N(R$^{32}$)C(=O)R$^{34}$, —(CR$^{30}$R$^{31}$)$_v$N(R$^{32}$)C(=O)OR$^{34}$, —(CR$^{30}$R$^{31}$)$_v$N(R$^{32}$)C(=O)NR$^{32}$R$^{33}$, —(CR$^{30}$R$^{31}$)$_w$N(R$^{32}$)C(=O) (CR$^{30}$R$^{31}$)$_v$NR$^{32}$R$^{33}$, —(CR$^{30}$R$^{31}$)$_v$N(R$^{32}$)S(=O)$_{0,1,2}$R$^{34}$, —(CR$^{30}$R$^{31}$)$_v$N(R$^{32}$)S(=O)$_{0,1,2}$NR$^{32}$R$^{33}$, —(CR$^{30}$R$^{31}$)$_v$S(=O)$_{0,1,2}$NR$^{32}$R$^{33}$, —(CR$^{30}$R$^{31}$)$_v$NR$^{32}$(CR$^{30}$R$^{31}$)$_w$NR$^{32}$R$^{33}$, —(CR$^{30}$R$^{31}$)$_v$N(R$^{32}$)CH(=NR$^{36}$), —(CR$^{30}$R$^{31}$)$_v$N(R$^{32}$)C(=NR$^{36}$)R$^{34}$, —(CR$^{30}$R$^{31}$)$_v$C(=NR$^{36}$)NR$^{32}$R$^{33}$, —(CR$^{30}$R$^{31}$)$_v$N(R$^{32}$)C(=NR$^{36}$)NR$^{32}$R$^{33}$, —(CR$^{30}$R$^{31}$)$_v$C(=NR$^{36}$)NR$^{32}$C(=NR$^{36}$)NR$^{32}$R$^{33}$, —(CR$^{30}$R$^{31}$)$_v$heteroaryl-NR$^{32}$R$^{33}$, —(CR$^{30}$R$^{31}$)$_v$heterocycloalkyl-NR$^{32}$R$^{33}$, —(CR$^{30}$R$^{31}$)$_v$heteroaryl-N(R$^{32}$)C(=NR$^{36}$)NR$^{32}$R$^{33}$, —(CR$^{30}$R$^{31}$)$_v$heterocycloalkyl-N(R$^{32}$)C(=NR$^{36}$)NR$^{32}$R$^{33}$, —(CR$^{30}$R$^{31}$)$_v$heteroaryl, —(CR$^{30}$R$^{31}$)$_v$heterocycloalkyl, —C(=O)OH, —C(=O)OR$^{34}$, —C(=O)NR$^{32}$R$^{33}$, —C(=O)NR$^{32}$(CR$^{30}$R$^{31}$)$_w$NR$^{32}$R$^{33}$, —C(=O)NR$^{32}$(CR$^{30}$R$^{31}$)$_w$OH, —C(=O)NR$^{32}$(CR$^{30}$R$^{31}$)$_w$OR$^{34}$, —C(=NR$^{36}$)NR$^{32}$R$^{33}$, —C(=NR$^{36}$)NR$^{32}$C(=O)R$^{34}$, —S(=O)$_{1,2}$R$^{34}$, —SR$^{35}$, —S(=O)$_{0,1,2}$(CR$^{30}$R$^{31}$)$_w$NR$^{32}$R$^{33}$, —S(=O)$_{0,1,2}$(CR$^{30}$R$^{31}$)$_w$OH, —S(=O)$_{0,1,2}$(CR$^{30}$R$^{31}$)$_w$OR$^{34}$, —S(=O)$_{0,1,2}$NR$^{32}$R$^{33}$, —S(=O)$_{0,1,2}$NR$^{32}$(CR$^{30}$R$^{31}$)$_w$NR$^{32}$R$^{33}$, —S(=O)$_{0,1,2}$(CR$^{30}$R$^{31}$)$_w$N(R$^{32}$)C(=NR$^{36}$)R$^{34}$, —S(=O)$_{0,1,2}$(CR$^{30}$R$^{31}$)$_v$C(=NR$^{36}$)NR$^{32}$R$^{33}$, —S(=O)$_{0,1,2}$(CR$^{30}$R$^{31}$)$_w$N(R$^{32}$)C(=NR$^{36}$)NR$^{32}$R$^{33}$, —S(=O)$_{0,1,2}$(CR$^{30}$R$^{31}$)$_v$C(=NR$^{36}$)NR$^{32}$C(=NR$^{36}$)NR$^{32}$R$^{33}$, —Si(R$^{34}$)$_3$, —NR$^{32}$R$^{33}$R$^{34+}$Q$^-$, —(CR$^{30}$R$^{31}$)$_v$NR$^{32}$R$^{33}$R$^{34+}$Q$^-$, —NR$^{32}$(CR$^{30}$R$^{31}$)$_w$NR$^{32}$R$^{33}$R$^{34+}$Q$^-$, —NR$^{32}$R$^{34+}$(CR$^{30}$R$^{31}$)$_w$NR$^{32}$R$^{33}$R$^{34+}$Q$^-_2$, —(CR$^{30}$R$^{31}$)$_v$(T)$^+$Q$^-$, or —O(CR$^{30}$R$^{31}$)$_w$NR$^{32}$R$^{33}$R$^{34+}$Q$^-$;

or two Ys taken together with the atoms to which they are attached form an optionally substituted cycloalkyl or an optionally substituted heterocycloalkyl;

T is pyridin-1-yl, pyrimidin-1-yl, or thiazol-3-yl;
Q is a pharmaceutically acceptable counterion;
n is 0-3;
m is 0-3;
p is 0-3;
each q is independently 2-6;
each v is independently 1-5; and
each w is independently 2-5.

Also provided herein are compounds of Formula (VIIa) or (VIIb), or a pharmaceutically acceptable salt, solvate, stereoisomer, tautomer, N-oxide, dimer, or trimer thereof:

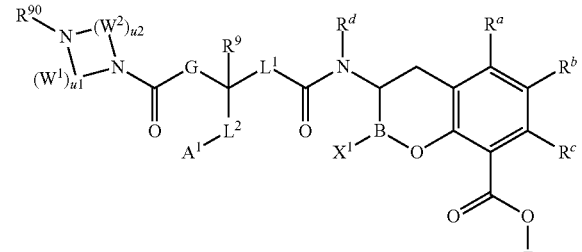

Formula (VIIa)

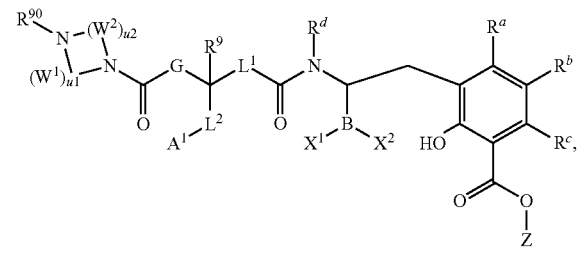

Formula (VIIb)

wherein:
G is —NR$^8$—, —C(R$^{10}$)$_2$—, or —C(R$^{10}$)$_2$NR$^8$—;
L$^1$ is —(CR$^1$R$^2$)$_n$—;
L$^2$ is —(CR$^1$R$^2$)$_m$—;
A$^1$ is hydrogen,

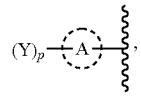

or Y;

Ring A is cycloalkyl, heterocycloalkyl, aryl, or heteroaryl;
R$^1$, R$^2$, and R$^9$ are independently hydrogen, halogen, optionally substituted alkyl, —OH, —OR$^{34}$, —SR$^{35}$, —NR$^{32}$R$^{33}$, —NR$^{32}$C(=O)R$^{34}$, —C(=O)NR$^{32}$R$^{33}$, —NR$^{32}$S(=O)$_2$R$^{34}$, —C(=O)OH, —C(=O)OR$^{34}$, optionally substituted cycloalkyl, optionally substituted heterocycloalkyl, optionally substituted aryl, or optionally substituted heteroaryl; or
R$^1$ and R$^2$ are taken together with the carbon to which they are attached to form an optionally substituted cycloalkyl or an optionally substituted heterocycloalkyl;
R$^8$ is hydrogen, optionally substituted alkyl, optionally substituted cycloalkyl, optionally substituted heterocycloalkyl, optionally substituted aryl, or optionally substituted heteroaryl; or
R$^8$ and R$^9$ are taken together with the atoms to which they are attached to form an optionally substituted heterocycloalkyl;
each R$^{10}$ is independently hydrogen, halogen, or optionally substituted alkyl;
each R$^{20}$ and R$^{21}$ are independently hydrogen, halogen, or optionally substituted alkyl;

$R^{22}$ and $R^{23}$ are independently hydrogen or optionally substituted alkyl; or $R^{22}$ and $R^{23}$ are taken together with the nitrogen to which they are attached to form an optionally substituted heterocycloalkyl;

$R^{24}$ is optionally substituted alkyl, optionally substituted cycloalkyl, optionally substituted heterocycloalkyl, optionally substituted aryl, or optionally substituted heteroaryl;

$R^{25}$ is hydrogen, optionally substituted alkyl, optionally substituted cycloalkyl, optionally substituted heterocycloalkyl, optionally substituted aryl, optionally substituted heteroaryl;

each $R^{30}$, $R^{31}$, $R^{50}$, and $R^{51}$ are independently hydrogen, halogen, optionally substituted alkyl, optionally substituted cycloalkyl, optionally substituted heterocycloalkyl, optionally substituted aryl, optionally substituted heteroaryl, —OH, —OR$^{24}$, —SR$^{25}$, —NR$^{22}$R$^{23}$, —NR$^{22}$C(=O)R$^{24}$, —C(=O)NR$^{22}$R$^{23}$, —NR$^{22}$S(=O)$_2$R$^{24}$, —C(=O)OH, or —C(=O)OR$^{24}$; or $R^{30}$ and $R^{31}$, or $R^{50}$ and $R^{51}$ are taken together with the carbon atom to which they are attached form an optionally substituted cycloalkyl; or two $R^{30}$ or two $R^{50}$ on adjacent carbons are taken together to form an alkenyl; or two $R^{30}$ and two $R^{31}$, or two $R^{50}$ and two $R^{5'}$ on adjacent carbons are taken together to form an alkynyl;

$R^{32}$, $R^{33}$, $R^{52}$, and $R^{53}$ are independently hydrogen, optionally substituted alkyl, optionally substituted cycloalkyl, optionally substituted heterocycloalkyl, optionally substituted aryl, optionally substituted heteroaryl, (poly-ethylene-glycol)-ethyl, optionally substituted saccharide, —CN, —OH, —S(=O)$_2$R$^{24}$, —S(=O)$_2$NR$^{22}$R$^{23}$, or —C(=O)R$^{24}$; or $R^{32}$ and $R^{33}$, or $R^{52}$ and $R^{53}$ are taken together with the nitrogen to which they are attached to form an optionally substituted heterocycloalkyl;

$R^{34}$, and $R^{54}$ are independently optionally substituted alkyl, optionally substituted cycloalkyl, optionally substituted heterocycloalkyl, optionally substituted aryl, or optionally substituted heteroaryl;

$R^{35}$ and $R^{55}$ are independently hydrogen, optionally substituted alkyl, optionally substituted cycloalkyl, optionally substituted heterocycloalkyl, optionally substituted aryl, optionally substituted heteroaryl;

$R^{36}$ and $R^{56}$ are independently hydrogen, —OH, —OR$^{24}$, —CN, —NO$_2$, —NR$^{22}$R$^{23}$, or optionally substituted alkyl;

each $R^{60}$ is independently —CH$_2$—, —CH(CH$_3$)—, —C(CH$_3$)$_2$—, or optionally substituted 1,1'-cyclopropylene;

each $R^{61}$ is independently optionally substituted alkyl, optionally substituted cycloalkyl, optionally substituted heterocycloalkyl, optionally substituted aryl, or optionally substituted heteroaryl; or two $R^{61}$ are taken together with the nitrogen to which they are attached to form an optionally substituted heterocycloalkyl;

$R^{90}$ is hydrogen, —OH, optionally substituted alkyl, optionally substituted alkoxy, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, —S(=O)$_2$R$^{24}$, —S(=O)$_2$NR$^{22}$R$^{23}$, or —C(=O)R$^{24}$ each $R^{91}$ is independently hydrogen, halogen, —OH, —CN, NH$_2$, NO$_2$, optionally substituted alkyl, optionally substituted alkoxy, optionally substituted cycloalkyl, optionally substituted heterocycloalkyl, optionally substituted aryl, or optionally substituted heteroaryl;

$R^a$, $R^b$, and $R^c$ are independently hydrogen, halogen, cyano, optionally substituted alkyl, optionally substituted cycloalkyl, optionally substituted heterocycloalkyl, optionally substituted aryl, optionally substituted heteroaryl, —OH, —OR$^{54}$, —O(CR$^{50}$R$^{51}$)NR$^{52}$R$^{53}$, —O(CR$^{50}$R$^{51}$)$_w$OH, —O(CR$^{50}$R$^{51}$)$_w$OR$^{54}$, —O(CR$^{50}$R$^{51}$)$_v$C(=O)OH, —O(CR$^{50}$R$^{51}$)$_v$C(=O)OR$^{54}$, —O(CR$^{50}$R$^{51}$)$_v$C(=O)NR$^{52}$R$^{53}$, —NR$^{52}$R$^{53}$, —NR$^{52}$(CR$^{50}$R$^{51}$)$_v$NR$^{52}$R$^{53}$, —NR$^{52}$(CR$^{50}$R$^{51}$)$_v$C(=O)OH, —NR$^{52}$(CR$^{50}$R$^{51}$)$_v$C(=O)OR$^{54}$, —NR$^{52}$(CR$^{50}$R$^{51}$)$_v$C(=O)NR$^{52}$R$^{53}$, —NR$^{52}$S(=O)$_{1,2}$R$^{54}$, —S(=O)$_{1,2}$R$^{54}$, —SR$^{55}$, —S(CR$^{50}$R$^{51}$)$_v$NR$^{52}$C(=NR$^{56}$)NR$^{52}$R$^{53}$, —S(CR$^{50}$R$^{51}$)$_v$NR$^{52}$CR$^{50}$(=NR$^{56}$), —S(CR$^{50}$R$^{51}$)C(=NR$^{56}$)NR$^{52}$R$^{53}$, —S(CR$^{50}$R$^{51}$)$_w$OH, —S(CR$^{50}$R$^{51}$)$_w$OR$^{54}$, —S(CR$^{50}$R$^{51}$)$_w$NR$^{52}$R$^{53}$, —S(CR$^{50}$R$^{51}$)$_v$C(=O)OH, —S(CR$^{50}$R$^{51}$)$_v$C(=O)OR$^{54}$, —S(CR$^{50}$R$^{51}$)$_v$C(=O)NR$^{52}$R$^{53}$, —C(=O)H, —C(=O)R$^{54}$, —C(=O)OH, —C(=O)OR$^{54}$, —C(=O)NR$^{52}$R$^{53}$, —(CR$^{50}$R$^{51}$)$_v$N(R$^{52}$)(CR$^{50}$R$^{51}$)$_v$C(=O)OH, —(CR$^{50}$R$^{51}$)$_w$OH, —(CR$^{50}$R$^{51}$)$_w$OR$^{54}$, —(CR$^{50}$R$^{51}$)$_v$C(=O)OH, —(CR$^{50}$R$^{51}$)$_v$C(=O)OR$^{54}$, —(CR$^{50}$R$^{51}$)$_v$C(=O)NR$^{52}$R$^{53}$, —(CR$^{50}$R$^{51}$)$_v$OC(=O)OR$^{54}$, —(CR$^{50}$R$^{51}$)SR$^{55}$, —(CR$^{50}$R$^{51}$)$_v$NR$^{52}$C(=NR$^{56}$), —(CR$^{50}$R$^{51}$)$_v$NR$^{52}$R$^{53}$, —(CR$^{50}$R$^{51}$)$_v$C(=NR$^{56}$)NR$^{52}$R$^{53}$, —(CR$^{50}$R$^{51}$)$^v$C(=O)NR$^{52}$R$^{53}$, —(CR$^{50}$R$^{51}$)$_v$heterocycloalkyl, or —(CR$^{50}$R$^{51}$)$_v$heteroaryl;

$R^d$ is hydrogen, —CN, —OH, —S(=O)$_2$R$^{24}$, —S(=O)$_2$NR$^{22}$R$^{23}$, —(CR$^{20}$R$^{21}$)C(=O)OH, —C(=O)R$^{24}$ optionally substituted alkyl, optionally substituted cycloalkyl, optionally substituted heterocycloalkyl, optionally substituted aryl, optionally substituted heteroaryl, (poly-ethylene-glycol)-ethyl, an optionally substituted saccharide;

$R^X$ is optionally substituted alkyl or optionally substituted cycloalkyl;

each $W^1$ and $W^2$ is independently —C(=O)— or —C(R$^{91}$)$_2$—;

$X^1$ and $X^2$ are independently —OH, —OR$^X$, or F; or $X^1$ and $X^2$ are taken together with the boron atom to which there are attached to form a cyclic boronate ester;

each Y is independently halogen, optionally substituted alkyl, optionally substituted cycloalkyl, optionally substituted heterocycloalkyl, optionally substituted aryl, optionally substituted heteroaryl, -heteroaryl-NR$^{32}$R$^{33}$, -heterocycloalkyl-NR$^{32}$R$^{33}$, -heteroaryl-N(R$^{32}$)C(=NR$^{32}$)NR$^{32}$R$^{33}$, -heterocycloalkyl-N(R$^{32}$)C(=NR$^{32}$)NR$^{32}$R$^{33}$, —OH, —OR$^{34}$, —O(CR$^{30}$R$^{31}$)$_w$OH, —O(CR$^{30}$R$^{31}$)$_w$OR$^{34}$, —O(CR$^{30}$R$^{31}$)$_w$NR$^{32}$R$^{33}$, —O(CR$^{30}$R$^{31}$)$_w$NR$^{32}$C(=O)R$^{34}$, —O(CR$^{30}$R$^{31}$)$_w$NR$^{32}$C(=O)OR$^{34}$, —O(CR$^{30}$R$^{31}$)$_w$NR$^{32}$C(=O)NR$^{32}$R$^{33}$, —O(CR$^{30}$R$^{31}$)$_w$C(=O)NR$^{32}$R$^{33}$, —O(CR$^{30}$R$^{31}$)$_w$NR$^{32}$S(=O)$_{0,1,2}$R$^{34}$, —O(CR$^{30}$R$^{31}$)$_w$NR$^{32}$S(=O)$_{0,1,2}$NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —O(CR$^{30}$R$^{31}$)$_v$C(=NR$^{36}$)NR$^{32}$R$^{31}$, —O(CR$^{30}$R$^{31}$)$_w$N(R$^{32}$)C(=NR$^{36}$)R$^{34}$, —O(CR$^{30}$R$^{31}$)$_v$C(=NR$^{36}$)NR$^{32}$C(=NR$^{36}$)NR$^{32}$R$^{33}$, —O(CR$^{30}$R$^{31}$)$_w$N(R$^{32}$)C(=NR$^{36}$)NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —OC(=O)R$^{34}$, —OC(=O)(CR$^{30}$R$^{31}$)$_v$NR$^{32}$R$^{33}$, —OC(=O)NR$^{32}$R$^{33}$, —OC(=O)OR$^{34}$, —OC(=O)NR$^{32}$ (CR³⁰R³¹)_wNR³²R³³, —O-heteroaryl, —O-heterocycloalkyl, —O(CR³⁰R³¹)_wheteroaryl, —O(CR³⁰R³¹)_w heterocycloalkyl, —O(CR³⁰R³¹)_wNR³²-heteroaryl, —O(CR³⁰R³¹)_wNR³²-heterocycloalkyl, —O(CR³⁰R³¹)_wO-heterocycloalkyl, —NR³²R³³, —NR³²(CR³⁰R³¹)_wNR³²R³³, —NR³²(CR³⁰R³¹)_wOH, —NR³²(CR³⁰R³¹)_wOR³⁴, —NR³²C(=O)R³⁴, —NR³²C(=O)OR³⁴, —N(R¹²)C(=O)(CR³⁰R³¹)_w NR³²R³³, —NR³²C(=O)NR³²R³³, —NR³²C(=O) NR³²(CR³⁰R³¹)_wNR³²R³³, —NR³²(CR³⁰R³¹)_wS(=O)_{0,1,2}R³⁴, —NR³²(CR³⁰R³¹)_wS(=O)_{0,1,2} NR³²R³³, —NR³²(CR³⁰R³¹)_wNR³²R³³S(=O)_{0,1,2}R³⁴, —NR³²(CR³⁰R³¹)_wNR³²S(=O)_{0,1,2}NR³²R³³, —NR³²C(=NR³⁶)NR³²R³³, —N(R³²)C(=NR³⁶)R³⁴, —NR³²(CR³⁰R³¹)_wN(R³²)C(=NR³⁶)R³⁴, —NR³²(CR³⁰R³¹)_vC(=NR³⁶)NR³²R³³, —NR³²(CR³⁰R³¹)_wN (R³²)C(=NR³⁶)NR³²R³³, —NR³²(CR³⁰R³¹)_wNR³²C (=O)NR³²R³³, —NR³²(CR³⁰R³¹)_wNR³²C(=O)OR³⁴, —NR³²S(=O)_{0,1,2}R³⁴, —NR³²(CR³⁰R³¹)_vCO₂H, —NR³²(CR³⁰R³¹)_vCO₂R³⁴, —NR³²(CR³⁰R³¹)_vC (=O)NR³²R³³, —N(R³²)-heteroaryl-NR³²R³³, —N(R³²)-heterocycloalkyl- NR³²R³³, —NR³² (CR³⁰R³¹)_vheteroaryl, —NR³²(CR³⁰R³¹)heterocycloalkyl, —NR³²(CR³⁰R³¹)_wNR³²-heteroaryl, —NR³² (CR³⁰R³¹)_wNR³²-heterocycloalkyl, —CN, —(CR³⁰R³¹)_vCN, —(CR³⁰R³¹)_vNR³²R³³, —(CR³⁰R³¹)_vOH, —(CR³⁰R³¹)_vOR³⁴, —(CR³⁰R³¹)_v OC(=O)R³⁴, —(CR³⁰R³¹)_vOC(=O)NR³²R³³, —(CR³⁰R³¹)_vO(CR³⁰R³¹)_wOR³⁴, —(CR³⁰R³¹)_vO (CR³⁰R³¹)_wOH, —(CR³⁰R³¹)_vO(CR³⁰R³¹)_wNR³²R³³, —(CR³⁰R³¹)_wNR³²(CR³⁰R³¹)_wOH, —(CR³⁰R³¹)_v NR³²(CR³⁰R³¹)_wOR³⁴, —(CR³⁰R³¹)_vC(=O) NR³²R³³, —(CR³⁰R³¹)_vC(=O)NR³²(CR³⁰R³¹)_w NR³²R³³, —(CR³⁰R³¹)_vC(=O)NR³²(CR³⁰R³¹)_w OR³⁴, —(CR³⁰R³¹)_vN(R³²)C(=O)R³⁴, —(CR³⁰R³¹)_v N(R³²)C(=O)OR³⁴, —(CR³⁰R³¹)_vN(R³²)C(=O) NR³²R³¹, —(CR³⁰R³¹)_vN(R³²)C(=O)(CR³⁰R³¹)_v NR³²R³³, —(CR³⁰R³¹)_vN(R³²)S(=O)_{0,1,2}R³⁴, —(CR³⁰R³¹)_vN(R³²)S(=O)_{0,1,2}NR³²R³³, —(CR³⁰R³¹)_vS(=O)_{0,1,2}NR³²R³³, —(CR³⁰R³¹)_vNR³² (CR³⁰R³¹)_wNR³²R³³, —(CR³⁰R³¹)_vN(R³²)CH (=NR³⁶), —(CR³⁰R³¹)_vN(R³²)C(=NR³⁶)R³⁴, —(CR³⁰R³¹)_vC(=NR³⁶)NR³²R³³, —(CR³⁰R³¹)_vN (R³²)C(=NR³⁶)NR³²R³³, —(CR³⁰R³¹)_vC(=NR³⁶) NR³²C(=NR³⁶)NR³²R³³, —(CR³⁰R³¹)_vheteroaryl-NR³²R³³, —(CR³⁰R³¹)_vheterocycloalkyl-NR³²R³³, —(CR³⁰R³¹)_vheteroaryl-N(R³²)C(=NR³⁶)NR³²R³³, —(CR³⁰R³¹)_vheterocycloalkyl-N(R³²)C(=NR³⁶) NR³²R³³, —(CR³⁰R³¹)_vheteroaryl, —(CR³⁰R³¹)_v heterocycloalkyl, —C(=O)OH, —C(=O)OR³⁴, —C(=O)NR³²R³³, —C(=O)NR³²(CR³⁰R³¹)_w NR³²R³³, —C(=O)NR³²(CR³⁰R³¹)_wOH, —C(=O) NR³²(CR³⁰R³¹)_wOR³⁴, —C(=NR³⁶)NR³²R³³, —C(=NR³⁶)NR³²C(=O)R³⁴, —S(=O)_{1,2}R³⁴, —SR³⁵, —S(=O)_{0,1,2}(CR³⁰R³¹)_wNR³²R³³, —S(=O)_{0,1,2}(CR³⁰R³¹)_wOH, —S(=O)_{0,1,2}(CR³⁰R³¹)_w OR³⁴, —S(=O)_{0,1,2}NR³²R³³, —S(=O)_{0,1,2}NR³² (CR³⁰R³¹)_wNR³²R³³, —S(=O)_{0,1,2}(CR³⁰R³¹)_wN(R³²) C(=NR³⁶)R³⁴, —S(=O)_{0,1,2}(CR³⁰R³¹)_vC(=NR³⁶) NR³²R³³, —S(=O)_{0,1,2}(CR³⁰R³¹)_wN(R³²)C(=NR³⁶) NR³²R³³, —S(=O)_{0,1,2}(CR³⁰R³¹)_vC(=NR³⁶)NR³²C (=NR³⁶)NR³²R³³, —Si(R³⁴)₃, —NR³²R³³R³⁴⁺Q⁻, —(CR³⁰R³¹)_wNR³²R³³R³⁴⁺Q⁻, —NR³²(CR³⁰R³¹)_w NR³²R³³R³⁴⁺Q⁻, —NR³²R³⁴⁺ (CR³⁰R³¹)_w NR³²R³³R³⁴⁺Q⁻₂, —(CR³⁰R³¹)_v(T)⁺Q⁻, or —(CR³⁰R⁻)_wN³²R³³⁺Q⁻;

or two Ys taken together with the atoms to which they are attached form an optionally substituted cycloalkyl or an optionally substituted heterocycloalkyl;

Z is hydrogen, R⁶¹, —(R⁶⁰)_qOR⁶¹, —(R⁶⁰)_qO(R⁶⁰)_q OR⁶¹, —R⁶⁰OC(=O)R⁶¹, —R⁶⁰OC(=O)OR⁶¹, —R⁶⁰OC(=O)NHR⁶¹, —R⁶⁰OC(=O)N(R⁶¹)₂, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

T is pyridin-1-yl, pyrimidin-1-yl, or thiazol-3-yl;

Q is a pharmaceutically acceptable counterion;

n is 0-3;

m is 0-3;

p is 0-3;

each q is independently 2-6;

u1 is 1-3;

u2 is 1-3;

each v is independently 1-5; and each w is independently 2-5.

Also disclosed herein is a pharmaceutical composition comprising a compound disclosed herein and a pharmaceutically acceptable excipient.

Also disclosed herein is a method of treating a bacterial infection in a subject, comprising administering to the subject an effective amount of a compound disclosed herein, or a pharmaceutically acceptable salt, solvate, stereoisomer, tautomer, N-oxide, dimer, or trimer thereof, or a pharmaceutical composition comprising a compound disclosed herein and a pharmaceutically acceptable excipient.

Also disclosed herein is method of inhibiting a bacterial penicillin binding protein in a human infected with a bacterial infection, comprising contacting said bacterial penicillin binding protein with an effective amount of compound disclosed herein, or a pharmaceutically acceptable salt, solvate, stereoisomer, tautomer, N-oxide, dimer, or trimer thereof, or a pharmaceutical composition comprising a compound disclosed herein and a pharmaceutically acceptable excipient.

Also disclosed herein is method of inhibiting a bacterial penicillin binding protein in a human infected with a bacterial infection, comprising contacting said bacterial penicillin binding protein with an effective amount of a compound of Formula (Ia) or Formula (Ib), or a pharmaceutically acceptable salt, solvate, stereoisomer, tautomer, N-oxide, dimer, or trimer thereof:

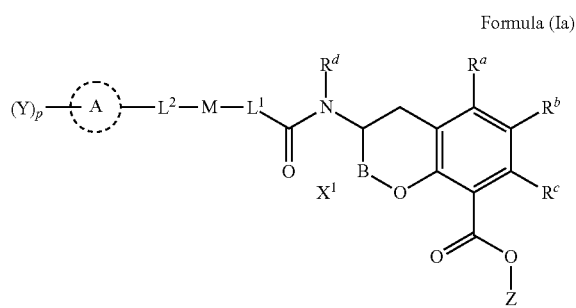

Formula (Ia)

-continued

Formula (Ib)

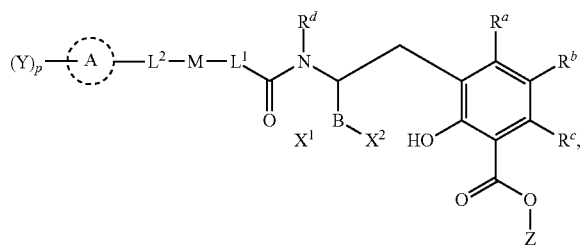

wherein:
$L^1$ is —$(CR^1R^2)_n$—;
$L^2$ is —$(CR^1R^2)_m$—;
Ring A is cycloalkyl, heterocycloalkyl, aryl, or heteroaryl;
M is

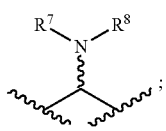

each $R^1$ and $R^2$ are independently hydrogen, halogen, optionally substituted alkyl, —OH, —$OR^{34}$, —$SR^{35}$, —$NR^{32}R^{33}$, —$NR^{32}C(=O)R^{34}$, —$C(=O)NR^{32}R^{33}$, —$NR^{32}S(=O)_2R^{34}$, —C(=O)OH, —$C(=O)OR^{34}$, optionally substituted cycloalkyl, optionally substituted heterocycloalkyl, optionally substituted aryl, or optionally substituted heteroaryl; or
$R^1$ and $R^2$ are taken together with the carbon to which they are attached to form an optionally substituted cycloalkyl;
$R^7$ and $R^8$ are independently hydrogen, optionally substituted alkyl, optionally substituted cycloalkyl, optionally substituted heterocycloalkyl, optionally substituted aryl, optionally substituted heteroaryl, —$S(=O)_2R^{44c}$, —$S(=O)_2NR^{42c}R^{43c}$, —$(CR^{40c}R^{41c})_vC(=O)OH$, —$(CR^{40c}R^{41c})_vC(=O)OR^{44c}$, —$(CR^{40c}R^{41c})_vC(=O)NR^{42c}R^{43c}$, or —$C(=O)R^{44c}$; or
$R^7$ and $R^8$ are taken together with the nitrogen to which they are attached to form an optionally substituted heterocycloalkyl;
each $R^{20}$ and $R^{21}$ are independently hydrogen, halogen, or optionally substituted alkyl;
$R^{22}$ and $R^{23}$ are independently hydrogen or optionally substituted alkyl; or
$R^{22}$ and $R^{23}$ are taken together with the nitrogen to which they are attached to form an optionally substituted heterocycloalkyl;
$R^{24}$ is optionally substituted alkyl, optionally substituted cycloalkyl, optionally substituted heterocycloalkyl, optionally substituted aryl, or optionally substituted heteroaryl;
$R^{25}$ is hydrogen, optionally substituted alkyl, optionally substituted cycloalkyl, optionally substituted heterocycloalkyl, optionally substituted aryl, optionally substituted heteroaryl;
each $R^{30}$, $R^{31}$, $R^{40c}$, $R^{41c}$, $R^{50}$, and $R^{51}$ are independently hydrogen, halogen, optionally substituted alkyl, optionally substituted cycloalkyl, optionally substituted heterocycloalkyl, optionally substituted aryl, optionally substituted heteroaryl, —OH, —$OR^{24}$, —$SR^{25}$, —$NR^{22}R^{23}$, —$NR^{22}C(=O)R^{24}$, —$C(=O)NR^{22}R^{23}$, —$NR^{22}S(=O)_2R^{24}$, —C(=O)OH, or —$C(=O)OR^{24}$; or
$R^{30}$ and $R^{31}$, $R^{40c}$ and $R^{41c}$, or $R^{50}$ and $R^{51}$ are taken together with the carbon atom to which they are attached form an optionally substituted cycloalkyl; or
two $R^{30}$, two $R^{40c}$, or two $R^{50}$ on adjacent carbons are taken together to form an alkenyl; or
two $R^{30}$ and two $R^{31}$, two $R^{40c}$ and two $R^{41c}$, or two $R^{50}$ and two $R^{51}$ on adjacent carbons are taken together to form an alkynyl;
$R^{32}$, $R^{33}$, $R^{42c}$, $R^{43c}$, $R^{52}$, or $R^{53}$ are independently hydrogen, optionally substituted alkyl, optionally substituted cycloalkyl, optionally substituted heterocycloalkyl, optionally substituted aryl, optionally substituted heteroaryl, (poly-ethylene-glycol)-ethyl, optionally substituted saccharide, —CN, —OH, —$S(=O)_2R^{24}$, —$S(=O)_2NR^{22}R^{23}$, or —$C(=O)R^{24}$; or
$R^{32}$ and $R^{33}$, $R^{42c}$ and $R^{43c}$, or $R^{52}$ and $R^{53}$ are taken together with the nitrogen to which they are attached to form an optionally substituted heterocycloalkyl;
$R^{34}$, $R^{44c}$, or $R^{54}$ are independently optionally substituted alkyl, optionally substituted cycloalkyl, optionally substituted heterocycloalkyl, optionally substituted aryl, or optionally substituted heteroaryl;
$R^{35}$ and $R^{55}$ are independently hydrogen, optionally substituted alkyl, optionally substituted cycloalkyl, optionally substituted heterocycloalkyl, optionally substituted aryl, optionally substituted heteroaryl;
$R^{36}$ and $R^{56}$ are independently hydrogen, —OH, —$OR^{24}$, —CN, —$NO_2$, —$NR^{22}R^{23}$, or optionally substituted alkyl;
Z is hydrogen, $R^{61}$, —$(R^{60})_qOR^{61}$, —$(R^{60})_qO(R^{60})_qOR^{61}$, —$R^{60}OC(O)R^{61}$, —$R^{60}OC(=O)OR^{61}$, —$R^{60}OC(=O)NHR^{61}$, —$R^{60}OC(=O)N(R^{61})_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;
each $R^{60}$ is independently —$CH_2$—, —$CH(CH_3)$—, —$C(CH_3)_2$—, or optionally substituted 1,1'-cyclopropylene;
each $R^{61}$ is independently optionally substituted alkyl, optionally substituted cycloalkyl, optionally substituted heterocycloalkyl, optionally substituted aryl, or optionally substituted heteroaryl; or
two $R^{61}$ are taken together with the nitrogen to which they are attached to form an optionally substituted heterocycloalkyl;
$R^a$, $R^b$, and $R^c$ are independently hydrogen, halogen, cyano, optionally substituted alkyl, optionally substituted cycloalkyl, optionally substituted heterocycloalkyl, optionally substituted aryl, optionally substituted heteroaryl, —OH, —$OR^{54}$, —$O(CR^{50}R^{51})_wNR^{52}R^{53}$, —$O(CR^{50}R^{51})_wOH$, —$O(CR^{50}R^{51})_wOR^{54}$, —$O(CR^{50}R^{51})_vC(=O)OH$, —$O(CR^{50}R^{51})_vC(=O)OR^{54}$, —$O(CR^{50}R^{51})_vC(=O)NR^{52}R^{53}$, —$NR^{52}R^{53}$, —$NR^{52}(CR^{50}R^{51})_wNR^{52}R^{53}$, —$NR^{52}(CR^{50}R^{51})_vC(=O)OH$, —$NR^{52}(CR^{50}R^{51})_vC(=O)OR^{54}$, —$NR^{52}(CR^{50}R^{51})_vC(=O)NR^{52}R^{53}$, —$NR^{52}S(=O)_{1,2}R^{54}$, —$S(=O)_{1,2}R^{54}$, —$SR^{55}$, —$S(CR^{50}R^{51})_wNR^{52}CR^{50}(=NR^{56})NR^{52}R^{53}$, —$S(NR^{56})$, —$S(CR^{50}R^{51})C(=NR^{56})NR^{52}R^{53}$, —$S(CR^{50}R^{51})_wOH$, —$S(CR^{50}R^{51})_wOR^{54}$, —$S(CR^{50}R^{51})_wNR^{52}R^{53}$, —$S(CR^{50}R^{51})_vC(=O)OH$, —S(CR$^{50}$R$^{51}$)$_v$C(=O)OR$^{54}$, —S(CR$^{50}$R$^{51}$)$_v$C(=O)NR$^{52}$R$^{53}$, —C(=O)H, —C(=O)R$^{54}$, —C(=O)OH, —C(=O)OR$^{54}$, —C(=O)NR$^{52}$R$^{53}$, —(CR$^{50}$R$^{51}$)$_v$N(R$^{52}$)(CR$^{50}$R$^{51}$)$_v$C(=O)OH, —(CR$^{50}$R$^{51}$)$_v$OH, —(CR$^{50}$R$^{51}$)$_v$OR$^{54}$, —(CR$^{50}$R$^{51}$)$_v$C(=O)OH, —(CR$^{50}$R$^{51}$)$_v$C(=O)OR$^{54}$, —(CR$^{50}$R$^{51}$)$_v$C(=O)NR$^{52}$R$^{53}$, —(CR$^{50}$R$^{51}$)$_v$OC(=O)R$^{54}$, —(CR$^{50}$R$^{51}$)$_v$SR$^{55}$, —(CR$^{50}$R$^{51}$)$_v$NR$^{52}$C(=NR$^{56}$), —(CR$^{50}$R$^{51}$)$_v$NR$^{52}$R$^{53}$, —(CR$^{50}$R$^{51}$)$_v$C(=NR$^{56}$)NR$^{52}$R$^{53}$, —(CR$^{50}$R$^{51}$)$_v$C(=O)NR$^{52}$R$^{53}$, —(CR$^{50}$R$^{51}$)$_v$heterocycloalkyl, or —(CR$^{50}$R$^{51}$)$_v$heteroaryl;

R$^d$ is hydrogen, —CN, —OH, —S(=O)$_2$R$^{24}$, —S(=O)$_2$NR$^{22}$R$^{23}$, —(CR$^{20}$R$^{21}$)$_v$C(=O)OH, —C(=O)R$^{24}$, optionally substituted alkyl, optionally substituted cycloalkyl, optionally substituted heterocycloalkyl, optionally substituted aryl, optionally substituted heteroaryl, (poly-ethylene-glycol)-ethyl, an optionally substituted saccharide;

R$^X$ is optionally substituted alkyl or optionally substituted cycloalkyl;

X$^1$ and X$^2$ are independently —OH, —OR$^X$, or F; or

X$^1$ and X$^2$ are taken together with the boron atom to which they are attached to form a cyclic boronate ester;

each Y is independently halogen, optionally substituted alkyl, optionally substituted cycloalkyl, optionally substituted heterocycloalkyl, optionally substituted aryl, optionally substituted heteroaryl, -heteroaryl-NR$^{32}$R$^{33}$, -heterocycloalkyl-NR$^{32}$R$^{33}$, -heteroaryl-N(R$^{32}$)C(=NR$^{32}$)NR$^{32}$R$^{33}$, -heterocycloalkyl-N(R$^{32}$)C(=NR$^{32}$)NR$^{32}$R$^{33}$, —OH, —OR$^{34}$, —O(CR$^{30}$R$^{31}$)$_w$OH, —O(CR$^{30}$R$^{31}$)$_w$OR$^{34}$, —O(CR$^{30}$R$^{31}$)$_w$NR$^{32}$R$^{33}$, —O(CR$^{30}$R$^{31}$)$_w$NR$^{32}$C(=O)R$^{34}$, —O(CR$^{30}$R$^{31}$)$_w$NR$^{32}$C(=O)OR$^{34}$, —O(CR$^{30}$R$^{31}$)$_w$NR$^{32}$C(=O)NR$^{32}$R$^{33}$, —O(CR$^{30}$R$^{31}$)$_w$C(=O)NR$^{32}$R$^{33}$, —O(CR$^{30}$R$^{31}$)$_w$NR$^{32}$S(=O)$_{0,1,2}$R$^{34}$, —O(CR$^{30}$R$^{31}$)$_w$NR$^{32}$S(=O)$_{0,1,2}$NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —O(CR$^{30}$R$^{31}$)$_v$C(=NR$^{36}$)NR$^{32}$R$^{33}$, —O(CR$^{30}$R$^{31}$)$_w$N(R$^{32}$)C(=NR$^{36}$)R$^{34}$, —O(CR$^{30}$R$^{31}$)$_v$C(=NR$^{36}$)NR$^{32}$C(=NR$^{36}$)NR$^{32}$R$^{33}$, —O(CR$^{30}$R$^{31}$)$_w$N(R$^{32}$)C(=NR$^{36}$)NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —OC(=O)R$^{34}$, —OC(=O)(CR$^{30}$R$^{31}$)$_v$NR$^{32}$R$^{33}$, —OC(=O)NR$^{32}$R$^{33}$, —OC(=O)OR$^{34}$, —OC(=O)NR$^{32}$(CR$^{30}$R$^{31}$)$_w$NR$^{32}$R$^{33}$, —O-heteroaryl, —O-heterocycloalkyl, —O(CR$^{30}$R$^{31}$)$_v$heteroaryl, —O(CR$^{30}$R$^{31}$)$_v$heterocycloalkyl, —O(CR$^{30}$R$^{31}$)$_w$NR$^{32}$-heteroaryl, —O(CR$^{30}$R$^{31}$)$_w$NR$^{32}$-heterocycloalkyl, —O(CR$^{30}$R$^{31}$)$_w$O-heterocycloalkyl, —NR$^{32}$R$^{33}$, —NR$^{32}$(CR$^{30}$R$^{31}$)$_w$NR$^{32}$R$^{33}$, —NR$^{32}$(CR$^{30}$R$^{31}$)$_w$OH, —NR$^{32}$(CR$^{30}$R$^{31}$)$_w$OR$^{34}$, —NR$^{32}$C(=O)R$^{34}$, —NR$^{32}$C(=O)OR$^{34}$, —N(R$^{32}$)C(=O)(CR$^{30}$R$^{31}$)$_v$NR$^{32}$R$^{33}$, —NR$^{32}$C(=O)NR$^{32}$R$^{33}$, —NR$^{32}$C(=O)NR$^{32}$(CR$^{30}$R$^{31}$)$_w$NR$^{32}$R$^{33}$, —NR$^{32}$(CR$^{30}$R$^{31}$)$_w$S(=O)$_{0,1,2}$R$^{34}$, —NR$^{32}$(CR$^{30}$R$^{31}$)$_w$S(=O)$_{0,1,2}$NR$^{32}$R$^{33}$, —NR$^{32}$(CR$^{30}$R$^{31}$)$_w$NR$^{32}$R$^{33}$S(=O)$_{0,1,2}$R$^{34}$, —NR$^{32}$(CR$^{30}$R$^{31}$)$_w$NR$^{32}$S(=O)$_{0,1,2}$NR$^{32}$R$^{33}$, —NR$^{32}$C(=NR$^{36}$)NR$^{32}$R$^{33}$, —N(R$^{32}$)C(=NR$^{36}$)R$^{34}$, —NR$^{32}$(CR$^{30}$R$^{31}$)$_w$N(R$^{32}$)C(=NR$^{36}$)R$^{34}$, —NR$^{32}$(CR$^{30}$R$^{31}$)$_v$C(=NR$^{36}$)NR$^{32}$R$^{33}$, —NR$^{32}$(CR$^{30}$R$^{31}$)$_w$N(R$^{32}$)C(=NR$^{36}$)NR$^{32}$R$^{33}$, —NR$^{32}$(CR$^{30}$R$^{31}$)$_w$NR$^{32}$C(=O)NR$^{32}$R$^{33}$, —NR$^{32}$(CR$^{30}$R$^{31}$)$_w$NR$^{32}$C(=O)OR$^{34}$, —NR$^{32}$S(=O)$_{0,1,2}$R$^{34}$, —NR$^{32}$(CR$^{30}$R$^{31}$)$_v$CO$_2$H, —NR$^{32}$(CR$^{30}$R$^{31}$)$_v$CO$_2$R$^{34}$, —NR$^{32}$(CR$^{30}$R$^{31}$)$_v$C(=O)NR$^{32}$R$^{33}$, —N(R$^{32}$)-heteroaryl-NR$^{32}$R$^{33}$, —N(R$^{32}$)-heterocycloalkyl-NR$^{32}$R$^{33}$, —NR$^{32}$(CR$^{30}$R$^{31}$)$_v$heteroaryl, —NR$^{32}$(CR$^{30}$R$^{31}$)$_w$heterocycloalkyl, —NR$^{32}$(CR$^{30}$R$^{31}$)$_w$NR$^{32}$-heteroaryl, —NR$^{32}$(CR$^{30}$R$^{31}$)$_w$NR$^{32}$-heterocycloalkyl, —CN, —(CR$^{30}$R$^{31}$)$_v$CN, —(CR$^{30}$R$^{31}$)$_v$NR$^{32}$R$^{33}$, —(CR$^{30}$R$^{31}$)$_v$OH, —(CR$^{30}$R$^{31}$)$_v$OR$^{34}$, —(CR$^{30}$R$^{31}$)$_v$OC(=O)R$^{34}$, —(CR$^{30}$R$^{31}$)$_v$OC(=O)NR$^{32}$R$^{33}$, —(CR$^{30}$R$^{31}$)$_v$O(CR$^{30}$R$^{31}$)$_w$OR$^{34}$, —(CR$^{30}$R$^{31}$)$_v$O(CR$^{30}$R$^{31}$)$_w$OH, —(CR$^{30}$R$^{31}$)$_v$O(CR$^{30}$R$^{31}$)$_w$NR$^{32}$R$^{33}$, —(CR$^{30}$R$^{31}$)$_v$NR$^{32}$(CR$^{30}$R$^{31}$)$_w$OH, —(CR$^{30}$R$^{31}$)$_v$NR$^{32}$(CR$^{30}$R$^{31}$)$_w$OR$^{34}$, —(CR$^{30}$R$^{31}$)$_v$C(=O)NR$^{32}$R$^{33}$, —(CR$^{30}$R$^{31}$)$_v$C(=O)NR$^{32}$(CR$^{30}$R$^{31}$)$_w$NR$^{32}$R$^{33}$, —(CR$^{30}$R$^{31}$)$_v$C(=O)NR$^{32}$(CR$^{30}$R$^{31}$)$_w$OR$^{34}$, —(CR$^{30}$R$^{31}$)$_v$N(R$^{32}$)C(=O)R$^{34}$, —(CR$^{30}$R$^{31}$)$_v$N(R$^{32}$)C(=O)OR$^{34}$, —(CR$^{30}$R$^{31}$)$_v$N(R$^{32}$)C(=O)NR$^{32}$R$^{33}$, —(CR$^{30}$R$^{31}$)$_v$N(R$^{32}$)C(=O) (CR$^{30}$R$^{31}$)$_v$NR$^{32}$R$^{33}$, —(CR$^{30}$R$^{31}$)$_v$N(R$^{32}$)S(=O)$_{0,1,2}$R$^{34}$, —(CR$^{30}$R$^{31}$)$_v$N(R$^{32}$)S(=O)$_{0,1,2}$NR$^{32}$R$^{33}$, —(CR$^{30}$R$^{31}$)$_v$S(=O)$_{0,1,2}$NR$^{32}$R$^{33}$, —(CR$^{30}$R$^{31}$)$_v$NR$^{32}$(CR$^{30}$R$^{31}$)$_w$NR$^{32}$R$^{33}$, —(CR$^{30}$R$^{31}$)$_v$N(R$^{32}$)CH(=NR$^{36}$), —(CR$^{30}$R$^{31}$)$_v$N(R$^{32}$)C(=NR$^{36}$)R$^{34}$, —(CR$^{30}$R$^{31}$)$_v$C(=NR$^{36}$)NR$^{32}$R$^{33}$, —(CR$^{30}$R$^{31}$)$_v$N(R$^{32}$)C(=NR$^{36}$)NR$^{32}$R$^{33}$, —(CR$^{30}$R$^{31}$)$_v$C(=NR$^{36}$)NR$^{32}$C(=NR$^{36}$)NR$^{32}$R$^{33}$, —(CR$^{30}$R$^{31}$)$_v$heteroaryl-NR$^{32}$R$^{33}$, —(CR$^{30}$R$^{31}$)$_v$heterocycloalkyl-NR$^{32}$R$^{33}$, —(CR$^{30}$R$^{31}$)$_v$heteroaryl-N(R$^{32}$)C(=NR$^{36}$)NR$^{32}$R$^{33}$, —(CR$^{30}$R$^{31}$)$_v$heterocycloalkyl-N(R$^{32}$)C(=NR$^{36}$)NR$^{32}$R$^{33}$, —(CR$^{30}$R$^{31}$)$_v$heteroaryl, —(CR$^{30}$R$^{31}$)$_v$heterocycloalkyl, —C(=O)OH, —C(=O)OR$^{34}$, —C(=O)NR$^{32}$R$^{33}$, —C(=O)NR$^{32}$(CR$^{30}$R$^{31}$)$_w$NR$^{32}$R$^{33}$, —C(=O)NR$^{32}$(CR$^{30}$R$^{31}$)$_w$OH, —C(=O)NR$^{32}$(CR$^{30}$R$^{31}$)$_w$OR$^{34}$, —C(=NR$^{36}$)NR$^{32}$R$^{33}$, —C(=NR$^{36}$)NR$^{32}$C(=O)R$^{34}$, —S(=O)$_{1,2}$R$^{34}$, —SR$^{35}$, —S(=O)$_{0,1,2}$(CR$^{30}$R$^{31}$)$_w$NR$^{32}$R$^{33}$, —S(=O)$_{0,1,2}$(CR$^{30}$R$^{31}$)$_w$OH, —S(=O)$_{0,1,2}$(CR$^{30}$R$^{31}$)$_w$OR$^{34}$, —S(=O)$_{0,1,2}$NR$^{32}$R$^{33}$, —S(=O)$_{0,1,2}$NR$^{32}$(CR$^{30}$R$^{31}$)$_w$NR$^{32}$R$^{33}$, —S(=O)$_{0,1,2}$(CR$^{30}$R$^{31}$)$_w$N(R$^{32}$)C(=NR$^{36}$)R$^{34}$, —S(=O)$_{0,1,2}$(CR$^{30}$R$^{31}$)$_v$C(=NR$^{36}$)NR$^{32}$R$^{33}$, —S(=O)$_{0,1,2}$(CR$^{30}$R$^{31}$)$_w$N(R$^{32}$)C(NR$^{36}$)NR$^{32}$R$^{33}$, —S(=O)$_{0,1,2}$(CR$^{30}$R$^{31}$)$_v$C(=NR$^{36}$)NR$^{32}$C(=NR$^{36}$)NR$^{32}$R$^{33}$, —Si(R$^{34}$)$_3$, —NR$^{32}$R$^{33}$R$^{34+}$Q$^-$, —(CR$^{30}$R$^{31}$)$_v$NR$^{32}$R$^{33}$R$^{34+}$Q$^-$, —NR$^{32}$(CR$^{30}$R$^{31}$)$_w$NR$^{32}$R$^{33}$R$^{34+}$Q$^-$, —NR$^{32}$R$^{34+}$(CR$^{30}$R$^{31}$)$_w$NR$^{32}$R$^{33}$R$^{34+}$Q$^-$$_2$, —(CR$^{30}$R$^{31}$)$_v$(T)$^+$Q$^-$, or —O(CR$^{30}$R$^{31}$)$_w$NR$^{32}$R$^{33}$R$^{34+}$Q$^-$;

or two Ys taken together with the atoms to which they are attached form an optionally substituted cycloalkyl or an optionally substituted heterocycloalkyl;

T is pyridin-1-yl, pyrimidin-1-yl, or thiazol-3-yl;

Q is a pharmaceutically acceptable counterion;

n is 0-3;

m is 0-3;

p is 0-3;

each q is independently 2-6;

each v is independently 1-5; and each w is independently 2-5.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Over the decades of clinical use of beta-lactam antibiotics, bacteria have evolved resistance mechanisms that compromise beta-lactam utility, including production of easily transferable, broad-spectrum beta-lactamases that are able to efficiently hydrolyze the beta lactam ring. These enzymes, now counting >1300 variants, have spread throughout Enterobacteriaceae. The rapid spread of this mechanism of bacterial resistance severely limits beta-lactam therapeutic options.

Novel non-beta-lactam compounds that inhibit the transpeptidase function of PBPs and are not degraded by beta-lactamases would represent a major advance in the treatment of resistant bacterial infections, essentially circumventing >70 years of bacterial evolution to protect the function of the penicillin-binding proteins in cell wall biosynthesis. The present invention is directed to certain boron-based compounds (boronic acids and cyclic boronic acid esters) which are PBP inhibitors and antibacterial compounds. The compounds and their pharmaceutically acceptable salts are useful for the treatment of bacterial infections, particularly antibiotic resistant bacterial infections. Some embodiments include compounds, compositions, pharmaceutical compositions, use, and preparation thereof.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The term "antibiotic" refers to a compound or composition which decreases the viability of a microorganism, or which inhibits the growth or proliferation of a microorganism. The phrase "inhibits the growth or proliferation" means increasing the generation time (i.e., the time required for the bacterial cell to divide or for the population to double) by at least about 2-fold. Preferred antibiotics are those which can increase the generation time by at least about 10-fold or more (e.g., at least about 100-fold or even indefinitely, as in total cell death). As used in this disclosure, an antibiotic is further intended to include an antimicrobial, bacteriostatic, or bactericidal agent. Examples of antibiotics suitable for use with respect to the present invention include penicillins, cephalosporins, and carbapenems.

The term "β-lactam antibiotic" refers to a compound with antibiotic properties that contains a β-lactam functionality. Non-limiting examples of β-lactam antibiotics useful with respect to the invention include penicillins, cephalosporins, penems, carbapenems, and monobactams.

The term "β-lactamase" denotes a protein capable of inactivating a β-lactam antibiotic. The β-lactamase can be an enzyme which catalyzes the hydrolysis of the β-lactam ring of a β-lactam antibiotic. Of particular interest herein are microbial β-lactamases. The β-lactamase may be, for example, a serine β-lactamase or a metallo-β-lactamase.

"Amino" refers to the —$NH_2$ substituent.
"Oxo" refers to the =O substituent.
"Oxime" refers to the =N—OH substituent.
"Thioxo" refers to the =S substituent.
"Alkyl" refers to a linear or branched hydrocarbon chain, which is fully saturated. Alkyl may have from one to thirty carbon atoms. An alkyl comprising up to 30 carbon atoms is referred to as a $C_1$-$C_{30}$ alkyl, likewise, for example, an alkyl comprising up to 12 carbon atoms is a $C_1$-$C_{12}$ alkyl. An alkyl comprising up to 6 carbons is a $C_1$-$C_6$ alkyl. Alkyl groups include, but are not limited to, $C_1$-$C_{30}$ alkyl, $C_1$-$C_{20}$ alkyl, $C_1$-$C_{15}$ alkyl, $C_1$-$C_{10}$ alkyl, $C_1$-$C_8$ alkyl, $C_1$-$C_6$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl, $C_4$-$C_8$ alkyl, and $C_5$-$C_{12}$ alkyl. In some embodiments, the alkyl group is $C_1$-$C_6$ alkyl. Representative alkyl groups include, but are not limited to, methyl, ethyl, n-propyl, 1-methylethyl (isopropyl), n-butyl, i-butyl, s-butyl, n-pentyl, 1,1-dimethylethyl (t-butyl), 2-ethylpropyl, and the like. Representative linear alkyl groups include, but are not limited to, methyl, ethyl, n-propyl, n-butyl, n-pentyl and the like. In certain embodiments, an alkyl group is optionally substituted by one or more of the following substituents: halogen, cyano, nitro, oxo, thioxo, imino, oximo, trimethylsilyl, —$OR^e$, —$SR^e$, —OC(O)—$R^e$, —$N(R^e)_2$, —C(O)$R^e$, —C(O)O$R^e$, —C(O)N($R^e$)$_2$, —N($R^e$)C(O)O$R^f$, —OC(O)—N$R^eR^f$, —N($R^e$)C(O)$R^f$, —N($R^e$)S(O)$_t$$R^f$ (where t is 1 or 2), —S(O)$_t$O$R^e$ (where t is 1 or 2), —S(O)$_t$R (where t is 1 or 2), —S(O)$_t$N($R^e$)$^2$ (where t is 1 or 2), aryl (optionally substituted as defined below), heteroaryl (optionally substituted as defined below), cycloalkyl (optionally substituted as defined below), and heterocycloalkyl (optionally substituted as defined below); where each $R^e$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, and each $R^f$ is independently alkyl, fluoroalkyl, cycloalkyl, cycloalkylalkyl, aryl, aralkyl, heterocycloalkyl, heterocycloalkylalkyl, heteroaryl or heteroarylalkyl. In some embodiments, the alkyl is substituted with an optionally substituted aryl to form an optionally substituted aralkyl. In some embodiments, the alkyl is substituted with an optionally substituted heteroaryl to form an optionally substituted heteroarylalkyl. In some embodiments, the alkyl is substituted with an optionally substituted cycloalkyl to form an optionally substituted cycloalkylalkyl. In some embodiments, the alkyl is substituted with an optionally substituted heterocycloalkyl to form an optionally substituted heterocycloalkylalkyl. In some embodiments, an alkyl group is optionally substituted with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —$CF_3$, —OH, —OMe, —$NH_2$, or —$NO_2$. In some embodiments, the alkyl is optionally substituted with oxo, halogen, —CN, —$CF_3$, —OH, or —OMe. In some embodiments, the alkyl is optionally substituted with halogen.

"Alkenyl" refers to a straight or branched hydrocarbon chain, containing at least one carbon-carbon double bond. In certain embodiments, alkenyl comprises two to twelve ($C_2$-$C_{12}$ alkenyl) carbon atoms, or two to eight carbon atoms ($C_2$-$C_8$ alkenyl), or two to six carbon atoms ($C_2$-$C_6$ alkenyl) or two to four carbon atoms ($C_2$-$C_4$ alkenyl). The alkenyl may be attached to the rest of the molecule by a single bond, for example, ethenyl (i.e., vinyl), prop-1-enyl (i.e., allyl), but-1-enyl, pent-1-enyl, penta-1,4-dienyl, and the like. Alkenyl may be attached to the rest of the molecule by a double bond, e.g., =$CH_2$, =$CH(CH_2)_3CH_3$. In certain embodiments, an alkenyl group is optionally substituted by one or more of the following substituents: halo, cyano, nitro, oxo, thioxo, imino, oximo, trimethylsilyl, —$OR^e$, —$SR^e$, —OC(O)—$R^e$, —$N(R^e)_2$, —$C(O)R^e$, —$C(O)OR^e$, —$C(O)N(R^e)_2$, —$N(R^e)C(O)OR^f$, —OC(O)—$NR^eR^f$, —$N(R^e)C(O)R^f$, —$N(R^e)S(O)_tR^f$ (where t is 1 or 2), —$S(O)_tOR^e$ (where t is 1 or 2), —$S(O)_tR^f$ (where t is 1 or 2), —$S(O)_tN(R^e)_2$ (where t is 1 or 2), aryl, heteroaryl, cycloalkyl, and heterocycloalkyl; where each $R^e$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, and each $R^f$ is independently alkyl, fluoroalkyl, cycloalkyl, cycloalkylalkyl, aryl, aralkyl, heterocycloalkyl, heterocycloalkylalkyl, heteroaryl or heteroarylalkyl. In some embodiments, an alkenyl group is optionally substituted with oxo, halogen, amino, nitrile, nitro, hydroxyl, haloalkyl, alkoxy, aryl, cycloalkyl, heterocycloalkyl, heteroaryl, and the like. In some embodiments, the alkenyl is optionally substituted with oxo, halogen, —CN, —$CF_3$, —OH, —OMe, —$NH_2$, or —$NO_2$. In some embodiments, the alkenyl is optionally substituted with oxo, halogen, —CN, —$CF_3$, —OH, or —OMe. In some embodiments, the alkenyl is optionally substituted with halogen.

"Alkynyl" refers to a straight or branched hydrocarbon chain group, containing at least one carbon-carbon triple bond. In certain embodiments, alkynyl comprises two to twelve ($C_2$-$C_{12}$ alkynyl) carbon atoms, or two to eight carbon atoms ($C_2$-$C_8$ alkynyl), or two to six carbon atoms ($C_2$-$C_6$ alkynyl) or two to four carbon atoms ($C_2$-$C_4$ alkynyl). The alkynyl may be attached to the rest of the molecule by a single bond, for example, ethynyl, propynyl, butynyl, pentynyl, hexynyl, and the like. In certain embodiments, an alkynyl group is optionally substituted by one or more of the following substituents: halo, cyano, nitro, oxo, thioxo, imino, oximo, trimethylsilanyl, —$OR^e$, —$SR^e$, —OC(O)—$R^e$, —$N(R^e)_2$, —$C(O)R^e$, —$C(O)OR^e$, —$C(O)N(R^e)_2$, —$N(R^e)C(O)OR^f$, —OC(O)—$NR^eR^f$, —$N(R^e)C(O)R^f$, —$N(R^e)S(O)_tR^f$ (where t is 1 or 2), —$S(O)_tOR^e$ (where t is 1 or 2), —$S(O)_tR^f$ (where t is 1 or 2), —$S(O)_tN(R^e)_2$ (where t is 1 or 2), aryl, heteroaryl, cycloalkyl, and heterocycloalkyl; where each $R^e$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, and each $R^f$ is independently alkyl, fluoroalkyl, cycloalkyl, cycloalkylalkyl, aryl, aralkyl, heterocycloalkyl, heterocycloalkylalkyl, heteroaryl or heteroarylalkyl. In some embodiments, an alkynyl group is optionally substituted with oxo, halogen, amino, nitrile, nitro, hydroxyl, haloalkyl, alkoxy, aryl, cycloalkyl, heterocycloalkyl, heteroaryl, and the like. In some embodiments, the alkynyl is optionally substituted with oxo, halogen, —CN, —$CF_3$, —OH, —OMe, —$NH_2$, or —$NO_2$. In some embodiments, the alkynyl is optionally substituted with oxo, halogen, —CN, —$CF_3$, —OH, or —OMe. In some embodiments, the alkynyl is optionally substituted with halogen.

"Alkylene" or "alkylene chain" refers to a straight or branched divalent hydrocarbon chain linking the rest of the molecule to a radical group, consisting solely of carbon and hydrogen, containing no unsaturation and having, for example, from one to twelve carbon atoms ($C_1$-$C_{12}$ alkylene), e.g., methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. In certain embodiments, an alkylene comprises one to eight carbon atoms ($C_1$-$C_8$ alkylene), or one to five carbon atoms ($C_1$-$C_5$ alkylene), or one to four carbon atoms ($C_1$-$C_4$ alkylene), or one to three carbon atoms ($C_1$-$C_3$ alkylene), or one to two carbon atoms ($C_1$-$C_2$ alkylene). In other embodiments, an alkylene comprises one carbon atom ($C_1$ alkylene), or two carbon atoms ($C_2$ alkylene). In certain embodiments, an alkylene comprises two to five carbon atoms (e.g., $C_2$-$C_5$ alkylene). In certain embodiments, an alkylene chain is optionally substituted by one or more of the following substituents: halo, cyano, nitro, oxo, thioxo, imino, oximo, trimethylsilyl, —$OR^e$, —$SR^e$, —OC(O)—$R^e$, —$N(R^e)_2$, —$C(O)R^e$, —$C(O)OR^e$, —$C(O)N(R^e)_2$, —$N(R^e)C(O)OR^f$, —OC(O)—$NR^eR^f$, —$N(R^e)C(O)R^f$, —$N(R^e)S(O)_tR^f$ (where t is 1 or 2), —$S(O)_tOR^e$ (where t is 1 or 2), —$S(O)_tR^f$ (where t is 1 or 2), —$S(O)_tN(R^e)_2$ (where t is 1 or 2), aryl, heteroaryl, cycloalkyl, and heterocycloalkyl; where each $R^e$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, and each $R^f$ is independently alkyl, fluoroalkyl, cycloalkyl, cycloalkylalkyl, aryl, aralkyl, heterocycloalkyl, heterocycloalkylalkyl, heteroaryl or heteroarylalkyl. In some embodiments, an alkylene group is optionally substituted with oxo, halogen, amino, nitrile, nitro, hydroxyl, haloalkyl, alkoxy, aryl, cycloalkyl, heterocycloalkyl, heteroaryl, and the like. In some embodiments, the alkylene is optionally substituted with oxo, halogen, —CN, —$CF_3$, —OH, —OMe, —$NH_2$, or —$NO_2$. In some embodiments, the alkylene is optionally substituted with oxo, halogen, —CN, —$CF_3$, —OH, or —OMe. In some embodiments, the alkylene is optionally substituted with halogen.

"Alkoxy" refers to a radical of the formula —O-alkyl where alkyl is as defined herein. Unless stated otherwise specifically in the specification, an alkoxy group may be optionally substituted as described above for alkyl.

"Aryl" refers to an aromatic monocyclic hydrocarbon or aromatic multicyclic hydrocarbon ring system by removing a hydrogen atom from a ring carbon atom. Aryl may include cycles with six to eighteen carbon atoms, where at least one of the rings in the ring system is aromatic, i.e., it contains a cyclic, delocalized (4n+2) π-electron system in accordance with the Hückel theory. In some embodiments, the aryl is a monocyclic, bicyclic, tricyclic or tetracyclic ring system, which may include fused ring system (when fused with a cycloalkyl or heterocycloalkyl ring, the aryl is bonded through an aromatic ring atom). In some embodiments, the aryl is a 6 to 10-membered aryl. In some embodiments, the aryl is a 6-membered aryl. In some embodiments, the aryl is a 10-membered aryl. The ring system from which aryl groups are derived include, but are not limited to, groups such as benzene, fluorene, indane, indene, tetralin and naphthalene. In certain embodiments, an aryl group is optionally substituted by one or more of the following substituents: alkyl, alkenyl, alkynyl, halogen, fluoroalkyl, hydroxyalkyl, aminoalkyl, cyano, nitro, aryl, aralkyl, aralkenyl, aralkynyl, cycloalkyl, cycloalkylalkyl, heterocycloalkyl, heterocycloalkylalkyl, heteroaryl, heteroarylalkyl, —$R^g$—$OR^e$, —$R^gC(=NR^e)N(R^e)_2$, —$R^g$—$OC(O)$—$R^e$, —$R^g$—$OC(O)$—$OR^e$, —$R^g$—$OC(O)$—$N(R^e)_2$, —$R^g$—$N(R^e)_2$, —$R^g$—$C(O)R^e$, —$R^g$—$C(O)OR^e$, —$R^g$—$C(O)N(R^e)_2$, —$R^g$—$O$—$R^h$—$C(O)N(R^e)_2$, —$R^g$—$N(R^e)C(O)OR^e$, —$R^g$—$N(R^e)C(O)R^e$, —$R^g$—$N(R^e)S(O)_tR^e$ (where t is 1 or 2), —$R^g$—$S(O)_tOR^e$ (where t is 1 or 2), —$R^g$—$S(O)_tR^e$ (where t is 1 or 2), and —$R^g$—$S(O)_tN(R^e)_2$ (where t is 1 or 2), where each $R^e$ is independently hydrogen, alkyl, fluoroalkyl, cycloalkyl, cycloalkylalkyl, aryl, aralkyl, heterocycloalkyl (optionally substituted with one or more alkyl groups), heterocycloalkylalkyl, heteroaryl or heteroarylalkyl, or two $R^e$ attached to the same nitrogen atom are combined to form a heterocycloalkyl, each $R^g$ is independently a direct bond or a straight or branched alkylene or alkenylene chain, and $R^h$ is a straight or branched alkylene or alkenylene chain, and where each of the above substituents is unsubstituted unless otherwise indicated. In some embodiments, an aryl is optionally substituted with halogen, amino, nitrile, nitro, hydroxyl, alkyl, haloalkyl, alkoxy, aryl, aralkyl, cycloalkyl, heterocycloalkyl, heteroaryl, and the like. In some embodiments, the aryl is optionally substituted with halogen, —CN, -Me, -Et, —$CF_3$, —OH, —OMe, —$NH_2$, —$NO_2$, or cyclopropyl. In some embodiments, the aryl is optionally substituted with oxo, halogen, —CN, -Me, -Et, —$CF_3$, —OH, —OMe, or cyclopropyl. In some embodiments, the aryl is optionally substituted with halogen.

"Aryloxy" refers to a radical bonded through an oxygen atom of the formula —O-aryl, where aryl is as described above.

"Aralkyl" refers to a radical of the formula —$R^h$-aryl where $R^h$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Boronate ester" refers to —$B(OR^k)_2$ wherein each $R^k$ are independently hydrogen, optionally substituted alkyl, optionally substituted cycloalkyl, optionally substituted heterocycloalkyl, optionally substituted aryl, optionally substituted heteroaryl, (poly ethylene glycol) ethyl, or an optionally substituted saccharide provided that they are not both hydrogen. In some embodiments, each $R^k$ is alkyl. In some embodiments, two $R^k$ may be taken together with the atom to which they are attached to form an optionally substituted heterocycle or a cyclic boronate ester. In some embodiments, the cyclic boronate ester is formed from pinanediol, pinacol, 1,2-ethanediol, 1,3-propanediol, 1,2-propanediol, 2,3-butanediol, 1,2-diisopropylethandiol, 5,6-decanediol, 1,2-dicyclohexylethanediol, diethanolamine, 1,2-diphenyl-1,2-ethanediol, 2,6,6-trimethylbicyclo[3.1.1]heptane-2,3-diol, or (1S,2S,3R,5S)-2,6,6-trimethylbicyclo[3.1.1]heptane-2,3-diol.

"Cycloalkyl" refers to a saturated or partially unsaturated, monocyclic or polycyclic hydrocarbon. In certain embodiments, the cycloalkyl includes fused (when fused with an aryl or a heteroaryl ring, the cycloalkyl is bonded through a non-aromatic ring atom) or bridged ring systems. In certain embodiments, the cycloalkyl comprises from three to twenty carbon atoms ($C_3$-$C_{20}$ cycloalkyl), or three to ten carbon atoms ($C_3$-$C_{10}$ cycloalkyl), or three to eight carbon atoms ($C_3$-$C_8$ cycloalkyl), or three to six carbon atoms ($C_3$-$C_6$ cycloalkyl). In some embodiments, the cycloalkyl is a 3- to 6-membered cycloalkyl. In some embodiments, the cycloalkyl is a 3- to 8-membered cycloalkyl. Examples of monocyclic cycloalkyls include, e.g., cyclopropyl, cyclobutyl, cyclopentyl, cyclohexyl, cycloheptyl, and cyclooctyl. Polycyclic cycloalkyl include, for example, adamantyl, norbornyl (i.e., bicyclo[2.2.1]heptanyl), norbornenyl, decalinyl, 7,7-dimethyl-bicyclo[2.2.1]heptanyl, and the like. In certain embodiments, the cycloalkyl is optionally substituted by one or more substituents independently selected from alkyl, alkenyl, alkynyl, halogen, fluoroalkyl, hydroxyalkyl, aminoalkyl, oxo, thioxo, cyano, nitro, aryl, aralkyl, aralkenyl, aralkynyl, cycloalkyl, cycloalkylalkyl, heterocycloalkyl, heterocycloalkylalkyl, heteroaryl, heteroarylalkyl, —$R^g$—$OR^e$, —$R^gC(=NR^e)N(R^e)_2$, —$R^g$—$OC(O)$—$R^e$, —$R^g$—$OC(O)$—$OR^e$, —$R^g$—$OC(O)$—$N(R^e)_2$, —$R^g$—$N(R^e)_2$, —$R^g$—$C(O)R^e$, —$R^g$—$C(O)OR^e$, —$R^g$—$C(O)N(R^e)_2$, —$R^g$—$O$—$R^h$—$C(O)N(R^e)_2$, —$R^g$—$N(R^e)C(O)OR^e$, —$R^g$—$N(R^e)C(O)R^e$, —$R^g$—$N(R^e)S(O)_tR^e$ (where t is 1 or 2), —$R^g$—$S(O)_tOR^e$ (where t is 1 or 2), —$R^g$—$S(O)_tR^e$ (where t is 1 or 2) and —$R^g$—$S(O)_tN(R^e)_2$ (where t is 1 or 2), where each $R^e$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each $R^g$ is independently a direct bond or a straight or branched alkylene or alkenylene chain, and $R^h$ is a straight or branched alkylene or alkenylene chain, and where each of the above substituents is unsubstituted unless otherwise indicated. In some embodiments, a cycloalkyl is optionally substituted with oxo, halogen, amino, nitrile, nitro, hydroxyl, alkyl, haloalkyl, alkoxy, aryl, aralkyl, cycloalkyl, heterocycloalkyl, heteroaryl, and the like. In some embodiments, the cycloalkyl is optionally substituted with oxo, halogen, —CN, -Me, -Et, —$CF_3$, —OH, —OMe, —$NH_2$, —$NO_2$, or cyclopropyl. In some embodiments, the cycloalkyl is optionally substituted with oxo, halogen, —CN, -Me, -Et, —$CF_3$, —OH, —OMe, or cyclopropyl. In some embodiments, the cycloalkyl is optionally substituted with halogen.

"Cycloalkylalkyl" refers to a radical of the formula —$R^h$-cycloalkyl where $R^h$ is an alkylene chain as defined above. The alkylene chain and the cycloalkyl radical are optionally substituted as described above.

"Halo" or "halogen" refers to bromo, chloro, fluoro, or iodo. In some embodiments, halogen refers to chloro or fluoro.

"Heterocycloalkyl" refers to a saturated or partially unsaturated ring that comprises two to twenty carbon atoms and at least one heteroatom. In certain embodiments, the heteroatoms are independently selected from N, O, Si, P, B, and S atoms. In certain embodiments, the heteroatoms are independently selected from N, O, and S atoms. The heterocycloalkyl may be selected from monocyclic or bicyclic, fused (when fused with an aryl or a heteroaryl ring, the heterocycloalkyl is bonded through a non-aromatic ring atom) or bridged ring systems. The heteroatoms in the heterocycloalkyl are optionally oxidized. One or more nitrogen atoms, if present, are optionally quaternized. The heterocycloalkyl is partially or fully saturated. The heterocycloalkyl is attached to the rest of the molecule through any atom of the heterocycloalkyl, valence permitting, such as any carbon or nitrogen atoms of the heterocycloalkyl. In certain embodiments, the heterocycloalkyl comprises from two to twenty carbon atoms ($C_2$-$C_{20}$ heterocycloalkyl), or two to ten carbon atoms ($C_2$-$C_{10}$ heterocycloalkyl), or two to eight carbon atoms ($C_2$-$C_8$ heterocycloalkyl), or two to six carbon atoms ($C_2$-$C_6$ heterocycloalkyl). In some embodiments, the heterocycloalkyl is a 3- to 6-membered heterocycloalkyl. In some embodiments, the heterocycloalkyl is a 3- to 8-membered heterocycloalkyl. In some embodiments, the heterocycloalkyl is a 5- to 6-membered heterocycloalkyl. In some embodiments, the heterocycloalkyl is a 5-membered heterocycloalkyl. In some embodiments, the heterocycloalkyl is a 6-membered heterocycloalkyl. Examples of heterocycloalkyl include, but are not limited to, azetidinyl, aziridyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. In some embodiments, the heterocycloalkyl is piperazinyl. In certain embodiments, a heterocycloalkyl group is optionally substituted by one or more of the following substituents selected from alkyl, alkenyl, alkynyl, halogen, fluoroalkyl, oxo, thioxo, cyano, nitro, optionally substituted aryl, optionally substituted aralkyl, optionally substituted aralkenyl, optionally substituted aralkynyl, optionally substituted cycloalkyl, optionally substituted cycloalkylalkyl, optionally substituted heterocycloalkyl, optionally substituted heterocycloalkylalkyl, optionally substituted heteroaryl, optionally substituted heteroarylalkyl, —$R^g$—$OR^e$, —$R^gC(=NR^e)N(R^e)_2$, —$R^g$—$OC(O)$—$R^e$, —$R^g$—$OC(O)$—$OR^e$, —$R^g$—$OC(O)$—$N(R^e)_2$, —$R^g$—$N(R^e)_2$, —$R^g$—$C(O)R^e$, —$R^g$—$C(O)OR^e$, —$R^g$—$C(O)N(R^e)_2$, —$R^g$—O—$R^h$—$C(O)N(R^e)_2$, —$R^g$—$N(R^e)C(O)OR^e$, —$R^g$—$N(R^e)C(O)R^e$, —$R^g$—$N(R^e)S(O)_tR^e$ (where t is 1 or 2), —$R^g$—$S(O)_tOR^e$ (where t is 1 or 2), —$R^g$—$S(O)_tR^e$ (where t is 1 or 2) and —$R^g$—$S(O)_tN(R^e)_2$ (where t is 1 or 2), where each $R^e$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each $R^g$ is independently a direct bond or a straight or branched alkylene or alkenylene chain, and $R^h$ is a straight or branched alkylene or alkenylene chain, and where each of the above substituents is unsubstituted unless otherwise indicated. In some embodiments, a heterocycloalkyl is optionally substituted with oxo, halogen, amino, nitrile, nitro, hydroxyl, alkyl, haloalkyl, alkoxy, aryl, aralkyl, cycloalkyl, heterocycloalkyl, heteroaryl, and the like. In some embodiments, the heterocycloalkyl is optionally substituted with oxo, halogen, —CN, -Me, -Et, —$CF_3$, —OH, —OMe, —$NH_2$, —$NO_2$, or cyclopropyl. In some embodiments, the heterocycloalkyl is optionally substituted with oxo, halogen, —CN, -Me, -Et, —$CF_3$, —OH, —OMe, or cyclopropyl. In some embodiments, the heterocycloalkyl is optionally substituted with halogen.

"Heterocycloalkylalkyl" refers to a radical of the formula —$R^h$-heterocycloalkyl where $R^h$ is an alkylene chain as defined above. If the heterocycloalkyl is a nitrogen-containing heterocycloalkyl, the heterocycloalkyl is optionally attached to the alkyl radical at the nitrogen atom. The alkylene chain of the heterocycloalkylalkyl radical is optionally substituted as defined above for an alkylene chain. The heterocycloalkyl part of the heterocycloalkylalkyl radical is optionally substituted as defined above for a heterocycloalkyl group.

"Heteroaryl" refers to a 5- to 14-membered ring system comprising hydrogen atoms, one to thirteen carbon atoms, one to six heteroatoms selected from the group consisting of nitrogen, oxygen, phosphorous and sulfur, and at least one aromatic ring. In some embodiments, the heteroaryl is a 5-membered heteroaryl. In some embodiments, the heteroaryl is a 6-membered heteroaryl. In some embodiments, the heteroaryl is a monocyclic, bicyclic, tricyclic or tetracyclic ring system, which may include fused ring systems (when fused with a cycloalkyl or heterocycloalkyl ring, the heteroaryl is bonded through an aromatic ring atom); and the nitrogen, carbon or sulfur atoms in the heteroaryl may be optionally oxidized; the nitrogen atom may be optionally quaternized. In some embodiments, the heteroaryl is a 5- to 10-membered heteroaryl. In some embodiments, the heteroaryl is a 5-membered heteroaryl. In some embodiments, the heteroaryl is a 6-membered heteroaryl. In some embodiments, the heteroaryl is a 10-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group is optionally substituted by one or more of the following substituents selected from alkyl, alkenyl, alkynyl, halogen, fluoroalkyl, hydroxyalkyl, aminoalkyl, haloalkenyl, haloalkynyl, cyano, nitro, aryl, aralkyl, aralkenyl, alkynyl, cycloalkyl, cycloalkylalkyl, heterocycloalkyl, heterocycloalkylalkyl, heteroaryl, heteroarylalkyl, —$R^g$—$OR^e$, —$R^gC(=NR^e)N(R^e)_2$, —$R^g$—$OC(O)$—$R^e$, —$R^g$—$OC(O)$—$OR^e$, —$R^g$—$OC(O)$—$N(R^e)_2$, —$R^g$—$N(R^e)_2$, —$R^g$—$C(O)R^e$, —$R^g$—$C(O)OR^e$, —$R^g$—$C(O)N(R^e)_2$, —$R^g$—O—$R^h$—$C(O)N(R^e)_2$, —R—$N(R^e)C(O)OR^e$, —$R^g$—$N(R^e)C(O)R^e$, —$R^g$—$N(R^e)S(O)_tR^e$ (where t is 1 or 2), —$R^g$—$S(O)_tOR^e$ (where t is 1 or 2), —$R^g$—$S(O)_tR^e$ (where t is 1 or 2) and —$R^g$—$S(O)_tN(R^e)_2$ (where t is 1 or 2), where each $R^e$ is independently hydrogen, alkyl, fluoroalkyl, cycloalkyl, cycloalkylalkyl, aryl, aralkyl, heterocycloalkyl, heterocycloalkylalkyl, heteroaryl or heteroarylalkyl, each $R^g$ is independently a direct bond or a straight or branched alkylene or alkenylene chain, and $R^h$ is a straight or branched alkylene or alkenylene chain, and where each of the above substituents is unsubstituted unless otherwise indicated. In some embodiments, a heteroaryl is optionally substituted with halogen, amino, nitrile, nitro, hydroxyl, alkyl, haloalkyl, alkoxy, aryl, aralkyl, cycloalkyl, heterocycloalkyl, heteroaryl, and the like. In some embodiments, the heteroaryl is optionally substituted with halogen, —CN, -Me, -Et, —$CF_3$, —OH, —OMe, —$NH_2$, —$NO_2$, or cyclopropyl. In some embodiments, the heteroaryl is optionally substituted with halogen, —CN, -Me, -Et, —$CF_3$, —OH, —OMe, or cyclopropyl. In some embodiments, the heteroaryl is optionally substituted with halogen.

"Heteroarylalkyl" refers to a radical of the formula —$R^h$-heteroaryl, where $R^h$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition. In some embodiments, treatment also includes prophylactic treatment (e.g., administration of a composition described herein when an individual is suspected to be suffering from a bacterial infection).

Compounds

Described herein are compounds that modulate the activity of beta-lactamase. In some embodiments, the compounds described herein inhibit beta-lactamase. In some embodiments, the compounds described herein inhibit penicillin binding protein. In certain embodiments, the compounds described herein are useful in the treatment of bacterial infections. In some embodiments, the bacterial infection is an upper or lower respiratory tract infection, a urinary tract infection, an intra-abdominal infection, or a skin infection.

In one aspect, provided herein are compounds of Formula (Ia) or Formula (Ib), or a pharmaceutically acceptable salt, solvate, stereoisomer, tautomer, N-oxide, dimer, or trimer thereof:

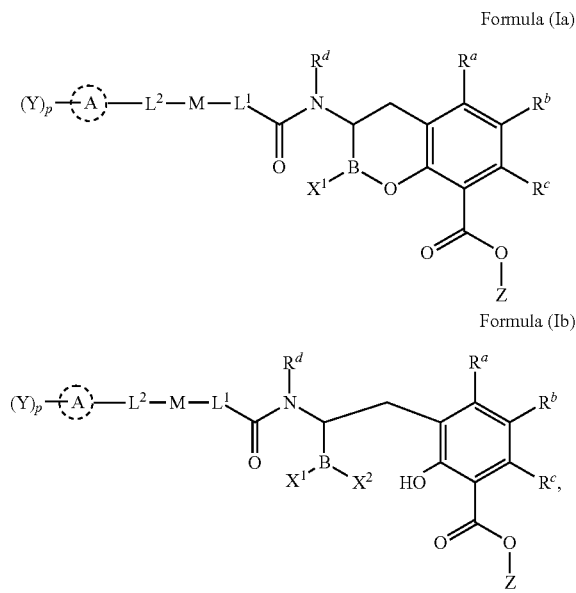

wherein:
L$^1$ is —(CR$^1$R$^2$)$_n$—;
L$^2$ is —(CR$^1$R$^2$)$_m$—;
Ring A is cycloalkyl, heterocycloalkyl, aryl, or heteroaryl;
M is

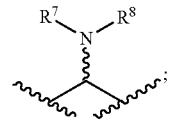

each R$^1$ and R$^2$ are independently hydrogen, halogen, optionally substituted alkyl, —OH, —OR$^{34}$, —SR$^{35}$, —NR$^{32}$R$^{33}$, —NR$^{32}$C(=O)R$^{34}$, —C(=O)NR$^{32}$R$^{33}$, —NR$^{32}$S(=O)$_2$R$^{34}$, —C(=O)OH, —C(=O)OR$^{34}$, optionally substituted cycloalkyl, optionally substituted heterocycloalkyl, optionally substituted aryl, or optionally substituted heteroaryl; or
R$^1$ and R$^2$ are taken together with the carbon to which they are attached to form an optionally substituted cycloalkyl;
R$^7$ and R$^8$ are independently hydrogen, optionally substituted alkyl, optionally substituted cycloalkyl, optionally substituted heterocycloalkyl, optionally substituted aryl, optionally substituted heteroaryl, —S(=O)$_2$R$^{44c}$, —S(=O)$_2$NR$^{42c}$R$^{43c}$, —(CR$^{40c}$R$^{41c}$)$_v$C(=O)OH, —(CR$^{40c}$R$^{41c}$)$_v$C(=O)OR$^{44c}$, —(CR$^{40c}$CR$^{41}$)$_v$C(=O)NR$^{42c}$CR$^{43c}$, or —C(=O)R$^{44c}$; or
R$^7$ and R$^8$ are taken together with the nitrogen to which they are attached to form an optionally substituted heterocycloalkyl;
each R$^{20}$ and R$^{21}$ are independently hydrogen, halogen, or optionally substituted alkyl;
R$^{22}$ and R$^{23}$ are independently hydrogen or optionally substituted alkyl; or
R$^{22}$ and R$^{23}$ are taken together with the nitrogen to which they are attached to form an optionally substituted heterocycloalkyl;
R$^{24}$ is optionally substituted alkyl, optionally substituted cycloalkyl, optionally substituted heterocycloalkyl, optionally substituted aryl, or optionally substituted heteroaryl;

$R^{25}$ is hydrogen, optionally substituted alkyl, optionally substituted cycloalkyl, optionally substituted heterocycloalkyl, optionally substituted aryl, optionally substituted heteroaryl;

each $R^{30}$, $R^{31}$, $R^{40c}$, $R^{41c}$, $R^{50}$, and $R^{51}$ are independently hydrogen, halogen, optionally substituted alkyl, optionally substituted cycloalkyl, optionally substituted heterocycloalkyl, optionally substituted aryl, optionally substituted heteroaryl, —OH, —OR$^{24}$, —SR$^{25}$, —NR$^{22}$R$^{23}$, —NR$^{22}$C(=O)R$^{24}$, —C(=O)NR$^{22}$R$^{23}$, —NR$^{22}$S(=O)$_2$R$^{24}$, —C(=O)OH, or —C(=O)OR$^{24}$; or $R^{30}$ and $R^{31}$, $R^{40c}$ and $R^{41c}$, or $R^{50}$ and $R^{51}$ are taken together with the carbon atom to which they are attached form an optionally substituted cycloalkyl; or two $R^{30}$, two $R^{40c}$, or two $R^{50}$ on adjacent carbons are taken together to form an alkenyl; or two $R^{30}$ and two $R^{31}$, two $R^{40c}$ and two $R^{41c}$, or two $R^{50}$ and two $R^{51}$ on adjacent carbons are taken together to form an alkynyl;

$R^{32}$, $R^{33}$, $R^{42c}$, $R^{43c}$, $R^{52}$, or $R^{53}$ are independently hydrogen, optionally substituted alkyl, optionally substituted cycloalkyl, optionally substituted heterocycloalkyl, optionally substituted aryl, optionally substituted heteroaryl, (poly-ethylene-glycol)-ethyl, optionally substituted saccharide, —CN, —OH, —S(=O)$_2$R$^{24}$, —S(=O)$_2$NR$^{22}$R$^{23}$, or —C(=O)R$^{24}$; or $R^{32}$ and $R^{33}$, $R^{42C}$ and $R^{43c}$, or $R^{52}$ and $R^{53}$ are taken together with the nitrogen to which they are attached to form an optionally substituted heterocycloalkyl;

$R^{34}$, $R^{44C}$, or $R^{54}$ are independently optionally substituted alkyl, optionally substituted cycloalkyl, optionally substituted heterocycloalkyl, optionally substituted aryl, or optionally substituted heteroaryl;

$R^{35}$ and $R^{55}$ are independently hydrogen, optionally substituted alkyl, optionally substituted cycloalkyl, optionally substituted heterocycloalkyl, optionally substituted aryl, optionally substituted heteroaryl;

$R^{36}$ and $R^{56}$ are independently hydrogen, —OH, —OR$^{24}$, —CN, —NO$_2$, —NR$^{22}$R$^{23}$, or optionally substituted alkyl;

Z is hydrogen, $R^{61}$, —(R$^{60}$)$_q$OR$^{61}$, —R$^{60}$)$_q$O(R$^{60}$)$_q$OR$^{61}$, —R$^{60}$OC(=O)R$^{61}$, —R$^{60}$OC(=O)OR$^{61}$, —R$^{60}$OC(=O)NHR$^{61}$, —R$^{60}$OC(=O)N(R$^{61}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each $R^{60}$ is independently —CH$_2$—, —CH(CH$_3$)—, —C(CH$_3$)$_2$—, or optionally substituted 1,1'-cyclopropylene;

each $R^{61}$ is independently optionally substituted alkyl, optionally substituted cycloalkyl, optionally substituted heterocycloalkyl, optionally substituted aryl, or optionally substituted heteroaryl; or two $R^{61}$ are taken together with the nitrogen to which they are attached to form an optionally substituted heterocycloalkyl;

$R^a$, $R^b$, and $R^c$ are independently hydrogen, halogen, cyano, optionally substituted alkyl, optionally substituted cycloalkyl, optionally substituted heterocycloalkyl, optionally substituted aryl, optionally substituted heteroaryl, —OH, —OR$^{54}$, —O(CR$^{50}$R$^{51}$)$_w$NR$^{52}$R$^{53}$, —O(CR$^{50}$R$^{51}$)$_w$OH, —O(CR$^{50}$R$^{51}$)$_w$OR$^{54}$, —O(CR$^{50}$R$^{51}$)$_w$C(=O)OH, —O(CR$^{50}$R$^{51}$)$_w$C(=O)OR$^{54}$, —O(CR$^{50}$R$^{51}$)$_v$C(=O)NR$^{52}$R$^{53}$, —NR$^{52}$R$^{53}$, —NR$^{52}$(CR$^{50}$R$^{51}$)$_w$NR$^{52}$R$^{53}$, —NR$^{52}$(CR$^{50}$R$^{51}$)$_v$C(=O)OH, —NR$^{52}$(CR$^{50}$R$^{51}$)$_v$C(=O)OR$^{54}$, —NR$^{52}$(CR$^{50}$R$^{51}$)$_v$C(=O)NR$^{52}$R$^{53}$, —NR$^{52}$S(=O)$_{1,2}$R$^{54}$, —S(=O)$_{1,2}$R$^{54}$, —SR$^{55}$, —S(CR$^{50}$R$^{51}$)$_w$NR$^{52}$C(=NR$^{56}$)NR$^{52}$R$^{53}$, —S(CR$^{50}$R$^{51}$)$_w$NR$^{52}$CR$^{50}$(=NR$^{56}$), —S(CR$^{50}$R$^{51}$)$_v$C(=NR$^{56}$)NR$^{52}$R$^{53}$, —S(CR$^{50}$R$^{51}$)$_w$OH, —S(CR$^{50}$R$^{51}$)$_w$OR$^{54}$, —S(CR$^{50}$R$^{51}$)$_w$NR$^{52}$R$^{53}$, —S(CR$^{50}$R$^{51}$)$_v$C(=O)OH, —S(CR$^{50}$R$^{51}$)$_v$C(=O)OR$^{54}$, —S(CR$^{50}$R$^{51}$)$_v$C(=O)NR$^{52}$R$^{53}$, —C(=O)H, —C(=O)R$^{54}$, —C(=O)OH, —C(=O)OR$^{54}$, —C(=O)NR$^{52}$R$^{53}$, —(CR$^{50}$R$^{51}$)$_v$N(R$^{52}$)(CR$^{50}$R$^{51}$)$_v$C(=O)OH, —(CR$^{50}$R$^{51}$)$_v$OH, —(CR$^{50}$R$^{51}$)$_v$OR$^{54}$, —(CR$^{50}$R$^{51}$)$_v$C(=O)OH, —(CR$^{50}$R$^{51}$)$_v$C(=O)OR$^{54}$, —(CR$^{50}$R$^{51}$)$_v$C(=O)NR$^{52}$R$^{53}$, —(CR$^{50}$R$^{51}$)$_v$OC(=O)R$^{51}$, —(CR$^{50}$R$^{51}$)$_v$SR$^{55}$, —(CR$^{50}$R$^{51}$)$_v$NR$^{52}$C(=NR$^{56}$), —(CR$^{50}$R$^{51}$)$_v$NR$^{52}$R$^{53}$, —(CR$^{50}$R$^{51}$)$_v$C(=NR$^{56}$)NR$^{52}$R$^{53}$, —(CR$^{50}$R$^{51}$)$_v$C(=O)NR$^{52}$R$^{53}$, —(CR$^{50}$R$^{51}$)$_v$heterocycloalkyl, or —(CR$^{50}$R$^{51}$)$_v$heteroaryl;

$R^d$ is hydrogen, —CN, —OH, —S(=O)$_2$R$^{24}$, —S(=O)$_2$NR$^{22}$R$^{23}$, —(CR$^{20}$R$^{21}$)$_v$C(=O)OH, —C(=O)R$^{24}$, optionally substituted alkyl, optionally substituted cycloalkyl, optionally substituted heterocycloalkyl, optionally substituted aryl, optionally substituted heteroaryl, (poly-ethylene-glycol)-ethyl, an optionally substituted saccharide;

$R^X$ is optionally substituted alkyl or optionally substituted cycloalkyl;

$X^1$ and $X^2$ are independently —OH, —OR$^X$, or F; or $X^1$ and $X^2$ are taken together with the boron atom to which they are attached to form a cyclic boronate ester;

each Y is independently halogen, optionally substituted alkyl, optionally substituted cycloalkyl, optionally substituted heterocycloalkyl, optionally substituted aryl, optionally substituted heteroaryl, -heteroaryl-NR$^{32}$R$^{33}$, -heterocycloalkyl-NR$^{32}$R$^{33}$, -heteroaryl-N(R$^{32}$)C(=NR$^{32}$)NR$^{32}$R$^{33}$, -heterocycloalkyl-N(R$^{32}$)C(=NR$^{32}$)NR$^{32}$R$^{33}$, —OH, —OR$^{34}$, —O(CR$^{30}$R$^{31}$)$_w$OH, —O(CR$^{30}$R$^{31}$)$_w$OR$^{34}$, —O(CR$^{30}$R$^{31}$)$_w$NR$^{32}$R$^{33}$, —O(CR$^{30}$R$^{31}$)$_w$NR$^{32}$C(=O)R$^{34}$, —O(CR$^{30}$R$^{31}$)$_w$NR$^{32}$C(=O)OR$^{34}$, —O(CR$^{30}$R$^{31}$)$_w$NR$^{32}$C(=O)NR$^{32}$R$^{33}$, —O(CR$^{30}$R$^{31}$)$_w$C(=O)NR$^{32}$R$^{33}$, —O(CR$^{30}$R$^{31}$)$_w$NR$^{32}$S(=O)$_{0,1,2}$R$^{34}$, —O(CR$^{30}$R$^{31}$)$_w$NR$^{32}$S(=O)$_{0,1,2}$NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —O(CR$^{30}$R$^{31}$)$_v$C(=NR$^{36}$)NR$^{32}$R$^{33}$, —O(CR$^{30}$R$^{31}$)$_w$N(R$^{32}$)C(=NR$^{36}$)R$^{34}$, —O(CR$^{30}$R$^{31}$)$_v$C(=NR$^{36}$)NR$^{32}$C(=NR$^{36}$)NR$^{32}$R$^{33}$, —O(CR$^{30}$R$^{31}$)$_w$N(R$^{32}$)C(=NR$^{36}$)NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —OC(=O)R$^{34}$, —OC(=O)(CR$^{30}$R$^{31}$)$_w$NR$^{32}$R$^{33}$, —OC(=O)NR$^{32}$R$^{33}$, —OC(=O)OR$^{34}$, —OC(=O)NR$^{32}$(CR$^{30}$R$^{31}$)$_w$NR$^{32}$R$^{33}$, —O-heteroaryl, —O-heterocycloalkyl, —O(CR$^{30}$R$^{31}$)$_v$heteroaryl, —O(CR$^{30}$R$^{31}$)$_v$heterocycloalkyl, —O(CR$^{30}$R$^{31}$)$_w$NR$^{32}$-heteroaryl, —O(CR$^{30}$R$^{31}$)$_w$NR$^{32}$-heterocycloalkyl, —O(CR$^{30}$R$^{31}$)$_w$O-heterocycloalkyl, —NR$^{32}$R$^{33}$, —NR$^{32}$(CR$^{30}$R$^{31}$)$_w$NR$^{32}$R$^{33}$, —NR$^{32}$(CR$^{30}$R$^{31}$)$_w$OH, —NR$^{32}$(CR$^{30}$R$^{31}$)$_w$OR$^{34}$, —NR$^{32}$C(=O)R$^{34}$, —NR$^{32}$C(=O)OR$^{34}$, —N(R$^{32}$)C(=O)(CR$^{30}$R$^{31}$)$_v$NR$^{32}$R$^{33}$, —NR$^{32}$C(=O)NR$^{32}$R$^{33}$, —NR$^{32}$C(=O)NR$^{32}$(CR$^{30}$R$^{31}$)$_w$NR$^{32}$R$^{33}$, —NR$^{32}$(CR$^{30}$R$^{31}$)$_w$S(=O)$_{0,1,2}$R$^{34}$, —NR$^{32}$(CR$^{30}$R$^{31}$)$_w$S(=O)$_{0,1,2}$NR$^{32}$R$^{33}$, —NR$^{32}$(CR$^{30}$R$^{31}$)$_w$NR$^{32}$R$^{33}$S(=O)$_{0,1,2}$R$^{34}$, —NR$^{32}$(CR$^{30}$R$^{31}$)$_w$NR$^{32}$S(=O)$_{0,1,2}$NR$^{32}$R$^{33}$, —NR$^{32}$C(=NR$^{36}$)NR$^{32}$R$^{33}$, —N(R$^{32}$)C(=NR$^{36}$)R$^{34}$, —NR$^{32}$(CR$^{30}$R$^{31}$)$_w$N(R$^{32}$)C(=NR$^{36}$)R$^{34}$, —NR$^{32}$(CR$^{30}$R$^{31}$)$_v$C(=NR$^{36}$)NR$^{32}$R$^{33}$, —NR$^{32}$(CR$^{30}$R$^{31}$)$_w$N $(R^{32})C(=NR^{36})NR^{32}R^{33}$, —$NR^{32}(CR^{30}R^{31})_w NR^{32}C(=O)NR^{32}R^{33}$, —$NR^{32}CR^{30}R^{31})_w NR^{32}C(=O)OR^{34}$, —$NR^{32}S(=O)_{0,1,2}R^{34}$, —$NR^{32}(CR^{30}R^{31})_v CO_2H$, —$NR^{32}(CR^{30}R^{31})_v CO_2R^{34}$, —$NR^{32}(CR^{30}R^{31})_v C(=O)NR^{32}R^{33}$, —$N(R^{32})$-heteroaryl-$NR^{32}R^{33}$, —$N(R^{32})$-heterocycloalkyl- $NR^{32}R^{33}$, —$NR^{32}(CR^{30}R^{31})_v$heteroaryl, —$NR^{32}(CR^{30}R^{31})_v$heterocycloalkyl, —$NR^{32}(CR^{30}R^{31})_w NR^{32}$-heteroaryl, —$NR^{32}(CR^{30}R^{31})_w NR^{32}$-heterocycloalkyl, —CN, —$(CR^{30}R^{31})_v CN$, —$(CR^{30}R^{31})_v NR^{32}R^{33}$, —$(CR^{30}R^{31})_v OH$, —$(CR^{30}R^{31})_v OR^{34}$, —$(CR^{30}R^{31})_v OC(=O)R^{34}$, —$(CR^{30}R^{31})_v OC(=O)NR^{32}R^{33}$, —$(CR^{30}R^{31})_v O(CR^{30}R^{31})_w OR^{34}$, —$(CR^{30}R^{31}))_v O(CR^{30}R^{31})_w OH$, —$(CR^{30}R^{31})_v O(CR^{30}R^{31})_w NR^{32}R^{33}$, —$(CR^{30}R^{31})_v NR^{32}(CR^{30}R^{31})_w OH$, —$(CR^{30}R^{31})_v NR^{32}(CR^{30}R^{31})_w OR^{34}$, —$(CR^{30}R^{31})_v C(=O)NR^{32}R^{33}$, —$(CR^{30}R^{31})_v C(=O)NR^{32}(CR^{30}R^{31})_w NR^{32}R^{33}$, —$(CR^{30}R^{31})_v C(=O)NR^{32}(CR^{30}R^{31})_w OR^{34}$, —$(CR^{30}R^{31})_v N(R^{32})C(=O)R^{34}$, —$(CR^{30}R^{31})_v N(R^{32})C(=O)OR^{34}$, —$(CR^{30}R^{31})_v N(R^{32})C(=O)NR^{32}R^{33}$, —$(CR^{30}R^{31})_v N(R^{32})C(=O)$ $(CR^{30}R^{31})_v NR^{32}R^{33}$, —$(CR^{30}R^{31})_v N(R^{32})S(=O)_{0,1,2}R^{34}$, —$(CR^{30}R^{31})_v N(R^{32})S(=O)_{0,1,2}NR^{32}R^{33}$, —$(CR^{30}R^{31})_v S(=O)_{0,1,2}NR^{32}R^{33}$, —$(CR^{30}R^{31})_v NR^{32}(CR^{30}R^{31})_w NR^{32}R^{33}$, —$(CR^{30}R^{31})_v N(R^{32})CH(=NR^{36})$, —$(CR^{30}R^{31})_v N(R^{32})C(=NR^{36})R^{34}$, —$(CR^{30}R^{31})_v C(=NR^{36})NR^{32}R^{33}$, —$(CR^{30}R^{31})_v N(R^{32})C(=NR^{36})NR^{32}R^{33}$, —$(CR^{30}R^{31})_v C(=NR^{36}) NR^{32}C(=NR^{36})NR^{32}R^{33}$, —$(CR^{30}R^{31})_v$heteroaryl-$NR^{32}R^{33}$, —$(CR^{30}R^{31})_v$heterocycloalkyl-$NR^{32}R^{33}$, —$(CR^{30}R^{31})_v$heteroaryl-$N(R^{32})C(=NR^{36})NR^{32}R^{33}$, —$(CR^{30}R^{31})_v$heterocycloalkyl-$N(R^{32})C(=NR^{36}) NR^{32}R^{33}$, —$(CR^{30}R^{31})_v$heteroaryl, —$(CR^{30}R^{31})_v$heterocycloalkyl, —C(=O)OH, —C(=O)OR^{34}, —C(=O)NR^{32}R^{33}, —C(=O)NR^{32}(CR^{30}R^{31})_w NR^{32}R^{33}, —C(=O)NR^{32}(CR^{30}R^{31})_w OH, —C(=O)NR^{32}(CR^{30}R^{31})_w OR^{34}, —C(=NR^{36})NR^{32}R^{33}, —C(=NR^{36})NR^{32}C(=O)R^{34}, —S(=O)_{1,2}R^{34}, —SR^{35}, —S(=O)_{0,1,2}(CR^{30}R^{31})_w NR^{32}R^{33}, —S(=O)_{0,1,2}(CR^{30}R^{31})_w OH, —S(=O)_{0,1,2}(CR^{30}R^{31})_w OR^{34}, —S(=O)_{0,1,2}NR^{32}R^{33}, —S(=O)_{0,1,2}NR^{32}(CR^{30}R^{31})_w NR^{32}R^{33}, —S(=O)_{0,1,2}(CR^{30}R^{31})_w N(R^{32})C(=NR^{36})R^{34}, —S(=O)_{0,1,2}(CR^{30}R^{31})_v C(=NR^{36})NR^{32}R^{33}, —S(=O)_{0,1,2}(CR^{30}R^{31})_w N(R^{32})C(=R^{36})NR^{32}R^{33}, —S(=O)_{0,1,2}(CR^{30}R^{31})_v C(=NR^{36}) NR^{32}C(=NR^{36})NR^{32}R^{33}, —Si(R^{34})_3, —NR^{32}R^{33}R^{34+}Q^-, —(CR^{30}R^{31})_v NR^{32}R^{33}R^{34+}Q^-, —NR^{32}(CR^{30}R^{31})_w NR^{32}R^{33}R^{34+}Q^-, —NR^{32}R^{34+}(CR^{30}R^{31})_w NR^{32}R^{33}R^{34+}Q^-_2, —(CR^{30}R^{31})_v(T)^+Q^-, or —O(CR^{30}R^{31})_w NR^{32}R^{33}R^{34+}Q^-$;

or two Ys taken together with the atoms to which they are attached form an optionally substituted cycloalkyl or an optionally substituted heterocycloalkyl;

T is pyridin-1-yl, pyrimidin-1-yl, or thiazol-3-yl;
Q is a pharmaceutically acceptable counterion;
n is 0-3;
m is 0-3;
p is 0-3;
each q is independently 2-6;
each v is independently 1-5; and each w is independently 2-5.

Also disclosed herein is a compound of Formula (Va) or (Vb), or a pharmaceutically acceptable salt, solvate, stereoisomer, tautomer, N-oxide, dimer, or trimer thereof:

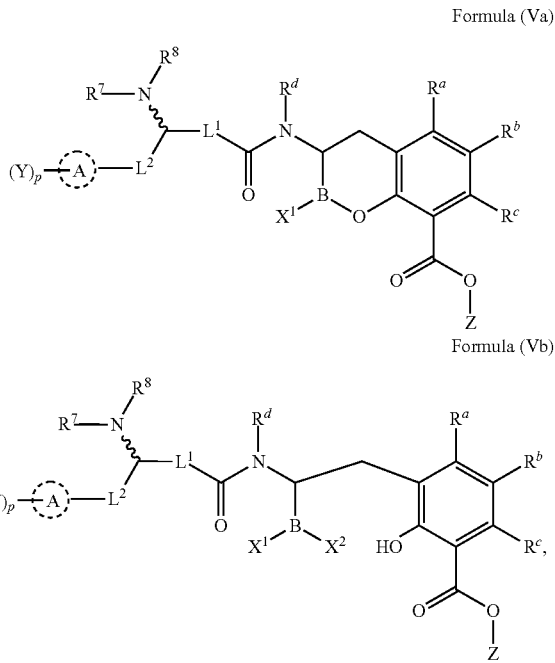

Formula (Va)

Formula (Vb)

wherein:
$L^1$ is —$(CR^1R^2)_n$—;
$L^2$ is —$(CR^1R^2)_m$—;
Ring A is cycloalkyl, heterocycloalkyl, aryl, or heteroaryl;
each $R^1$ and $R^2$ are independently hydrogen, halogen, optionally substituted alkyl, —OH, —$OR^{34}$, —$SR^{35}$, —$NR^{32}R^{33}$, —$NR^{32}C(=O)R^{34}$, —$C(=O)NR^{32}R^{33}$, —$NR^{32}S(=O)_2R^{34}$, —C(=O)OH, —$C(=O)OR^{34}$, optionally substituted cycloalkyl, optionally substituted heterocycloalkyl, optionally substituted aryl, or optionally substituted heteroaryl; or $R^1$ and $R^2$ are taken together with the carbon to which they are attached to form an optionally substituted cycloalkyl;

$R^7$ and $R^8$ are independently hydrogen, optionally substituted alkyl, optionally substituted cycloalkyl, optionally substituted heterocycloalkyl, optionally substituted aryl, optionally substituted heteroaryl, —$S(=O)_2R^{44c}$, —$S(=O)_2NR^{42c}R^{43c}$, —$(CR^{40c}R^{41c})_v C(=O)OH$, —$(CR^{40c}R^{41c})_v C(=O)OR^{44c}$, —$(CR^{40c}R^{41c})_v C(=O) NR^{42c}R^{43c}$, or —$C(=O)R^{44c}$; or $R^7$ and $R^8$ are taken together with the nitrogen to which they are attached to form an optionally substituted heterocycloalkyl;

each $R^{20}$ and $R^{21}$ are independently hydrogen, halogen, or optionally substituted alkyl;

$R^{22}$ and $R^{23}$ are independently hydrogen or optionally substituted alkyl; or $R^{22}$ and $R^{23}$ are taken together with the nitrogen to which they are attached to form an optionally substituted heterocycloalkyl;

$R^{24}$ is optionally substituted alkyl, optionally substituted cycloalkyl, optionally substituted heterocycloalkyl, optionally substituted aryl, or optionally substituted heteroaryl;

$R^{25}$ is hydrogen, optionally substituted alkyl, optionally substituted cycloalkyl, optionally substituted heterocycloalkyl, optionally substituted aryl, optionally substituted heteroaryl;

each $R^{30}$, $R^{31}$, $R^{40c}$, $R^{41c}$, $R^{50}$, and $R^{51}$ are independently hydrogen, halogen, optionally substituted alkyl, optionally substituted cycloalkyl, optionally substituted heterocycloalkyl, optionally substituted aryl, optionally substituted heteroaryl, —OH, —OR$^{24}$, —SR$^{25}$, —NR$^{22}$R$^{23}$, —NR$^{22}$C(=O)R$^{24}$, —C(=O)NR$^{22}$R$^{23}$, —NR$^{22}$S(=O)$_2$R$^{24}$, —C(=O)OH, or —C(=O)OR$^{24}$; or $R^{30}$ and $R^{31}$, $R^{40c}$ and $R^{41c}$, or $R^{50}$ and $R^{51}$ are taken together with the carbon atom to which they are attached form an optionally substituted cycloalkyl; or two $R^{30}$, two $R^{40c}$, or two $R^{50}$ on adjacent carbons are taken together to form an alkenyl; or two $R^{30}$ and two $R^{31}$, two $R^{40c}$ and two $R^{41c}$, or two $R^{50}$ and two $R^{51}$ on adjacent carbons are taken together to form an alkynyl;

$R^{32}$, $R^{33}$, $R^{42c}$, $R^{43c}$, $R^{52}$, or $R^{53}$ are independently hydrogen, optionally substituted alkyl, optionally substituted cycloalkyl, optionally substituted heterocycloalkyl, optionally substituted aryl, optionally substituted heteroaryl, (poly-ethylene-glycol)-ethyl, optionally substituted saccharide, —CN, —OH, —S(=O)$_2$R$^{24}$, —S(=O)$_2$NR$^{22}$R$^{23}$, or —C(=O)R$^{24}$; or $R^{32}$ and $R^{33}$, $R^{42c}$ and $R^{43c}$ or $R^{52}$ and $R^{53}$ are taken together with the nitrogen to which they are attached to form an optionally substituted heterocycloalkyl;

$R^{34}$, $R^{44c}$, or $R^{54}$ are independently optionally substituted alkyl, optionally substituted cycloalkyl, optionally substituted heterocycloalkyl, optionally substituted aryl, or optionally substituted heteroaryl;

$R^{35}$ and $R^{55}$ are independently hydrogen, optionally substituted alkyl, optionally substituted cycloalkyl, optionally substituted heterocycloalkyl, optionally substituted aryl, optionally substituted heteroaryl; $R^{36}$ and $R^{56}$ are independently hydrogen, —OH, —OR$^{24}$, —CN, —NO$_2$, —NR$^{22}$R$^{23}$, or optionally substituted alkyl;

Z is hydrogen, $R^{61}$, —(R$^{60}$)$_q$OR$^{61}$, —(R$^{60}$)$_q$O(R$^{60}$)$_q$OR$^{61}$, —R$^{60}$OC(=O)R$^{61}$, —R$^{60}$OC(=O)OR$^{61}$, —R$^{60}$OC(=O)NHR$^{61}$, —R$^{60}$OC(=O)N(R$^{61}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each $R^{60}$ is independently —CH$_2$—, —CH(CH$_3$)—, —C(CH$_3$)$_2$—, or optionally substituted 1,1'-cyclopropylene;

each $R^{61}$ is independently optionally substituted alkyl, optionally substituted cycloalkyl, optionally substituted heterocycloalkyl, optionally substituted aryl, or optionally substituted heteroaryl; or two $R^{61}$ are taken together with the nitrogen to which they are attached to form an optionally substituted heterocycloalkyl;

$R^a$, $R^b$, and $R^c$ are independently hydrogen, halogen, cyano, optionally substituted alkyl, optionally substituted cycloalkyl, optionally substituted heterocycloalkyl, optionally substituted aryl, optionally substituted heteroaryl, —OH, —OR$^{54}$, —O(CR$^{50}$R$^{51}$)NR$^{52}$R$^{53}$, —O(CR$^{50}$R$^{51}$)$_w$OH, —O(CR$^{50}$R$^{51}$)$_w$OR$^{54}$, —O(CR$^{50}$R$^{51}$)$_v$C(=O)OH, —O(CR$^{50}$R$^{51}$)$_v$C(=O)OR$^{54}$, —O(CR$^{50}$R$^{51}$)$_v$C(=O)NR$^{52}$R$^{53}$, —NR$^{52}$R$^{53}$, —NR$^{52}$(CR$^{50}$R$^{51}$)$_v$NR$^{52}$R$^{53}$, —NR$^{52}$(CR$^{50}$R$^{51}$)$_v$C(=O)OH, —NR$^{52}$(CR$^{50}$R$^{51}$)$_v$C(=O)OR$^{54}$, —NR$^{52}$(CR$^{50}$R$^{51}$)$_v$C(=O)NR$^{52}$R$^{53}$, —NR$^{52}$S(=O)$_{1,2}$R$^{54}$, —S(=O)$_{1,2}$R$^{54}$, —SR$^{55}$, —S(CR$^{50}$R$^{51}$)$_v$NR$^{52}$C(=NR$^{56}$)NR$^{52}$R$^{53}$, —S(CR$^{50}$R$^{51}$)'$^{v}$NR$^{52}$CR$^{50}$(=NR$^{56}$), —S(CR$^{50}$R$^{51}$)$_v$C(=NR$^{56}$)NR$^{52}$R$^{53}$, —S(CR$^{50}$R$^{51}$)$_w$OH, —S(CR$^{50}$R$^{51}$)$_w$OR$^{54}$, —S(CR$^{50}$R$^{51}$)$_w$NR$^{52}$R$^{53}$, —S(CR$^{50}$R$^{51}$) C(=O)OH, —S(CR$^{50}$R$^{51}$)$_v$C(=O)OR$^{54}$, —S(CR$^{50}$R$^{51}$)$_v$C(=O)NR$^{52}$R$^{53}$, —C(=O)H, —C(=O)R$^{54}$, —C(=O)OH, —C(=O)OR$^{54}$, —C(=O)NR$^{52}$R$^{53}$, —(CR$^{50}$R$^{51}$)$_v$N(R$^{52}$)(CR$^{50}$R$^{51}$)$_v$C(=O)OH, —(CR$^{50}$R$^{51}$)$_v$OH, —(CR$^{50}$R$^{51}$)$_v$OR$^{54}$, —(CR$^{50}$R$^{51}$)$_v$C(=O)OH, —(CR$^{50}$R$^{51}$)$_v$C(=O)OR$^{54}$, —(CR$^{50}$R$^{51}$)$_v$C(=O)NR$^{52}$R$^{53}$, —(CR$^{50}$R$^{51}$)$_v$OC(=O)R$^{54}$, —(CR$^{50}$R$^{51}$)$_v$SR$^{55}$, —(CR$^{50}$R$^{51}$)$_v$NR$^{52}$C(=NR$^{56}$), —(CR$^{50}$R$^{51}$)$_v$NR$^{52}$R$^{53}$, —(CR$^{50}$R$^{51}$)$_v$C(=NR$^{56}$)NR$^{52}$R$^{53}$, —(CR$^{50}$R$^{51}$)$_v$C(=O)NR$^{52}$R$^{53}$, —(CR$^{50}$R$^{51}$)$_v$heterocycloalkyl, or —(CR$^{50}$R$^{51}$)$_v$heteroaryl;

$R^d$ is hydrogen, —CN, —OH, —S(=O)$_2$R$^{24}$, —S(=O)$_2$NR$^{22}$R$^{23}$, —(CR$^{20}$R$^{21}$)$_v$C(=O)OH, —C(=O)R$^{24}$, optionally substituted alkyl, optionally substituted cycloalkyl, optionally substituted heterocycloalkyl, optionally substituted aryl, optionally substituted heteroaryl, (poly-ethylene-glycol)-ethyl, an optionally substituted saccharide;

$R^X$ is optionally substituted alkyl or optionally substituted cycloalkyl;

$X^1$ and $X^2$ are independently —OH, —OR$^X$, or F; or $X^1$ and $X^2$ are taken together with the boron atom to which they are attached to form a cyclic boronate ester;

each Y is halogen, optionally substituted alkyl, optionally substituted cycloalkyl, optionally substituted heterocycloalkyl, optionally substituted aryl, optionally substituted heteroaryl, -heteroaryl-NR$^{32}$R$^{33}$, -heterocycloalkyl-NR$^{32}$R$^{33}$, -heteroaryl-N(R$^{32}$)C(=NR$^{32}$)NR$^{32}$R$^{33}$, -heterocycloalkyl-N(R$^{32}$)C(=NR$^{32}$)NR$^{32}$R$^{33}$, —OH, —OR$^{34}$, —O(CR$^{30}$R$^{31}$)$_w$OH, —O(CR$^{30}$R$^{31}$)$_w$OR$^{34}$, —O(CR$^{30}$R$^{31}$)$_w$NR$^{32}$R$^{33}$, —O(CR$^{30}$R$^{31}$)$_w$NR$^{32}$C(=O)R$^{34}$, —O(CR$^{30}$R$^{31}$)$_w$NR$^{32}$C(=O)OR$^{34}$, —O(CR$^{30}$R$^{31}$)$_w$NR$^{32}$C(=O)NR$^{32}$R$^{33}$, —O(CR$^{30}$R$^{31}$)$_w$C(=O)NR$^{32}$R$^{33}$, —O(CR$^{30}$R$^{31}$)$_w$NR$^{32}$S(=O)$_{0,1,2}$R$^{34}$, —O(CR$^{30}$R$^{31}$)$_w$NR$^{32}$S(=O)$_{0,1,2}$NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —O(CR$^{30}$R$^{31}$)$_v$C(=NR$^{36}$)NR$^{32}$R$^{33}$, —O(CR$^{30}$R$^{31}$)$_w$N(R$^{32}$)C(=NR$^{36}$)R$^{34}$, —O(CR$^{30}$R$^{31}$)$_v$C(=NR$^{36}$)NR$^{32}$C(=NR$^{36}$)NR$^{32}$R$^{33}$, —O(CR$^{30}$R$^{31}$)$_w$N(R$^{32}$)C(=NR$^{36}$)NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —OC(=O)R$^{34}$, —OC(=O)(CR$^{30}$R$^{31}$)$_w$NR$^{32}$R$^{33}$, —OC(=O)NR$^{32}$R$^{33}$, —OC(=O)OR$^{34}$, —OC(=O)NR$^{32}$(CR$^{30}$R$^{31}$)$_w$NR$^{32}$R$^{33}$, —O-heteroaryl, —O-heterocycloalkyl, —O(CR$^{30}$R$^{31}$)$_v$ heteroaryl, —O(CR$^{30}$R$^{31}$)$_v$heterocycloalkyl, —O(CR$^{30}$R$^{31}$)$_w$NR$^{32}$-heteroaryl, —O(CR$^{30}$R$^{31}$)$_w$ NR$^{32}$-heterocycloalkyl, —O(CR$^{30}$R$^{31}$)$_w$O-heterocycloalkyl, —NR$^{32}$R$^{33}$, —NR$^{32}$(CR$^{30}$R$^{31}$)$_w$NR$^{32}$R$^{33}$, —NR$^{32}$(CR$^{30}$R$^{31}$)$_w$OH, —NR$^{32}$(CR$^{30}$R$^{31}$)$_w$OR$^{34}$, —NR$^{32}$C(=O)R$^{34}$, —NR$^{32}$C(=O)OR$^{34}$, —N(R$^{32}$)C(=O)(CR$^{30}$R$^{31}$)$_v$NR$^{32}$R$^{33}$, —NR$^{32}$C(=O)NR$^{32}$R$^{33}$, —NR$^{32}$C(=O)NR$^{32}$(CR$^{30}$R$^{31}$)$_w$NR$^{32}$R$^{33}$, —NR$^{32}$(CR$^{30}$R$^{31}$)$_w$S(=O)$_{0,1,2}$R$^{34}$, —NR$^{32}$(CR$^{30}$R$^{31}$)$_w$S(=O)$_{0,1,2}$NR$^{32}$R$^{33}$, —NR$^{32}$(CR$^{30}$R$^{31}$)$_w$NR$^{32}$R$^{33}$S(=O)$_{0,1,2}$R$^{34}$, —NR$^{32}$(CR$^{30}$R$^{31}$)$_w$NR$^{32}$S(=O)$_{0,1,2}$NR$^{32}$R$^{33}$, —NR$^{32}$C(=NR$^{36}$)NR$^{32}$R$^{33}$, —N(R$^{32}$)C(=NR$^{36}$)R$^{34}$, —NR$^{32}$(CR$^{30}$R$^{31}$)$_w$N(R$^{32}$)C(=NR$^{36}$)R$^{34}$, —NR$^{32}$(CR$^{30}$R$^{31}$)$_v$C(=NR$^{36}$)NR$^{32}$R$^{33}$, —NR$^{32}$(CR$^{30}$R$^{31}$)$_w$N(R$^{32}$)C(=NR$^{36}$)NR$^{32}$R$^{33}$, —NR$^{32}$(CR$^{30}$R$^{31}$)$_w$NR$^{32}$C(=O)NR$^{32}$R$^{33}$, —NR$^{32}$(CR$^{30}$R$^{31}$)$_w$NR$^{32}$C(=O)OR$^{34}$, —NR$^{32}$S(=O)$_{0,1,2}$R$^{34}$, —NR$^{32}$(CR$^{30}$R$^{31}$)$_v$CO$_2$H, —NR$^{32}$(CR$^{30}$R$^{31}$)$_v$CO$_2$R$^{34}$, —NR$^{32}$(CR$^{30}$R$^{31}$)$_v$C —(=O)NR$^{32}$R$^{33}$, —N(R$^{32}$)-heteroaryl-NR$^{32}$R$^{33}$, —N(R$^{32}$)-heterocycloalkyl-NR$^{32}$R$^{33}$, —NR$^{32}$(CR$^{30}$R$^{31}$)$_w$heteroaryl, —NR$^{32}$(CR$^{30}$R$^{31}$)$_w$heterocycloalkyl, —NR$^{32}$(CR$^{30}$R$^{31}$)$_w$NR$^{32}$-heteroaryl, —NR$^{32}$(CR$^{30}$R$^{31}$)$_w$NR$^{32}$-heterocycloalkyl, —CN, —(CR$^{30}$R$^{31}$)$_v$CN, —(CR$^{30}$R$^{31}$)$_v$NR$^{32}$R$^{33}$, —(CR$^{30}$R$^{31}$)$_v$OH, —(CR$^{30}$R$^{31}$)$_v$OR$^{34}$, —(CR$^{30}$R$^{31}$)$_v$OC(=O)R$^{34}$, —(CR$^{30}$R$^{31}$)$_v$OC(=O)NR$^{32}$R$^{33}$, —(CR$^{30}$R$^{31}$)$_v$O(CR$^{30}$R$^{31}$)$_w$OR$^{34}$, —(CR$^{30}$R$^{31}$)$_v$O(CR$^{30}$R$^{31}$)$_w$OH, —(CR$^{30}$R$^{31}$)$_v$O(CR$^{30}$R$^{31}$)$_w$NR$^{32}$R$^{33}$, —(CR$^{30}$R$^{31}$)$_v$NR$^{32}$(CR$^{30}$R$^{31}$)$_w$OH, —(CR$^{30}$R$^{31}$)$_v$NR$^{32}$(CR$^{30}$R$^{31}$)$_w$OR$^{34}$, —(CR$^{30}$R$^{31}$)$_v$C(=O)NR$^{32}$R$^{33}$, —(CR$^{30}$R$^{31}$)$_v$C(=O)NR$^{32}$(CR$^{30}$R$^{31}$)$_w$NR$^{32}$R$^{33}$, —(CR$^{30}$R$^{31}$)$_v$C(=O)NR$^{32}$(CR$^{30}$R$^{31}$)$_w$OR$^{34}$, —(CR$^{30}$R$^{31}$)$_v$N(R$^{32}$)C(=O)R$^{34}$, —(CR$^{30}$R$^{31}$)$_v$N(R$^{32}$)C(=O)OR$^{34}$, —(CR$^{30}$R$^{31}$)$_v$N(R$^{32}$)C(=O)NR$^{32}$R$^{33}$, —(CR$^{30}$R$^{31}$)$_v$N(R$^{32}$)C(=O)(CR$^{30}$R$^{31}$)$_v$NR$^{32}$R$^{33}$, —(CR$^{30}$R$^{31}$)$_v$N(R$^{32}$)S(=O)$_{0,1,2}$R$^{34}$, —(CR$^{30}$R$^{31}$)$_v$N(R$^{32}$)S(=O)$_{0,1,2}$NR$^{32}$R$^{33}$, —(CR$^{30}$R$^{31}$)$_v$S(=O)$_{0,1,2}$NR$^{32}$R$^{33}$, —(CR$^{30}$R$^{31}$)$_v$NR$^{32}$(CR$^{30}$R$^{31}$)$_w$NR$^{32}$R$^{33}$, —(CR$^{30}$R$^{31}$)$_v$N(R$^{32}$)CH(=NR$^{36}$), —(CR$^{30}$R$^{31}$)$_v$N(R$^{32}$)C(=NR$^{36}$)R$^{34}$, —(CR$^{30}$R$^{31}$)$_v$N(R$^{32}$)C(=NR$^{36}$)NR$^{32}$R$^{33}$, —(CR$^{30}$R$^{31}$)$_v$C(=NR$^{36}$)NR$^{32}$R$^{33}$, —(CR$^{30}$R$^{31}$)$_v$C(=NR$^{36}$)NR$^{32}$C(=NR$^{36}$)NR$^{32}$R$^{33}$, —(CR$^{30}$R$^{31}$)$_v$heteroaryl-NR$^{32}$R$^{32}$R$^{33}$, —(CR$^{30}$R$^{31}$)$_v$heterocycloalkyl-NR$^{32}$R$^{33}$, —(CR$^{30}$R$^{31}$)$_v$heteroaryl-N(R$^{32}$)C(=NR$^{36}$)NR$^{32}$R$^{33}$, —(CR$^{30}$R$^{31}$)$_v$heterocycloalkyl-N(R$^{32}$)C(=NR$^{36}$)NR$^{32}$R$^{33}$, —(CR$^{30}$R$^{31}$)$_v$heteroaryl, —(CR$^{30}$R$^{31}$)$_v$heterocycloalkyl, —C(=O)OH, —C(=O)OR$^{34}$, —C(=O)NR$^{32}$R$^{33}$, —C(=O)NR$^{32}$(CR$^{30}$R$^{31}$)$_w$NR$^{32}$R$^{33}$, —C(=O)NR$^{32}$(CR$^{30}$R$^{31}$)$_w$OH, —C(=O)NR$^{32}$(CR$^{30}$R$^{31}$)$_w$OR$^{34}$, —C(=NR$^{36}$)NR$^{32}$R$^{33}$, —C(=NR$^{36}$)NR$^{32}$C(=O)R$^{34}$, —S(=O)$_{1,2}$R$^{34}$, —SR$^{35}$, —S(=O)$_{0,1,2}$(CR$^{30}$R$^{31}$)$_w$NR$^{32}$R$^{33}$, —S(=O)$_{0,1,2}$(CR$^{30}$R$^{31}$)$_w$OH, —S(=O)$_{0,1,2}$(CR$^{30}$R$^{31}$)$_w$OR$^{34}$, —S(=O)$_{0,1,2}$NR$^{32}$R$^{33}$, —S(=O)$_{0,1,2}$NR$^{32}$(CR$^{30}$R$^{31}$)$_w$NR$^{32}$R$^{33}$, —S(=O)$_{0,1,2}$(CR$^{30}$R$^{31}$)$_w$N(R$^{32}$)C(=NR$^{36}$)R$^{34}$, —S(=O)$_{0,1,2}$(CR$^{30}$R$^{31}$)$_v$C(=NR$^{36}$)NR$^{32}$R$^{33}$, —S(=O)$_{0,1,2}$(CR$^{30}$R$^{31}$)$_w$N(R$^{32}$)C(=NR$^{36}$)NR$^{32}$R$^{33}$, —S(=O)$_{0,1,2}$(CR$^{30}$R$^{31}$)$_v$C(=NR$^{36}$)NR$^{32}$C(=NR$^{36}$)NR$^{32}$R$^{33}$, —Si(R$^{34}$)$_3$, —NR$^{32}$R$^{33}$R$^{34+}$Q$^-$, —(CR$^{30}$R$^{31}$)$_v$NR$^{32}$R$^{33}$R$^{34+}$Q$^-$, —NR$^{32}$(CR$^{30}$R$^{31}$)$_w$NR$^{32}$R$^{33}$R$^{34+}$Q$^-$, —NR$^{32}$R$^{34+}$(CR$^{30}$R$^{31}$)$_w$NR$^{32}$R$^{33}$R$^{34+}$Q$^-_2$, —(CR$^{30}$R$^{31}$)$_v$(T)$^+$Q$^-$, or —O(CR$^{30}$R$^{31}$)$_w$NR$^{32}$R$^{33}$R$^{34+}$Q$^-$;

or two Ys taken together with the atoms to which they are attached form an optionally substituted cycloalkyl or an optionally substituted heterocycloalkyl;

T is pyridin-1-yl, pyrimidin-1-yl, or thiazol-3-yl;
Q is a pharmaceutically acceptable counterion;
n is 0-3;
m is 0-3;
p is 0-3;
each q is independently 2-6;
each v is independently 1-5; and each w is independently 2-5.

In some embodiments of a compound of Formula (Ia), (Va), (Ib), or (Vb), the compound is not 3-(2-amino-2-phenylacetamido)-2-hydroxy-3,4-dihydro-2H-benzo[e][1,2]oxaborinine-8-carboxylic acid/3-(2-(2-amino-2-phenylacetamido)-2-boronoethyl)-2-hydroxybenzoic acid.

In some embodiments of a compound of Formula (Ia), (Va), (Ib), or (Vb), R$^7$ and R$^8$ are not hydrogen when Ring A is benzene. In some embodiments of a compound of Formula (Ia), (Va), (Ib), or (Vb), R$^7$ and R$^8$ are not hydrogen when p is 0. In some embodiments of a compound of Formula (Ia), (Va), (Ib), or (Vb), Ring A is not benzene when p is 0.

In some embodiments of a compound of Formula (Ia), (Va), (Ib), or (Vb), R$^7$ and R$^8$ are independently hydrogen, optionally substituted heterocycloalkyl, —(CR$^{40c}$R$^{41c}$)$_v$C(=O)OH, or —C(=O)R$^{44c}$. In some embodiments of a compound of Formula (Ia), (Va), (Ib), or (Vb), R$^7$ and R$^8$ are independently hydrogen, optionally substituted heterocycloalkyl, or —(CR$^{40c}$R$^{41c}$)$_v$C(=O)OH. In some embodiments of a compound of Formula (Ia), (Va), (Ib), or (Vb), R$^7$ and R$^8$ are hydrogen. In some embodiments of a compound of Formula (Ia), (Va), (Ib), or (Vb), R$^7$ and R$^8$ are not hydrogen. In some embodiments of a compound of Formula (Ia), (Va), (Ib), or (Vb), at least one of R$^7$ and R$^8$ is not hydrogen. In some embodiments of a compound of Formula (Ia), (Va), (Ib), or (Vb), R$^7$ and R$^8$ are as defined above and R$^{40c}$ and R$^{41c}$ are independently hydrogen or alkyl. In some embodiments of a compound of Formula (Ia), (Va), (Ib), or (Vb), R$^7$ and R$^8$ are as defined above and v is 1 or 2. In some embodiments of a compound of Formula (Ia), (Va), (Ib), or (Vb), R$^8$ is hydrogen and R$^7$ is —C(=O)R$^{44c}$. In some embodiments of a compound of Formula (Ia), (Va), (Ib), or (Vb), R$^7$ is as defined above and R$^{44c}$ is optionally substituted heterocycloalkyl.

Also disclosed herein is a compound of Formula (VIa) or (VIb), or a pharmaceutically acceptable salt, solvate, stereoisomer, tautomer, N-oxide, dimer, or trimer thereof:

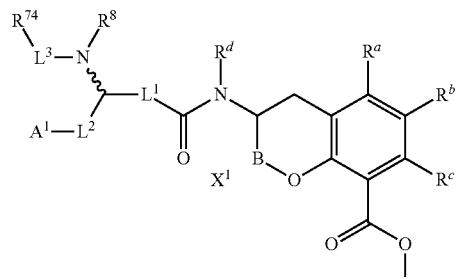

Formula (VIa)

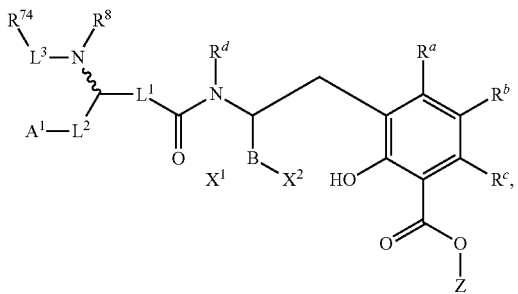

Formula (VIb)

wherein:
L$^1$ is —(CR$^1$R$^2$)$_n$—;
L$^2$ is —(CR$^1$R$^2$)$_m$—;
L$^3$ is —C(=O)—, —S(=O)—, or —S(=O)$_2$—;
A$^1$ is hydrogen,

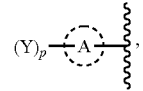

or Y;

Ring A is cycloalkyl, heterocycloalkyl, aryl, or heteroaryl;

each $R^1$ and $R^2$ are independently hydrogen, halogen, optionally substituted alkyl, —OH, —OR$^{34}$, —SR$^{35}$, —NR$^{32}$R$^{33}$, —NR$^{32}$C(=O)R$^{34}$, —C(=O)NR$^{32}$R$^{33}$, —NR$^{32}$S(=O)$_2$R$^{34}$, —C(=O)OH, —C(=O)OR$^{34}$, optionally substituted cycloalkyl, optionally substituted heterocycloalkyl, optionally substituted aryl, or optionally substituted heteroaryl; or $R^1$ and $R^2$ are taken together with the carbon to which they are attached to form an optionally substituted cycloalkyl;

$R^8$ is hydrogen, optionally substituted alkyl, optionally substituted cycloalkyl, optionally substituted heterocycloalkyl, optionally substituted aryl, or optionally substituted heteroaryl;

each $R^{20}$ and $R^{21}$ are independently hydrogen, halogen, or optionally substituted alkyl;

$R^{22}$ and $R^{23}$ are independently hydrogen or optionally substituted alkyl; or $R^{22}$ and $R^{23}$ are taken together with the nitrogen to which they are attached to form an optionally substituted heterocycloalkyl;

$R^{24}$ is optionally substituted alkyl, optionally substituted cycloalkyl, optionally substituted heterocycloalkyl, optionally substituted aryl, or optionally substituted heteroaryl;

$R^{25}$ is hydrogen, optionally substituted alkyl, optionally substituted cycloalkyl, optionally substituted heterocycloalkyl, optionally substituted aryl, optionally substituted heteroaryl;

each $R^{30}$, $R^{31}$, $R^{50}$, and $R^{51}$ are independently hydrogen, halogen, optionally substituted alkyl, optionally substituted cycloalkyl, optionally substituted heterocycloalkyl, optionally substituted aryl, optionally substituted heteroaryl, —OH, —OR$^{24}$, —SR$^{25}$, —NR$^{22}$R$^{23}$, —NR$^{22}$C(=O)R$^{24}$, —C(=O)NR$^{22}$R$^{23}$, —NR$^{22}$S(=O)$_2$R$^{24}$, —C(=O)OH, or —C(=O)OR$^{24}$; or $R^{30}$ and $R^{31}$, or $R^{50}$ and $R^{51}$ are taken together with the carbon atom to which they are attached form an optionally substituted cycloalkyl; or two $R^{30}$ or two $R^{50}$ on adjacent carbons are taken together to form an alkenyl; or two $R^{30}$ and two $R^{31}$, or two $R^{50}$ and two $R^{51}$ on adjacent carbons are taken together to form an alkynyl;

$R^{32}$, $R^{33}$, $R^{52}$, $R^{53}$, $R^{82}$, and $R^{83}$ are independently hydrogen, optionally substituted alkyl, optionally substituted cycloalkyl, optionally substituted heterocycloalkyl, optionally substituted aryl, optionally substituted heteroaryl, (poly-ethylene-glycol)-ethyl, optionally substituted saccharide, —CN, —OH, —S(=O)$_2$R$^{24}$, —S(=O)$_2$NR$^{22}$R$^{23}$, or —C(=O)R$^{24}$; or $R^{32}$ and $R^{33}$, or $R^{52}$ and $R^{53}$, or $R^{82}$ and $R^{83}$ are taken together with the nitrogen to which they are attached to form an optionally substituted heterocycloalkyl;

$R^{34}$, $R^{54}$, and $R^{84}$ are independently optionally substituted alkyl, optionally substituted cycloalkyl, optionally substituted heterocycloalkyl, optionally substituted aryl, or optionally substituted heteroaryl;

$R^{35}$ and $R^{55}$ are independently hydrogen, optionally substituted alkyl, optionally substituted cycloalkyl, optionally substituted heterocycloalkyl, optionally substituted aryl, optionally substituted heteroaryl;

$R^{36}$ and $R^{56}$ are independently hydrogen, —OH, —OR$^{24}$, —CN, —NO$_2$, —NR$^{22}$R$^{23}$, or optionally substituted alkyl;

Z is hydrogen, $R^{61}$, —(R$^{60}$)$_q$OR$^{61}$, —(R$^{60}$)$_q$O(R$^{60}$)$_q$OR$^{61}$, —R$^{60}$OC(=O)R$^{61}$, —R$^{60}$OC(=O)OR$^{61}$, —R$^{60}$OC(=O)NHR$^{61}$, —R$^{60}$OC(=O)N(R$^{61}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each $R^{60}$ is independently —CH$_2$—, —CH(CH$_3$)—, —C(CH$_3$)$_2$—, or optionally substituted 1,1'-cyclopropylene;

each $R^{61}$ is independently optionally substituted alkyl, optionally substituted cycloalkyl, optionally substituted heterocycloalkyl, optionally substituted aryl, or optionally substituted heteroaryl; or two $R^{61}$ are taken together with the nitrogen to which they are attached to form an optionally substituted heterocycloalkyl; $R^{74}$ is optionally substituted alkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, —OH, —OR$^{84}$, —NR$^{82}$R$^{83}$, —C(=O)OH, or —C(=O)OR$^{84}$;

$R^a$, $R^b$, and $R^c$ are independently hydrogen, halogen, cyano, optionally substituted alkyl, optionally substituted cycloalkyl, optionally substituted heterocycloalkyl, optionally substituted aryl, optionally substituted heteroaryl, —OH, —OR$^{54}$, —O(CR$^{50}$R$^{51}$)$_w$NR$^{52}$R$^{53}$, —O(CR$^{50}$R$^{51}$)$_w$OH, —O(CR$^{50}$R$^{51}$)$_w$OR$^{54}$, —O(CR$^{50}$R$^{51}$)$_v$C(=O)OH, —O(CR$^{50}$R$^{51}$)$_v$C(=O)OR$^{54}$, —O(CR$^{50}$R$^{51}$)$_v$C(=O)NR$^{52}$R$^{53}$, —NR$^{52}$R$^{53}$, —NR$^{52}$(CR$^{50}$R$^{51}$)$_w$NR$^{52}$R$^{53}$, —NR$^{52}$(CR$^{50}$R$^{51}$)$_v$C(=O)OH, —NR$^{52}$(CR$^{50}$R$^{51}$)$_v$C(=O)OR$^{54}$, —NR$^{52}$(CR$^{50}$R$^{51}$)$_v$C(=O)NR$^{52}$R$^{53}$, —NR$^{52}$S(=O)$_{1,2}$R$^{54}$, —S(=O)$_{1,2}$R$^{54}$, —SR$^{55}$, —S(CR$^{50}$R$^{51}$)$_v$NR$^{52}$C(=NR$^{56}$)NR$^{52}$R$^{53}$, —S(CR$^{50}$R$^{51}$)$^v$NR$^{52}$CR$^{50}$(=NR$^{56}$), —S(CR$^{50}$R$^{51}$)$_v$C(=NR$^{56}$)NR$^{52}$R$^{53}$, —S(CR$^{50}$R$^{51}$)$_w$OH, —S(CR$^{50}$R$^{51}$)$_w$OR$^{54}$, —S(CR$^{50}$R$^{51}$)$_w$NR$^{52}$R$^{53}$, —S(CR$^{50}$R$^{51}$)$_v$C(=O)OH, —S(CR$^{50}$R$^{51}$)$_v$C(=O)OR$^{54}$, —S(CR$^{50}$R$^{51}$)$_v$C(=O)NR$^{52}$R$^{53}$, —C(=O)H, —C(=O)R$^{54}$, —C(=O)OH, —C(=O)OR$^{54}$, —C(=O)NR$^{52}$R$^{53}$, —(CR$^{50}$R$^{51}$)$_v$N(R$^{52}$)(CR$^{50}$R$^{51}$)$_v$C(=O)OH, —(CR$^{50}$R$^{51}$)$_v$OH, —(CR$^{50}$R$^{51}$)$_v$OR$^{54}$, —(CR$^{50}$R$^{51}$)$_v$C(=O)OH, —(CR$^{50}$R$^{51}$)$_v$C(=O)OR$^{54}$, —(CR$^{50}$R$^{51}$)$_v$C(=O)NR$^{52}$R$^{53}$, —(CR$^{50}$R$^{51}$)$_v$OC(=O)R$^{54}$, —(CR$^{50}$R$^{51}$)$_v$SR$^{55}$, —(CR$^{50}$R$^{51}$)NR$^{52}$C(=NR$^{56}$), —(CR$^{50}$R$^{51}$)$_v$NR$^{52}$R$^{53}$, —(CR$^{50}$R$^{51}$)$_v$C(=NR$^{56}$)NR$^{52}$R$^{53}$, —(CR$^{50}$R$^{51}$)$_v$C(=O)NR$^{52}$R$^{53}$, —(CR$^{50}$R$^{51}$)$_v$heterocycloalkyl, or —(CR$^{50}$R$^{51}$)$_v$heteroaryl;

$R^d$ is hydrogen, —CN, —OH, —S(=O)$_2$R$^{24}$, —S(=O)$_2$NR$^{22}$R$^{23}$, —(CR$^{20}$R$^{21}$)$_v$C(=O)OH, —C(=O)R$^{24}$, optionally substituted alkyl, optionally substituted cycloalkyl, optionally substituted heterocycloalkyl, optionally substituted aryl, optionally substituted heteroaryl, (poly-ethylene-glycol)-ethyl, an optionally substituted saccharide;

$R^X$ is optionally substituted alkyl or optionally substituted cycloalkyl;

$X^1$ and $X^2$ are independently —OH, —OR$^X$, or F; or $X^1$ and $X^2$ are taken together with the boron atom to which they are attached to form a cyclic boronate ester;

each Y is independently halogen, optionally substituted alkyl, optionally substituted cycloalkyl, optionally substituted heterocycloalkyl, optionally substituted aryl, optionally substituted heteroaryl, -heteroaryl-$NR^{32}R^{33}$, -heterocycloalkyl-$NR^{32}R^{33}$, -heteroaryl-$N(R^{32})C(=NR^{32})NR^{32}R^{33}$, -heterocycloalkyl-$N(R^{32})C(=NR^{32})NR^{32}R^{33}$, —OH, —$OR^{34}$, —$O(CR^{30}R^{31})_w$OH, —$O(CR^{30}R^{31})_w$$OR^{34}$, —$O(CR^{30}R^{31})_w$$NR^{32}R^{33}$, —$O(CR^{30}R^{31})_w$$NR^{32}C(=O)R^{34}$, —$O(CR^{30}R^{31})_w$$NR^{32}C(=O)OR^{34}$, —$O(CR^{30}R^{31})_w$$NR^{32}C(=O)NR^{32}R^{33}$, —$O(CR^{30}R^{31})_w$$C(=O)NR^{32}R^{33}$, —$O(CR^{30}R^{31})_w$$NR^{32}S(=O)_{0,1,2}R^{34}$, —$O(CR^{30}R^{31})_w$$NR^{32}S(=O)_{0,1,2}NR^{32}R^{33}$, —$O(CR^{30}R^{31})_w$$S(=O)_{0,1,2}R^{34}$, —$O(CR^{30}R^{31})_w$$S(=O)^{0,1,2}NR^{32}R^{33}$, —$O(CR^{30}R^{31})_v$$C(=NR^{36})NR^{32}R^{33}$, —$O(CR^{30}R^{31})_w$$N(R^{32})C(=NR^{36})R^{34}$, —$O(CR^{30}R^{31})_v$$C(=NR^{36})NR^{32}C(=NR^{36})NR^{32}R^{33}$, —$O(CR^{30}R^{31})_w$$N(R^{32})C(=NR^{36})NR^{32}R^{33}$, —$O(CR^{30}R^{31})_w$$S(=O)_{0,1,2}R^{34}$, —$O(CR^{30}R^{31})_w$$S(=O)_{0,1,2}NR^{32}R^{33}$, —$OC(=O)R^{34}$, —$OC(=O)(CR^{30}R^{31})_v$$NR^{32}R^{33}$, —$OC(=O)NR^{32}R^{33}$, —$OC(=O)OR^{34}$, —$OC(=O)NR^{32}(CR^{30}R^{31})_w$$NR^{32}R^{33}$, —O-heteroaryl, —O-heterocycloalkyl, —$O(CR^{30}R^{31})_v$heteroaryl, —$O(CR^{30}R^{31})_v$heterocycloalkyl, —$O(CR^{30}R^{31})_w$$NR^{32}$-heteroaryl, —$O(CR^{30}R^{31})_w$$NR^{32}$-heterocycloalkyl, —$O(CR^{30}R^{31})_v$O-heteroaryl, —$NR^{32}R^{33}$, —$NR^{32}(CR^{30}R^{31})_w$$NR^{32}R^{33}$, —$NR^{32}(CR^{30}R^{31})_w$OH, —$NR^{32}(CR^{30}R^{31})_w$$OR^{34}$, —$NR^{32}C(=O)R^{34}$, —$NR^{32}C(=O)OR^{34}$, —$N(R^{32})C(=O)(CR^{30}R^{31})_v$$NR^{32}R^{33}$, —$NR^{32}C(=O)NR^{32}R^{33}$, —$NR^{32}C(=O)NR^{32}(CR^{30}R^{31})_w$$NR^{32}R^{33}$, —$NR^{32}(CR^{30}R^{31})_w$$S(=O)_{0,1,2}R^{34}$, —$NR^{32}(CR^{30}R^{31})_w$$S(=O)_{0,1,2}NR^{32}R^{33}$, —$NR^{32}(CR^{30}R^{31})_w$$NR^{32}R^{33}S(=O)_{0,1,2}R^{34}$, —$NR^{32}(CR^{30}R^{31})_w$$NR^{32}S(=O)_{0,1,2}NR^{32}R^{33}$, —$NR^{32}C(=NR^{36})NR^{32}R^{33}$, —$N(R^{32})C(=NR^{36})R^{34}$, —$NR^{32}(CR^{30}R^{31})_w$$N(R^{32})C(=NR^{36})R^{34}$, —$NR^{32}(CR^{30}R^{31})_v$$C(=NR^{36})NR^{32}R^{33}$, —$NR^{32}(CR^{30}R^{31})_w$$N(R^{32})C(=NR^{36})NR^{32}R^{33}$, —$NR^{32}(CR^{30}R^{31})_w$$NR^{32}C(=O)NR^{32}R^{33}$, —$NR^{32}(CR^{30}R^{31})_w$$NR^{32}C(=O)OR^{34}$, —$NR^{32}S(=O)_{0,1,2}R^{34}$, —$NR^{32}(CR^{30}R^{31})_v$$CO_2H$, —$NR^{32}(CR^{30}R^{31})_v$$CO_2R^{34}$, —$NR^{32}(CR^{30}R^{31})_v$$C(=O)NR^{32}R^{33}$, —$N(R^{32})$-heteroaryl-$NR^{32}R^{33}$, —$N(R^{32})$-heterocycloalkyl-$NR^{32}R^{33}$, —$NR^{32}(CR^{30}R^{31})_v$heteroaryl, —$NR^{32}(CR^{30}R^{31})_v$heterocycloalkyl, —$NR^{32}(CR^{30}R^{31})_w$$NR^{32}$-heteroaryl, —$NR^{32}(CR^{30}R^{31})_w$$NR^{32}$-heterocycloalkyl, —CN, —$(CR^{30}R^{31})_v$CN, —$(CR^{30}R^{31})_v$$NR^{32}R^{33}$, —$(CR^{30}R^{31})_v$OH, —$(CR^{30}R^{31})_v$$OR^{34}$, —$(CR^{30}R^{31})_v$$OC(=O)R^{34}$, —$(CR^{30}R^{31})_v$$OC(=O)NR^{32}R^{33}$, —$(CR^{30}R^{31})_v$$O(CR^{30}R^{31})_w$$OR^{34}$, —$(CR^{30}R^{31})_v$$O(CR^{30}R^{31})_w$OH, —$(CR^{30}R^{31})_v$$O(CR^{30}R^{31})_w$$NR^{32}R^{33}$, —$(CR^{30}R^{31})_v$$NR^{32}(CR^{30}R^{31})_w$OH, —$(CR^{30}R^{31})_v$$NR^{32}(CR^{30}R^{31})_w$$OR^{34}$, —$(CR^{30}R^{31})_v$$C(=O)NR^{32}R^{33}$, —$(CR^{30}R^{31})_v$$C(=O)NR^{32}(CR^{30}R^{31})_w$$NR^{32}R^{33}$, —$(CR^{30}R^{31})_v$$C(=O)NR^{32}(CR^{30}R^{31})_w$$OR^{34}$, —$(CR^{30}R^{31})_v$$N(R^{32})C(=O)R^{34}$, —$(CR^{30}R^{31})_v$$N(R^{32})C(=O)OR^{34}$, —$(CR^{30}R^{31})_v$$N(R^{32})C(=O)NR^{32}R^{33}$, —$(CR^{30}R^{31})_v$$N(R^{32})C(=O)(CR^{30}R^{31})_v$$NR^{32}R^{33}$, —$(CR^{30}R^{31})_v$$N(R^{32})S(=O)_{0,1,2}R^{34}$, —$(CR^{30}R^{31})_v$$N(R^{32})S(=O)_{0,1,2}NR^{32}R^{33}$, —$(CR^{30}R^{31})_v$$S(=O)_{0,1,2}NR^{32}R^{33}$, —$(CR^{30}R^{31})_v$$NR^{32}(CR^{30}R^{31})_w$$NR^{32}R^{33}$, —$(CR^{30}R^{31})_v$$N(R^{32})CH(=NR^{36})$, —$(CR^{30}R^{31})_v$$N(R^{32})C(=NR^{36})R^{34}$, —$(CR^{30}R^{31})_v$$C(=NR^{36})NR^{32}R^{33}$, —$(CR^{30}R^{31})_v$$N(R^{32})C(=NR^{36})NR^{32}R^{33}$, —$(CR^{30}R^{31})_v$$C(=NR^{36})NR^{32}C(=NR^{36})NR^{32}R^{33}$, —$(CR^{30}R^{31})_v$heteroaryl-$NR^{32}R^{33}$, —$(CR^{30}R^{31})_v$heterocycloalkyl-$NR^{32}R^{33}$, —$(CR^{30}R^{31})_v$heteroaryl-$N(R^{32})C(=NR^{36})NR^{32}R^{33}$, —$(CR^{30}R^{31})_v$heterocycloalkyl-$N(R^{32})C(=NR^{36})NR^{32}R^{33}$, —$(CR^{30}R^{31})_v$heteroaryl, —$(CR^{30}R^{31})_v$heterocycloalkyl, —$C(=O)OH$, —$C(=O)OR^{34}$, —$C(=O)NR^{32}R^{33}$, —$C(=O)NR^{32}(CR^{30}R^{31})_w$$NR^{32}R^{33}$, —$C(=O)NR^{32}(CR^{30}R^{31})_w$OH, —$C(=O)NR^{32}(CR^{30}R^{31})_w$$OR^{34}$, —$C(=NR^{36})NR^{32}R^{33}$, —$C(=NR^{36})NR^{32}C(=O)R^{34}$, —$S(=O)_{1,2}R^{34}$, —$SR^{35}$, —$S(=O)_{0,1,2}(CR^{30}R^{31})_w$$NR^{32}R^{33}$, —$S(=O)_{0,1,2}(CR^{30}R^{31})_w$OH, —$S(=O)_{0,1,2}(CR^{30}R^{31})_w$$OR^{34}$, —$S(=O)_{0,1,2}NR^{32}R^{33}$, —$S(=O)_{0,1,2}NR^{32}(CR^{30}R^{31})_w$$NR^{32}R^{33}$, —$S(=O)_{0,1,2}(CR^{30}R^{31})_w$$N(R^{32})C(=NR^{36})R^{34}$, —$S(=O)_{0,1,2}(CR^{30}R^{31})_v$$C(=NR^{36})NR^{32}R^{33}$, —$S(=O)_{0,1,2}(CR^{30}R^{31})_w$$N(R^{32})C(NR^{36})NR^{32}R^{33}$, —$S(=O)_{0,1,2}(CR^{30}R^{31})_v$$C(=NR^{36})NR^{32}C(=NR^{36})NR^{32}R^{33}$, —$Si(R^{34})_3$, —$NR^{32}R^{33}R^{34+}Q^-$, —$(CR^{30}R^{31})_v$$NR^{32}R^{33}R^{34+}Q^-$, —$NR^{32}(CR^{30}R^{31})_w$$NR^{32}R^{33}R^{34+}Q^-$, —$NR^{32}R^{34+}(CR^{30}R^{31})_w$$NR^{32}R^{33}R^{34+}Q^-_2$, —$(CR^{30}R^{31})_v(T)^+Q^-$, or —$O(CR^{30}R^{31})_w$$NR^{32}R^{33}R^{34+}Q^-$;

or two Ys taken together with the atoms to which they are attached form an optionally substituted cycloalkyl or an optionally substituted heterocycloalkyl;

T is pyridin-1-yl, pyrimidin-1-yl, or thiazol-3-yl;

Q is a pharmaceutically acceptable counterion;

n is 0-3;

m is 0-3;

p is 0-3;

each q is independently 2-6;

each v is independently 1-5; and each w is independently 2-5.

In some embodiments of a compound of Formula (VIa) or (VIb), $L^3$ is —C(=O)— or —S(=O)$_2$—. In some embodiments of a compound of Formula (VIa) or (VIb), $L^3$ is —C(=O)—. In some embodiments of a compound of Formula (VIa) or (VIb), $L^3$ is —S(=O)$_2$—. In some embodiments of a compound of Formula (VIa) or (VIb), $L^3$ is —S(=O)—.

In some embodiments of a compound of Formula (VIa) or (VIb), $R^8$ is hydrogen or optionally substituted alkyl. In some embodiments of a compound of Formula (VIa) or (VIb), $R^8$ is hydrogen.

In some embodiments of a compound of Formula (VIa) or (VIb), $R^{74}$ is optionally substituted alkyl, optionally substituted heterocycloalkyl, optionally substituted heteroaryl, optionally substituted heteroaralkyl, —$NR^{82}R^{83}$, or —$C(=O)OR^{84}$. In some embodiments of a compound of Formula (VIa) or (VIb), $R^{74}$ is optionally substituted heteroaryl. In some embodiments of a compound of Formula (VIa) or (VIb), the heteroaryl is thiazole, pyridine, or pyrimidine. In some embodiments of a compound of Formula (VIa) or (VIb), $R^{74}$ is optionally substituted heterocycloalkyl. In some embodiments of a compound of Formula (VIa) or (VIb), the heterocycloalkyl is piperazine, morpholine, or imidazolidine. In some embodiments of a compound of Formula (VIa) or (VIb), $R^{74}$ is optionally substituted piperazine.

In some embodiments of a compound of Formula (VIa) or (VIb), $R^{74}$ is —$NR^{82}R^{83}$.

In some embodiments of a compound of Formula (VIa) or (VIb), $R^{82}$ and $R^{83}$ are independently hydrogen, optionally substituted alkyl, or optionally substituted heteroaryl. In some embodiments of a compound of Formula (VIa) or (VIb), $R^{82}$ and $R^{83}$ are independently hydrogen or optionally substituted alkyl. In some embodiments of a compound of Formula (VIa) or (VIb), $R^{82}$ and $R^{83}$ are both optionally substituted alkyl. In some embodiments of a compound of Formula (VIa) or (VIb), $R^{82}$ is hydrogen and and $R^{83}$ optionally substituted alkyl or optionally substituted heteroaryl.

In some embodiments of a compound of Formula (VIa) or (VIb), $R^{82}$ and $R^{83}$ are taken together with the nitrogen to which they are attached to form an optionally substituted heterocycloalkyl. In some embodiments of a compound of Formula (VIa) or (VIb), the heterocycloalkyl is piperazine, morpholine, or imidazolidine. In some embodiments of a compound of Formula (VIa) or (VIb), $R^{74}$ is optionally substituted piperazine.

In some embodiments of a compound of Formula (VIa) or (VIb), $R^{74}$ is

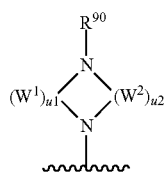

wherein:
- each $W^1$ and $W^2$ is independently —C(=O)— or —C($R^{91}$)$_2$—;
- $R^{90}$ is hydrogen, —OH, optionally substituted alkyl, optionally substituted alkoxy, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, —S(O)$_2$R$^{24}$, —S(=O)$_2$NR$^{22}$R$^{23}$, or —C(=O)R$^{24}$;
- each $R^{91}$ is independently hydrogen, halogen, —OH, —CN, NH$_2$, NO$_2$, optionally substituted alkyl, optionally substituted alkoxy, optionally substituted cycloalkyl, optionally substituted heterocycloalkyl, optionally substituted aryl, or optionally substituted heteroaryl;
- u1 is 1-3; and
- u2 is 1-3.

In some embodiments of a compound of Formula (VIa) or (VIb), u1 is 1. In some embodiments of a compound of Formula (VIa) or (VIb), u1 is 2. In some embodiments of a compound of Formula (VIa) or (VIb), u1 is 3. In some embodiments of a compound of Formula (VIa) or (VIb), u1 is 1. In some embodiments of a compound of Formula (VIa) or (VIb), u1 is 2. In some embodiments of a compound of Formula (VIa) or (VIb), u1 is 3. In some embodiments of a compound of Formula (VIa) or (VIb), u2 is 1. In some embodiments of a compound of Formula (VIa) or (VIb), u2 is 2. In some embodiments of a compound of Formula (VIa) or (VIb), u2 is 3. In some embodiments of a compound of Formula (VIa) or (VIb), u1 is 1 and u2 is 1. In some embodiments of a compound of Formula (VIa) or (VIb), u1 is 2 and u2 is 1. In some embodiments of a compound of Formula (VIa) or (VIb), u1 is 2 and u2 is 2. In some embodiments of a compound of Formula (VIa) or (VIb), u1 is 1 and u2 is 3. In some embodiments of a compound of Formula (VIa) or (VIb), u1 is 2 and u2 is 3. In some embodiments of a compound of Formula (VIa) or (VIb), u1 is 3 and u2 is 3.

In some embodiments of a compound of Formula (VIa) or (VIb), u1 is 2; each $W^1$ is —C($R^{91}$)$_2$—; u2 is 2; and each $W^2$ is —C(=O)—. In some embodiments of a compound of Formula (VIa) or (VIb), u1 is 2; each $W^1$ is —C($R^{91}$)$_2$—; u2 is 1; and $W^2$ is —C(=O)—. In some embodiments of a compound of Formula (VIa) or (VIb), u1 is 2; each $W^1$ is —C($R^{91}$)$_2$—; u2 is 2; and one $W^2$ is —C($R^{91}$)$_2$— and one $W^2$ is —C(=O)—. In some embodiments of a compound of Formula (VIa) or (VIb), u1 is 2; one $W^1$ is —C($R^{91}$)$_2$— and one $W^1$ is —C(=O)—; u2 is 2; and one $W^2$ is —C($R^{91}$)$_2$— and one $W^2$ is —C(=O)—.

In some embodiments of a compound of Formula (VIa) or (VIb), $R^{90}$ is hydrogen, optionally substituted alkyl, optionally substituted cycloalkyl, optionally substituted aralkyl, —S(=O)$_2$R$^{24}$, or —C(=O)R$^{24}$. In some embodiments of a compound of Formula (VIa) or (VIb), $R^{90}$ is optionally substituted alkyl. In some embodiments of a compound of Formula (VIa) or (VIb), $R^{90}$ is —H, —OH,

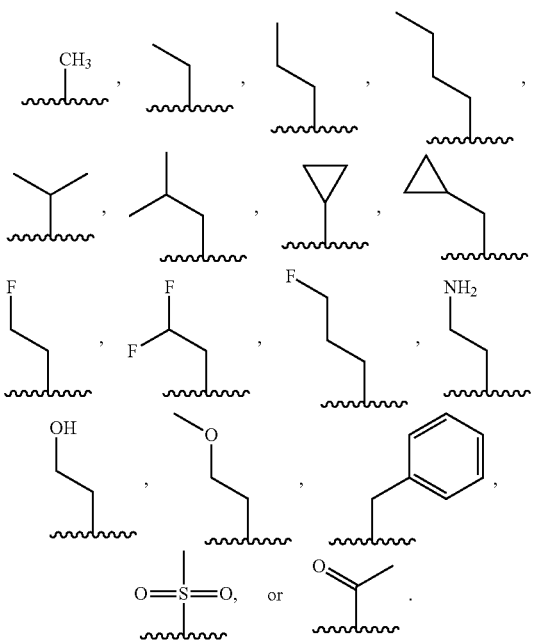

In some embodiments of a compound of Formula (VIa) or (VIb), $R^{90}$ is ethyl.

In some embodiments of a compound of Formula (VIa) or (VIb), each $R^{91}$ is independently hydrogen, halogen, or optionally substituted alkyl. In some embodiments of a compound of Formula (VIa) or (VIb), each $R^{91}$ is hydrogen.

In some embodiments of a compound of Formula (VIa) or (VIb), $R^{74}$ is:

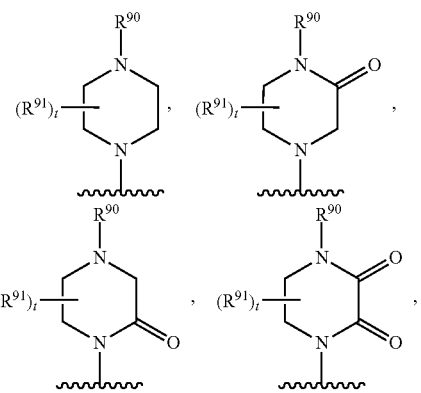

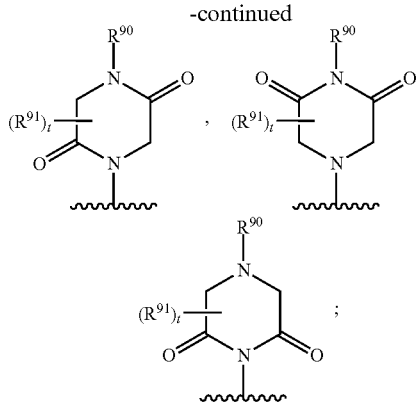

wherein

R$^{90}$ is hydrogen, —OH, optionally substituted alkyl, optionally substituted alkoxy, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, —S(=O)$_2$R$^{24}$, —S(=O)$_2$NR$^{22}$R$^{23}$, or —C(=O)R$^{24}$ each R$^{91}$ is independently hydrogen, halogen, —OH, —CN, NH$_2$, NO$_2$, optionally substituted alkyl, optionally substituted alkoxy, optionally substituted cycloalkyl, optionally substituted heterocycloalkyl, optionally substituted aryl, or optionally substituted heteroaryl; and t is 1-4.

In some embodiments of a compound of Formula (VIa) or (VIb), R$^{74}$ is:

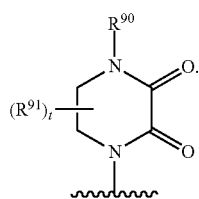

In some embodiments of a compound of Formula (VIa) or (VIb), t is 0. In some embodiments of a compound of Formula (VIa) or (VIb), t is 1. In some embodiments of a compound of Formula (VIa) or (VIb), t is 2. In some embodiments of a compound of Formula (VIa) or (VIb), t is 3. In some embodiments of a compound of Formula (VIa) or (VIb), t is 4.

In some embodiments of a compound of Formula (VIa) or (VIb), R$^{90}$ is hydrogen, optionally substituted alkyl, optionally substituted cycloalkyl, optionally substituted aralkyl, or —S(=O)$_2$R$^{24}$. In some embodiments of a compound of Formula (VIa) or (VIb), R$^{90}$ is hydrogen, optionally substituted alkyl, optionally substituted cycloalkyl, or optionally substituted aralkyl. In some embodiments of a compound of Formula (VIa) or (VIb), R$^{90}$ is optionally substituted alkyl. In some embodiments of a compound of Formula (VIa) or (VIb), R$^{90}$ is methyl, ethyl, propyl, or butyl. In some embodiments of a compound of Formula (VIa) or (VIb), R$^{90}$ is ethyl.

In some embodiments of a compound of Formula (VIa) or (VIb), R$^{90}$ is —H, —OH,

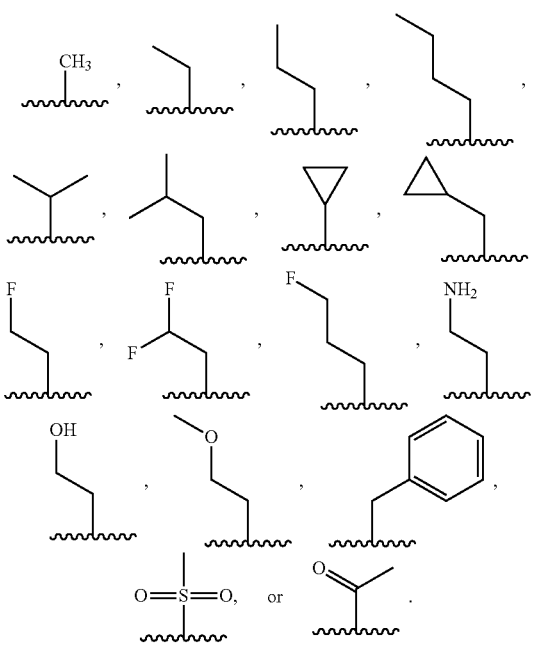

In some embodiments of a compound of Formula (VIa) or (VIb), each R$^{91}$ is independently hydrogen, halogen, or optionally substituted alkyl. In some embodiments of a compound of Formula (VIa) or (VIb), each R$^{91}$ is independently hydrogen or halogen. In some embodiments of a compound of Formula (VIa) or (VIb), each R$^{91}$ is hydrogen.

In some embodiments of a compound of Formula (VIa) or (VIb), R$^{74}$ is:

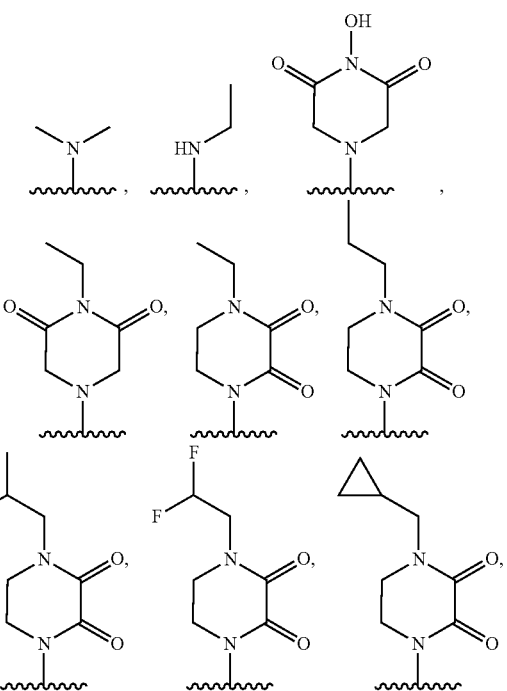

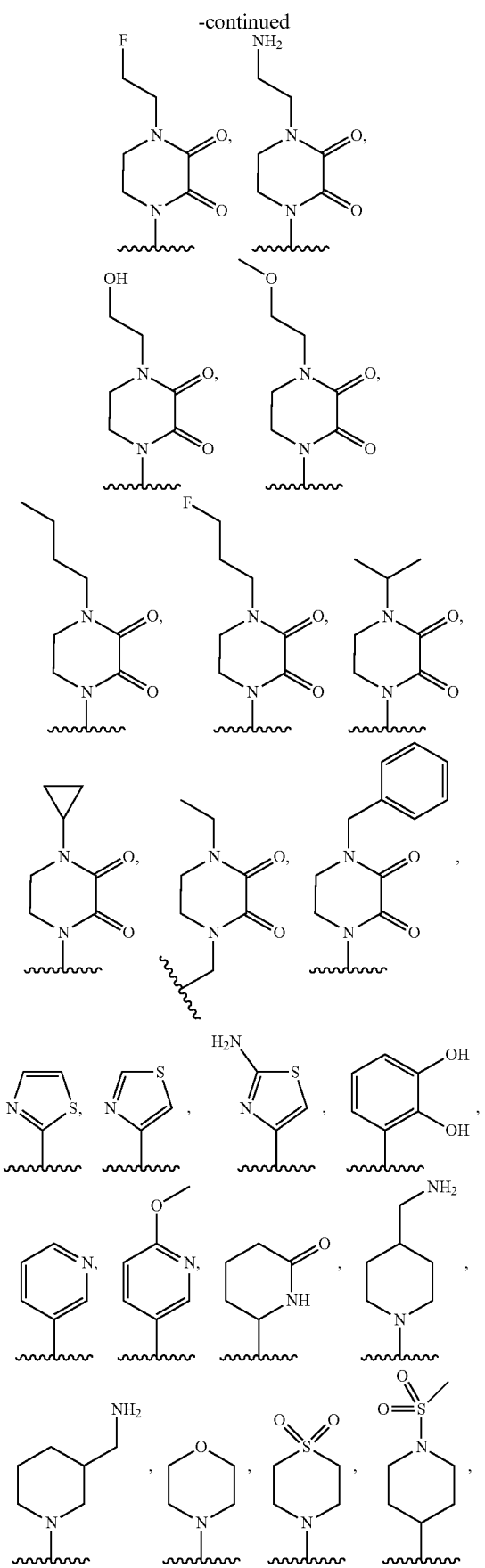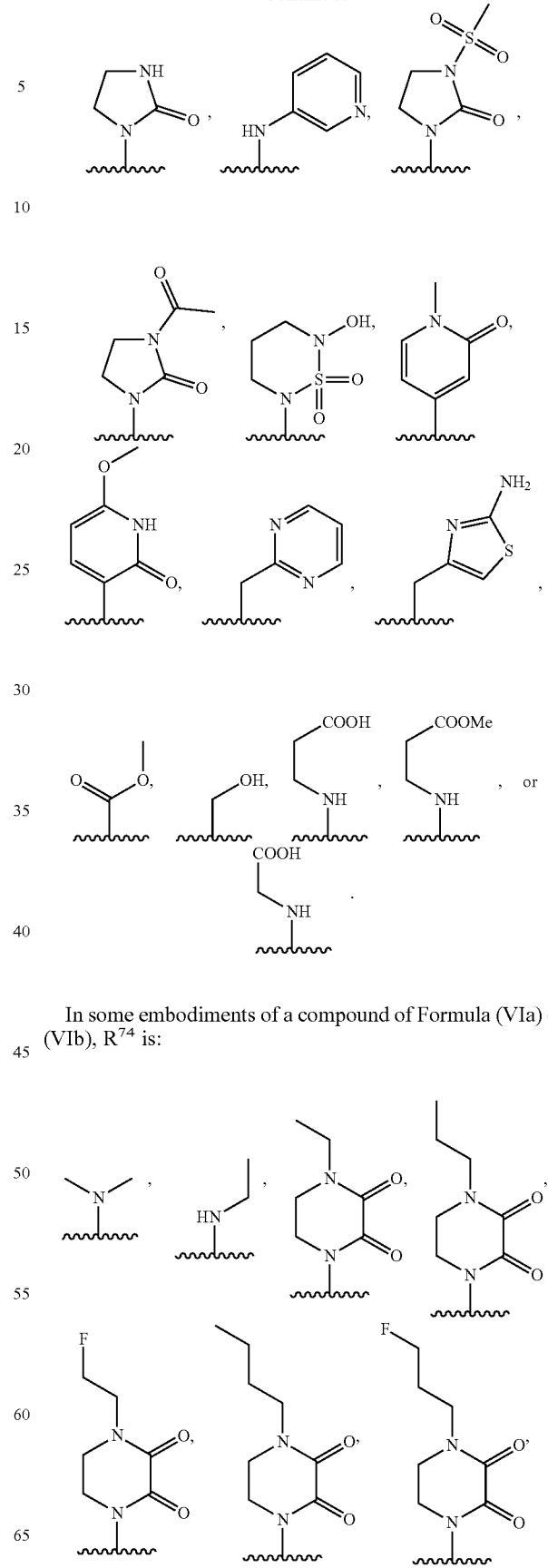
In some embodiments of a compound of Formula (VIa) or (VIb), $R^{74}$ is:

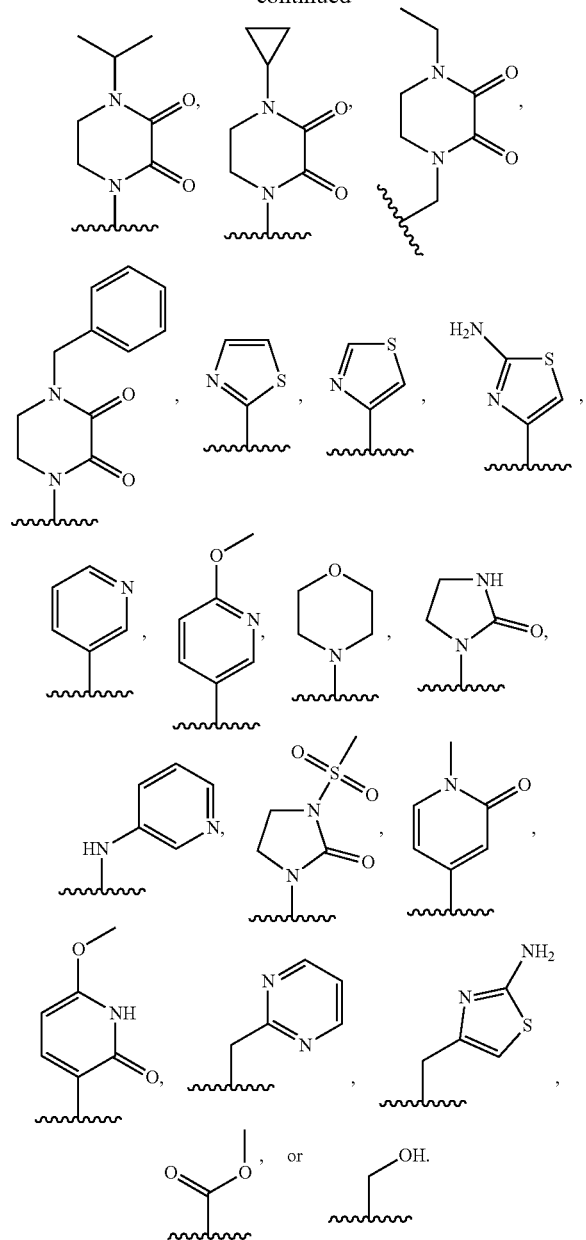

Also disclosed herein is a compound of Formula (VIIa) or (VIIb), or a pharmaceutically acceptable salt, solvate, stereoisomer, tautomer, N-oxide, dimer, or trimer thereof:

Formula (VIIa)

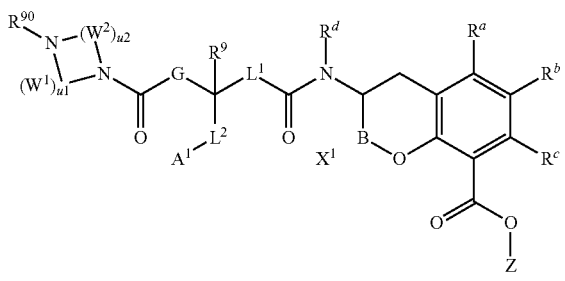

Formula (VIIb)

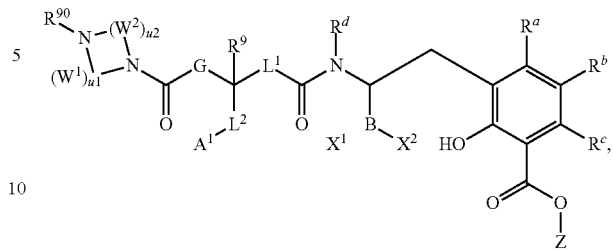

wherein:
G is —NR$^8$—, —C(R$^{10}$)$_2$—, or —C(R$^{10}$)$_2$NR$^8$—;
L$^1$ is —(CR$^1$R$^2$)$_n$—;
L$^2$ is —(CR$^1$R$^2$)$_m$—;
A$^1$ is hydrogen,

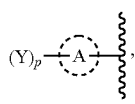

or Y;
Ring A is cycloalkyl, heterocycloalkyl, aryl, or heteroaryl;
R$^1$, R$^2$, and R$^9$ are independently hydrogen, halogen, optionally substituted alkyl, —OH, —OR$^{34}$, —SR$^{35}$, —NR$^{32}$R$^{33}$, —NR$^{32}$C(=O)R$^{34}$, —C(=O)NR$^{32}$R$^{33}$, —NR$^{32}$S(=O)$_2$R$^{34}$, —C(=O)OH, —C(=O)OR$^{34}$, optionally substituted cycloalkyl, optionally substituted heterocycloalkyl, optionally substituted aryl, or optionally substituted heteroaryl; or
R$^1$ and R$^2$ are taken together with the carbon to which they are attached to form an optionally substituted cycloalkyl or an optionally substituted heterocycloalkyl;
R$^8$ is hydrogen, optionally substituted alkyl, optionally substituted cycloalkyl, optionally substituted heterocycloalkyl, optionally substituted aryl, or optionally substituted heteroaryl; or
R$^8$ and R$^9$ are taken together with the atoms to which they are attached to form an optionally substituted heterocycloalkyl;
each R$^{10}$ is independently hydrogen, halogen, or optionally substituted alkyl;
each R$^{20}$ and R$^{21}$ are independently hydrogen, halogen, or optionally substituted alkyl;
R$^{22}$ and R$^{23}$ are independently hydrogen or optionally substituted alkyl; or
R$^{22}$ and R$^{23}$ are taken together with the nitrogen to which they are attached to form an optionally substituted heterocycloalkyl;
R$^{24}$ is optionally substituted alkyl, optionally substituted cycloalkyl, optionally substituted heterocycloalkyl, optionally substituted aryl, or optionally substituted heteroaryl;
R$^{25}$ is hydrogen, optionally substituted alkyl, optionally substituted cycloalkyl, optionally substituted heterocycloalkyl, optionally substituted aryl, optionally substituted heteroaryl;
each R$^{30}$, R$^{31}$, R$^{50}$, and R$^{51}$ are independently hydrogen, halogen, optionally substituted alkyl, optionally substituted cycloalkyl, optionally substituted heterocycloalkyl, optionally substituted aryl, optionally substituted heteroaryl, —OH, —OR$^{24}$, —SR$^{25}$, —NR$^{22}$R$^{23}$, —NR$^{22}$C(=O)R$^{24}$, —C(=O)NR$^{22}$R$^{23}$, —NR$^{22}$S(=O)$_2$R$^{24}$, —C(=O)OH, or —C(=O)OR$^{24}$; or R$^{30}$ and R$^{31}$, or R$^{50}$ and R$^{51}$ are taken together with the carbon atom to which they are attached form an optionally substituted cycloalkyl; or two R$^{30}$ or two R$^{50}$ on adjacent carbons are taken together to form an alkenyl; or two R$^{30}$ and two R$^{31}$, or two R$^{50}$ and two R$^{51}$ on adjacent carbons are taken together to form an alkynyl;

R$^{32}$, R$^3$, R$^{52}$, and R$^{53}$ are independently hydrogen, optionally substituted alkyl, optionally substituted cycloalkyl, optionally substituted heterocycloalkyl, optionally substituted aryl, optionally substituted heteroaryl, (poly-ethylene-glycol)-ethyl, optionally substituted saccharide, —CN, —OH, —S(=O)$_2$R$^{24}$, —S(=O)$_2$NR$^{22}$R$^{23}$, or —C(=O)R$^{24}$; or R$^{32}$ and R$^{33}$, or R$^{52}$ and R$^{53}$ are taken together with the nitrogen to which they are attached to form an optionally substituted heterocycloalkyl;

R$^{34}$, and R$^{54}$ are independently optionally substituted alkyl, optionally substituted cycloalkyl, optionally substituted heterocycloalkyl, optionally substituted aryl, or optionally substituted heteroaryl;

R$^{35}$ and R$^{55}$ are independently hydrogen, optionally substituted alkyl, optionally substituted cycloalkyl, optionally substituted heterocycloalkyl, optionally substituted aryl, optionally substituted heteroaryl;

R$^{36}$ and R$^{56}$ are independently hydrogen, —OH, —OR$^{24}$, —CN, —NO$_2$, —NR$^{22}$R$^{23}$, or optionally substituted alkyl;

each R$^{60}$ is independently —CH$_2$—, —CH(CH$_3$)—, —C(CH$_3$)$_2$—, or optionally substituted 1,1'-cyclopropylene;

each R$^{61}$ is independently optionally substituted alkyl, optionally substituted cycloalkyl, optionally substituted heterocycloalkyl, optionally substituted aryl, or optionally substituted heteroaryl; or two R$^{61}$ are taken together with the nitrogen to which they are attached to form an optionally substituted heterocycloalkyl;

R$^{90}$ is hydrogen, —OH, optionally substituted alkyl, optionally substituted alkoxy, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, —S(=O)$_2$R$^{24}$, —S(=O)$_2$NR$^{22}$R$^{23}$, or —C(=O)R$^{24}$;

each R$^{91}$ is independently hydrogen, halogen, —OH, —CN, NH$_2$, NO$_2$, optionally substituted alkyl, optionally substituted alkoxy, optionally substituted cycloalkyl, optionally substituted heterocycloalkyl, optionally substituted aryl, or optionally substituted heteroaryl;

R$^a$, R$^b$, and R$^c$ are independently hydrogen, halogen, cyano, optionally substituted alkyl, optionally substituted cycloalkyl, optionally substituted heterocycloalkyl, optionally substituted aryl, optionally substituted heteroaryl, —OH, —OR$^{54}$, —O(CR$^{50}$R$^{51}$)$_v$NR$^{52}$R$^{53}$, —O(CR$^{50}$R$^{51}$)$_w$OH, —O(CR$^{50}$R$^{51}$)$_v$OR$^{54}$, —O(CR$^{50}$R$^{51}$)$_v$C(=O)OH, —O(CR$^{50}$R$^{51}$)$_v$C(=O)OR$^{54}$, —O(CR$^{50}$R$^{51}$)$_v$C(=O)NR$^{52}$R$^{53}$, —NR$^{52}$R$^{53}$, —NR$^{52}$(CR$^{50}$R$^{51}$)$_w$NR$^{52}$R$^{53}$, —NR$^{52}$(CR$^{50}$R$^{51}$)$_v$C(=O)OH, —NR$^{52}$(CR$^{50}$R$^{51}$)$_v$C(=O)OR$^{54}$, —NR$^{52}$(CR$^{50}$R$^{51}$)$_v$C(=O)NR$^{52}$R$^{53}$, —NR$^{52}$S(=O)$_{1,2}$R$^{54}$, —S(=O)$_{1,2}$R$^{54}$, —SR$^{55}$, —S(CR$^{50}$R$^{51}$)$_v$NR$^{52}$C(=NR$^{56}$)NR$^{52}$R$^{53}$, —S(CR$^{50}$R$^{51}$)$_w$NR$^{52}$CR$^{50}$(=NR$^{56}$), —S(CR$^{50}$R$^{51}$)$_v$C(=NR$^{56}$)NR$^{52}$R$^{53}$, —S(CR$^{50}$R$^{51}$)$_w$OH, —S(CR$^{50}$R$^{51}$)$_w$OR$^{54}$, —S(CR$^{50}$R$^{51}$)$_w$NR$^{52}$R$^{53}$, —S(CR$^{50}$R$^{51}$)$_v$C(=O)OH, —S(CR$^{50}$R$^{51}$)$_v$C(=O)OR$^{54}$, —S(CR$^{50}$R$^{51}$)$_v$C(=O)NR$^{52}$R$^{53}$, —C(=O)H, —C(=O)R$^{54}$, —C(=O)OH, —C(=O)OR$^{54}$, —C(=O)NR$^{52}$R$^{53}$, —(CR$^{50}$R$^{51}$)$_v$N(R$^{52}$)(CR$^{50}$R$^{51}$)$_v$C(=O)OH, —(CR$^{50}$R$^{51}$)$_v$OH, —(CR$^{50}$R$^{51}$)$_v$OR$^{54}$, —(CR$^{50}$R$^{51}$)$_v$C(=O)OH, —(CR$^{50}$R$^{51}$)$_v$C(=O)OR$^{54}$, —(CR$^{50}$R$^{51}$)$_v$C(=O)NR$^{52}$R$^{53}$, —(CR$^{50}$R$^{51}$)$_v$OC(=O)R$^{54}$, —(CR$^{50}$R$^{51}$)$_v$SR$^{55}$, —(CR$^{50}$R$^{51}$)$_v$NR$^{52}$C(=NR$^{56}$), —(CR$^{50}$R$^{51}$)$_v$NR$^{52}$R$^{53}$, —(CR$^{50}$R$^{51}$)$_v$C(=NR$^{56}$)NR$^{52}$R$^{53}$, —(CR$^{50}$R$^{51}$)$_v$C(=O)NR$^{52}$R$^{53}$, —(CR$^{50}$R$^{51}$)$_v$heterocycloalkyl, or —(CR$^{50}$R$^{51}$)$_v$heteroaryl;

R$^d$ is hydrogen, —CN, —OH, —S(=O)$_2$R$^{24}$, —S(=O)$_2$NR$^{22}$R$^{23}$, —(CR$^{20}$R$^{21}$)$_v$C(=O)OH, —C(=O)R$^{24}$, optionally substituted alkyl, optionally substituted cycloalkyl, optionally substituted heterocycloalkyl, optionally substituted aryl, optionally substituted heteroaryl, (poly-ethylene-glycol)-ethyl, an optionally substituted saccharide;

R$^X$ is optionally substituted alkyl or optionally substituted cycloalkyl;

each W$^1$ and W$^2$ is independently —C(=O)— or —C(R$^{91}$)$_2$—;

X$^1$ and X$^2$ are independently —OH, —OR$^X$, or F; or

X$^1$ and X$^2$ are taken together with the boron atom to which there are attached to form a cyclic boronate ester;

each Y is independently halogen, optionally substituted alkyl, optionally substituted cycloalkyl, optionally substituted heterocycloalkyl, optionally substituted aryl, optionally substituted heteroaryl, -heteroaryl-NR$^{32}$R$^{33}$, -heterocycloalkyl-NR$^{32}$R$^{33}$, -heteroaryl-N(R$^{32}$)C(=NR$^{32}$)NR$^{32}$R$^{33}$, -heterocycloalkyl-N(R$^{32}$)C(=NR$^{32}$)NR$^{32}$R$^{33}$, —OH, —OR$^{34}$, —O(CR$^{30}$R$^{31}$)$_w$OH, —O(CR$^{30}$R$^{31}$)$_w$OR$^{34}$, —O(CR$^{30}$R$^{31}$)$_w$NR$^{32}$R$^{33}$, —O(CR$^{30}$R$^{31}$)$_w$NR$^{32}$C(=O)R$^{34}$, —O(CR$^{30}$R$^{31}$)$_w$NR$^{32}$C(=O)OR$^{34}$, —O(CR$^{30}$R$^{31}$)$_w$NR$^{32}$C(=O)NR$^{32}$R$^{33}$, —O(CR$^{30}$R$^{31}$)$_w$C(=O)NR$^{32}$R$^{33}$, —O(CR$^{30}$R$^{31}$)$_w$NR$^{32}$S(=O)$_{0,1,2}$R$^{34}$, —O(CR$^{30}$R$^{31}$)$_w$NR$^{32}$S(=O)$_{0,1,2}$NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —O(CR$^{30}$R$^{31}$)$_v$C(=NR$^{36}$)NR$^{32}$R$^{33}$, —O(CR$^{30}$R$^{31}$)$_w$N(R$^{32}$)C(=NR$^{36}$)R$^{34}$, —O(CR$^{30}$R$^{31}$)$_v$C(=NR$^{36}$)NR$^{32}$R$^{33}$, —O(CR$^{30}$R$^{31}$)$_w$N(R$^{32}$)C(=NR$^{36}$)NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —OC(=O)R$^{34}$, —OC(=O)(CR$^{30}$R$^{31}$)$_{NR}{}^{32}$R$^{33}$, —OC(=O)NR$^{32}$R$^{33}$, —OC(=O)OR$^{34}$, —OC(=O)NR$^{32}$(CR$^{30}$R$^{31}$)$_w$NR$^{32}$R$^{33}$, —O-heteroaryl, —O-heterocycloalkyl, —O(CR$^{30}$R$^{31}$)$_v$heteroaryl, —O(CR$^{30}$R$^{31}$)$_v$heterocycloalkyl, —O(CR$^{30}$R$^{31}$)$_w$NR$^{32}$-heteroaryl, —O(CR$^{30}$R$^{31}$)$_w$NR$^{32}$-heterocycloalkyl, —O(CR$^{30}$R$^{31}$)$_w$O-heterocycloalkyl, —NR$^{32}$R$^{33}$, —NR$^{32}$(CR$^{30}$R$^{31}$)$_w$NR$^{32}$R$^{33}$, —NR$^{32}$(CR$^{30}$R$^{31}$)$_w$OH, —NR$^{32}$(CR$^{30}$R$^{31}$)$_w$OR$^{34}$, —NR$^{32}$C(=O)R$^{34}$, —NR$^{32}$C(=O)OR$^{34}$, —N(R$^{32}$)C(=O)(CR$^{30}$R$^{31}$)$_v$NR$^{32}$R$^{33}$, —NR$^{32}$C(=O)NR$^{32}$R$^{33}$, —NR$^{32}$C(=O)NR$^{32}$(CR$^{30}$R$^{31}$)$_w$R$^{32}$R$^{33}$, —NR$^{32}$(CR$^{30}$R$^{31}$)$_w$S(=O)$_{0,1,2}$R$^{34}$, —NR$^{32}$(CR$^{30}$R$^{31}$)$_w$S(=O)$_{0,1,2}$NR$^{32}$R$^{33}$, —NR$^{32}$(CR$^{30}$R$^{31}$)$_w$NR$^{32}$R$^{33}$S(=O)$_{0,1,2}$R$^{34}$, —NR$^{32}$(CR$^{30}$R$^{31}$)$_w$NR$^{32}$S(=O)$_{0,1,2}$NR$^{32}$R$^{33}$, —NR$^{32}$C(=NR$^{36}$)NR$^{32}$R$^{33}$, —N(R$^{32}$)C(=NR$^{36}$)R$^{34}$, —NR$^{32}$(CR$^{30}$R$^{31}$)$_w$N(R$^{32}$)C(=NR$^{36}$)R$^{34}$, —NR$^{32}$(CR$^{30}$R$^{31}$)$_v$C(=NR$^{36}$)NR$^{32}$R$^{33}$, —NR$^{32}$(CR$^{30}$R$^{31}$)$_w$N(R$^{32}$)C(=NR$^{36}$)NR$^{32}$R$^{33}$, —NR$^{32}$(CR$^{30}$R$^{31}$)$_w$NR$^{32}$C(=O)NR$^{32}$R$^{33}$, —NR$^{32}$(CR$^{30}$R$^{31}$)$_w$NR$^{32}$C(=O)OR$^{34}$, —NR$^{32}$S(=O)$_{0,1,2}$R$^{34}$, —NR$^{32}$(CR$^{30}$R$^{31}$)$_v$CO$_2$H, —NR³²(CR³⁰R³¹)ᵥCO₂R³⁴, —NR³²(CR³⁰R³¹)ᵥC(=O)NR³²R³³, —N(R³²)-heteroaryl-NR³²R³³, —N(R³²)-heterocycloalkyl-NR³²R³³, —NR³²(CR³⁰R³¹)ᵥheteroaryl, —NR³²(CR³⁰R³¹)ᵥheterocycloalkyl, —NR³²(CR³⁰R³¹)ᵥNR³²-heteroaryl, —NR³²(CR³⁰R³¹)ᵥNR³²-heterocycloalkyl, —CN, —(CR³⁰R³¹)ᵥCN, —(CR³⁰R³¹)ᵥNR³²R³³, —(CR³⁰R³¹)ᵥOH, —(CR³⁰R³¹)ᵥOR³⁴, —(CR³⁰R³¹)ᵥOC(=O)R³⁴, —(CR³⁰R³¹)ᵥOC(=O)NR³²R³³, —(CR³⁰R³¹)ᵥO(CR³⁰R³¹)ᵥOR³⁴, —(CR³⁰R³¹)ᵥO(CR³⁰R³¹)ᵥOH, —(CR³⁰R³¹)ᵥO(CR³⁰R³¹)ᵥNR³²R³³, —(CR³⁰R³¹)ᵥNR³²(CR³⁰R³¹)ᵥOH, —(CR³⁰R³¹)ᵥNR³²(CR³⁰R³¹)ᵥOR³⁴, —(CR³⁰R³¹)ᵥC(=O)NR³²R³³, —(CR³⁰R³¹)ᵥC(=O)NR³²(CR³⁰R³¹)ᵥNR³²R³³, —(CR³⁰R³¹)ᵥC(=O)NR³²(CR³⁰R³¹)ᵥOR³⁴, —(CR³⁰R³¹)ᵥN(R³²)C(=O)R³⁴, —(CR³⁰R³¹)ᵥN(R³²)C(=O)OR³⁴, —(CR³⁰R³¹)ᵥN(R³²)C(=O)NR³²R³³, —(CR³⁰R³¹)ᵥN(R³²)C(=O)(CR³⁰R³¹)ᵥNR³²R³³, —(CR³⁰R³¹)ᵥN(R³²)S(=O)₀,₁,₂R³⁴, —(CR³⁰R³¹)ᵥN(R³²)S(=O)₀,₁,₂NR³²R³³, —(CR³⁰R³¹)ᵥS(=O)₀,₁,₂NR³²R³³, —(CR³⁰R³¹)ᵥNR³²(CR³⁰R³¹)ᵥNR³²R³³, —(CR³⁰R³¹)ᵥN(R³²)CH(=NR³⁶), —(CR³⁰R³¹)ᵥN(R³²)C(=NR³⁶)R³⁴, —(CR³⁰R³¹)ᵥC(=NR³⁶)NR³²R³³, —(CR³⁰R³¹)ᵥN(R³²)C(=NR³⁶)NR³²R³³, —(CR³⁰R³¹)ᵥC(=NR³⁶)NR³²C(=NR³⁶)NR³²R³³ (CR³⁰R³¹)ᵥheteroaryl-NR³²R³³, —(CR³⁰R³¹)ᵥheterocycloalkyl-NR³²R³³, —(CR³⁰R³¹)ᵥheteroaryl-N(R³²)C(=NR³⁶)NR³²R³³, —(CR³⁰R³¹)ᵥheterocycloalkyl-N(R³²)C(=NR³⁶)NR³²R³³, —(CR³⁰R³¹)ᵥheteroaryl, —(CR³⁰R³¹)ᵥheterocycloalkyl, —C(=O)OH, —C(=O)OR³⁴, —C(=O)NR³²R³³, —C(=O)NR³²(CR³⁰R³¹)ᵥNR³²R³³, —C(=O)NR³²(CR³⁰R³¹)ᵥOH, —C(=O)NR³²(CR³⁰R³¹)ᵥOR³⁴, —C(=NR³⁶)NR³²R³³, —C(=NR³⁶)NR³²C(=O)R³⁴, —S(=O)₀,₁,₂R³⁴, —SR³⁵, —S(=O)₀,₁,₂(CR³⁰R³¹)ᵥNR³²R³³, —S(=O)₀,₁,₂(CR³⁰R³¹)ᵥOH, —S(=O)₀,₁,₂(CR³⁰R³¹)ᵥOR³⁴, —S(=O)₀,₁,₂NR³²R³³, —S(=O)₀,₁,₂NR³²(CR³⁰R³¹)ᵥ NR³²R³³, —S(=O)₀,₁,₂(CR³⁰R³¹)ᵥN(R³²)C(=NR³⁶)R³⁴, —S(=O)₀,₁,₂(CR³⁰R³¹)ᵥC(=NR³⁶)NR³²R³³, —S(=O)₀,₁,₂(CR³⁰R³¹)ᵥN(R³²)C(=NR³⁶)NR³²R³³, —S(=O)₀,₁,₂(CR³⁰R³¹)ᵥC(=NR³⁶)NR³²C(=NR³⁶)NR³²R³³, —Si(R³⁴)₃, —NR³²R³³R³⁴⁺Q⁻, —(CR³⁰R³¹)ᵥNR³²R³³R³⁴⁺Q⁻, —NR³²(CR³⁰R³¹)ᵥ NR³²R³³R³⁴⁺Q⁻, —NR³²R³⁴⁺(CR³⁰R³¹)ᵥ NR³²R³³R³⁴⁺Q⁻₂, —(CR³⁰R³¹)ᵥ(T)⁺Q⁻, or —O(CR³⁰R³¹)ᵥNR³²R³³R³⁴⁺Q⁻;

or two Ys taken together with the atoms to which they are attached form an optionally substituted cycloalkyl or an optionally substituted heterocycloalkyl;

Z is hydrogen, R⁶¹, —(R⁶⁰)qOR⁶¹, —(R⁶⁰)qO(R⁶⁰)qOR⁶¹, —R⁶⁰OC(=O)R⁶¹, —R⁶⁰OC(=O)OR⁶¹, —R⁶⁰OC(=O)NHR⁶¹, —R⁶⁰OC(=O)N(R⁶¹)₂, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

T is pyridin-1-yl, pyrimidin-1-yl, or thiazol-3-yl;
Q is a pharmaceutically acceptable counterion;
n is 0-3;
m is 0-3;
p is 0-3;
each q is independently 2-6;
u1 is 1-3;
u2 is 1-3;
each v is independently 1-5; and
each w is independently 2-5.

In some embodiments of a compound of Formula (VIIa) or (VIIb), G is —NR⁸— or —CH₂NR⁸—. In some embodiments of a compound of Formula (VIIa) or (VIIb), G is —CH₂—. In some embodiments of a compound of Formula (VIIa) or (VIIb), G is —NR⁸—. In some embodiments of a compound of Formula (VIIa) or (VIIb), G is —CH₂NR⁸—. In some embodiments of a compound of Formula (VIIa) or (VIIb), R⁹ is hydrogen or optionally substituted alkyl. In some embodiments of a compound of Formula (VIIa) or (VIIb), R⁹ is optionally substituted alkyl. In some embodiments of a compound of Formula (VIIa) or (VIIb), R⁹ is methyl. In some embodiments of a compound of Formula (VIIa) or (VIIb), R⁹ is hydrogen. In some embodiments of a compound of Formula (VIIa) or (VIIb), and R⁹ are taken together with the atoms to which they are attached to form an optionally substituted heterocycloalkyl. In some embodiments of a compound of Formula (VIIa) or (VIIb), and R⁹ are taken together with the atoms to which they are attached to form an optionally substituted heterocycloalkyl selected from pyrrolidine and azetidine. In some embodiments of a compound of Formula (VIIa) or (VIIb), G is —NR⁸— and the heterocycloalkyl formed when R⁸ and R⁹ are taken together with the atoms to which they are attached is pyrrolidine. In some embodiments of a compound of Formula (VIIa) or (VIIb), G is —CH₂NR⁸— and the heterocycloalkyl formed when R⁸ and R⁹ are taken together with the atoms to which they are attached is azetidine.

In some embodiments the compound of Formula (VIIa) or (VIIb) is of Formula (VIIa-1) or (VIIb-1), or a pharmaceutically acceptable salt, solvate, stereoisomer, tautomer, N-oxide, dimer, or trimer thereof:

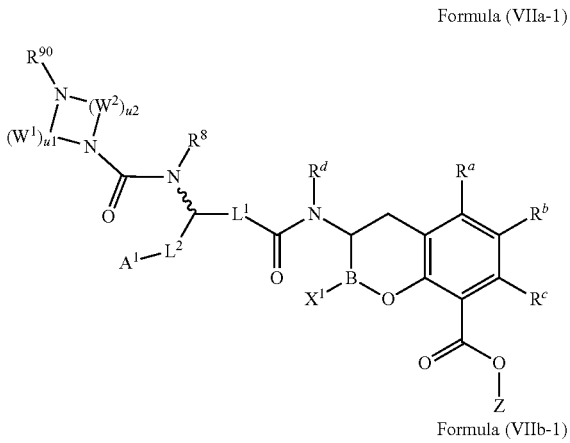

Formula (VIIa-1)

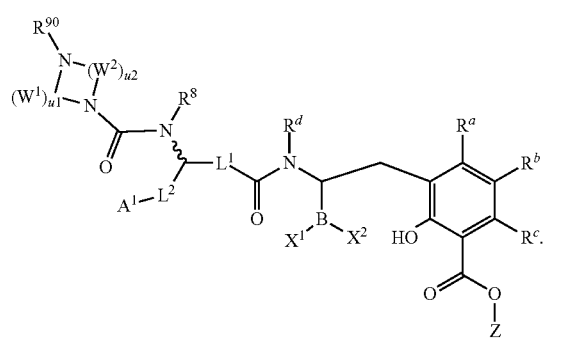

Formula (VIIb-1)

In some embodiments of a compound of Formula (VIIa), (VIIa-1), (VIIb), or (VIIb-1), u1 is 1. In some embodiments of a compound of Formula (VIIa), (VIIa-1), (VIIb), or (VIIb-1), u1 is 2. In some embodiments of a compound of Formula (VIIa), (VIIa-1), (VIIb), or (VIIb-1), u1 is 3. In some embodiments of a compound of Formula (VIIa), (VIIa-1), (VIIb), or (VIIb-1), u1 is 1. In some embodiments of a compound of Formula (VIIa), (VIIa-1), (VIIb), or (VIIb-1), u1 is 2. In some embodiments of a compound of Formula (VIIa), (VIIa-1), (VIIb), or (VIIb-1), u1 is 3. In some embodiments of a compound of Formula (VIIa), (VIIa-1), (VIIb), or (VIIb-1), u2 is 1. In some embodiments of a compound of Formula (VIIa), (VIIa-1), (VIIb), or (VIIb-1), u2 is 2. In some embodiments of a compound of Formula (VIIa), (VIIa-1), (VIIb), or (VIIb-1), u2 is 3. In some embodiments of a compound of Formula (VIIa), (VIIa-1), (VIIb), or (VIIb-1), u1 is 1 and u2 is 1. In some embodiments of a compound of Formula (VIIa), (VIIa-1), (VIIb), or (VIIb-1), u1 is 2 and u2 is 1. In some embodiments of a compound of Formula (VIIa), (VIIa-1), (VIIb), or (VIIb-1), u1 is 2 and u2 is 2. In some embodiments of a compound of Formula (VIIa), (VIIa-1), (VIIb), or (VIIb-1), u1 is 1 and u2 is 3. In some embodiments of a compound of Formula (VIIa), (VIIa-1), (VIIb), or (VIIb-1), u1 is 2 and u2 is 3. In some embodiments of a compound of Formula (VIIa), (VIIa-1), (VIIb), or (VIIb-1), u1 is 3 and u2 is 3.

In some embodiments of a compound of Formula (VIIa), (VIIa-1), (VIIb), or (VIIb-1), u1 is 2; each $W^1$ is —C($R^{91}$)$_2$—; u2 is 2; and each $W^2$ is —C(=O)—. In some embodiments of a compound of Formula (VIIa), (VIIa-1), (VIIb), or (VIIb-1), u1 is 2; each $W^1$ is —C($R^{91}$)$_2$—; u2 is 1; and $W^2$ is —C(=O)—. In some embodiments of a compound of Formula (VIIa), (VIIa-1), (VIIb), or (VIIb-1), u1 is 2; each $W^1$ is —C($R^{91}$)$_2$—; u2 is 2; and one $W^2$ is —C($R^{91}$)$_2$— and one $W^2$ is —C(=O)—. In some embodiments of a compound of Formula (VIIa), (VIIa-1), (VIIb), or (VIIb-1), u1 is 2; one $W^1$ is —C($R^{91}$)$_2$— and one $W^1$ is —C(=O)—; u2 is 2; and one $W^2$ is —C($R^{91}$)$_2$— and one $W^2$ is —C(=O)—.

In some embodiments of a compound of Formula (VIIa), (VIIa-1), (VIIb), or (VIIb-1), $R^{90}$ is hydrogen, optionally substituted alkyl, optionally substituted cycloalkyl, optionally substituted aralkyl, —S(=O)$_2$$R^{24}$, or —C(=O)$R^{24}$. In some embodiments of a compound of Formula (VIIa), (VIIa-1), (VIIb), or (VIIb-1), $R^{90}$ is optionally substituted alkyl. In some embodiments of a compound of Formula (VIIa), (VIIa-1), (VIIb), or (VIIb-1), $R^{90}$ is —H, —OH,

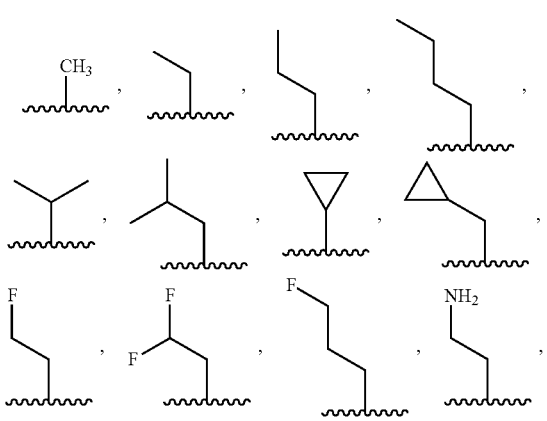

In some embodiments of a compound of Formula (VIIa), (VIIa-1), (VIIb), or (VIIb-1), $R^{90}$ is ethyl.

In some embodiments of a compound of Formula (VIIa), (VIIa-1), (VIIb), or (VIIb-1), each $R^{91}$ is independently hydrogen, halogen, or optionally substituted alkyl. In some embodiments of a compound of Formula (VIIa), (VIIa-1), (VIIb), or (VIIb-1), each $R^{91}$ is hydrogen.

In some embodiments of a compound of Formula (VIa), (VIIa), (VIIa-1), (VIb), (VIIb), or (VIIb-1), $A^1$ is

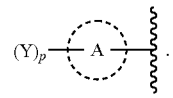

In some embodiments of a compound of Formula (VIa), (VIIa), (VIIa-1), (VIb), (VIIb), or (VIIb-1), $A^1$ is hydrogen. In some embodiments of a compound of Formula (VIa), (VIIa), (VIIa-1), (VIb), (VIIb), or (VIIb-1), $A^1$ is Y. In some embodiments of a compound of Formula (VIa), (VIIa), (VIIa-1), (VIb), (VIIb), or (VIIb-1), $A^1$ is halogen, alkyl, —OH, —O$R^{34}$, —O(C$R^{30}R^{31}$)$_w$OH, —O(C$R^{30}R^{31}$)$_w$O$R^{34}$, —O(C$R^{30}R^{31}$)$_w$N$R^{32}R^{33}$, —O(C$R^{30}R^{31}$)$_w$N$R^{32}$C(=O)$R^{34}$, —O(C$R^{30}R^{31}$)$_w$N$R^{32}$C(=O)O$R^{34}$, —O(C$R^{30}R^{31}$)$_w$N$R^{32}$C(=O)N$R^{32}R^{33}$, —O(C$R^{30}R^{31}$)$_v$C(=O)N$R^{32}R^{33}$, —O(C$R^{30}R^{31}$)$_v$C(=N$R^{36}$)N$R^{32}R^{33}$, —O(C$R^{30}R^{31}$)$_w$N($R^{32}$)C(=N$R^{36}$)$R^{34}$, —O(C$R^{30}R^{31}$)$_v$C(=N$R^{36}$)N$R^{32}$C(=N$R^{36}$)N$R^{32}R^{33}$, —O(C$R^{30}R^{31}$)$_w$N($R^{32}$)C(=N$R^{36}$)N$R^{32}R^{33}$, —N$R^{32}$(C$R^{30}R^{31}$)$_w$N$R^{32}R^{33}$, —N$R^{32}$(C$R^{30}R^{31}$)$_w$OH, —N$R^{32}$(C$R^{30}R^{31}$)$_w$O$R^{34}$, —N$R^{32}$C(=O)$R^{34}$, —N$R^{32}$C(=O)O$R^{34}$, —N($R^{32}$)C(=O)(C$R^{30}R^{31}$)$_w$N$R^{32}R^{33}$, —N$R^{32}$C(=O)N$R^{32}R^{33}$, —N$R^{32}$C(=O)N$R^{32}$(C$R^{30}R^{31}$)$_w$N$R^{32}R^{33}$, —N$R^{32}$C(=N$R^{36}$)N$R^{32}R^{33}$, —N($R^{32}$)C(=N$R^{36}$)$R^{34}$, —N$R^{32}$(C$R^{30}R^{31}$)$_w$N($R^{32}$)C(=N$R^{36}$)$R^{34}$, —N$R^{32}$(C$R^{30}R^{31}$)$_v$C(=N$R^{36}$)N$R^{32}R^{33}$, —N$R^{32}$(C$R^{30}R^{31}$)$_w$N($R^{32}$)C(=N$R^{36}$)N$R^{32}R^{33}$, —N$R^{32}$(C$R^{30}R^{31}$)$_w$N$R^{32}$C(=O)N$R^{32}R^{33}$, —N$R^{32}$(C$R^{30}R^{31}$)$_w$N$R^{32}$C(=O)O$R^{34}$, —N$R^{32}$(C$R^{30}R^{31}$)$_v$CO$_2$H, —N$R^{32}$(C$R^{30}R^{31}$)$_v$CO$_2R^{34}$, —N$R^{32}$(C$R^{30}R^{31}$)$_v$C(=O)N$R^{32}R^{33}$, —N($R^{32}$)-heteroaryl-N$R^{32}R^{33}$, —N($R^{32}$)-heterocycloalkyl-N$R^{32}R^{33}$, —N$R^{32}$(C$R^{30}R^{31}$)$_v$heteroaryl, —N$R^{32}$(C$R^{30}R^{31}$)$_v$heterocycloalkyl, —CN, —(C$R^{30}R^{31}$)$_v$CN, —(C$R^{30}R^{31}$)$_v$N$R^{32}R^{33}$, —C(=O)OH, —C(=O)O$R^{34}$, —C(=O)N$R^{32}R^{33}$, —C(=O)N$R^{32}$(C$R^{30}R^{31}$)$_w$N$R^{32}R^{33}$, —C(=O)N$R^{32}$(C$R^{30}R^{31}$)$_w$OH, —C(=O)N$R^{32}$(C$R^{30}R^{31}$)$_w$O$R^{34}$, —C(=N$R^{36}$)N$R^{32}R^{33}$, —C(=N$R^{36}$)N$R^{32}$C(=O)$R^{34}$, or S$R^{35}$.

In some embodiments of a compound of Formula (VIa), (VIIa), (VIIa-1), (VIb), (VIIb), or (VIIb-1), $A^1$ is halogen, alkyl, —OH, —O$R^{34}$, —N$R^{32}R^{33}$, —N$R^{32}$(C$R^{30}R^{31}$)$_w$N$R^{32}R^{33}$, —N$R^{32}$(C$R^{30}R^{31}$)$_w$OH, —N$R^{32}$(C$R^{30}R^{31}$)$_w$O$R^{34}$, —N$R^{32}$C(=O)$R^{34}$, —N$R^{32}$C(=O)O$R^{34}$, —N($R^{32}$)C(=O)(C$R^{30}R^{31}$)$_w$N$R^{32}R^{33}$, —N$R^{32}$C(=O)N$R^{32}R^{33}$, —N$R^{32}$C(=O)N$R^{32}$(C$R^{30}R^{31}$)$_w$N$R^{32}R^{33}$, —N$R^{32}$C (=NR$^{36}$)NR$^{32}$R$^{33}$, —N(R$^{32}$)C(=NR$^{36}$)R$^{34}$, —NR$^{32}$(CR$^{30}$R$^{31}$)$_w$N(R$^{32}$)C(=NR$^{36}$)R$^{34}$, —NR$^{32}$(CR$^{30}$R$^{31}$)$_v$C(=NR$^{36}$)NR$^{32}$R$^{33}$, —NR$^{32}$(CR$^{30}$R$^{31}$)$_w$N(R$^{32}$)C(=NR$^{36}$)NR$^{32}$R$^{33}$, —NR$^{32}$(CR$^{30}$R$^{31}$)$_w$NR$^{32}$C(=O)NR$^{32}$R$^{33}$, —NR$^{32}$(CR$^{30}$R$^{31}$)$_w$NR$^{32}$C(=O)OR$^{34}$, —NR$^{32}$(CR$^{30}$R$^{31}$)$_v$CO$_2$H, —NR$^{32}$(CR$^{30}$R$^{31}$)$_v$CO$_2$R$^{34}$, —NR$^{32}$(CR$^{30}$R$^{31}$)$_v$C(=O)NR$^{32}$R$^{33}$, —NR$^{32}$(CR$^{30}$R$^{31}$)$_v$heteroaryl, —NR$^{32}$(CR$^{30}$R$^{31}$)$_v$heterocycloalkyl, —C(=O)OH, —C(=O)OR$^{34}$, —C(=O)NR$^{32}$R$^{33}$, —C(=O)NR$^{32}$(CR$^{30}$R$^{31}$)$_w$NR$^{32}$R$^{33}$, —C(=O)NR$^{32}$(CR$^{30}$R$^{31}$)$_w$OH, —C(=O)NR$^{32}$(CR$^{30}$R$^{31}$)$_w$OR$^{34}$, —C(=NR$^{36}$)NR$^{32}$R$^{33}$, —C(=NR$^{36}$)NR$^{32}$C(=O)R$^{34}$, or SR$^{35}$.

In some embodiments of a compound of Formula (VIa), (VIIa), (VIIa-1), (VIb), (VIIb), or (VIIb-1), A$^1$ is hydrogen, halogen, —NR$^{32}$R$^{33}$, —OH, —OR$^{34}$, —NR$^{32}$(CR$^{30}$R$^{31}$)$_w$NR$^{32}$R$^{33}$, —NR$^{32}$C(=NR$^{36}$)NR$^{32}$R$^{33}$, —SR$^{35}$, —NR$^{32}$(CR$^{31}$R$^{31}$)$_v$CO$_2$H, —NR$^{32}$(CR$^{30}$R$^{31}$)$_v$C(=O)NR$^{32}$R$^{33}$, —C(=O)OH, —C(=O)OR$^{34}$, or —C(=O)NR$^{32}$R$^{33}$.

In some embodiments of a compound of Formula (VIa), (VIIa), (VIIa-1), (VIb), (VIIb), or (VIIb-1), A$^1$ is —NR$^{32}$R$^{33}$, —OH, —NR$^{32}$C(=NR$^{36}$)NR$^{32}$R$^{33}$, —C(=O)OH, or —C(=O)NR$^{32}$R$^{33}$. In some embodiments of a compound of Formula (VIa), (VIIa), (VIIa-1), (VIb), (VIIb), or (VIIb-1), A$^1$ is hydrogen, —NR$^{32}$R$^{33}$, —OH, —NR$^{32}$C(=NR$^{36}$)NR$^{32}$R$^{33}$, —C(=O)OH, or —C(=O)NR$^{32}$R$^{33}$. In some embodiments of a compound of Formula (VIa), (VIIa), (VIIa-1), (VIb), (VIIb), or (VIIb-1), A$^1$ is hydrogen, —NR$^{32}$R$^{33}$, —OH, —C(=O)OH, or —C(=O)NR$^{32}$R$^{33}$.

In some embodiments of a compound of Formula (Ia), (Va)-(VIIa), (VIIa-1), (Ib), (Vb)-(VIIb), or (VIIb-1), Ring A is cyclopropane, cyclobutane, cyclopentane, cyclohexane, cycloheptane, cyclooctane, cyclopentene, cyclohexene, cycloheptene, and cyclooctene, wherein the olefin functionality of the cyclopentene, cyclohexene, cycloheptene, and cyclooctene is not directly attached to an oxygen, sulfur, or nitrogen substituent. In some embodiments of a compound of Formula (Ia), (Va)-(VIIa), (VIIa-1), (Ib), (Vb)-(VIIb), or (VIIb-1), Ring A is cyclopropane, cyclobutane, cyclopentane, or cyclohexane.

In some embodiments of a compound of Formula (Ia), (Va)-(VIIa), (VIIa-1), (Ib), (Vb)-(VIIb), or (VIIb-1), Ring A is azetidine, aziridine, oxirane, oxetane, thietane, pyrrolidine, oxazolidine, isoxazolidine, thiazolidine, isothiazolidine, imidazolidine, pyrazolidine, 2,5-dihydro-1H-pyrrole, 3,4-dihydro-2H-pyrrole, 4,5-dihydrooxazole, 4,5-dihydroisoxazole, 4,5-dihydrothiazole, 4,5-dihydroisothiazole, 4,5-dihydro-1H-pyrazole, 4,5-dihydro-1H-imidazole, 2,5-dihydro-1H-pyrrole, piperidine, morpholine, thiomorpholine, tetrahydrothiopyran, tetrahydropyran, tetrahydrofuran, 1,4-oxathiane, piperazine, hexahydropyrimidine, hexahydropyridazine, 1,4,5,6-tetrahydropyrimidine, 1,3-oxazinane, 5,6-dihydro-4H-1,3-oxazine, 1,3-thiazinane, 5,6-dihydro-4H-1,3-thiazine, 1,4,5,6-tetrahydropyridazine, 1,2,3,6-tetrahydropyrazine, 1,2,3,6-tetrahydropyridine, 1,2,3,6-tetrahydropyridazine, azepane, 1,3-oxazepane, 1,4-oxazepane, 1,3-diazepane, 1,4-diazepane, 1,3-thiazepane, 1,4-thiazepane, diazepane, oxazepane, thiazepane, 3,4,5,6-tetrahydro-2H-azepine, 4,5,6,7-tetrahydro-1H-1,3-diazepine, 4,5,6,7-tetrahydro-1,3-oxazepine, 4,5,6,7-tetrahydro-1,3-thiazepine, 2,3,4,7-tetrahydro-H-1,3-diazepine, or 2,3,4,7-tetrahydro-1,3-oxazepine. In some embodiments of a compound of Formula (Ia), (Va)-(VIIa), (VIIa-1), (Ib), (Vb)-(VIIb), or (VIIb-1), Ring A is pyrrolidine, piperidine, morpholine, or piperazine. In some embodiments of a compound of Formula (Ia), (Va)-(VIIa), (VIIa-1), (Ib), (Vb)-(VIIb), or (VIIb-1), Ring A is a 5-membered heterocycloalkyl bearing at least one nitrogen atom. In some embodiments of a compound of Formula (Ia), (Va)-(VIIa), (VIIa-1), (Ib), (Vb)-(VIIb), or (VIIb-1), Ring A is a 5-membered heterocycloalkyl bearing at least one oxygen atom. In some embodiments of a compound of Formula (Ia), (Va)-(VIIa), (VIIa-1), (Ib), (Vb)-(VIIb), or (VIIb-1), Ring A is a 5-membered heterocycloalkyl bearing at least one oxygen atom and one nitrogen atom.

In some embodiments of a compound of Formula (Ia), (Va)-(VIIa), (VIIa-1), (Ib), (Vb)-(VIIb), or (VIIb-1), Ring A is benzene, naphthalene, pyridine, pyrimidine, pyrazine, pyridazine, triazine, thiophene, furan, pyrrole, pyrazole, triazole, tetrazole, imidazole, thiazole, isothiazole, oxazole, isoxazole, indole, thiadiazole, oxadiazole, indazole, azaindole, azaindoline, indolizine, imidazopyridine, pyrazolopyridine, thiazolo-pyridine, pyrrolo-pyrimidine, thienopyrazole, benzimidazole, benzothiazole, benzoxazole, benzofuran, benzisoxazole, benzisothiazole, quinoline, isoquinoline, quinoxaline, quinazoline, cinnoline, benzotriazine, napthyridine, pyrido-pyrimidine, pyrido-pyrazine, pyridopyridazine, isoxazolo-pyridine, or oxazolo-pyridine. In some embodiments of a compound of Formula (Ia), (Va)-(VIIa), (VIIa-1), (Ib), (Vb)-(VIIb), or (VIIb-1), Ring A is benzene, pyridine, thiazole, triazole, tetrazole, oxadiazole, or thiadiazole. In some embodiments of a compound of Formula (Ia), (Va)-(VIIa), (VIIa-1), (Ib), (Vb)-(VIIb), or (VIIb-1), Ring A is benzene, pyridine, thiazole, triazole, tetrazole, imidazole, oxadiazole, or thiadiazole. In some embodiments of a compound of Formula (Ia), (Va)-(VIIa), (VIIa-1), (Ib), (Vb)-(VIIb), or (VIIb-1), Ring A is thiazole. In some embodiments of a compound of Formula (Ia), (Va)-(VIIa), (VIIa-1), (Ib), (Vb)-(VIIb), or (VIIb-1), Ring A is not benzene.

In some embodiments of a compound of Formula (Ia), (Va)-(VIIa), (VIIa-1), (Ib), (Vb)-(VIIb), or (VIIb-1), Ring A is a 5-membered heteroaryl bearing at least two nitrogen atoms. In some embodiments of a compound of Formula (Ia), (Va)-(VIIa), (VIIa-1), (Ib), (Vb)-(VIIb), or (VIIb-1), Ring A is a 5-membered heteroaryl bearing at least three nitrogen atoms. In some embodiments of a compound of Formula (Ia), (Va)-(VIIa), (VIIa-1), (Ib), (Vb)-(VIIb), or (VIIb-1), Ring A is a 5-membered heteroaryl bearing four nitrogen atoms. In some embodiments of a compound of Formula (Ia), (Va)-(VIIa), (VIIa-1), (Ib), (Vb)-(VIIb), or (VIIb-1), Ring A is a 5-membered heteroaryl bearing only nitrogen atoms as heteroatoms. In some embodiments of a compound of Formula (Ia), (Va)-(VIIa), (VIIa-1), (Ib), (Vb)-(VIIb), or (VIIb-1), Ring A is a 5-membered heteroaryl bearing at least one oxygen atom. In some embodiments of a compound of Formula (Ia), (Va)-(VIIa), (VIIa-1), (Ib), (Vb)-(VIIb), or (VIIb-1), Ring A is a 5-membered heteroaryl bearing at least one sulfur atom.

In some embodiments of a compound of Formula (Ia), (Va)-(VIIa), (VIIa-1), (Ib), (Vb)-(VIIb), or (VIIb-1), is:

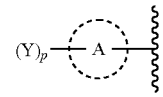

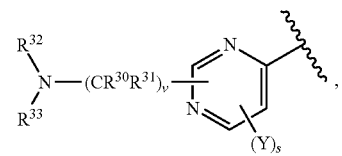

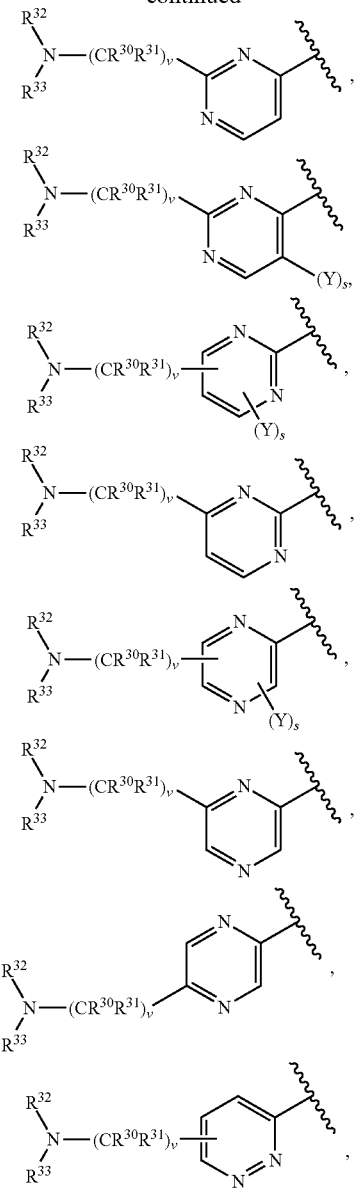
wherein s is 0-2.
In some embodiments of a compound of Formula (Ia), (Va)-(VIIa), (VIIa-1), (Ib), (Vb)-(VIIb), or (VIIb-1),
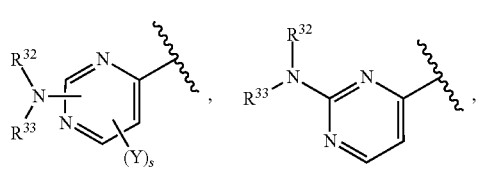
is:
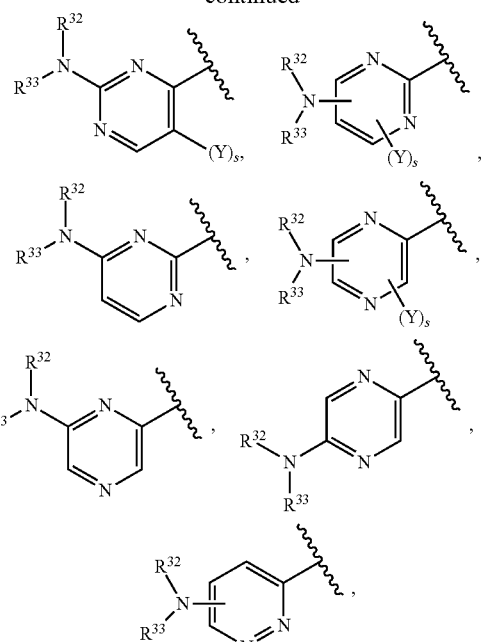
wherein s is 0-2.
In some embodiments of a compound of Formula (Ia), (Va)-(VIIa), (VIIa-1), (Ib), (Vb)-(VIIb), or (VIIb-1),
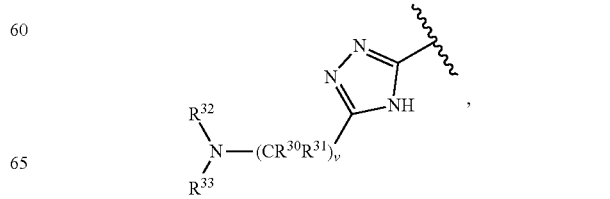
is:
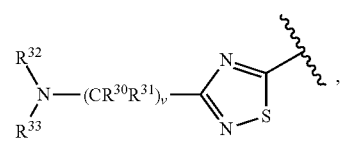
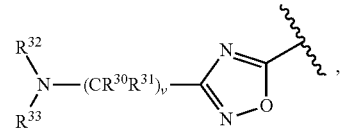
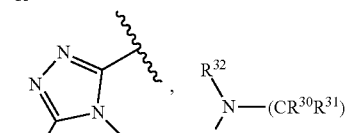
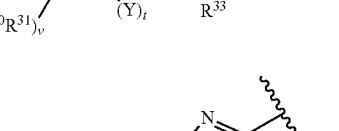
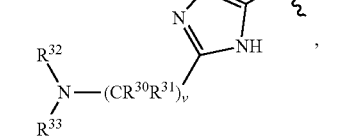

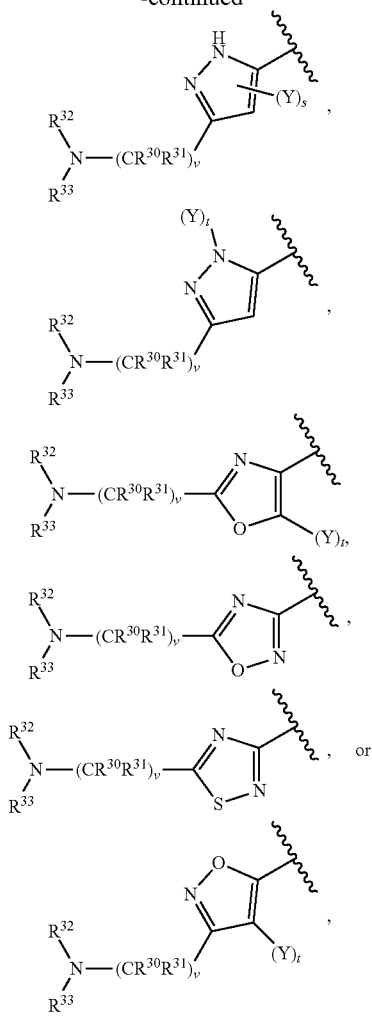
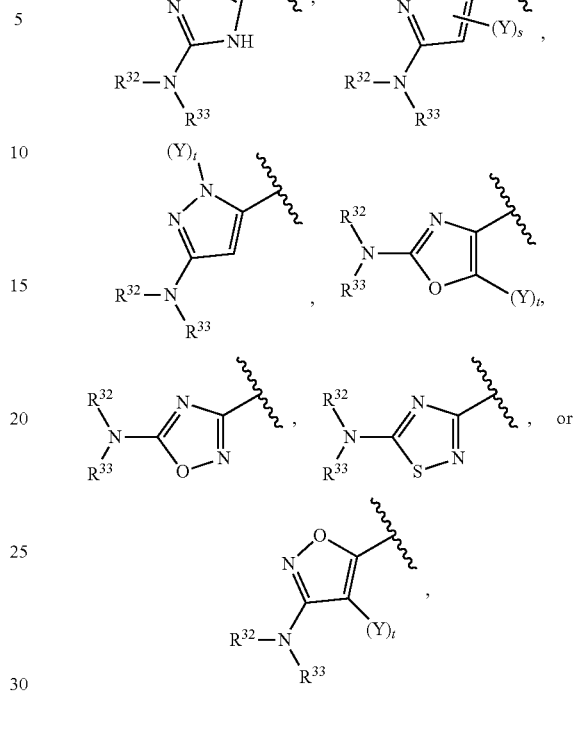
wherein s is 0-2 and t is 0-1.
In some embodiments of a compound of Formula (Ia), (Va)-(VIIa), (VIIa-1), (Ib), (Vb)-(VIIb), or (VIIb-1),
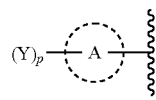
is:
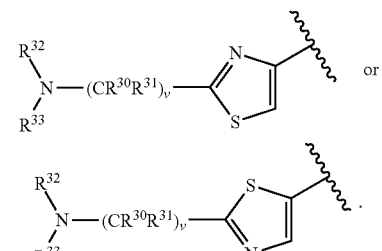
In some embodiments of a compound of Formula (Ia), (Va)-(VIIa), (VIIa-1), (Ib), (Vb)-(VIIb), or (VIIb-1),
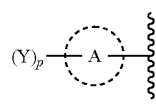
wherein s is 0-2 and t is 0-1.
In some embodiments of a compound of Formula (Ia), (Va)-(VIIa), (VIIa-1), (Ib), (Vb)-(VIIb), or (VIIb-1),
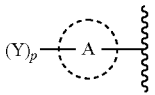
is:
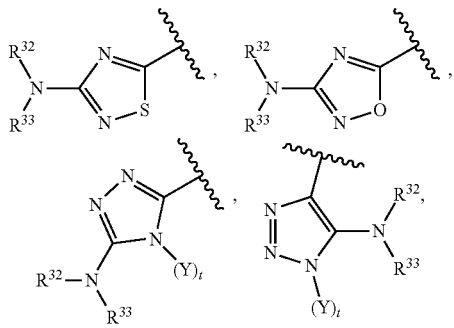

is:

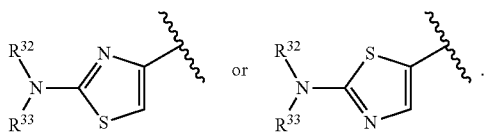

In some embodiments of a compound of Formula (Ia), (Va)-(VIIa), (VIIa-1), (Ib), (Vb)-(VIIb), or (VIIb-1),

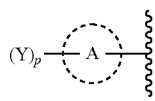

is:

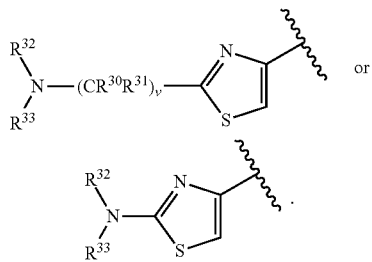

In some embodiments of a compound of Formula (Ia), (Va)-(VIIa), (VIIa-1), (Ib), (Vb)-(VIIb), or (VIIb-1), $R^a$, $R^b$, and $R^c$ are independently hydrogen, optionally substituted alkyl, fluoro, chloro, —OH, —OR$^{54}$, —C(=O)H, —C(=O)OH, —(CR$^{50}$R$^{51}$)$_v$N(R$^{52}$)(CR$^{50}$R$^{51}$)$_v$C(=O)OH, —(CR$^{50}$R$^{51}$)OH, —(CR$^{50}$R$^{51}$)$_v$C(=O)OH, —(CR$^{50}$R$^{51}$)$_v$C(=O)OR$^{54}$, or —(CR$^{50}$R$^{51}$)$_v$heterocycloalkyl. In some embodiments of a compound of Formula (Ia), (Va)-(VIIa), (VIIa-1), (Ib), (Vb)-(VIIb), or (VIIb-1), $R^a$, $R^b$, and $R^c$ are independently hydrogen, fluoro, chloro, optionally substituted alkyl, —(CR$^{50}$R$^{51}$)$_v$C(=O)OH, or —(CR$^{50}$R$^{51}$)$_v$heterocycloalkyl. In some embodiments of a compound of Formula (Ia), (Va)-(VIIa), (VIIa-1), (Ib), (Vb)-(VIIb), or (VIIb-1), $R^a$, $R^b$, and $R^c$ are hydrogen.

In some embodiments of a compound of Formula (Ia), (Va)-(VIIa), (VIIa-1), (Ib), (Vb)-(VIIb), or (VIIb-1), at least one of $R^a$, $R^b$, and $R^c$ is halogen, cyano, optionally substituted alkyl, optionally substituted cycloalkyl, optionally substituted heterocycloalkyl, optionally substituted aryl, optionally substituted heteroaryl, —OH, —OR$^{54}$, —O(CR$^{50}$R$^{51}$)$_w$NR$^{52}$R$^{53}$, —O(CR$^{50}$R$^{51}$)$_w$OH, —O(CR$^{50}$R$^{51}$)$_w$OR$^{54}$, —O(CR$^{50}$R$^{51}$)C(=O)OH, —O(CR$^{50}$R$^{51}$)C(=O)OR$^{54}$, —O(CR$^{50}$R$^{51}$)$_v$C(=O)NR$^{52}$R$^{53}$, —NR$^{52}$R$^{53}$, —NR$^{52}$(CR$^{50}$R$^{51}$)$_w$NR$^{52}$R$^{53}$, —NR$^{52}$(CR$^{50}$R$^{51}$)$_v$C(=O)OH, —NR$^{52}$(CR$^{50}$R$^{51}$)$_v$C(=O)OR$^{54}$, —NR$^{52}$(CR$^{50}$R$^{51}$)$_v$C(=O)NR$^{52}$R$^{53}$, —NR$^{52}$S(=O)$_{1,2}$R$^{54}$, —S(=O)$_{1,2}$R$^{54}$, —SR$^{55}$, —S(CR$^{50}$R$^{51}$)$_v$NR$^{52}$C(=NR$^{56}$)NR$^{52}$R$^{53}$, —S(CR$^{50}$R$^{51}$)NR$^{52}$CR$^{50}$(=NR$^{56}$), —S(CR$^{50}$R$^{51}$)$_v$C(=NR$^{56}$)NR$^{52}$R$^{53}$, —S(CR$^{50}$R$^{51}$)$_w$OH, —S(CR$^{50}$R$^{51}$)$_w$OR$^{54}$, —S(CR$^{50}$R$^{51}$)$_w$NR$^{52}$R$^{53}$, —S(CR$^{50}$R$^{51}$)$_v$C(=O)OH, —S(CR$^{50}$R$^{51}$)C(=O)OR$^{54}$, —S(CR$^{50}$R$^{51}$)C(=O)NR$^{52}$R$^{53}$, —C(=O)H, —C(=O)R$^{54}$, —C(=O)OH, —C(=O)OR$^{54}$, —C(=O) NR$^{52}$R$^{53}$, —(CR$^{50}$R$^{51}$)$_v$N(R$^{52}$)(CR$^{50}$R$^{51}$)$_v$C(=O)OH, —(CR$^{50}$R$^{51}$)$_v$OH, —(CR$^{50}$R$^{51}$)$_v$OR$^{54}$, —(CR$^{50}$R$^{51}$)$_v$C(=O)OH, —(CR$^{50}$R$^{51}$)$_v$C(=O)OR$^{54}$, —(CR$^{50}$R$^{51}$)$_v$C(=O)NR$^{52}$R$^{53}$, —(CR$^{50}$R$^{51}$)$_v$OC(=O)R$^{54}$, —(CR$^{50}$R$^{51}$)$_v$SR$^{55}$, —(CR$^{50}$R$^{51}$)$_v$NR$^{52}$C(=NR$^{56}$), —(CR$^{50}$R$^{51}$)$_v$NR$^{52}$R$^{53}$, —(CR$^{50}$R$^{51}$)$_v$C(=NR$^{56}$)NR$^{52}$R$^{53}$, —(CR$^{50}$R$^{51}$)$_v$C(=O)NR$^{52}$R$^{53}$, —(CR$^{50}$R$^{51}$)$_v$heterocycloalkyl, or —(CR$^{50}$R$^{51}$)$_v$heteroaryl.

In some embodiments of a compound of Formula (Ia), (Va)-(VIIa), (VIIa-1), (Ib), (Vb)-(VIIb), or (VIIb-1), at least one of $R^a$, $R^b$, or $R^c$ is optionally substituted alkyl, fluoro, chloro, —OH, —OR$^{54}$, —C(=O)H, —C(=O)OH, —(CR$^{50}$R$^{51}$)$_v$N(R$^{52}$)(CR$^{50}$R$^{51}$)$_v$C(=O)OH, —(CR$^{50}$R$^{51}$)OH, —(CR$^{50}$R$^{51}$)$_v$C(=O)OH, or —(CR$^{50}$R$^{51}$)$_v$C(=O)OR$^{54}$, or —(CR$^{50}$R$^{51}$)$_v$heterocycloalkyl. In some embodiments of a compound of Formula (Ia), (Va)-(VIIa), (VIIa-1), (Ib), (Vb)-(VIIb), or (VIIb-1), at least one of $R^a$, $R^b$, or $R^c$ is alkyl optionally substituted with heterocycloalkyl (optionally substituted with optionally substituted alkyl). In some embodiments of a compound of Formula (Ia), (Va)-(VIIa), (VIIa-1), (Ib), (Vb)-(VIIb), or (VIIb-1), at least one of $R^a$, $R^b$, or $R^c$ is —(CR$^{50}$R$^{51}$)$_v$heterocycloalkyl optionally substituted with optionally substituted alkyl.

In some embodiments of a compound of Formula (Ia), (Va)-(VIIa), (VIIa-1), (Ib), (Vb)-(VIIb), or (VIIb-1), $R^a$, $R^b$, or $R^c$ are defined as above, $R^{50}$ and $R^{51}$ are independently hydrogen or optionally substituted alkyl; or two $R^{50}$ on adjacent carbon form an alkenyl; $R^{52}$ and $R^{53}$ are independently hydrogen or optionally substituted alkyl; or $R^{52}$ and $R^{53}$ are taken together with the nitrogen to which they are attached to form an optionally substituted heterocycloalkyl; $R^{54}$ is optionally substituted alkyl; $R^{55}$ is hydrogen or optionally substituted alkyl; $R^{56}$ is hydrogen or optionally substituted alkyl; each v is independently 1 or 2; and each w is independently 2 or 3.

In some embodiments of a compound of Formula (Ia), (Va)-(VIIa), (VIIa-1), (Ib), (Vb)-(VIIb), or (VIIb-1), $R^a$ is hydrogen. In some embodiments of a compound of Formula (Ia), (Va)-(VIIa), (VIIa-1), (Ib), (Vb)-(VIIb), or (VIIb-1), $R^b$ is hydrogen. In some embodiments of a compound of Formula (Ia), (Va)-(VIIa), (VIIa-1), (Ib), (Vb)-(VIIb), or (VIIb-1), $R^c$ is hydrogen. In some embodiments of a compound of Formula (Ia), (Va)-(VIIa), (VIIa-1), (Ib), (Vb)-(VIIb), or (VIIb-1), $R^a$ is not hydrogen. In some embodiments of a compound of Formula (Ia), (Va)-(VIIa), (VIIa-1), (Ib), (Vb)-(VIIb), or (VIIb-1), $R^b$ is not hydrogen. In some embodiments of a compound of Formula (Ia), (Va)-(VIIa), (VIIa-1), (Ib), (Vb)-(VIIb), or (VIIb-1), R is not hydrogen. In some embodiments of a compound of Formula (Ia), (Va)-(VIIa), (VIIa-1), (Ib), (Vb)-(VIIb), or (VIIb-1), $R^a$ and $R^b$ are hydrogen. In some embodiments of a compound of Formula (Ia), (Va)-(VIIa), (VIIa-1), (Ib), (Vb)-(VIIb), or (VIIb-1), $R^a$ and $R^c$ are hydrogen. In some embodiments of a compound of Formula (Ia), (Va)-(VIIa), (VIIa-1), (Ib), (Vb)-(VIIb), or (VIIb-1), $R^b$ and $R^c$ are hydrogen.

In some embodiments of a compound of Formula (Ia), (Va)-(VIIa), (VIIa-1), (Ib), (Vb)-(VIIb), or (VIIb-1), $X^1$ is —OH and $X^2$ is —OH when present. In some embodiments of a compound of Formula (Ia), (Va)-(VIIa), (VIIa-1), (Ib), (Vb)-(VIIb), or (VIIb-1), $X^1$ and $X^2$ are taken together with the boron atom to which they are attached to form a cyclic boronate ester.

In some embodiments of a compound of Formula (Ia), (Va)-(VIIa), (VIIa-1), (Ib), (Vb)-(VIIb), or (VIIb-1), $R^d$ is hydrogen or alkyl. In some embodiments of a compound of Formula (Ia), (Va)-(VIIa), (VIIa-1), (Ib), (Vb)-(VIIb), or (VIIb-1), $R^d$ is hydrogen. In some embodiments of a compound of Formula (Ia), (Va)-(VIIa), (VIIa-1), (Ib), (Vb)-(VIIb), or (VIIb-1), $R^d$ is alkyl.

In some embodiments of a compound of Formula (Ia), (Va)-(VIIa), (VIIa-1), (Ib), (Vb)-(VIIb), or (VIIb-1), n is 0. In some embodiments of a compound of Formula (Ia), (Va)-(VIIa), (VIIa-1), (Ib), (Vb)-(VIIb), or (VIIb-1), n is 1. In some embodiments of a compound of Formula (Ia), (Va)-(VIIa), (VIIa-1), (Ib), (Vb)-(VIIb), or (VIIb-1), n is 2. In some embodiments of a compound of Formula (Ia), (Va)-(VIIa), (VIIa-1), (Ib), (Vb)-(VIIb), or (VIIb-1), n is 3. In some embodiments of a compound of Formula (Ia), (Va)-(VIIa), (VIIa-1), (Ib), (Vb)-(VIIb), or (VIIb-1), m is 0. In some embodiments of a compound of Formula (Ia), (Va)-(VIIa), (VIIa-1), (Ib), (Vb)-(VIIb), or (VIIb-1), m is 1. In some embodiments of a compound of Formula (Ia), (Va)-(VIIa), (VIIa-1), (Ib), (Vb)-(VIIb), or (VIIb-1), m is 2. In some embodiments of a compound of Formula (Ia), (Va)-(VIIa), (VIIa-1), (Ib), (Vb)-(VIIb), or (VIIb-1), m is 3. In some embodiments of a compound of Formula (Ia), (Va)-(VIIa), (VIIa-1), (Ib), (Vb)-(VIIb), or (VIIb-1), n is 0 or 1 and m is 0 or 1. In some embodiments of a compound of Formula (Ia), (Va)-(VIIa), (VIIa-1), (Ib), (Vb)-(VIIb), or (VIIb-1), n is 0 and m is 0. In some embodiments of a compound of Formula (Ia), (Va)-(VIIa), (VIIa-1), (Ib), (Vb)-(VIIb), or (VIIb-1), n is 0 and m is 1. In some embodiments of a compound of Formula (Ia), (Va)-(VIIa), (VIIa-1), (Ib), (Vb)-(VIIb), or (VIIb-1), n is 1 and m is 0. In some embodiments of a compound of Formula (Ia), (Va)-(VIIa), (VIIa-1), (Ib), (Vb)-(VIIb), or (VIIb-1), n is 2 and m is 0. In some embodiments of a compound of Formula (Ia), (Va)-(VIIa), (VIIa-1), (Ib), (Vb)-(VIIb), or (VIIb-1), n is 0 and m is 2.

In some embodiments of a compound of Formula (Ia), (Va)-(VIIa), (VIIa-1), (Ib), (Vb)-(VIIb), or (VIIb-1), each $R^1$ and $R^2$ are independently hydrogen, —OH, fluoro, chloro, bromo, or optionally substituted alkyl.

In some embodiments of a compound of Formula (Ia), (Va)-(VIIa), (VIIa-1), (Ib), (Vb)-(VIIb), or (VIIb-1), each $R^1$ and $R^2$ are independently hydrogen, fluoro, chloro, bromo, or optionally substituted alkyl. In some embodiments of a compound of Formula (Ia), (Va)-(VIIa), (VIIa-1), (Ib), (Vb)-(VIIb), or (VIIb-1), each $R^1$ and $R^2$ are hydrogen.

In some embodiments of a compound of Formula (Ia), (Va)-(VIIa), (VIIa-1), (Ib), (Vb)-(VIIb), or (VIIb-1), Z is hydrogen. In some embodiments of a compound of Formula (Ia), (Va)-(VIIa), (VIIa-1), (Ib), (Vb)-(VIIb), or (VIIb-1), Z is $R^{61}$; and $R^{61}$ is optionally substituted alkyl. In some embodiments of a compound of Formula (Ia), (Va)-(VIIa), (VIIa-1), (Ib), (Vb)-(VIIb), or (VIIb-1), Z is —$R^{60}$OC(=O)$R^{61}$ or —$R^{60}$OC(=O)O$R^{61}$; $R^{60}$ is —CH$_2$— or —CH(CH$_3$)—; and $R^{61}$ is optionally substituted alkyl, optionally substituted cycloalkyl, or optionally substituted heterocycloalkyl.

In some embodiments of a compound of Formula (Ia), (Va)-(VIIa), (VIIa-1), (Ib), (Vb)-(VIIb), or (VIIb-1), at least one Y is halogen, alkyl, optionally substituted heteroaryl, —OH, —OR$^{34}$, —O(CR$^{30}$R$^{31}$)$_w$OH, —O(CR$^{30}$R$^{31}$)$_w$OR$^{34}$, —O(CR$^{30}$R$^{31}$)$_w$NR$^{32}$R$^{33}$, —O(CR$^{30}$R$^{31}$)$_w$NR$^{32}$C(=O)R$^{34}$, —O(CR$^{30}$R$^{31}$)$_w$NR$^{32}$C(=O)OR$^{34}$, —O(CR$^{30}$R$^{31}$)$_w$NR$^{32}$C(=O)NR$^{32}$R$^{33}$, —O(CR$^{30}$R$^{31}$)$_w$C(=O)NR$^{32}$R$^{33}$, —O(CR$^{30}$R$^{31}$)$_v$C(=NR$^{36}$)NR$^{32}$R$^{33}$, —O(CR$^{30}$R$^{31}$)$_w$N(R$^{32}$)C(=NR$^{36}$)R$^{34}$, —O(CR$^{30}$R$^{31}$)$_v$C(=NR$^{36}$)NR$^{32}$C(=NR$^{36}$)NR$^{32}$R$^{33}$, —O(CR$^{30}$R$^{31}$)$_w$N(R$^{32}$)C(=NR$^{36}$)NR$^{32}$R$^{33}$, —NR$^{32}$R$^{33}$, —NR$^{32}$(CR$^{30}$R$^{31}$)$_w$NR$^{32}$R$^{33}$, —NR$^{32}$(CR$^{30}$R$^{31}$)$_w$OH, —NR$^{32}$(CR$^{30}$R$^{31}$)$_w$OR$^{34}$, —NR$^{32}$C(=O)R$^{34}$, —NR$^{32}$C(=O)OR$^{34}$, —N(R$^{32}$)C(=O)(CR$^{30}$R$^{31}$)$_v$NR$^{32}$R$^{33}$, —NR$^{32}$C(=O)NR$^{32}$R$^{33}$, —NR$^{32}$C (=O)NR$^{32}$(CR$^{30}$R$^{31}$)$_w$NR$^{32}$R$^{33}$, —NR$^{32}$C(=NR$^{36}$)NR$^{32}$R$^{33}$, —N(R$^{32}$)C(=NR$^{36}$)R$^{34}$, —NR$^{32}$(CR$^{30}$R$^{31}$)$_w$N(R$^{32}$)C(=NR$^{36}$)R$^{34}$, —NR$^{32}$(CR$^{30}$R$^{31}$)$_v$C(=NR$^{36}$)NR$^{32}$R$^{33}$, —NR$^{32}$(CR$^{30}$R$^{31}$)$_w$N(R$^{32}$)C(=NR$^{36}$)NR$^{32}$R$^{33}$, —NR$^{32}$(CR$^{30}$R$^{31}$)$_w$NR$^{32}$C(=O)NR$^{32}$R$^{33}$, —NR$^{32}$(CR$^{30}$R$^{31}$)$_w$NR$^{32}$C(=O)NR$^{32}$R$^{33}$, —NR$^{32}$(CR$^{30}$R$^{31}$)$_w$NR$^{32}$C(=O)OR$^{34}$, —NR$^{32}$(CR$^{30}$R$^{31}$)$_v$CO$_2$H, —NR$^{32}$(CR$^{30}$R$^{31}$)$_v$CO$_2$R$^{34}$, —NR$^{32}$(CR$^{30}$R$^{31}$)$_v$C(=O)NR$^{32}$R$^{33}$, —N(R$^{32}$)-heteroaryl-NR$^{32}$R$^{33}$, —N(R$^{32}$)-heterocycloalkyl-NR$^{32}$R$^{33}$, —NR$^{32}$(CR$^{30}$R$^{31}$)$_v$heteroaryl, —NR$^{32}$(CR$^{30}$R$^{31}$)$_v$heterocycloalkyl, —CN, —(CR$^{30}$R$^{31}$)$_v$CN, —(CR$^{30}$R$^{31}$)$_v$NR$^{32}$R$^{33}$, —(CR$^{30}$R$^{31}$)$_v$OH, —(CR$^{30}$R$^{31}$)$_v$OR$^{34}$, —(CR$^{30}$R$^{31}$)$_v$OC(=O)R$^{34}$, —(CR$^{30}$R$^{31}$)$_v$OC(=O)NR$^{32}$R$^{33}$, —(CR$^{30}$R$^{31}$)$_v$O(CR$^{30}$R$^{31}$)$_w$OR$^{34}$, —(CR$^{30}$R$^{31}$)$_v$O(CR$^{30}$R$^{31}$)$_w$OH, —(CR$^{30}$R$^{31}$)$_v$O(CR$^{30}$R$^{31}$)$_w$NR$^{32}$R$^{33}$, —(CR$^{30}$R$^{31}$)$_v$NR$^{32}$(CR$^{30}$R$^{31}$)$_w$OH, —(CR$^{30}$R$^{31}$)$_v$NR$^{32}$(CR$^{30}$R$^{31}$)$_w$OR$^{34}$, —(CR$^{30}$R$^{31}$)$_v$C(=O)NR$^{32}$R$^{33}$, —(CR$^{30}$R$^{31}$)$_v$C(=O)NR$^{32}$(CR$^{30}$R$^{31}$)$_w$NR$^{32}$R$^{33}$, —(CR$^{30}$R$^{31}$)$_v$C(=O)NR$^{32}$(CR$^{30}$R$^{31}$)$_w$OR$^{34}$, —(CR$^{30}$R$^{31}$)$_v$N(R$^{32}$)C(=O)R$^{34}$, —(CR$^{30}$R$^{31}$)$_v$N(R$^{32}$)C(=O)OR$^{34}$, —(CR$^{30}$R$^{31}$)$_v$N(R$^{32}$)C(=O)NR$^{32}$R$^{33}$, —(CR$^{30}$R$^{31}$)$_v$N(R$^{32}$)C(=O)(CR$^{30}$R$^{31}$)$_v$NR$^{32}$R$^{33}$, —(CR$^{30}$R$^{31}$)$_v$NR$^{32}$(CR$^{30}$R$^{31}$)$_w$NR$^{32}$R$^{33}$, —(CR$^{30}$R$^{31}$)$_v$N(R$^{32}$)CH(=NR$^{36}$), —(CR$^{30}$R$^{31}$)$_v$N(R$^{32}$)C(=NR$^{36}$)R$^{34}$, —(CR$^{30}$R$^{31}$)$_v$C(=NR$^{36}$)NR$^{32}$R$^{33}$, —(CR$^{30}$R$^{31}$)$_v$N(R$^{32}$)C(=NR$^{36}$)NR$^{32}$R$^{33}$, —(CR$^{30}$R$^{31}$)$_v$C(=NR$^{36}$)NR$^{32}$C(=NR$^{36}$)NR$^{32}$R$^{33}$, —(CR$^{30}$R$^{31}$)$_v$heteroaryl-NR$^{32}$R$^{33}$, —C(=O)OH, —C(=O)OR$^{34}$, —C(=O)NR$^{32}$R$^{33}$, —C(=O)NR$^{32}$(CR$^{30}$R$^{31}$)$_w$NR$^{32}$R$^{33}$, —C(=O)NR$^{32}$(CR$^{30}$R$^{31}$)$_w$OH, —C(=O)NR$^{32}$(CR$^{30}$R$^{31}$)$_w$OR$^{34}$, —C(=NR$^{36}$)NR$^{32}$R$^{33}$, —C(=NR$^{36}$)NR$^{32}$C(=O)R$^{34}$, or SR$^{35}$.

In some embodiments of a compound of Formula (Ia), (Va)-(VIIa), (VIIa-1), (Ib), (Vb)-(VIIb), or (VIIb-1), each Y is independently halogen, optionally substituted heteroaryl, —NR$^{32}$R$^{33}$, —OH, —OR$^{34}$, —NR$^{32}$(CR$^{30}$R$^{31}$)$_w$NR$^{32}$R$^{33}$, —NR$^{32}$C(=NR$^{36}$)NR$^{32}$R$^{33}$, —(CR$^{30}$R$^{31}$)$_v$NR$^{32}$R$^{33}$, —$SR^{35}$, —$NR^{32}(CR^{31}R^{31})_vCO_2H$, —$NR^{32}(CR^{30}R^{31})_vC(=O)NR^{32}R^{33}$, or —$NR^{32}(CR^{30}R^{31})_v$heteroaryl; or two Ys taken together with the atoms to which they are attached form an optionally substituted heterocycloalkyl. In some embodiments of a compound of Formula (Ia), (Va)-(VIIa), (VIIa-1), (Ib), (Vb)-(VIIb), or (VIIb-1), each Y is independently —$NR^{32}R^{33}$. In some embodiments of a compound of Formula (Ia), (Va)-(VIIa), (VIIa-1), (Ib), (Vb)-(VIIb), or (VIIb-1), each Y is independently —$(CR^{30}R^{31})_vNR^{32}R^{33}$. In some embodiments of a compound of Formula (Ia), (Va)-(VIIa), (VIIa-1), (Ib), (Vb)-(VIIb), or (VIIb-1), each Y is independently —$NR^{32}(CR^{30}R^{31})_wNR^{32}R^{33}$. In some embodiments of a compound of Formula (Ia), (Va)-(VIIa), (VIIa-1), (Ib), (Vb)-(VIIb), or (VIIb-1), each Y is independently —OH. In some embodiments of a compound of Formula (Ia), (Va)-(VIIa), (VIIa-1), (Ib), (Vb)-(VIIb), or (VIIb-1), each Y is independently halogen, —$NR^{32}R^{33}$, —OH, —$OR^{34}$, —$NR^{32}(CR^{30}R^{31})_wNR^{32}R^{33}$, —C(=O)OH, or —C(=O)$NR^{32}R^{33}$. In some embodiments of a compound of Formula (Ia), (Va)-(VIIa), (VIIa-1), (Ib), (Vb)-(VIIb), or (VIIb-1), each Y is independently halogen, —$NR^{32}R^{33}$, —OH, —$OR^{34}$, or —$NR^{32}(CR^{30}R^{31})_wNR^{32}R^{33}$. In some embodiments of a compound of Formula (Ia), (Va)-(VIIa), (VIIa-1), (Ib), (Vb)-(VIIb), or (VIIb-1), each Y is independently halogen, —$NR^{32}R^{33}$, —OH, —C(=O)OH, or —C(=O)$NR^{32}R^{33}$. In some embodiments of a compound of Formula (Ia), (Va)-(VIIa), (VIIa-1), (Ib), (Vb)-(VIIb), or (VIIb-1), each Y is independently —OH or —$OR^{34}$.

In some embodiments of a compound of Formula (Ia), (Va)-(VIIa), (VIIa-1), (Ib), (Vb)-(VIIb), or (VIIb-1), two Ys taken together with the atoms to which they are attached form an optionally substituted cycloalkyl or an optionally substituted heterocycloalkyl. In some embodiments of a compound of Formula (Ia), (Va)-(VIIa), (VIIa-1), (Ib), (Vb)-(VIIb), or (VIIb-1), two Ys taken together with the atoms to which they are attached form a heterocycloalkyl optionally substituted with alkyl or halogen.

In some embodiments of a compound of Formula (Ia), (Va)-(VIIa), (VIIa-1), (Ib), (Vb)-(VIIb), or (VIIb-1), Y is defined as above and $R^{30}$ and $R^{31}$ are independently hydrogen or optionally substituted alkyl; or two $R^{30}$ on adjacent carbon form an alkenyl. In some embodiments of a compound of Formula (Ia), (Va)-(VIIa), (VIIa-1), (Ib), (Vb)-(VIIb), or (VIIb-1), Y is defined as above and $R^{32}$ and $R^{33}$ are independently hydrogen or optionally substituted alkyl; or $R^{32}$ and $R^{33}$ are taken together with the nitrogen to which they are attached to form an optionally substituted heterocycloalkyl. In some embodiments of a compound of Formula (Ia), (Va)-(VIIa), (VIIa-1), (Ib), (Vb)-(VIIb), or (VIIb-1), Y is defined as above and $R^{34}$ is optionally substituted alkyl. In some embodiments of a compound of Formula (Ia), (Va)-(VIIa), (VIIa-1), (Ib), (Vb)-(VIIb), or (VIIb-1), Y is defined as above and $R^{35}$ is hydrogen or optionally substituted alkyl. In some embodiments of a compound of Formula (Ia), (Va)-(VIIa), (VIIa-1), (Ib), (Vb)-(VIIb), or (VIIb-1), Y is defined as above and $R^{36}$ is hydrogen or optionally substituted alkyl. In some embodiments of a compound of Formula (Ia), (Va)-(VIIa), (VIIa-1), (Ib), (Vb)-(VIIb), or (VIIb-1), Y is defined as above and each v is independently 1 or 2. In some embodiments of a compound of Formula (Ia), (Va)-(VIIa), (VIIa-1), (Ib), (Vb)-(VIIb), or (VIIb-1), Y is defined as above and each w is independently 2 or 3.

In some embodiments of a compound of Formula (Ia), (Va)-(VIIa), (VIIa-1), (Ib), (Vb)-(VIIb), or (VIIb-1), Y is defined as above, $R^{30}$ and $R^{31}$ are independently hydrogen or optionally substituted alkyl; or two $R^{30}$ on adjacent carbon form an alkenyl; $R^{32}$ and $R^{33}$ are independently hydrogen or optionally substituted alkyl; or $R^{32}$ and $R^{33}$ are taken together with the nitrogen to which they are attached to form an optionally substituted heterocycloalkyl; $R^{34}$ is optionally substituted alkyl; $R^{35}$ is hydrogen or optionally substituted alkyl; $R^{36}$ is hydrogen or optionally substituted alkyl; each v is independently 1 or 2; and each w is independently 2 or 3.

In some embodiments of a compound of Formula (Ia), (Va)-(VIIa), (VIIa-1), (Ib), (Vb)-(VIIb), or (VIIb-1), each Y is defined by the inclusion of non-hydrogen atoms. In some embodiments, each Y comprises at least 1, 2, 3, 4, 5, 6, 7, 8, 9, 10, 12, 14, 16, 18, 20, 24, 28, 32, 36, 40, 50, or 60 non-hydrogen atoms. In some embodiments of a compound of Formula (Ia), (Va)-(VIIa), (VIIa-1), (Ib), (Vb)-(VIIb), or (VIIb-1), each Y comprises fewer than 50, 40, 36, 32, 28, 24, 20, 18, 16, 14, 12, 10, 9, 8, 7, 6, 5, 4, 3 or 2 non-hydrogen atoms. In some embodiments of a compound of Formula (Ia), (Va)-(VIIa), (VIIa-1), (Ib), (Vb)-(VIIb), or (VIIb-1), each Y is independently a group comprising 1-50 non-hydrogen atoms. In some embodiments of a compound of Formula (Ia), (Va)-(VIIa), (VIIa-1), (Ib), (Vb)-(VIIb), or (VIIb-1), non-hydrogen atoms are atoms generally found in organic molecules. In some embodiments of a compound of Formula (Ia), (Va)-(VIIa), (VIIa-1), (Ib), (Vb)-(VIIb), or (VIIb-1), non-hydrogen atoms are atoms selected from the group consisting of halogen, C, N, O, S, and P. In some embodiments of a compound of Formula (Ia), (Va)-(VIIa), (VIIa-1), (Ib), (Vb)-(VIIb), or (VIIb-1), each Y is independently a group comprising 1-50 non-hydrogen atoms selected from the group consisting of halogen, C, N, O, S, and P. In some embodiments of a compound of Formula (Ia), (Va)-(VIIa), (VIIa-1), (Ib), (Vb)-(VIIb), or (VIIb-1), each Y is independently a group comprising 1-50 non-hydrogen atoms selected from the group consisting of halogen, C, N, and O.

In some embodiments of a compound of Formula (Ia), (Va)-(VIIa), (VIIa-1), (Ib), (Vb)-(VIIb), or (VIIb-1), each Y is defined by its molecular formula. In some embodiments of a compound of Formula (Ia), (Va)-(VIIa), (VIIa-1), (Ib), (Vb)-(VIIb), or (VIIb-1), each Y has the formula $C_aH_bN_cO_d$; wherein each a is independently 0-30; each b is independently 1-69; each c is independently 1-8; and each d is independently 0-10. In some embodiments of a compound of Formula (Ia), (Va)-(VIIa), (VIIa-1), (Ib), (Vb)-(VIIb), or (VIIb-1), each Y has the formula $C_aH_bN_cO_d$; wherein each a is independently 0-10; each b is independently 1-25; each c is independently 1-4; and each d is independently 0-3. In some embodiments of a compound of Formula (Ia), (Va)-(VIIa), (VIIa-1), (Ib), (Vb)-(VIIb), or (VIIb-1), each c is 2. In some embodiments of a compound of Formula (Ia), (Va)-(VIIa), (VIIa-1), (Ib), (Vb)-(VIIb), or (VIIb-1), each c is at least 2.

In some embodiments of a compound of Formula (Ia), (Va)-(VIIa), (VIIa-1), (Ib), (Vb)-(VIIb), or (VIIb-1), each Y is defined by its molecular weight. In some embodiments of a compound of Formula (Ia), (Va)-(VIIa), (VIIa-1), (Ib), (Vb)-(VIIb), or (VIIb-1), each Y has a molecular weight of less than 500, 450, 400, 350, 300, 250, 200, 190, 180, 170, 160, 150, 140, 130, 120, 110, 100, 90, 80, 75, 70, or 50 daltons. In some embodiments of a compound of Formula (Ia), (Va)-(VIIa), (VIIa-1), (Ib), (Vb)-(VIIb), or (VIIb-1), each Y has a molecular weight of less than 200 daltons. In some embodiments of a compound of Formula (Ia), (Va)-(VIIa), (VIIa-1), (Ib), (Vb)-(VIIb), or (VIIb-1), each Y has a molecular weight of less than 150 daltons. In some embodiments of a compound of Formula (Ia), (Va)-(VIIa), (VIIa-1), (Ib), (Vb)-(VIIb), or (VIIb-1), each Y has a molecular weight between 30 and 280 daltons.

In some embodiments of a compound of Formula (Ia), (Va)-(VIIa), (VIIa-1), (Ib), (Vb)-(VIIb), or (VIIb-1), p is 0, 1, or 2. In some embodiments of a compound of Formula (Ia), (Va)-(VIIa), (VIIa-1), (Ib), (Vb)-(VIIb), or (VIIb-1), p is 1, 2, or 3. In some embodiments of a compound of Formula (Ia), (Va)-(VIIa), (VIIa-1), (Ib), (Vb)-(VIIb), or (VIIb-1), p is 2 or 3. In some embodiments of a compound of Formula (Ia), (Va)-(VIIa), (VIIa-1), (Ib), (Vb)-(VIIb), or (VIIb-1), p is 0. In some embodiments of a compound of Formula (Ia), (Va)-(VIIa), (VIIa-1), (Ib), (Vb)-(VIIb), or (VIIb-1), p is 1. In some embodiments of a compound of Formula (Ia), (Va)-(VIIa), (VIIa-1), (Ib), (Vb)-(VIIb), or (VIIb-1), p is 2. In some embodiments of a compound of Formula (Ia), (Va)-(VIIa), (VIIa-1), (Ib), (Vb)-(VIIb), or (VIIb-1), p is 3.

In some embodiments of a compound of Formula (Ia), (Va)-(VIIa), (VIIa-1), (Ib), (Vb)-(VIIb), or (VIIb-1), v is 1. In some embodiments of a compound of Formula (Ia), (Va)-(VIIa), (VIIa-1), (Ib), (Vb)-(VIIb), or (VIIb-1), v is 2. In some embodiments of a compound of Formula (Ia), (Va)-(VIIa), (VIIa-1), (Ib), (Vb)-(VIIb), or (VIIb-1), v is 3. In some embodiments of a compound of Formula (Ia), (Va)-(VIIa), (VIIa-1), (Ib), (Vb)-(VIIb), or (VIIb-1), v is 4. In some embodiments of a compound of Formula (Ia), (Va)-(VIIa), (VIIa-1), (Ib), (Vb)-(VIIb), or (VIIb-1), v is 5.

In some embodiments of a compound of Formula (Ia), (Va)-(VIIa), (VIIa-1), (Ib), (Vb)-(VIIb), or (VIIb-1), w is 2. In some embodiments of a compound of Formula (Ia), (Va)-(VIIa), (VIIa-1), (Ib), (Vb)-(VIIb), or (VIIb-1), w is 3. In some embodiments of a compound of Formula (Ia), (Va)-(VIIa), (VIIa-1), (Ib), (Vb)-(VIIb), or (VIIb-1), w is 4. In some embodiments of a compound of Formula (Ia), (Va)-(VIIa), (VIIa-1), (Ib), (Vb)-(VIIb), or (VIIb-1), w is 5.

Preparation of Compounds

Described herein are compounds of Formula (Ia), (Va)-(VIIa), (VIIa-1), (Ib), (Vb)-(VIIb), or (VIIb-1) that inhibit the activity of penicillin-binding proteins, and processes for their preparation. Also described herein are pharmaceutically acceptable salt, solvate, stereoisomer, tautomer, N-oxide, dimer, or trimer of compounds of Formula (Ia), (Va)-(VIIa), (VIIa-1), (Ib), (Vb)-(VIIb), or (VIIb-1).

Compounds of Formula (Ia), (Va)-(VIIa), (VIIa-1), (Ib), (Vb)-(VIIb), or (VIIb-1) may be synthesized using standard synthetic reactions known to those of skill in the art or using methods known in the art. The reactions can be employed in a linear sequence to provide the compounds or they may be used to synthesize fragments which are subsequently joined by the methods known in the art.

The starting material used for the synthesis of the compounds described herein may be synthesized or can be obtained from commercial sources. The compounds described herein, and other related compounds having different substituents can be synthesized using techniques and materials known to those of skill in the art, such as described, for example, in March, ADVANCED ORGANIC CHEMISTRY 4$^{th}$ Ed., (Wiley 1992); Carey and Sundberg, ADVANCED ORGANIC CHEMISTRY 4$^{th}$ Ed., Vols. A and B (Plenum 2000, 2001); Green and Wuts, PROTECTIVE GROUPS IN ORGANIC SYNTHESIS 3$^{rd}$ Ed., (Wiley 1999); Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); and Larock's Comprehensive Organic Transformations (VCH Publishers Inc., 1989) (all of which are incorporated by reference in their entirety). General methods for the preparation of compound as disclosed herein may be derived from known reactions in the field, and the reactions may be modified by the use of appropriate reagents and conditions, as would be recognized by the skilled person, for the introduction of the various moieties found in the formulae as provided herein.

The products of the reactions may be isolated and purified, if desired, using conventional techniques, including, but not limited to, filtration, distillation, crystallization, chromatography, and the like. Such materials may be characterized using conventional means, including physical constants and spectral data.

Further Forms of Compounds Disclosed Herein

Isomers/Stereoisomers

In some embodiments, due to the oxophilic nature of the boron atom, the compounds described herein may convert to, or exist in equilibrium with, alternate forms, particularly in milieu that contain water (aqueous solution, plasma, etc.). Accordingly, the compounds described herein may exist in an equilibrium between the "closed" cyclic form shown in Formula (Ia), (IIa), (IIIa), or (IIIa-1) and the "open" acyclic form shown in Formula (Ib), (IIb), (IIIb), or (IIIb-1). In addition the compounds described herein may associate into intramolecular dimers, trimers, and related combinations.

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Compounds described herein may be prepared as a single isomer or a mixture of isomers.

Tautomers

In some situations, compounds described herein exist as tautomers. The compounds described herein include all possible tautomers within the formulas described herein. A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

useful in drug and/or substrate tissue distribution assays. Tritiated, i. e., $^3$H and carbon-14, i. e., $^{14}$C, isotopes are particularly preferred for their ease of preparation and detectability. Further, substitution with heavy isotopes such as deuterium, i.e., $^2$H, produces certain therapeutic advantages resulting from greater metabolic stability, for example increased in vivo half-life or reduced dosage requirements. In some embodiments, the isotopically labeled compounds,

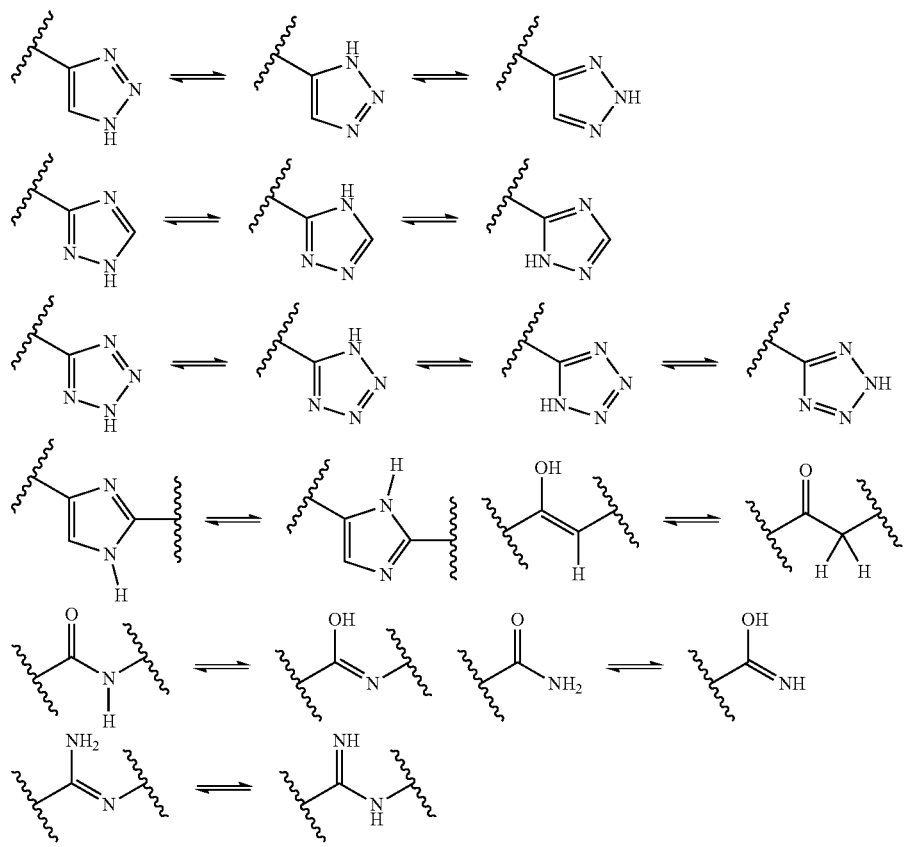

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorous, sulfur, fluorine, and chloride, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds described herein which contain the aforementioned isotopes and/or other isotopes of other atoms are within the scope of this invention. Certain isotopically-labeled compounds, for example those into which radioactive isotopes such as $^3$H and $^{14}$C are incorporated, are pharmaceutically acceptable salt, ester, prodrug, solvate, hydrate, or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds described herein, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate, and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid. In some embodiments, other acids, such as oxalic, while not in themselves pharmaceutically acceptable, are employed in the preparation of salts useful as intermediates in obtaining the compounds described herein and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+(C_{1-4}$ alkyl$)_4$, and the like.

Representative organic amines useful for the formation of base addition salts include ethylamine, diethylamine, ethylenediamine, ethanolamine, diethanolamine, piperazine, and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran, or methanol. In addition, the compounds provided herein can exist in unsolvated as well as solvated forms. In general, the solvated forms are considered equivalent to the unsolvated forms for the purposes of the compounds and methods provided herein.

Pharmaceutical Compositions/Formulations

In another aspect, provided herein are pharmaceutical compositions comprising a compound described herein, or a pharmaceutically acceptable salt, solvate, stereoisomer, tautomer, N-oxide, dimer, or trimer thereof, and a pharmaceutically acceptable excipient. In some embodiments, the pharmaceutical composition further comprises a beta-lactam antibiotic. In certain embodiments, the beta-lactam antibiotic is a penicillin, cephalosporin, carbapenem, monobactam, bridged monobactam, or a combination thereof.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound described herein with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including, but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, liquids, gels, syrups, elixirs, slurries, suspensions, self-emulsifying dispersions, solid solutions, liposomal dispersions, aerosols, solid oral dosage forms, powders, immediate release formulations, controlled release formulations, fast melt formulations, tablets, capsules, pills, powders, dragees, effervescent formulations, lyophilized formulations, delayed release formulations, extended release formulations, pulsatile release formulations, multiparticulate formulations, and mixed immediate and controlled release formulations.

Combination Treatment

The compounds described herein may be used in combination with one or more antibiotics in the treatment of bacterial infections. Such antibiotics may be administered, by a route and in an amount commonly used therefore, contemporaneously or sequentially with a compound described herein. When a compound described herein is used contemporaneously with one or more antibiotic, a pharmaceutical composition in unit dosage form containing such other drugs and the compound of the present invention is preferred. However, the combination therapy may also include therapies in which the compound described herein and one or more antibiotic are administered on different overlapping schedules. It is also contemplated that when used in combination with one or more antibiotics, the antibiotics may be used in lower doses than when each is used singly.

Accordingly, the pharmaceutical compositions of the present invention also include those that contain one or more antibiotics, in addition to a compound described herein. In some embodiments, a pharmaceutical composition comprising a compound described herein further comprises a beta-lactam antibiotic. In certain embodiments, the beta-lactam antibiotic is a penicillin, cephalosporin, carbapenem, monobactam, bridged monobactam, or a combination thereof.

In some embodiments, the compounds described herein are used in combination with one or more antibiotics in the treatment of bacterial infections. In certain embodiments, the bacterial infection is a upper or lower respiratory tract infection, a urinary tract infection, a intra-abdominal infection, or a skin infection. In some embodiments, the one or more antibiotics are selected from β-lactam antibiotics. β-Lactam antibiotics include, but are not limited to, penicillins, penems, carbapenems, cephalosporins, cephamycins, monobactams, or combinations thereof. Penicillins include, but are not limited to, amoxicillin, ampicillin, azidocillin, azlocillin, bacampicillin, benzathinebenzylpenicillin, benzathinephenoxymethylpenicillin, benzylpenicillin (G), carbenicillin, carindacillin, clometocillin, cloxacillin, dicloxacillin, epicillin, flucloxacillin, hetacillin, mecillinam, metampicillin, meticillin, mezlocillin, nafcillin, oxacillin, penamecillin, pheneticillin, phenoxymethylpenicillin (V), piperacillin, pivampicillin, pivmecillinam, procaine benzylpenicillin, propicillin, sulbenicillin, talampicillin, temocillin, and ticarcillin. Penems include, but are not limited to, faropenem. Carbapenems include, but are not limited to, biapenem, ertapenem, doripenem, imipenem, meropenem, and panipenem. Cephalosporins/Cephamycins include, but are not limited to, cefacetrile, cefaclor, cefadroxil, cefalexin, cefaloglycin, cefalonium, cefaloridine, cefalotin, cefamandole, cefapirin, cefatrizine, cefazaflur, cefazedone, cefazolin, cefbuperazone, cefcapene, cefdaloxime, cefdinir, cefditoren, cefepime, cefetamet, cefixime, cefmenoxime, cefmetazole, cefminox, cefodizime, cefonicid, cefoperazone, ceforanide, cefotaxime, cefotetan, cefotiam, cefovecin, cefoxitin, cefozopran, cefpimizole, cefpiramide, cefpirome, cefpodoxime, cefprozil, cefquinome, cefquinome, cefradine, cefroxadine, cefsulodin, ceftarolinefosamil, ceftazidime, cefteram, ceftezole, ceftibuten, ceftiofur, ceftiolene, ceftizoxime, ceftobiprole, ceftriaxone, cefuroxime, cefuzonam, flomoxef, latamoxef, and loracarbef. Monobactams include, but are not limited to, aztreonam, carumonam, nocardicinA, and tigemonam.

Methods

The present disclosure also provides methods for inhibiting bacterial growth, such methods comprising contacting a bacterial cell culture, or a bacterially infected cell culture, tissue, or organism, with a penicillin-binding protein inhibitor described herein. Preferably, the bacteria to be inhibited by administration of a penicillin-binding protein inhibitor described herein are bacteria that are resistant to beta-lactam antibiotics. The term "resistant" is well-understood by those of ordinary skill in the art (see, e g Payne et al., *Antimicrobial Agents and Chemotherapy* 38 767-772 (1994), Hanaki et al., *Antimicrobial Agents and Chemotherapy* 30 1120-1126 (1995)). In some embodiments, the penicillin-binding protein inhibitor described herein is used to treat a bacterial infection that is resistant to beta-lactam antibiotic. In some embodiments, the penicillin-binding protein inhibitor described herein is used to treat a bacterial infection that has developed beta-lactamase enzymes.

These methods are useful for inhibiting bacterial growth in a variety of contexts. In certain embodiments, a compound described herein is administered to an experimental cell culture in vitro to prevent the growth of beta-lactam resistant bacteria. In some embodiments, a compound described herein is administered to a mammal, including a human, to prevent the growth of beta-lactam resistant bacteria in vivo. The method according to this embodiment comprises administering a therapeutically effective amount of a penicillin-binding protein inhibitor described herein for a therapeutically effective period of time to a mammal, including a human. Preferably, the penicillin-binding protein inhibitor described herein is administered in the form of a pharmaceutical composition as described above.

In another aspect provided herein are methods of treating a bacterial infection, which method comprises administering to a subject a pharmaceutical composition comprising a compound described herein, or a pharmaceutically acceptable salt thereof, and a pharmaceutically acceptable excipient. In some embodiments, the methods of treating a bacterial infection in a subject comprises administering to the subject a pharmaceutical composition as described herein. In some embodiments, the bacterial infection is an upper or lower respiratory tract infection, a urinary tract infection, an intra-abdominal infection, or a skin infection.

In some embodiments, the infection that is treated or prevented comprises a bacteria that includes *Pseudomonas* aeruginosa, *Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacterfreundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilusinfluenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacterjejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella kingae, Moraxella catarrhalis, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtheriae, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus.*

In some embodiments, the infection that is treated or prevented comprises a bacteria that includes *Pseudomonas aeruginosa, Pseudomonas fluorescens, Stenotrophomonas maltophilia, Escherichia coli, Citrobacterfreundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacterjejuni, Campylobacter coli, Vibrio cholerae, Vibrio parahaemolyticus, Legionella pneumophila, Listeria monocytogenes, Neisseria gonorrhoeae, Neisseria meningitidis, Moraxella catarrhalis, Bacteroides fragilis, Bacteroides vulgatus, Bacteroides ovalus, Bacteroides thetaiotaomicron, Bacteroides uniformis, Bacteroides eggerthii,* or *Bacteroides splanchnicus.*

In some embodiments of the methods described herein, the compound described herein is not administered with a β-lactam antibiotic. In some embodiments of the methods described herein, the compound described herein is not administered with a β-lactamase inhibitor. In some embodiments of the methods described herein, the compound described herein is not administered with a combination of a β-lactam antibiotic and a β-lactamase inhibitor.

EXAMPLES

General Examples for the Preparation of Compounds of Formula (Ia), (Va)-(VIIa), (VIIa-1), (Ib), (Vb)-(VIIb), or (VIIb-1)

The starting materials and intermediates for the compounds of this invention may be prepared by the application or adaptation of the methods described below, their obvious chemical equivalents, or, for example, as described in literature such as The Science of Synthesis, Volumes 1-8. Editors E. M. Carreira et al. Thieme publishers (2001-2008). The use of protective groups may be as described in methodology compendia such as *Greene's Protective Groups in Organic Synthesis*, Fourth Edition. John Wiley & Sons, Inc. 2006.

Certain compounds of Formula I (Scheme 1) are prepared from the corresponding functional-group-protected boronic acid esters A by treatment with a Lewis acid in a solvent such as dichloromethane, at a temperature between −78 OC and 0° C. followed by an aqueous quench.

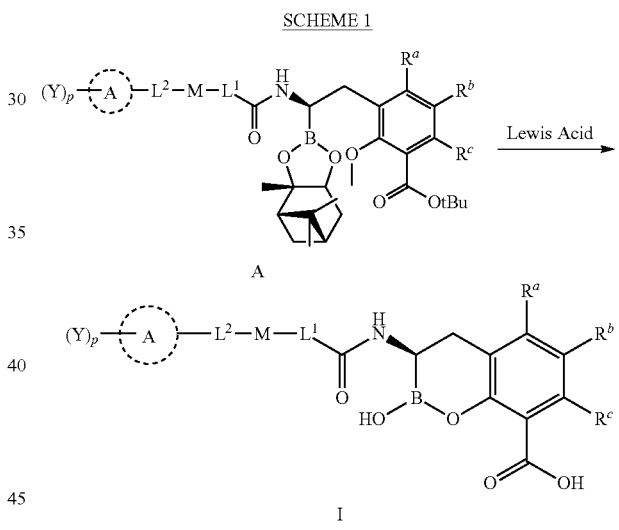

Amide intermediates A may be prepared according to the route outlined in Scheme 2. Chloro-boronates B, prepared by methods described previously (e.g. see WO2014089365), is reacted with silylamine bases such as lithium hexamethyldisilazide, and the intermediate silylamine is treated with carboxylic acids C under amide coupling conditions (such as with carbodiimide dehydrating reagents, HATU, or other coupling reagents) to provide protected amides A. Alternatively, the above silyamine intermediate is allowed to react with acid chlorides to provide A. Carboxylic acids (C) or acid chlorides (D) may be obtained from commercial sources, prepared according to known methods in the literature, or prepared by a number of different reaction sequences. Formation of the acid chloride (D) involves treatment of (C) with a chlorinating agent such as thionyl chloride, phosphorous pentachloride or oxalyl chloride, in a solvent such as dichloromethane, in the presence of a catalyst such as DMF, at around room temperature. In certain cases, DMF is also used as a co-solvent. Formation of the anhydride (E) involves treatment of (C) with a sterically hindered acid chloride or chloroformate, such as trimethylacetyl chloride or isopropylchloroformate, in an inert solvent such as dichloromethane, in the presence of a non-nucleophilic base, such as triethyl amine or diisopropylamine at room temperature or below. Formation of the activated ester (F) involves treatment of (C) with an activating reagent system such as EDCI, DCC/HOBt, HATU, BOP reagents or TBTU, in a solvent such as DMF, DMA, NMP or dichloromethane at room temperature or below (*International Journal of Pharmaceutical Sciences Review and Research* (2011), 8(1), 108-119).

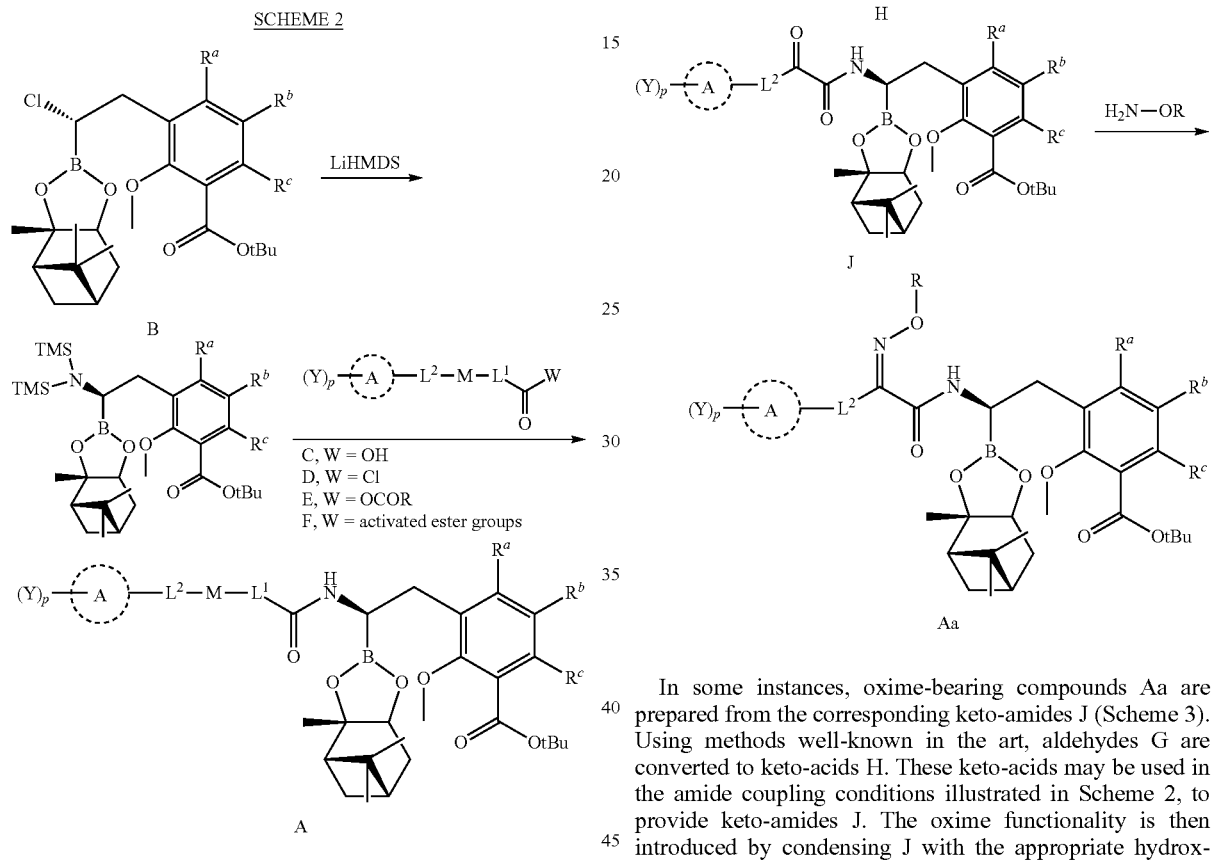

In some instances, oxime-bearing compounds Aa are prepared from the corresponding keto-amides J (Scheme 3). Using methods well-known in the art, aldehydes G are converted to keto-acids H. These keto-acids may be used in the amide coupling conditions illustrated in Scheme 2, to provide keto-amides J. The oxime functionality is then introduced by condensing J with the appropriate hydroxylamine.

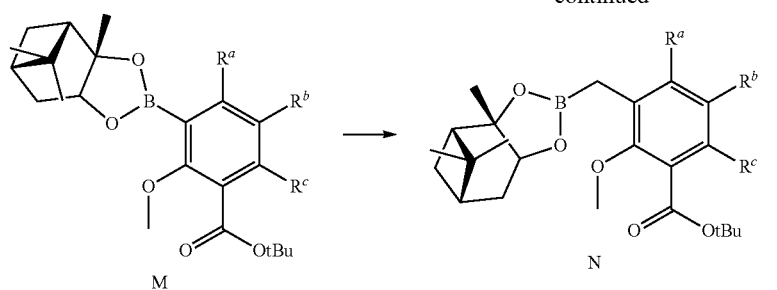

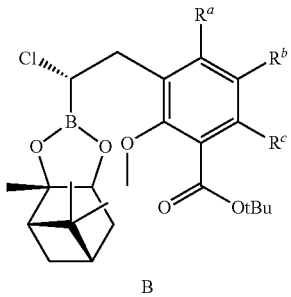

Chloroboronates B may be prepared from aryl halides or aryl triflates K (X=Br, I or OTf) in the manner described in Scheme 4. Compounds K (X=Br, I or OTf) may be converted into boronic acids L by treatment with alkyl lithium reagents, for example n-butyllithium, and then quenching the intermediate aryllithium species with trialkylboronates, followed by aqueous work-up. The boronic acids L may be converted into protected boronate esters M by treatment with 1,2-diols, such as (+)-pinanediol or pinacol. Alternatively, aryl halides K may be converted to boronate esters M by transition-metal-catalyzed reaction with diboron compounds, for example bis[(+)-pinanediolato]diboron and palladium catalysts. Two sequential Matteson reactions, as described previously, provide chloroboronates B bearing a wide range of substituents $R^a$, $R^b$, and $R^c$. Another variant consists of reaction of K with chloromethyl boronate J and isopropylmagnesium chloride to provide desired intermediate N directly.

While there are common themes and strategies among the illustrative examples cited below, the selection of an appropriate reaction sequence (including protecting group requirements) is dictated by the nature and arrangement of the functionality present in the target molecule and, therefore, may involve obvious adaptations of the illustrated methods in order to be applied in a particular case.

General Method A: Deprotection with Boron Trichloride or Boron Tribromide

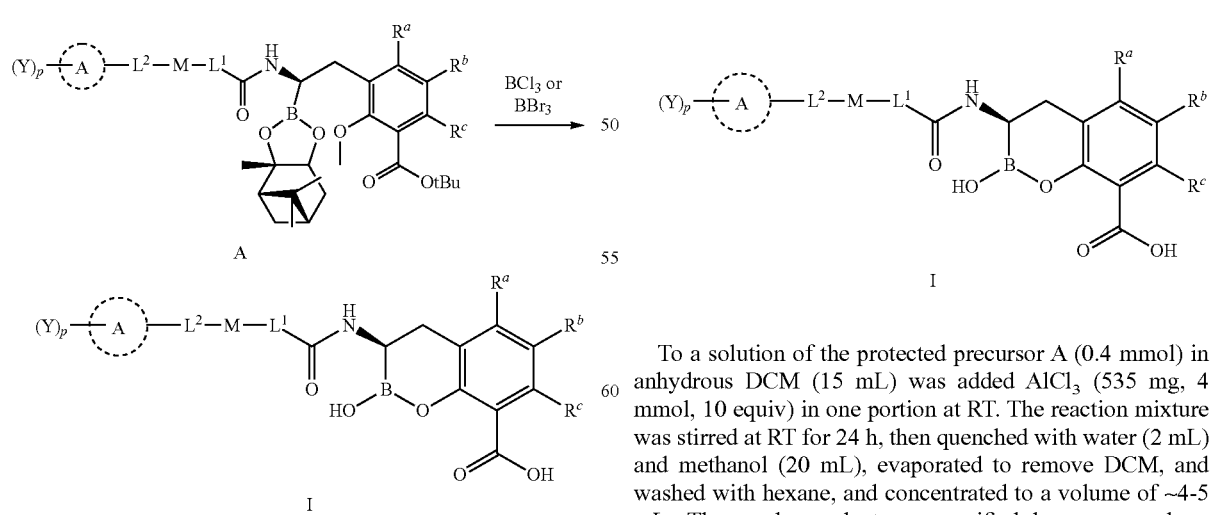

To a solution of the protected precursor A (0.4 mmol) in anhydrous DCM (15 mL) at −78° C. under argon was added dropwise $BCl_3$ or $BBr_3$ (1.0 M in DCM, 2.4-4 mL, 2.4-4 mmol, 6-10 equiv). The reaction mixture was allowed to slowly warmed to 0° C. over 1 h, and stirred between 0-5° C. for an additional 1-2 h, then quenched with water (2 mL) and methanol (20 mL), evaporated to remove DCM, washed with hexane, and concentrated to a volume of ~4-5 mL. The crude product was purified by reverse phase preparative HPLC and dried using lyophilization to afford the product I.

General Method B: Deprotection with Aluminum Chloride

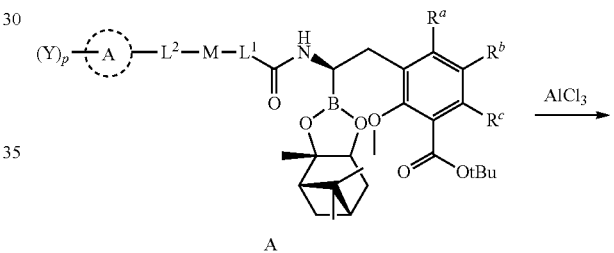

To a solution of the protected precursor A (0.4 mmol) in anhydrous DCM (15 mL) was added $AlCl_3$ (535 mg, 4 mmol, 10 equiv) in one portion at RT. The reaction mixture was stirred at RT for 24 h, then quenched with water (2 mL) and methanol (20 mL), evaporated to remove DCM, and washed with hexane, and concentrated to a volume of ~4-5 mL. The crude product was purified by reverse phase preparative HPLC and dried using lyophilization to afford the product I.

General Method C: Conversion of Chloro-Boronates to Amides

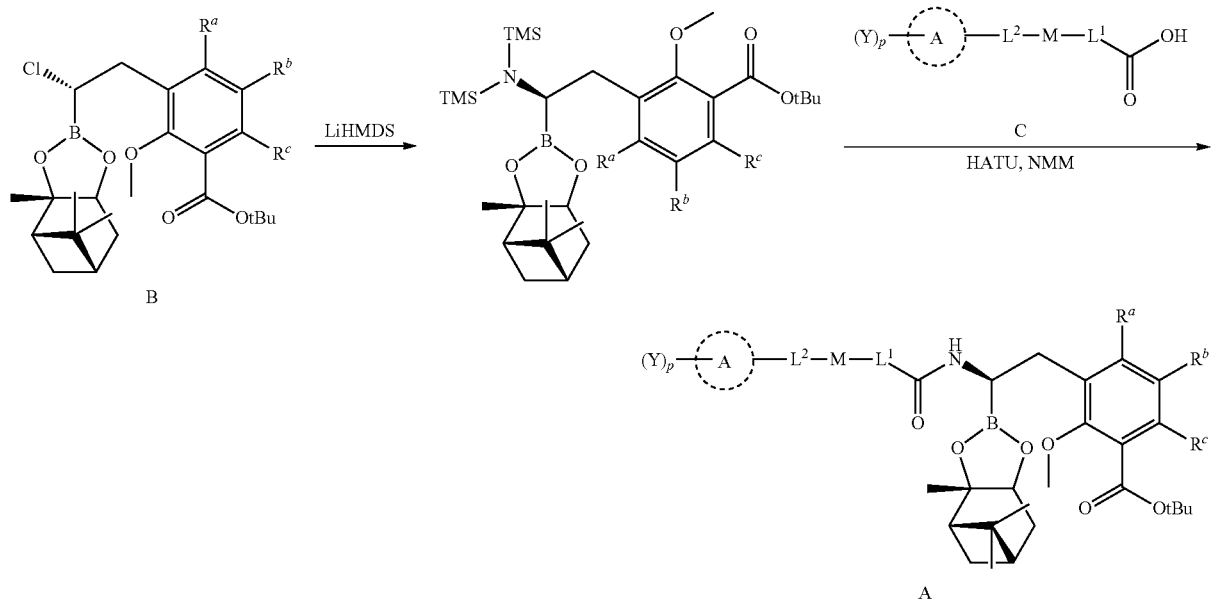

To a solution of the chloride B (4 mmol) in anhydrous THF (16 mL) was added dropwise LiHMDS (1.0 M in THF, 4.5 mL, 4.5 mmol) at −60° C. under argon. The reaction mixture was allowed to slowly warmed to 0° C. over 45 min, and stirred at RT for an additional 2 h.

In a separate flask was charged the carboxylic acid C (4.2 mmol) and anhydrous DMA (20 mL), to this mixture was added HATU (1.68 g, 4.4 mmol) followed by NMM (0.49 mL, 4.4 mmol). The reaction mixture was stirred at RT for 2 h, at which time the solution from the above reaction was added to the flask, and the reaction mixture was stirred at RT overnight, then diluted with EtOAc, washed with water, brine, and dried over $Na_2SO_4$, concentrated in vacuo to afford the crude product, which was purified by flash chromatography on silica gel (hexane-EtOAc, 20:1-1:1, or hexane-acetone, 10:1-1:1, or DCM-MeOH, 30:1-10:1) to afford the product A.

SYNTHETIC EXAMPLES

Example 1A: (R,Z)-3-(2-(2-aminothiazol-4-yl)-2-(hydroxyimino)acetamido)-2-hydroxy-3,4-dihydro-2H-benzo[e][1,2]oxaborinine-8-carboxylic acid

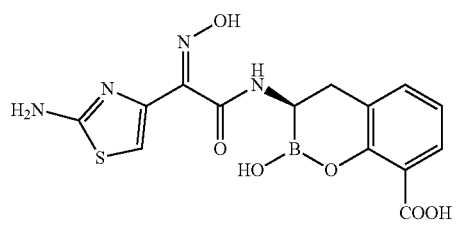 [SMILES: Nc1nc(/C(=N/O)C(=O)N[C@H]2Cc3cccc(C(=O)O)c3OB2O)cs1]

Step 1. Synthesis of ethyl 2-(2-((tert-butoxycarbonyl)amino)thiazol-4-yl)-2-oxoacetate

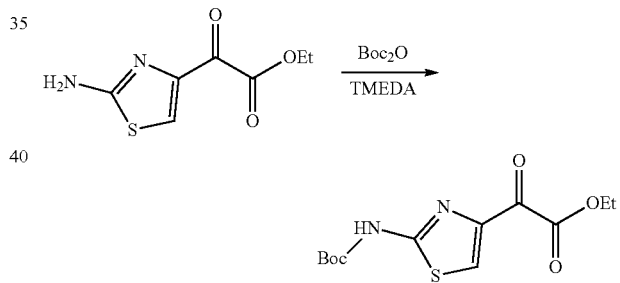

To ethyl 2-(2-amino-4-thiazolyl)-2-oxoacetate (11.2 g, 56 mmol) in $CH_3CN$ (300 mL) was added TMEDA (26 mL, 175 mmol) followed by $Boc_2O$ (13.4 g, 61.4 mmol). The reaction mixture was stirred at RT overnight, then concentrated, and purified by flash chromatography on silica gel (hexane-EtOAc, 10:1-2:1) to afford the product, 11 g. ESI-MS m/z 301 (MH)$^+$.

Step 2. Synthesis of ethyl 2-((benzyloxy)imino)-2-(2-((tert-butoxycarbonyl)amino)thiazol-4-yl)acetate

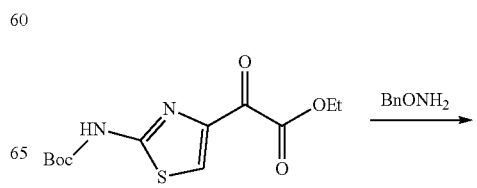

-continued

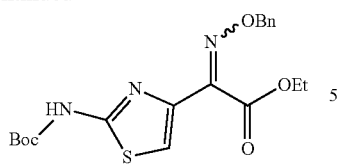

To the above product (11 g, 36.7 mmol) in EtOH (500 mL) was added O-benzylhydroxylamine hydrochloride (10 g, 62.5 mmol), the reaction mixture was stirred at RT overnight, concentrated in vacuo. The residue was dissolved in DCM, washed with saturated aqueous NaHCO$_3$, dried over Na$_2$SO$_4$, concentrated. The crude product was purified by flash chromatography on silica gel (hexane-EtOAc, 20:1-2:1) to afford the product as an inseparable mixture of Z and E isomers, 14.68 g. ESI-MS m/z 406 (MH)$^+$.

Step 3. Synthesis of (Z)- and (E)-2-((benzyloxy)imino)-2-(2-((tert-butoxycarbonyl)amino)thiazol-4-yl)acetic acid

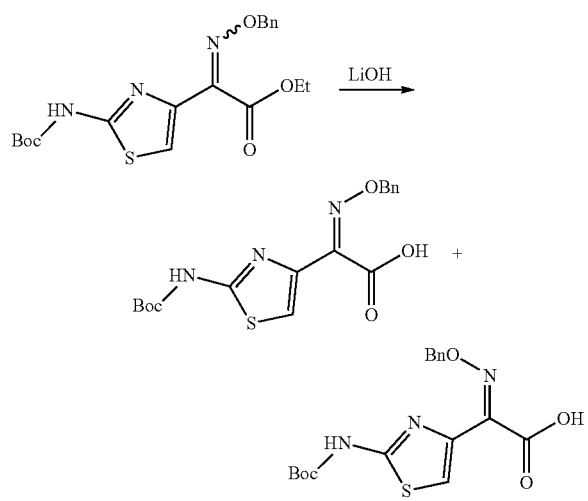

To the above product (14.68 g, 36.3 mmol) in THF (200 mL) and water (200 mL) was added LiOH.H$_2$O (840 mg, 20 mmol), the reaction mixture was stirred at RT for 2 h, then added more LiOH.H$_2$O (2.2 g, 52.4 mmol), and stirred for 1 h. LC/MS showed the minor, E isomer was completely hydrolyzed (the E isomer was less hindered and hydrolyzed much faster than Z isomer). The reaction mixture was extracted with diethyl ether. The aqueous was acidified with 1 N HCl to pH~3, extracted with DCM. The organic extracts were washed with brine, dried over Na$_2$SO$_4$, concentrated in vacuo to afford the E-oxime acid, 3.47 g. ESI-MS m/z 378 (MH)$^+$.

The ether extracts were combined and concentrated. The residue was dissolved in THF (150 mL), MeOH (150 mL) and water (150 mL), and treated with LiOH.H$_2$O (4.41 g, 105 mmol) at RT for 2 days, then concentrated, acidified with 1 N HCl to pH~3, the precipitated solid was collected by filtration, washed with water, and dried in vacuo to yield the pure Z-oxime acid, 9.3 g. ESI-MS m/z 378 (MH)$^+$.

Step 4. Synthesis of tert-butyl 3-(2-((Z)-2-((benzyloxy)imino)-2-(2-((tert-butoxycarbonyl)amino)thiazol-4-yl)acetamido)-2-((3aS,4S,6R)-3a,5,5-trimethylhexahydro-4,6-methanobenzo[d][1,3,2]dioxaborol-2-yl)ethyl)-2-methoxybenzoate

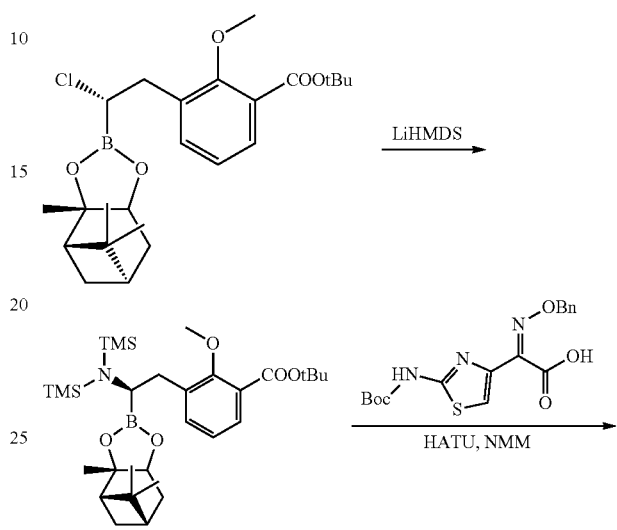

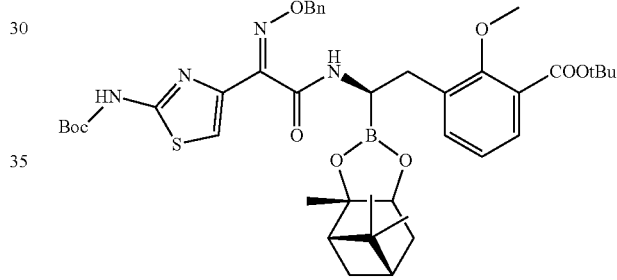

By following General Method C, the chloride (prepared as previous reported, WO2014089365) was treated with LiHMDS, and then coupled with the (Z)-oxime acid from above reaction in the presence of HATU and NMM, yielding the title compound. ESI-MS m/z 789 (MH)$^+$.

Step 5. Synthesis of (R,Z)-3-(2-(2-aminothiazol-4-yl)-2-(hydroxyimino)acetamido)-2-hydroxy-3,4-dihydro-2H-benzo[e][1,2]oxaborinine-8-carboxylic acid

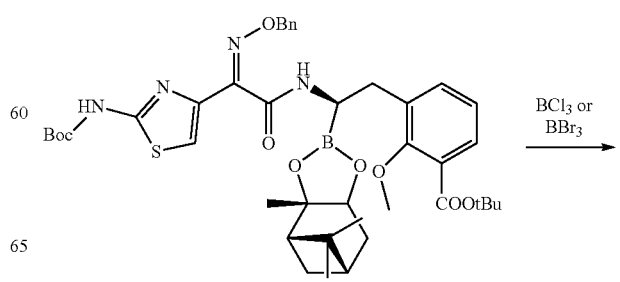

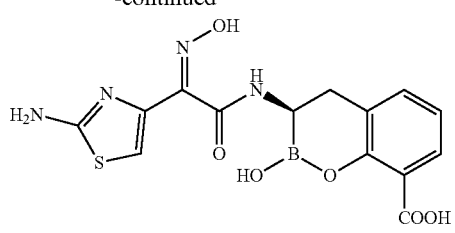

The title compound was prepared by treatment of the above product with either BCl₃ or BBr₃ by following General Method A. ESI-MS m/z 377 (MH)⁺.

Example 1: (R)-3-((R)-2-amino-3-phenylpropanamido)-2-hydroxy-3,4-dihydro-2H-benzo[e][1,2]oxaborinine-8-carboxylic acid

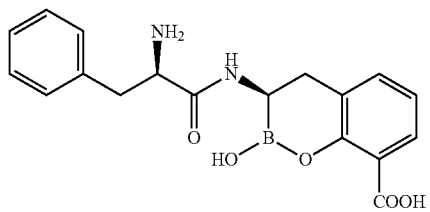 [SMILES: N[C@H](Cc1ccccc1)C(=O)N[C@H]1Cc2cccc(C(=O)O)c2OB1O]

In a similar manner to the synthesis of Example 1A, the title compound was prepared from Boc-D-phenylalanine. ESI-MS m/z 355 (MH)⁺.

Example 2: (R)-3-((R)-2-amino-2-phenylacetamido)-2-hydroxy-3,4-dihydro-2H-benzo[e][1,2]oxaborinine-8-carboxylic acid

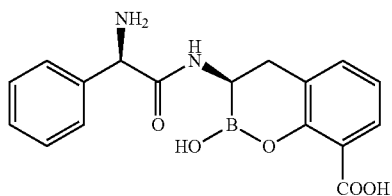 [SMILES: N[C@@H](C(=O)N[C@H]1Cc2cccc(C(=O)O)c2OB1O)c1ccccc1]

Example 3: (R)-3-((S)-2-amino-2-phenylacetamido)-2-hydroxy-3,4-dihydro-2H-benzo[e][1,2]oxaborinine-8-carboxylic acid

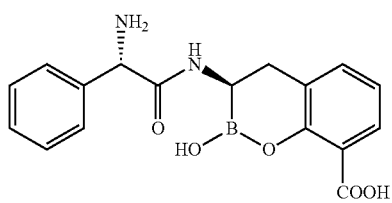

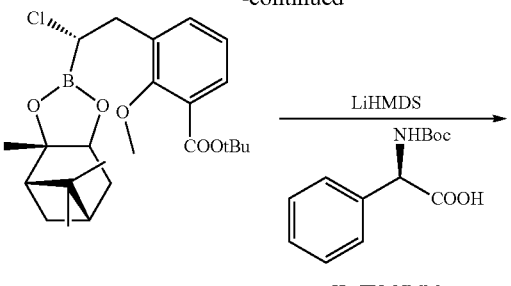

By following General Method C, the chloride was treated with LiHMDS, and then coupled with Boc-D-α-phenylglycine in the presence of HATU and NMM to yield two products after purification by flash chromatography on silica gel (hexane-Et₂O, 4:1-1:2), which were tentatively assigned as the two diastereomers (Boc-D-α-phenylglycine racemized during the reaction). ESI-MS m/z 663 (MH)⁺.

These two products were treated with BCl₃ to afford the two title compounds. ESI-MS m/z 341 (MH)⁺.

Example 4: (R)-3-((R)-2-amino-2-(4-methoxyphenyl)acetamido)-2-hydroxy-3,4-dihydro-2H-benzo[e][1,2]oxaborinine-8-carboxylic acid

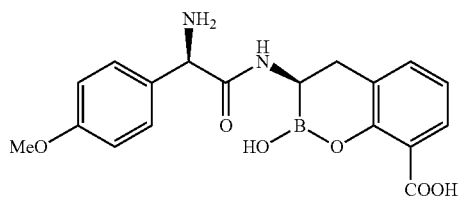

Example 5: (R)-3-((S)-2-amino-2-(4-methoxyphenyl)acetamido)-2-hydroxy-3,4-dihydro-2H-benzo[e][1,2]oxaborinine-8-carboxylic acid

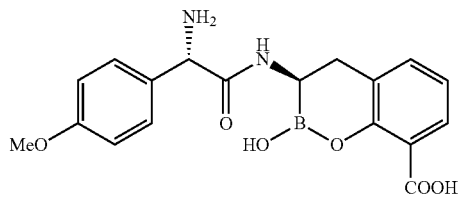

Step 1. Synthesis of (R)-2-((tert-butoxycarbonyl)amino)-2-(4-methoxyphenyl)acetic acid

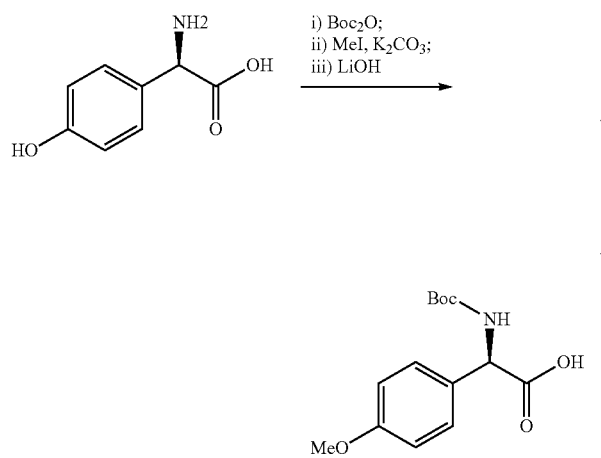

Step 1a. Boc Protection

To 4-hydroxy-D-phenylglycine (5 g, 30 mmol) in dioxane (30 mL) and water (30 mL) was added 1 N NaOH (31 mL, 31 mmol), followed by Boc$_2$O (8.3 g, 38 mmol) in dioxane (30 mL). The reaction mixture was stirred at RT overnight, concentrated, acidified with 1 N HCl to pH~2-3, extracted with EtOAc. The organic extracts were washed with brine, dried over Na$_2$SO$_4$, and concentrated to give the Boc-protected product, which was used for the next step without further purification. ESI-MS m/z 290 (M+Na)$^+$.

Step 1b. Methylation

To the above crude product in DMF (120 mL) was added K$_2$CO$_3$ (10.35 g, 75 mmol) followed by MeI (5.6 mL, 90 mmol). The reaction mixture was stirred at RT overnight, poured into water and extracted with diethyl ether. The ether extracts were washed with water, brine, dried over Na$_2$SO$_4$, and concentrated to give the crude product, which was used for the next step without further purification. ESI-MS m/z 318 (M+Na)$^+$.

Step 1c. Hydrolysis of Methyl Ester

The above crude product was dissolved in THF (60 mL) and water (60 mL), treated with LiOH.H$_2$O (1.93 g, 46 mmol) at RT overnight, standard workup afforded the title compound, 7.9 g. ESI-MS m/z 304 (M+Na)$^+$.

Step 2. Synthesis of (R)-3-((R)-2-amino-2-(4-methoxyphenyl)acetamido)-2-hydroxy-3,4-dihydro-2H-benzo[e][1,2]oxaborinine-8-carboxylic acid and (R)-3-((S)-2-amino-2-(4-methoxyphenyl)acetamido)-2-hydroxy-3,4-dihydro-2H-benzo[e][1,2]oxaborinine-8-carboxylic acid In a similar manner to the synthesis of Example 2 and Example 3, Example 4 and Example 5 were prepared from the above acid. MS m/z 371 (MH)$^+$.

Example 6: (R)-3-((R)-2-amino-2-(4-hydroxyphenyl)acetamido)-2-hydroxy-3,4-dihydro-2H-benzo[e][1,2]oxaborinine-8-carboxylic acid

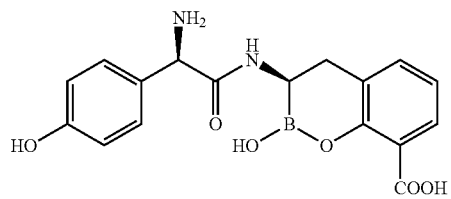 [SMILES: N[C@@H](C(=O)N[C@H]1Cc2cccc(C(=O)O)c2OB1O)c1ccc(O)cc1]

Example 7: (R)-3-((S)-2-amino-2-(4-hydroxyphenyl)acetamido)-2-hydroxy-3,4-dihydro-2H-benzo[e][1,2]oxaborinine-8-carboxylic acid

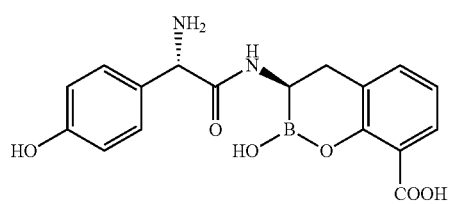 [SMILES: N[C@H](C(=O)N[C@H]1Cc2cccc(C(=O)O)c2OB1O)c1ccc(O)cc1]

In a similar manner to the synthesis of Example 4 and Example 5, and in the last deprotection step using BBr$_3$ instead of BCl$_3$, Example 6 and Example 7 were prepared. MS m/z 357 (MH)$^+$.

Example 8: (R)-3-((R)-2-amino-2-(2-aminothiazol-4-yl)acetamido)-2-hydroxy-3,4-dihydro-2H-benzo[e][1,2]oxaborinine-8-carboxylic acid

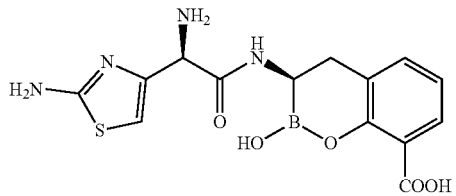 [SMILES: Nc1nc([C@@H](N)C(=O)N[C@H]2Cc3cccc(C(=O)O)c3OB2O)cs1]

Example 9: (R)-3-((S)-2-amino-2-(2-aminothiazol-4-yl)acetamido)-2-hydroxy-3,4-dihydro-2H-benzo[e][1,2]oxaborinine-8-carboxylic acid

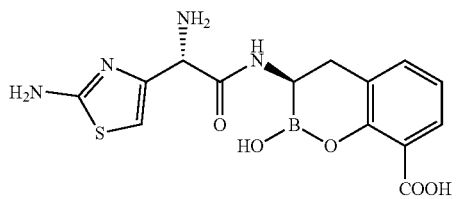 [SMILES: Nc1nc([C@H](N)C(=O)N[C@H]2Cc3cccc(C(=O)O)c3OB2O)cs1]

Step 1. Synthesis of ethyl 2-(2-aminothiazol-4-yl)-2-((tert-butoxycarbonyl)amino)acetate

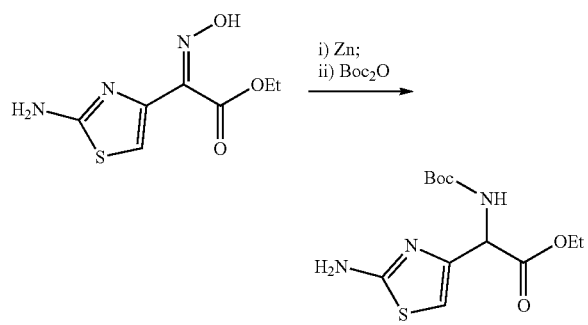

To ethyl 2-amino-α-(hydroxyimino)-4-thiazoleacetate (4.4 g, 20 mmol) in 50% HCOOH (40 mL) and MeOH (20 mL) was added zinc dust (3 g, 46 mmol) at 0° C. The reaction mixture was stirred 0° C. for 3 h, filtered through a pad of Celite, the filtrate was concentrated. To this concentrated mixture was added water (80 mL), basified with $K_2CO_3$ to pH~8-9, then THF (100 mL) was added to the resulting solution followed by $Boc_2O$ (5.24 g, 24 mmol). The reaction was stirred at 0° C. for 1 h, then warmed to RT, added more $Boc_2O$ (1.9 g, 8.7 mmol), stirred for an additional 1 h 40 min, extracted with EtOAc. The organic extracts were dried over $Na_2SO_4$, and concentrated. The crude product was purified by flash chromatography on silica gel (hexane-EtOAc, 10:1-1:3) to afford the title compound, 4.5 g. ESI-MS m/z 302 (MH)+.

Step 2. Synthesis of ethyl 2-((tert-butoxycarbonyl)amino)-2-(2-((tert-butoxycarbonyl)amino)thiazol-4-yl)acetate

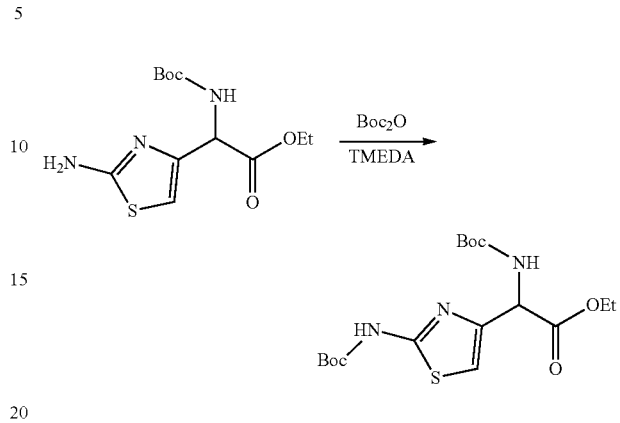

The above product (2.3 g, 7.64 mmol) was dissolved in $CH_3CN$ (50 mL), reacted with $Boc_2O$ (1.9 g, 8.7 mmol) in the presence of TMEDA (3.6 mL, 24 mmol) at RT overnight, then concentrated, and purified by flash chromatography on silica gel (hexane-EtOAc, 10:1-3:2) to afford the title compound, 1.46 g. ESI-MS m/z 402 (MH)+.

Step 3. Synthesis of 2-((tert-butoxycarbonyl)amino)-2-(2-((tert-butoxycarbonyl)amino)thiazol-4-yl)acetic acid

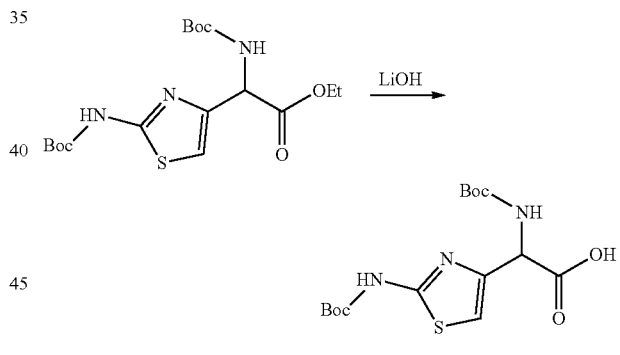

The above product (1.43 g, 3.57 mmol) was dissolved in THF (20 mL) and water (20 mL), treated with $LiOH \cdot H_2O$ (420 mg, 10 mmol) at RT for 2 h, concentrated, acidified with 1 N HCl to pH~3-4, the solid was collected by filtration, dried in vacuo to afford the title compound, 1.3 g. ESI-MS m/z 374 (MH)+.

Step 4. Synthesis of (R)-3-((R)-2-amino-2-(2-aminothiazol-4-yl)acetamido)-2-hydroxy-3,4-dihydro-2H-benzo[e][1,2]oxaborinine-8-carboxylic acid and (R)-3-((S)-2-amino-2-(2-aminothiazol-4-yl)acetamido)-2-hydroxy-3,4-dihydro-2H-benzo[e][1,2]oxaborinine-8-carboxylic acid In a similar manner to the synthesis of Example 2 and Example 3, Example 8 and Example 9 were prepared from the above acid. MS m/z 363 (MH)+.

Example 10: (3R)-3-(2-(2-aminothiazol-4-yl)-2-((carboxymethyl)amino)acetamido)-2-hydroxy-3,4-dihydro-2H-benzo[e][1,2]oxaborinine-8-carboxylic acid

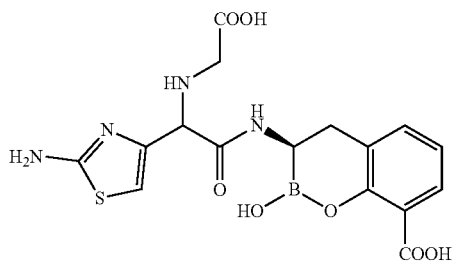 [SMILES: Nc1nc(C(NCC(=O)O)C(=O)N[C@H]2Cc3cccc(C(=O)O)c3OB2O)cs1]

Step 1. Synthesis of ethyl 2-bromo-2-(2-((tert-butoxycarbonyl)amino)thiazol-4-yl)acetate

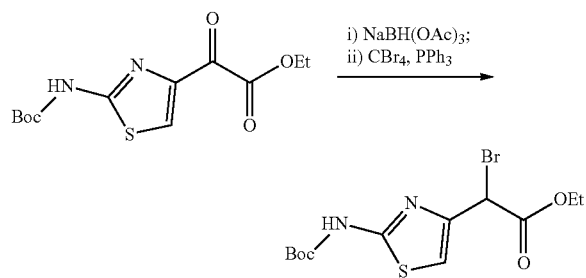

To a solution of ethyl 2-(2-((tert-butoxycarbonyl)amino)thiazol-4-yl)-2-oxoacetate (6 g, 20 mmol) in DCE (200 mL) was added HOAc (2.9 mL, 49.5 mmol) followed by NaBH(OAc)₃ (10.5 g, 49.5 mmol). The reaction mixture was stirred at RT for 1 h, quenched with saturated aqueous NaHCO₃, the organic layer was separated, dried over Na₂SO₄, concentrated to give the alcohol, which was used for the next step without further purification. ESI-MS m/z 303 (MH)⁺.

To the above crude alcohol in DCM (150 mL) was added triphenylphosphine (11 g, 42 mmol), followed by CBr₄ (13.86 g, 42 mmol) at 0° C. under argon. The reaction mixture was stirred at 0° C. for 1 h, then concentrated, and purified by flash chromatography on silica gel (hexane-EtOAc, 20:1-3:1) to afford the title compound, 1.5 g. ESI-MS m/z 365/367 (MH/MH+2)⁺.

Step 2. Synthesis of ethyl 2-((2-(tert-butoxy)-2-oxoethyl)(tert-butoxycarbonyl)amino)-2-(2-((tert-butoxycarbonyl)amino)thiazol-4-yl)acetate

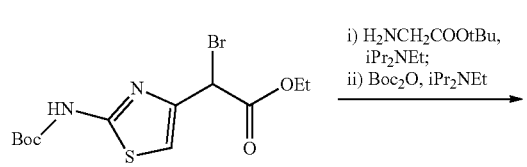

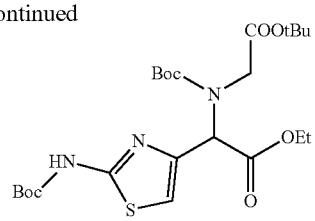

To a mixture of glycine tert-butyl ester hydrochloride (790 mg, 4.7 mmol) in DCM (4 mL) was added saturated aqueous NaHCO₃, extracted with DCM. The organic extracts were combined, dried over Na₂SO₄, concentrated to give glycine tert-butyl ester (free base), 465 mg, as a solid. To this solid was added THF (4 mL) and DCM (3 mL), iPr₂NEt (0.41 mL, 2.36 mmol), followed by dropwise addition of the above bromide (430 mg, 1.18 mmol) in THF (4 mL). The reaction mixture was stirred at RT for 2 h, concentrated to a volume of ~4 mL, stirred for an additional 2 days. To this resulting mixture was added iPr₂NEt (0.615 mL, 3.54 mmol) followed by Boc₂O (772 mg, 3.54 mmol) and THF (4 mL). The reaction mixture was stirred at RT for 3 days, and DCM (3 mL) was added, the resulting clear yellow solution was stirred at RT for an additional 2 h, then concentrated, and purified by flash chromatography on silica gel (DCM-EtOAc, 50:1-5:1) to afford the title compound, 457 mg. ESI-MS m/z 516 (MH)⁺.

Step 3. Synthesis of 2-((2-(tert-butoxy)-2-oxoethyl)(tert-butoxycarbonyl)amino)-2-(2-((tert-butoxycarbonyl)amino)thiazol-4-yl)acetic acid The above product (379 mg, 0.74 mmol) was hydrolyzed with LiOH.H₂O (55.6 mg, 1.32 mmol) under standard reaction condition to give the title acid, 312 mg. ESI-MS m/z 488 (MH)⁺.

Step 4. Synthesis of (3R)-3-(2-(2-aminothiazol-4-yl)-2-((carboxymethyl)amino)acetamido)-2-hydroxy-3,4-dihydro-2H-benzo[e][1,2]oxaborinine-8-carboxylic acid In a similar manner to the synthesis of Example 1A, the title compound was prepared from the above acid. ESI-MS m/z 421 (MH)⁺.

Example 11: (R)-3-((R)-2-(4-ethyl-2,3-dioxopiperazine-1-carboxamido)-2-phenylacetamido)-2-hydroxy-3,4-dihydro-2H-benzo[e][1,2]oxaborinine-8-carboxylic acid

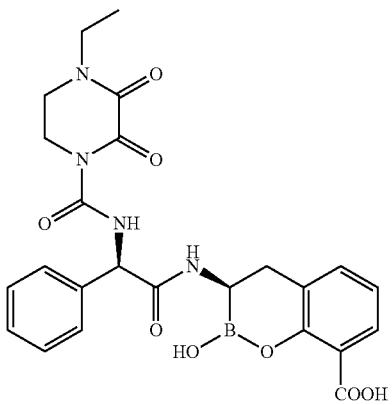 [SMILES: CCN1CCN(C(=O)N[C@@H](C(=O)N[C@H]2Cc3cccc(C(=O)O)c3OB2O)c2ccccc2)C(=O)C1=O]

The title compound was prepared from the commercially available (R)-2-(4-ethyl-2,3-dioxopiperazine-1-carboxamido)-2-phenylacetic acid by following the General Method C and General Method A. ESI-MS m/z 509 (MH)$^+$.

Example 12: (3R)-3-(2-(2-aminothiazol-4-yl)-2-(4-ethyl-2,3-dioxopiperazine-1-carboxamido)acetamido)-2-hydroxy-3,4-dihydro-2H-benzo[e][1,2]oxaborinine-8-carboxylic acid

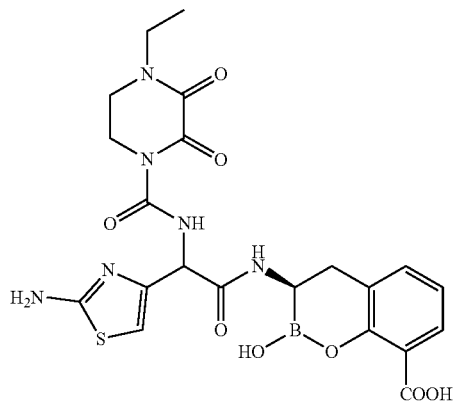 [SMILES: CCN1CCN(C(=O)NC(C(=O)N[C@H]2Cc3cccc(C(=O)O)c3OB2O)c2csc(N)n2)C(=O)C1=O]

Step 1. Synthesis of ethyl 2-(2-(((benzyloxy)carbonyl)amino)thiazol-4-yl)-2-((tert-butoxycarbonyl)amino)acetate

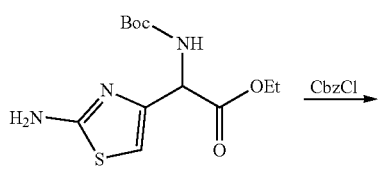

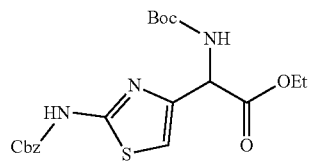

By following standard procedures for CBZ protection of an amine, the title compound was prepared from ethyl 2-(2-aminothiazol-4-yl)-2-((tert-butoxycarbonyl)amino)acetate (from Step 1 of Example 8, Example 9). ESI-MS m/z 436 (MH)$^+$.

Step 2. Synthesis of 2-(2-(((benzyloxy)carbonyl)amino)thiazol-4-yl)-2-((tert-butoxycarbonyl)amino)acetic acid

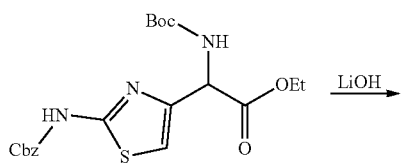

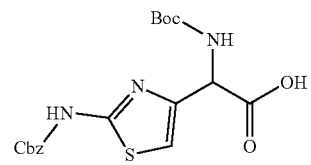

The above product (6.53 g, 15 mmol) in THF (100 mL) and water (100 mL) was treated with lithium hydroxide monohydrate (1.89 g, 45 mmol) at RT for 2 h, then concentrated in vacuo, acidified with 1 N HCl to pH~3-4. The precipitated solid was collected by filtration, washed with water, and dried in vacuo to afford the title compound, 5.8 g. ESI-MS m/z 408 (MH)$^+$.

Step 3. Synthesis of 2-amino-2-(2-(((benzyloxy)carbonyl)amino)thiazol-4-yl)acetic acid

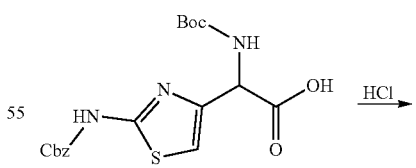

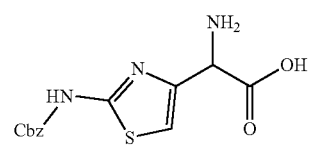

To a solution of the above product (5.8 g, 14.25 mmol) in DCM (120 mL) was added 4.0 M HCl in dioxane solution (60 mL, 240 mmol). The reaction mixture was stirred at RT overnight, diluted with diethyl ether. The precipitated solid was collected by filtration, washed with diethyl ether, and dried in vacuo to afford the title compound as the HCl salt, 4.86 g. ESI-MS m/z 308 (MH)+.

Step 4. Synthesis of 2-(2-(((benzyloxy)carbonyl)amino)thiazol-4-yl)-2-(4-ethyl-2,3-dioxopiperazine-1-carboxamido)acetic acid

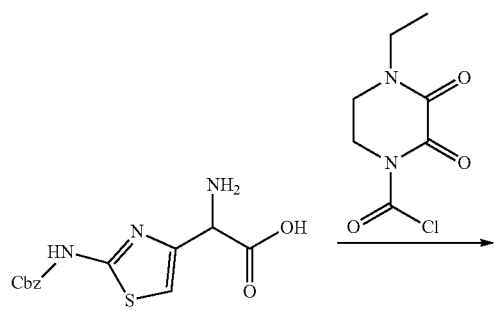

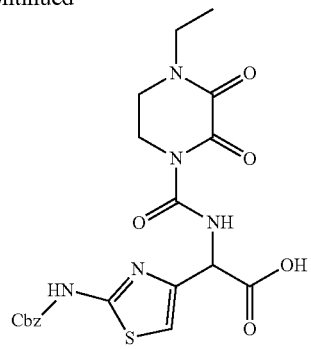

To a solution of the above amino acid (2.06 g, 6 mmol) in THF (60 mL) and water (60 mL) was added a solution of NaOH (480 mg, 12 mmol) in water (5 mL) at 0° C., followed by aqueous saturated $NaHCO_3$ (20 mL), a solution of 4-ethyl-2,3-dioxopiperazine-1-carbonyl chloride (1.54 g, 7.5 mmol) in THF (8 mL), and MeOH (160 mL). The reaction mixture was stirred between 0-10° C. for 1.5 h, then concentrated in vacuo, acidified with 1 N HCl to pH~2, extracted with EtOAc. The organic extracts were combined, dried over $Na_2SO_4$, concentrated in vacuo to afford the crude product, 2.3 g, which was used directly for the next Step without further purification. ESI-MS m/z 476 (MH)+.

Step 5. Synthesis of (3R)-3-(2-(2-aminothiazol-4-yl)-2-(4-ethyl-2,3-dioxopiperazine-1-carboxamido)acetamido)-2-hydroxy-3,4-dihydro-2H-benzo[e][1,2]oxaborinine-8-carboxylic acid

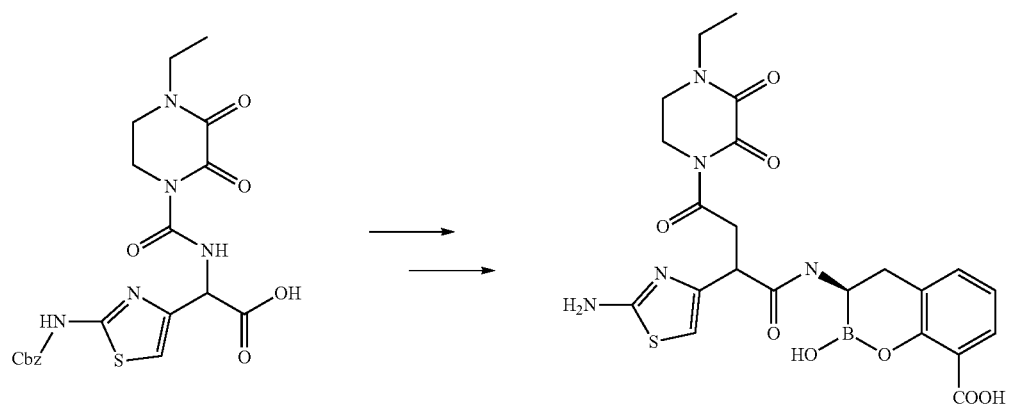 [SMILES: CCN1CCN(C(=O)NC(C(=O)O)c2csc(NC(=O)OCc3ccccc3)n2)C(=O)C1=O ; CCN1CCN(C(=O)CC(C(=O)N[C@H]2Cc3cccc(C(=O)O)c3OB2O)c2csc(N)n2)C(=O)C1=O]

The title compound was prepared from the above acid by following the General Method C and General Method A. ESI-MS m/z 531 (MH)+.

Example 13: (R)-3-(2-(2-aminothiazol-4-yl)-2-((2-(3-(5,5-difluoro-7,9-dimethyl-5H-4λ⁴,5λ⁴-dipyrrolo[1,2-c:2',1'-f][1,3,2]diazaborinin-3-yl)propanamido)ethoxy)imino)acetamido)-2-hydroxy-3,4-dihydro-2H-benzo[e][1,2]oxaborinine-8-carboxylic acid Step 1. Synthesis of (R,Z)-3-(2-((2-aminoethoxy)imino)-2-(2-aminothiazol-4-yl)acetamido)-2-hydroxy-3,4-dihydro-2H-benzo[e][1,2]oxaborinine-8-carboxylic acid

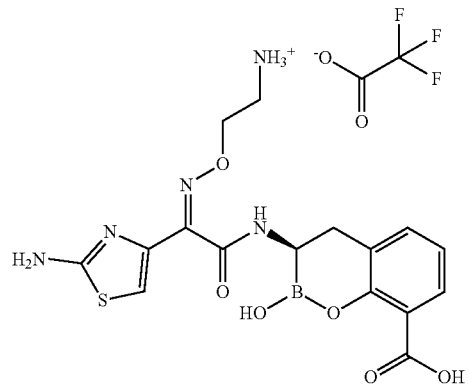

The title compound was prepared according to the method of Example 1A, utilizing tert-butyl (2-(aminooxy)ethyl) carbamate in place of O-benzylhydroxylaminehydrochloride in Step 2, followed by TFA-mediated deprotection of the Boc group, to provide the trifluoroacetate salt as a yellow powder. ESI-MS m/z 420 (MH)+.

Step 2. Synthesis of (R)-3-(2-(2-aminothiazol-4-yl)-2-((2-(3-(5,5-difluoro-7,9-dimethyl-5H-4λ⁴,5λ⁴-dipyrrolo[1,2-c:2',1'-f][1,3,2]diazaborinin-3-yl)propanamido)ethoxy)imino)acetamido)-2-hydroxy-3,4-dihydro-2H-benzo[e][1,2]oxaborinine-8-carboxylic acid

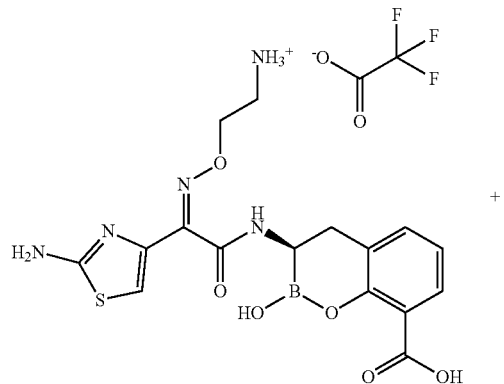

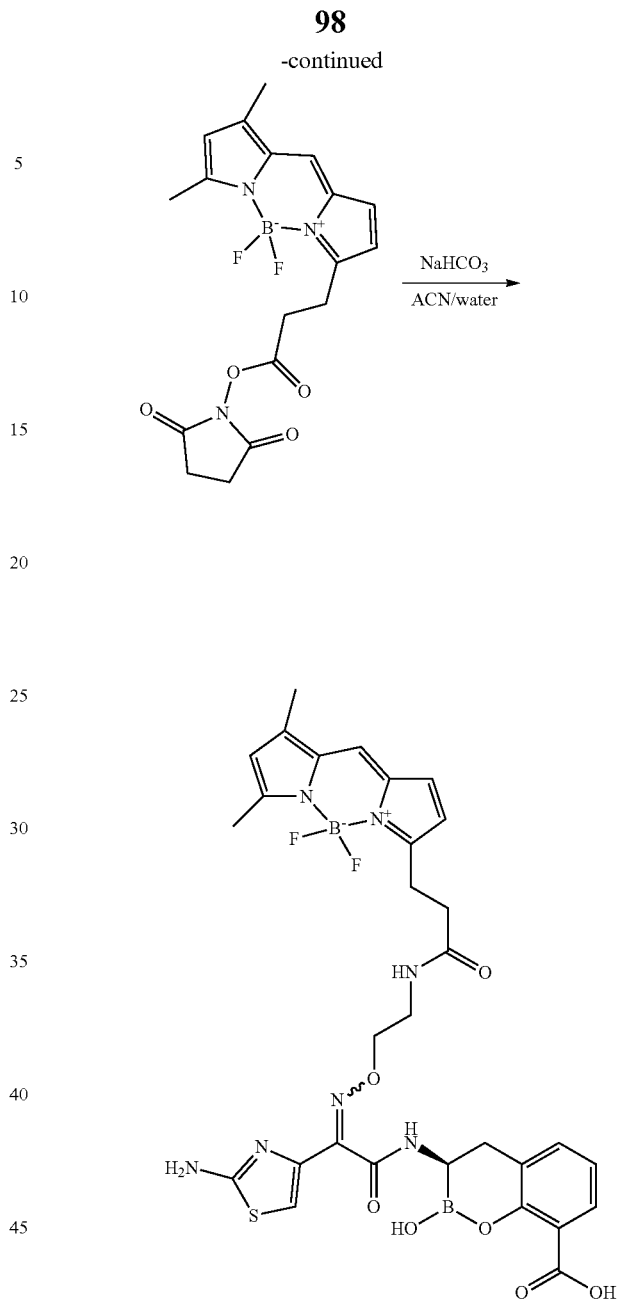

The title compound was prepared using an adaption of a literature procedure (Li, Z., et al., Proc. Nat. Acad. Sci. 2013, 100, 414-419). To a stirred solution of the compound of Step 1 (15.8 mg. 0.03 mmol) and 2,5-dioxopyrrolidin-1-yl 3-(5,5-difluoro-7,9-dimethyl-5H-4λ⁴,5λ⁴-dipyrrolo[1,2-c:2',1'-f][1,3,2]diazaborinin-3-yl)propanoate (BODIPY® FL succinimidyl ester; 7.8 mg, 0.02 mmol) in 1 mL of a 9/1 (v/v) mixture of acetonitrile and water, was added a 1 M aqueous solution of NaHCO₃ (0.1 mL, 0.1 mmol) at 0° C. The reaction mixture was allowed to warm to room temperature and stirred for 5 h. The desired product was isolated by submitting the reaction mixture directly to reverse-phase flash chromatography (C18-Silica gel, water-acetonitrile 0-50% gradient, modified with 0.1% TFA) followed by lyophilization: 12.3 mg orange-red solid (yield: 88%), 1:1 mixture of E/Z oxime-ether isomers; ESI-MS m/z 694.2 (M+H)+.

Example 14: (3R)-3-(2-(2-aminothiazol-4-yl)-2-(3,3-dimethylureido)acetamido)-2-hydroxy-3,4-dihydro-2H-benzo[e][1,2]oxaborinine-8-carboxylic acid

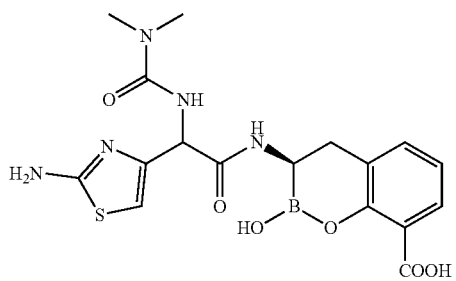 [SMILES: CN(C)C(=O)NC(C(=O)N[C@H]1Cc2cccc(C(=O)O)c2OB1O)c1csc(N)n1]

Step 1. Synthesis of ethyl 2-amino-2-(2-(((benzyloxy)carbonyl)amino)thiazol-4-yl)acetate

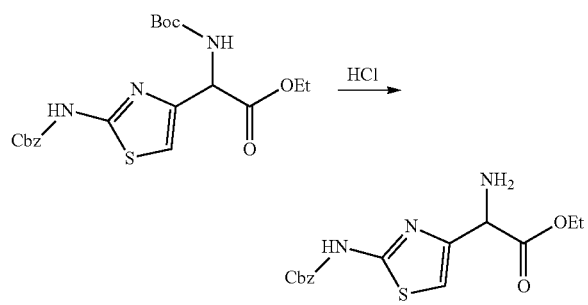

Ethyl 2-(2-(((benzyloxy)carbonyl)amino)thiazol-4-yl)-2-((tert-butoxycarbonyl)amino)acetate (from step 1 of Example 12) (12 g, 27.6 mmol) was dissolved in DCM (200 mL), treated with 4.0 M HCl in dioxane solution (100 mL, 400 mmol) at RT overnight. The reaction mixture was concentrated, the solid was washed with diethyl ether and hexane, and dried in vacuo to afford the title compound as the HCl salt (10 g). ESI-MS m/z 336 (MH)$^+$.

Step 2. Synthesis of ethyl 2-(2-(((benzyloxy)carbonyl)amino)thiazol-4-yl)-2-(3,3-dimethylureido)acetate

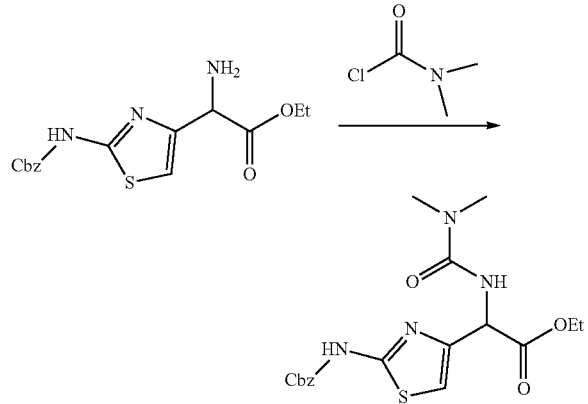

To the above product (1.49 g, 4 mmol) in DCM (40 mL) was added diisopropylethylamine (2.09 mL, 12 mmol), followed by dimethylcarbamyl chloride (0.44 mL, 4.8 mmol). The reaction mixture was stirred at RT overnight, added 4-DMAP (156 mg, 1.28 mmol) and more dimethylcarbamyl chloride (0.88 mL, 9.6 mmol). The reaction mixture was stirred at RT overnight, washed with aqueous saturated NaHCO$_3$, dried over Na$_2$SO$_4$, concentrated. To the residue was added a mixed solvent of hexane and EtOAc (3:1), the solid was collected by filtration, dried in vacuo to afford the product, 1.27 g. ESI-MS m/z 407 (MH)$^+$.

Step 3. Synthesis of 2-(2-(((benzyloxy)carbonyl)amino)thiazol-4-yl)-2-(3,3-dimethylureido)acetic acid

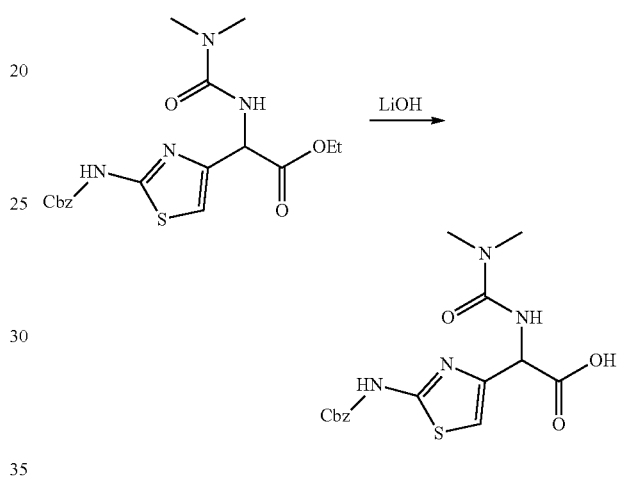

The above product (1.27 g, 3.13 mmol) was hydrolyzed with LiOH.H$_2$O (420 mg, 10 mmol) under standard reaction condition to give the title acid, 1.09 g. ESI-MS m/z 379 (MH)$^+$.

Step 4. Synthesis of (3R)-3-(2-(2-aminothiazol-4-yl)-2-(3,3-dimethylureido)acetamido)-2-hydroxy-3,4-dihydro-2H-benzo[e][1,2]oxaborinine-8-carboxylic acid

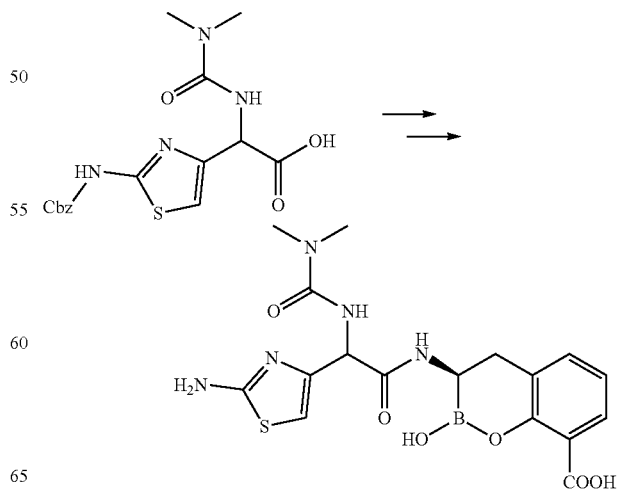

The title compound was prepared from the above acid by following the General Method C and General Method A. ESI-MS m/z 434 (MH)+.

Example 15: (3R)-3-(2-(2-aminothiazol-4-yl)-2-(thiazole-2-carboxamido)acetamido)-2-hydroxy-3,4-dihydro-2H-benzo[e][1,2]oxaborinine-8-carboxylic acid

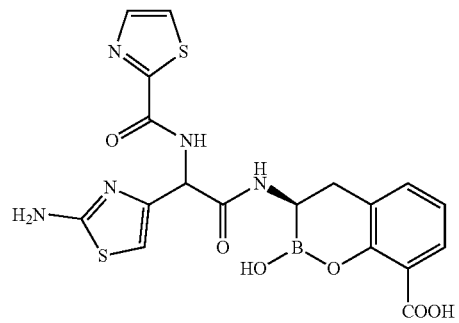 [SMILES: Nc1nc(C(NC(=O)c2nccs2)C(=O)N[C@H]2Cc3cccc(C(=O)O)c3OB2O)cs1]

Step 1. Synthesis of ethyl 2-(2-(((benzyloxy)carbonyl)amino)thiazol-4-yl)-2-(thiazole-2-carboxamido)acetate

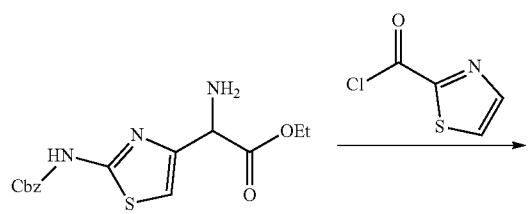

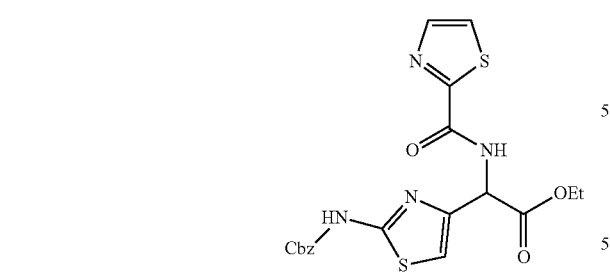

To ethyl 2-amino-2-(2-(((benzyloxy)carbonyl)amino)thiazol-4-yl)acetate hydrochloride (from step 1 of Example 14) (1.49 g, 4 mmol) in DCM (40 mL) was added diisopropylethylamine (2.09 mL, 12 mmol), followed by thiazole-2-carbonyl chloride (738 mL, 5 mmol). The reaction mixture was stirred at RT for 1.5 h, washed with aqueous saturated NaHCO₃, dried over Na₂SO₄, concentrated, and purified by flash chromatography on silica gel (hexane-EtOAc, 10:1-2:1) to afford the product, 1.66 g. ESI-MS m/z 397 (MH)+.

Step 2. Synthesis of (3R)-3-(2-(2-aminothiazol-4-yl)-2-(thiazole-2-carboxamido)acetamido)-2-hydroxy-3,4-dihydro-2H-benzo[e][1,2]oxaborinine-8-carboxylic acid

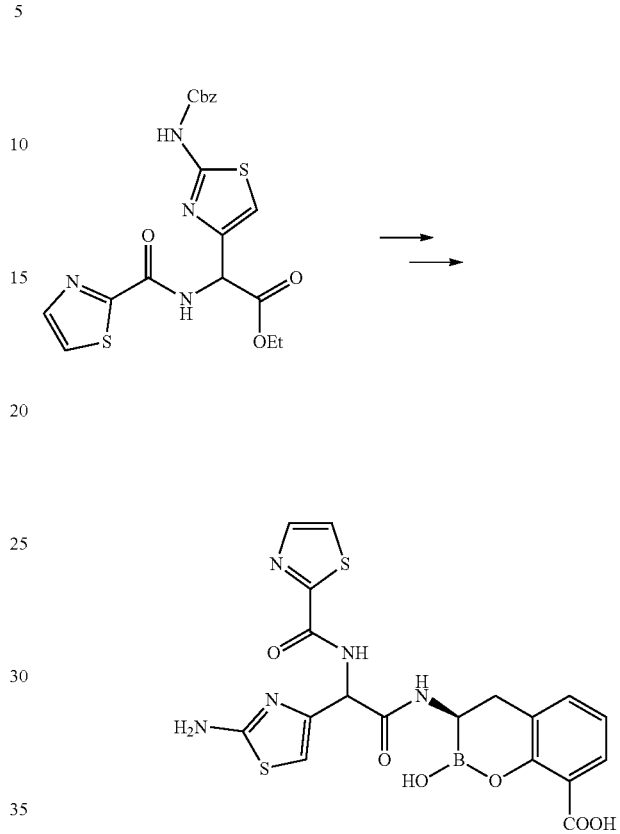

In a similar manner to the synthesis of Example 14, the title compound was prepared from the above product. ESI-MS m/z 474 (MH)+.

Example 16: (3R)-3-(2-(2-aminothiazol-4-yl)-2-(thiazole-4-carboxamido)acetamido)-2-hydroxy-3,4-dihydro-2H-benzo[e][1,2]oxaborinine-8-carboxylic acid

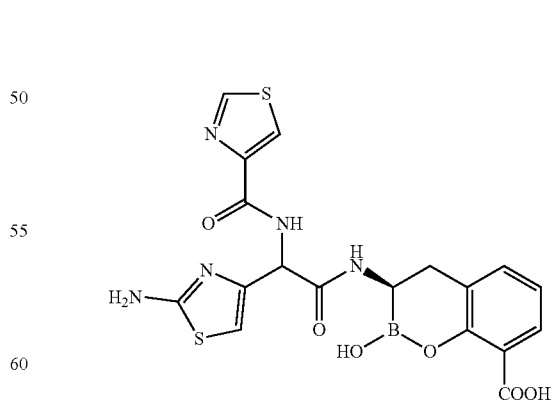

In a similar manner to the synthesis of Example 15, utilizing 1,3-thiazole-4-carbonyl chloride in place of thiazole-2-carbonyl chloride in Step 1, the title compound was prepared. ESI-MS m/z 474 (MH)+.

Example 17: (3R)-3-(2-(2-aminothiazol-4-yl)-2-(2-aminothiazole-4-carboxamido)acetamido)-2-hydroxy-3,4-dihydro-2H-benzo[e][1,2]oxaborinine-8-carboxylic acid

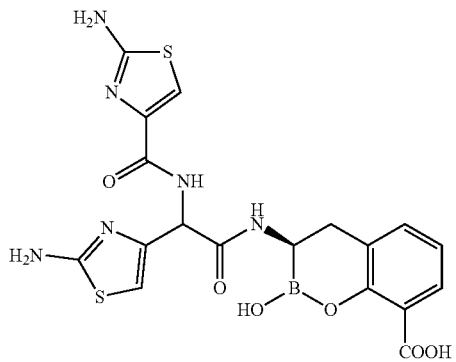 [SMILES: Nc1nc(C(=O)NC(C(=O)N[C@H]2Cc3cccc(C(=O)O)c3OB2O)c2csc(N)n2)cs1]

Step 1. Synthesis of ethyl 2-(2-(((benzyloxy)carbonyl)amino)thiazol-4-yl)-2-(2-((tert-butoxycarbonyl)amino)thiazole-4-carboxamido)acetate

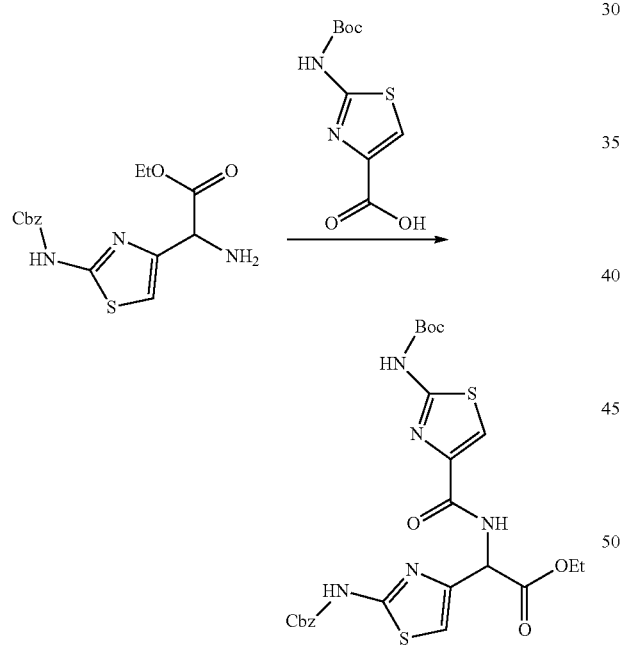

To ethyl 2-amino-2-(2-(((benzyloxy)carbonyl)amino)thiazol-4-yl)acetate hydrochloride (from step 1 of Example 14) (1.49 g, 4 mmol) in DCM (80 mL) was added triethylamine (2.79 mL, 20 mmol), followed by 2-((tert-butoxycarbonyl)amino)thiazole-4-carboxylic acid (1.15 g, 4.7 mmol) and the Mukaiyama reagent (2-chloro-1-methylpyridinium iodide) (1.32 g, 5.17 mmol). The reaction mixture was stirred at RT overnight, washed with aqueous saturated NaHCO$_3$, dried over Na$_2$SO$_4$, concentrated, and purified by flash chromatography on silica gel (hexane-EtOAc, 4:1-1:1) to afford the product, 2.2 g. ESI-MS m/z 562 (MH)$^+$.

Step 2. Synthesis of (3R)-3-(2-(2-aminothiazol-4-yl)-2-(2-aminothiazole-4-carboxamido)acetamido)-2-hydroxy-3,4-dihydro-2H-benzo[e][1,2]oxaborinine-8-carboxylic acid

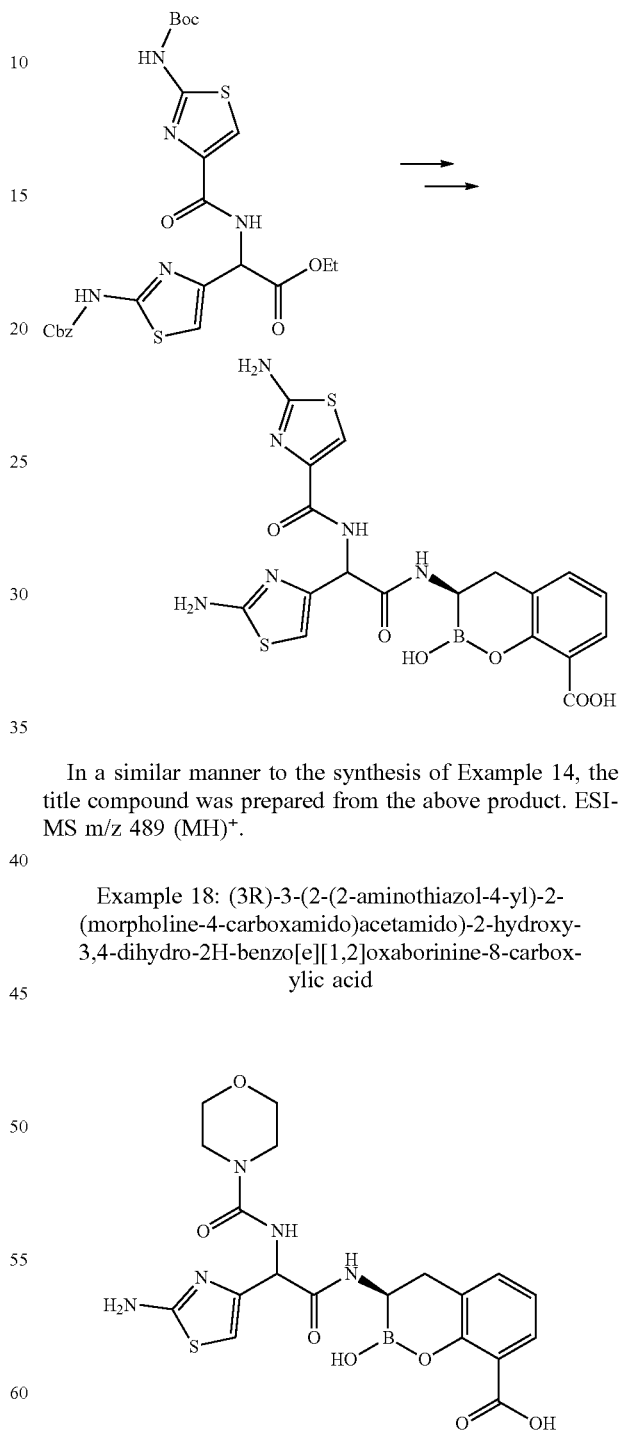

In a similar manner to the synthesis of Example 14, the title compound was prepared from the above product. ESI-MS m/z 489 (MH)$^+$.

Example 18: (3R)-3-(2-(2-aminothiazol-4-yl)-2-(morpholine-4-carboxamido)acetamido)-2-hydroxy-3,4-dihydro-2H-benzo[e][1,2]oxaborinine-8-carboxylic acid In a similar manner to the synthesis of Example 14, utilizing 4-morpholinecarbonyl chloride in place of dimethylcarbamyl chloride in Step 2, the title compound was prepared. ESI-MS m/z 476 (MH)$^+$.

Example 19: (3R)-3-(2-(2-aminothiazol-4-yl)-2-(2-oxoimidazolidine-1-carboxamido)acetamido)-2-hydroxy-3,4-dihydro-2H-benzo[e][1,2]oxaborinine-8-carboxylic acid

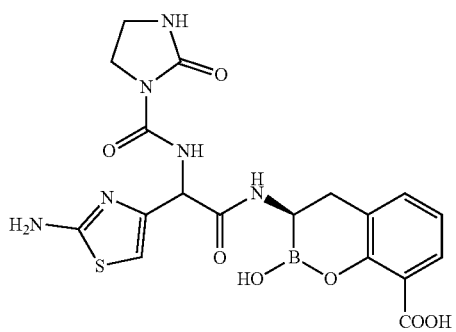 [SMILES: Nc1nc(C(NC(=O)N2CCNC2=O)C(=O)N[C@H]2Cc3cccc(C(=O)O)c3OB2O)cs1]

In a similar manner to the synthesis of Example 12, utilizing 2-oxoimidazolidine-1-carbonyl chloride in place of 4-ethyl-2,3-dioxopiperazine-1-carbonyl chloride in Step 4, the title compound was prepared. ESI-MS m/z 475 (MH)+.

Example 20: (3R)-3-(2-(2-aminothiazol-4-yl)-2-(3-(methylsulfonyl)-2-oxoimidazolidine-1-carboxamido)acetamido)-2-hydroxy-3,4-dihydro-2H-benzo[e][1,2]oxaborinine-8-carboxylic acid

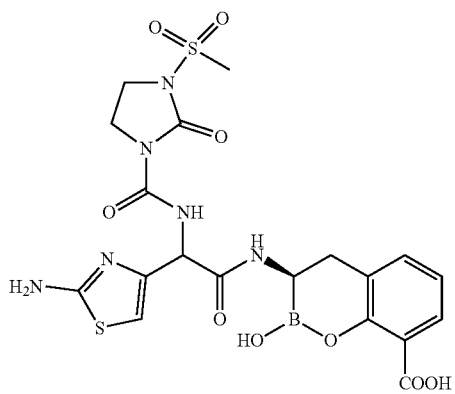 [SMILES: CS(=O)(=O)N1CCN(C(=O)NC(C(=O)N[C@H]2Cc3cccc(C(=O)O)c3OB2O)c2csc(N)n2)C1=O]

In a similar manner to the synthesis of Example 12, utilizing 3-(methylsulfonyl)-2-oxoimidazolidine-1-carbonyl chloride in place of 4-ethyl-2,3-dioxopiperazine-1-carbonyl chloride in Step 4, the title compound was prepared. ESI-MS m/z 553 (MH)+.

Example 21: (3R)-3-(2-(2-aminothiazol-4-yl)-2-(2-(pyrimidin-2-yl)acetamido)acetamido)-2-hydroxy-3,4-dihydro-2H-benzo[e][1,2]oxaborinine-8-carboxylic acid

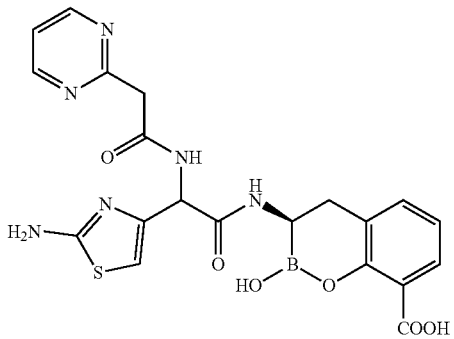 [SMILES: Nc1nc(C(NC(=O)Cc2ncccn2)C(=O)N[C@H]2Cc3cccc(C(=O)O)c3OB2O)cs1]

In a similar manner to the synthesis of Example 17, utilizing 2-pyrimidineacetic acid in place of 2-((tert-butoxycarbonyl)amino)thiazole-4-carboxylic acid in Step 1, the title compound was prepared. ESI-MS m/z 483 (MH)+.

Example 22: (3R)-3-(2-(2-aminothiazol-4-yl)-2-(2-(2-aminothiazol-4-yl)acetamido)acetamido)-2-hydroxy-3,4-dihydro-2H-benzo[e][1,2]oxaborinine-8-carboxylic acid

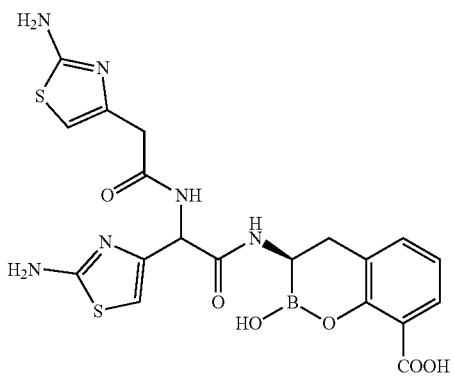 [SMILES: Nc1nc(CC(=O)NC(C(=O)N[C@H]2Cc3cccc(C(=O)O)c3OB2O)c2csc(N)n2)cs1]

In a similar manner to the synthesis of Example 17, utilizing 2-(2-((tert-butoxycarbonyl)amino)thiazol-4-yl)acetic acid in place of 2-((tert-butoxycarbonyl)amino)thiazole-4-carboxylic acid in Step 1, the title compound was prepared. ESI-MS m/z 503 (MH)+.

Example 23: (3R)-3-(2-(2-aminothiazol-4-yl)-2-((N,N-dimethylsulfamoyl)amino)acetamido)-2-hydroxy-3,4-dihydro-2H-benzo[e][1,2]oxaborinine-8-carboxylic acid

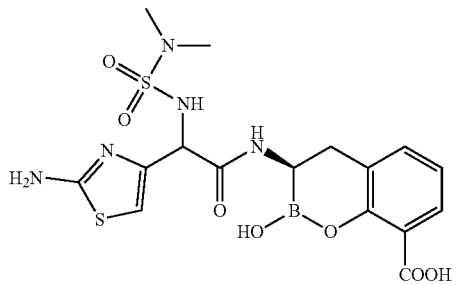 [SMILES: CN(C)S(=O)(=O)NC(C(=O)N[C@H]1Cc2cccc(C(=O)O)c2OB1O)c1csc(N)n1]

Step 1. Synthesis of ethyl 2-(2-(((benzyloxy)carbonyl)amino)thiazol-4-yl)-2-((N,N-dimethylsulfamoyl)amino)acetate

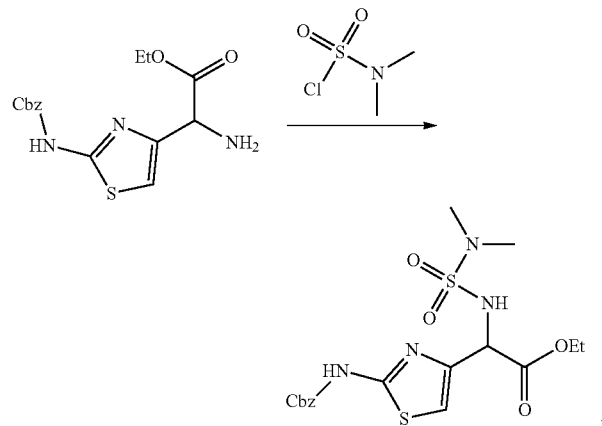

To ethyl 2-amino-2-(2-(((benzyloxy)carbonyl)amino)thiazol-4-yl)acetate hydrochloride (from step 1 of Example 14) (2.98 g, 8 mmol) in DCM (60 mL) was added diisopropylethylamine (5.6 mL, 32 mmol), followed by N,N-dimethylsulfamoyl chloride (2.58 mL, 24 mmol) and 4-DMAP (292 mg, 2.4 mmol). The reaction mixture was refluxed overnight, cooled to RT, washed with aqueous saturated NaHCO₃, dried over Na₂SO₄, concentrated, and purified by flash chromatography on silica gel (hexane-acetone, 10:1-1:1) to afford the product, 1 g. ESI-MS m/z 443 (MH)⁺.

Step 2. Synthesis of (3R)-3-(2-(2-aminothiazol-4-yl)-2-((N,N-dimethylsulfamoyl)amino)acetamido)-2-hydroxy-3,4-dihydro-2H-benzo[e][1,2]oxaborinine-8-carboxylic acid

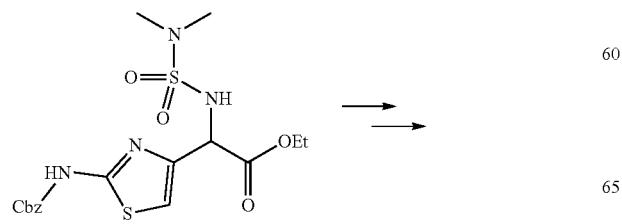

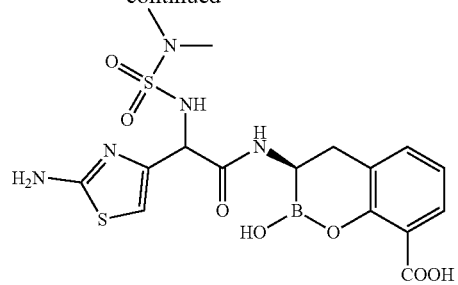

In a similar manner to the synthesis of Example 14, the title compound was prepared from the above product. ESI-MS m/z 474 (MH)⁺.

Example 24: (3R)-3-(2-(2-aminothiazol-4-yl)-2-(morpholine-4-sulfonamido)acetamido)-2-hydroxy-3,4-dihydro-2H-benzo[e][1,2]oxaborinine-8-carboxylic acid

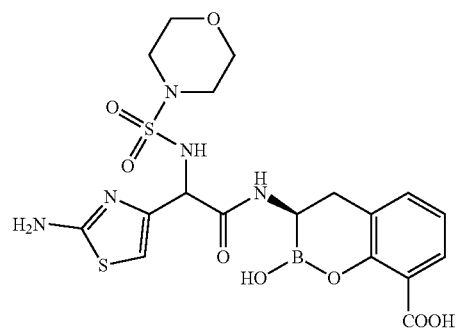 [SMILES: Nc1nc(C(NS(=O)(=O)N2CCOCC2)C(=O)N[C@H]2Cc3cccc(C(=O)O)c3OB2O)cs1]

In a similar manner to the synthesis of Example 23, utilizing morpholine-4-sulfonyl chloride in place of N,N-dimethylsulfamoyl chloride in Step 1, the title compound was prepared. ESI-MS m/z 512 (MH)⁺.

Example 25: (3R)-3-(2-(2-aminothiazol-4-yl)-2-(3-ethylureido)acetamido)-2-hydroxy-3,4-dihydro-2H-benzo[e][1,2]oxaborinine-8-carboxylic acid

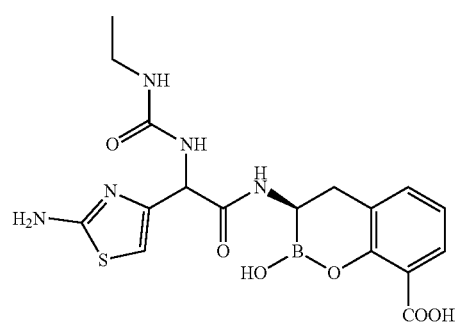 [SMILES: CCNC(=O)NC(C(=O)N[C@H]1Cc2cccc(C(=O)O)c2OB1O)c1csc(N)n1]

Step 1. Synthesis of tert-butyl 3-((2R)-2-(2-(2-(((benzyloxy)carbonyl)amino)thiazol-4-yl)-2-((tert-butoxycarbonyl)amino)acetamido)-2-((3aS,4S,6R)-3a,5,5-trimethylhexahydro-4,6-methanobenzo[d][1,3,2]dioxaborol-2-yl)ethyl)-2-methoxybenzoate

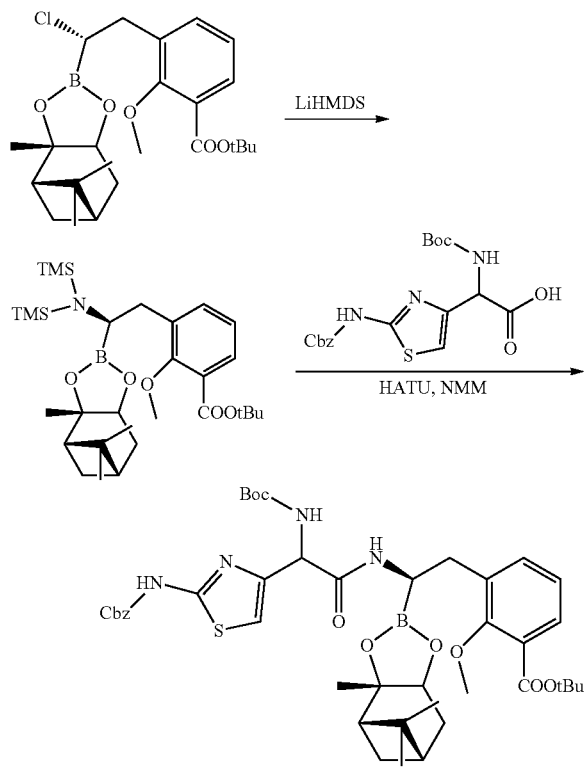

By following the general procedure C, the chloride (prepared as previous reported, WO 2014/089365) was treated with LiHMDS, and then coupled with 2-(2-(((benzyloxy)carbonyl)amino)thiazol-4-yl)-2-((tert-butoxycarbonyl)amino)acetic acid (from step 2 of Example 12) in the presence of HATU and NMM, yielding the title compound. ESI-MS m/z 819 (MH)⁺.

Step 2. Synthesis of tert-butyl 3-((2R)-2-(2-amino-2-(2-(((benzyloxy)carbonyl)amino)thiazol-4-yl)acetamido)-2-((3aS,4S,6R)-3a,5,5-trimethylhexahydro-4,6-methanobenzo[d][1,3,2]dioxaborol-2-yl)ethyl)-2-methoxybenzoate

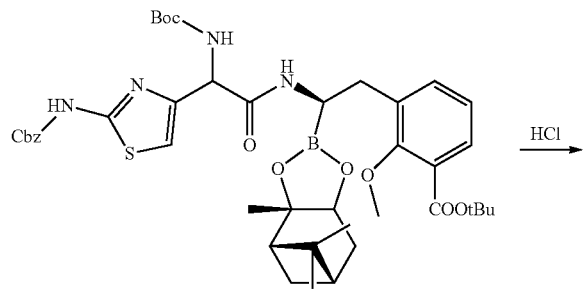

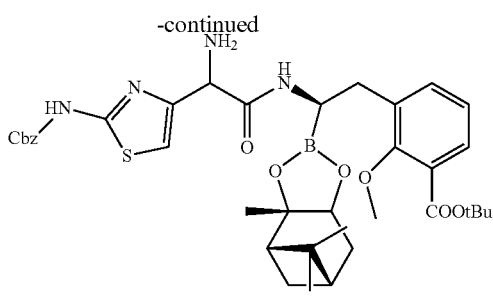

To above product (3 g, 3.66 mmol) was added cold solution of 1.0 M HCl in diethyl ether (100 mL, 100 mmol). The reaction mixture was stirred at RT overnight, and concentrated in vacuo, the residue was washed with hexane, dried in vacuo to afford the title compound as the HCl salt, which was used directly for the next step without further purification. ESI-MS m/z 719 (MH)⁺.

Step 3. Synthesis of tert-butyl 3-((2R)-2-(2-(2-(((benzyloxy)carbonyl)amino)thiazol-4-yl)-2-(3-ethylureido)acetamido)-2-((3aS,4S,6R)-3a,5,5-trimethylhexahydro-4,6-methanobenzo[d][1,3,2]dioxaborol-2-yl)ethyl)-2-methoxybenzoate

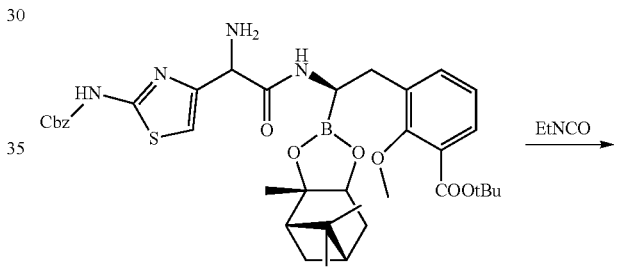

To above product (604 mg, 0.8 mmol) at 0° C. was added diisopropylethylamine (0.21 mL, 1.2 mmol) followed by a DCM (1 mL) solution of ethyl isocyanate (71 mg, 1 mmol). The reaction mixture was allowed to warm up to RT over 1.5 h, washed with water and brine, dried over Na₂SO₄, concentrated, and purified by flash chromatography on silica gel (hexane-acetone, 2:1-1:3) to yield the product, 270 mg. ESI-MS m/z 790 (MH)⁺.

Step 4. Synthesis of (3R)-3-(2-(2-aminothiazol-4-yl)-2-(3-ethylureido)acetamido)-2-hydroxy-3,4-dihydro-2H-benzo[e][1,2]oxaborinine-8-carboxylic acid

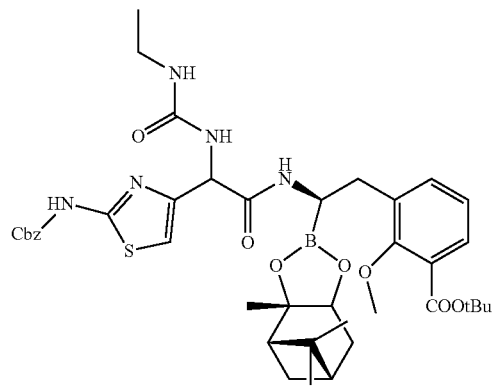

By following the General Method A, the above product was treated with BCl₃ to afford the title compound. ESI-MS m/z 434 (MH)⁺.

Example 26: (3R)-3-(2-(2-aminothiazol-4-yl)-2-(sulfamoylamino)acetamido)-2-hydroxy-3,4-dihydro-2H-benzo[e][1,2]oxaborinine-8-carboxylic acid

Step 1. Synthesis of tert-butyl 3-((2R)-2-(2-(2-(((benzyloxy)carbonyl)amino)thiazol-4-yl)-2-((N-(tert-butoxycarbonyl)sulfamoyl)amino)acetamido)-2-((3aS,4S,6R)-3a,5,5-trimethylhexahydro-4,6-methanobenzo[d][1,3,2]dioxaborol-2-yl)ethyl)-2-methoxybenzoate

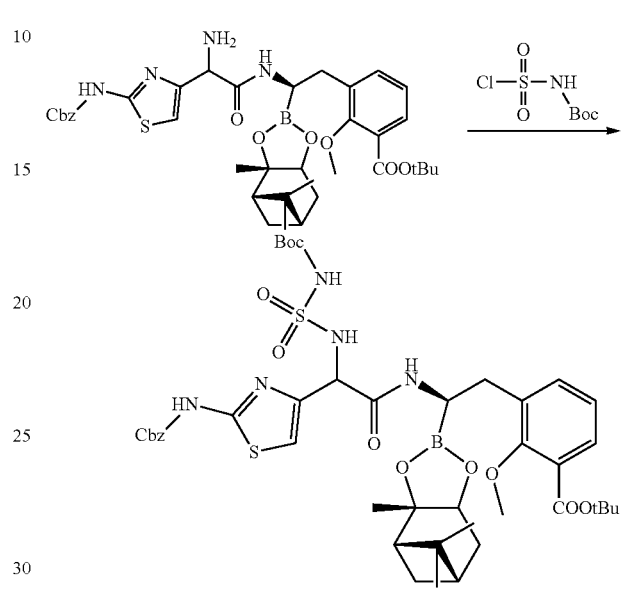

To a DCM (5 mL) solution of chlorosulfonylisocyanate (156 mg, 1.1 mmol) at 0° C. was added a DCM (1 mL) solution of tBuOH (82 mg, 1.1 mmol). After stirred at 0° C. for 30 min, the reaction mixture and diisopropylethylamine (0.21 mL, 1.2 mmol) were added to a cold DCM (10 mL) solution of the amine intermediate (product from step 2 of Example 25) (755 mg, 1 mmol) and diisopropylethylamine (0.19 mL, 1.1 mmol). The reaction mixture was stirred at RT for 2 h, washed with water and brine, dried over Na₂SO₄, concentrated, and purified by flash chromatography on silica gel (hexane-acetone, 10:1-1:1) to yield the product, 480 mg. ESI-MS m/z 898 (MH)⁺.

Step 2. Synthesis of (3R)-3-(2-(2-aminothiazol-4-yl)-2-(sulfamoylamino)acetamido)-2-hydroxy-3,4-dihydro-2H-benzo[e][1,2]oxaborinine-8-carboxylic acid

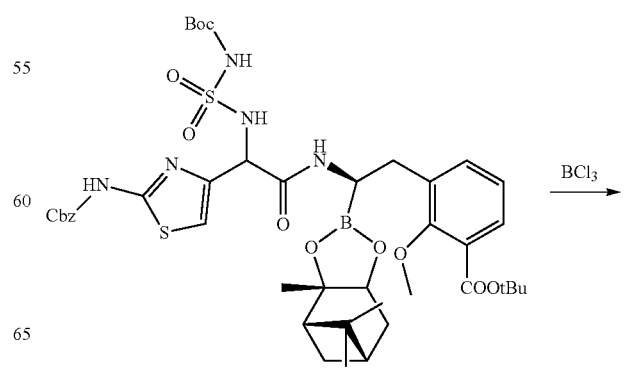

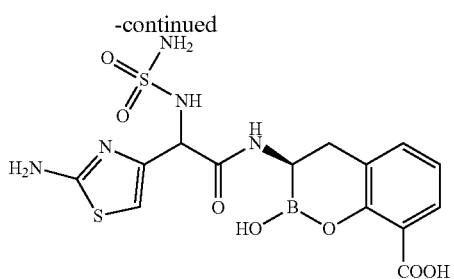

By following the General Method A, the above product was treated with BCl₃ to afford the title compound. ESI-MS m/z 442 (MH)⁺.

Example 27: (3R)-3-(2-(2-aminothiazol-4-yl)-2-(3-ethylureido)acetamido)-2-hydroxy-3,4-dihydro-2H-benzo[e][1,2]oxaborinine-8-carboxylic acid

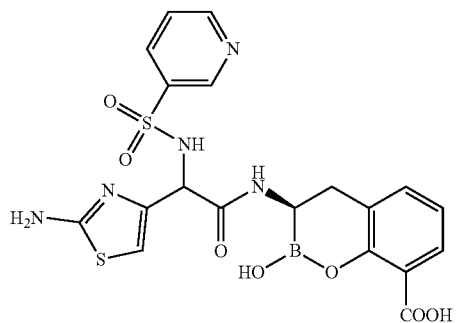 [SMILES: Nc1nc(C(NS(=O)(=O)c2cccnc2)C(=O)N[C@H]2Cc3cccc(C(=O)O)c3OB2O)cs1]

Step 1. Synthesis of tert-butyl 3-((2R)-2-(2-(2-(((benzyloxy)carbonyl)amino)thiazol-4-yl)-2-(pyridine-3-sulfonamido)acetamido)-2-((3aS,4S,6R)-3a,5,5-trimethylhexahydro-4,6-methanobenzo[d][1,3,2]dioxaborol-2-yl)ethyl)-2-methoxybenzoate

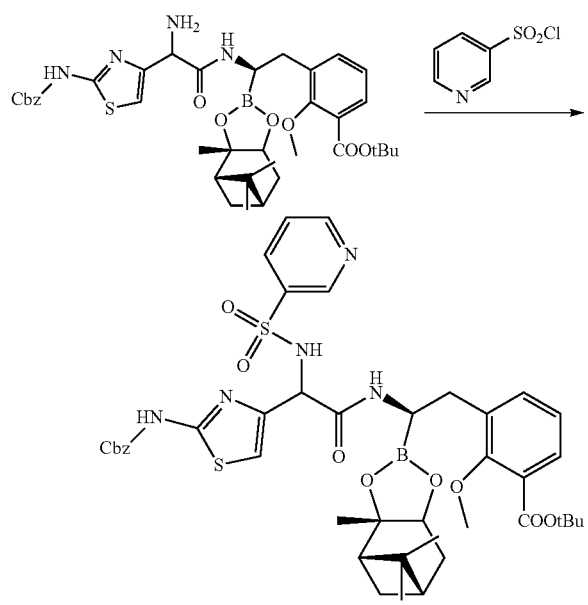

To the amine intermediate (product from step 2 of Example 25) (604 mg, 0.8 mmol) at 0° C. was added diisopropylethylamine (0.37 mL, 2.1 mmol) followed by a DCM (1 mL) solution of pyridine-3-sulfonyl chloride (178 mg, 1 mmol). The reaction mixture was allowed to warm up to RT over 1.5 h, washed with water and brine, dried over Na₂SO₄, concentrated, and purified by flash chromatography on silica gel (hexane-acetone, 4:1-2:3) to yield the product, 260 mg. ESI-MS m/z 860 (MH)⁺.

Step 2. Synthesis of (3R)-3-(2-(2-aminothiazol-4-yl)-2-(pyridine-3-sulfonamido)acetamido)-2-hydroxy-3,4-dihydro-2H-benzo[e][1,2]oxaborinine-8-carboxylic acid

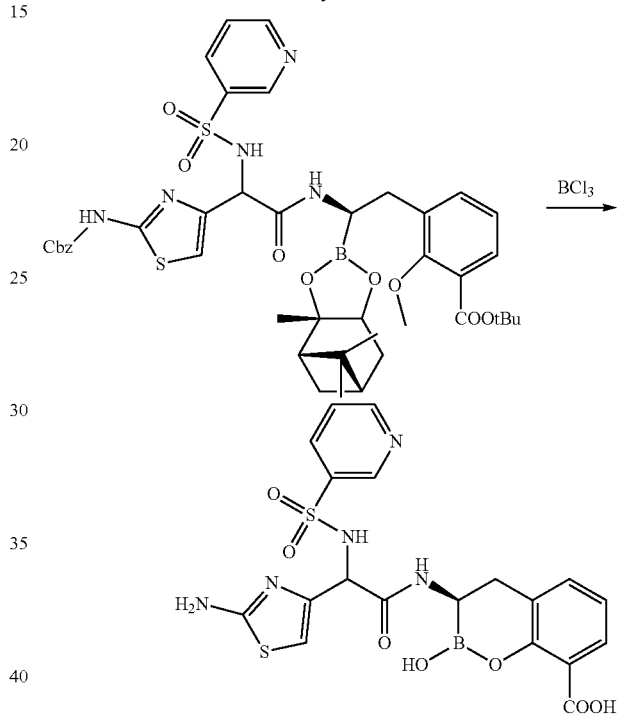

By following the General Method A, the above product was treated with BCl₃ to afford the title compound. ESI-MS m/z 504 (MH)⁺.

Example 28: (3R)-3-(2-(2-aminothiazol-4-yl)-2-(2-methoxy-2-oxoacetamido)acetamido)-2-hydroxy-3,4-dihydro-2H-benzo[e][1,2]oxaborinine-8-carboxylic acid

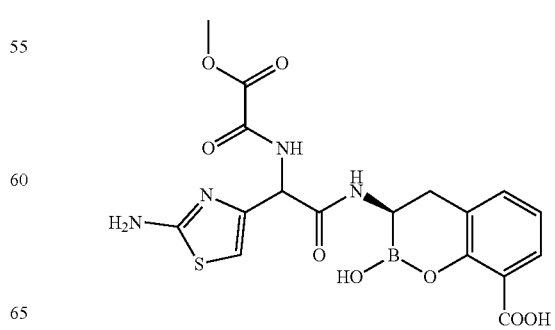

In a similar manner to the synthesis of Example 27, utilizing methyl chlorooxoacetate in place of pyridine-3-sulfonyl chloride in Step 1, the title compound was prepared. ESI-MS m/z 449 (MH)⁺.

Example 29: (3R)-3-(2-(2-aminothiazol-4-yl)-2-(2-hydroxyacetamido)acetamido)-2-hydroxy-3,4-dihydro-2H-benzo[e][1,2]oxaborinine-8-carboxylic acid

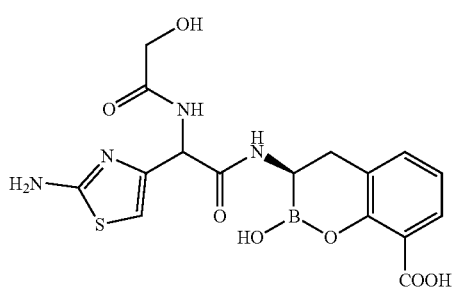 [SMILES: Nc1nc(C(NC(=O)CO)C(=O)N[C@H]2Cc3cccc(C(=O)O)c3OB2O)cs1]

In a similar manner to the synthesis of Example 27, utilizing benzyloxyacetyl chloride in place of pyridine-3-sulfonyl chloride in Step 1, the title compound was prepared. ESI-MS m/z 421 (MH)⁺.

Example 30: (3R)-3-(2-(2-aminothiazol-4-yl)-2-(3-(pyridin-3-yl)ureido)acetamido)-2-hydroxy-3,4-dihydro-2H-benzo[e][1,2]oxaborinine-8-carboxylic acid

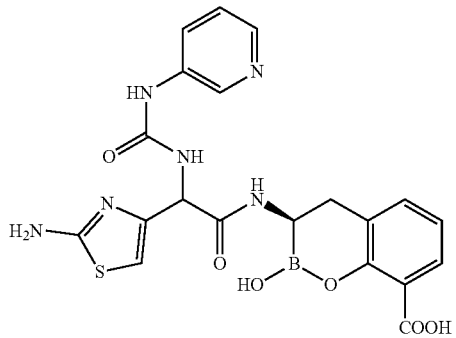 [SMILES: Nc1nc(C(NC(=O)Nc2cccnc2)C(=O)N[C@H]2Cc3cccc(C(=O)O)c3OB2O)cs1]

In a similar manner to the synthesis of Example 25, utilizing 3-isocyanatopyridine in place of ethyl isocyanate in Step 3, the title compound was prepared. ESI-MS m/z 483 (MH)⁺.

Example 31: (R)-3-((S)-2-(4-Ethyl-2,3-dioxopiperazine-1-carboxamido)propanamido)-2-hydroxy-3,4-dihydro-2H-benzo[e][1,2]oxaborinine-8-carboxylic acid

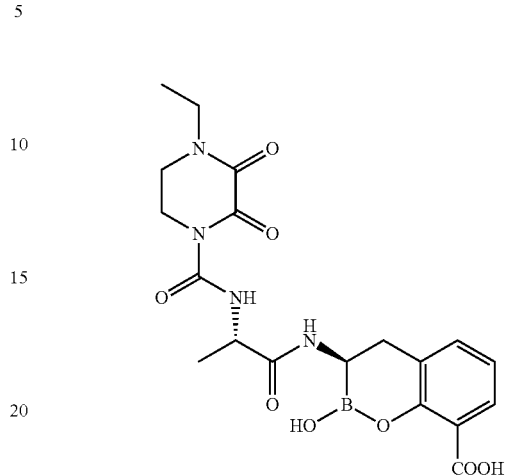

Step 1. Synthesis of (4-Ethyl-2,3-dioxopiperazine-1-carbonyl)-L-alanine

To a stirred solution of L-alanine (178 mg, 2.0 mmol) in a mixture (40 mL) of tetrahydrofuran (THF) and water (1:1, v/v) was added a saturated solution of sodium bicarbonate in water (6 mL) at 0° C. 4-Ethyl-2,3-dioxopiperazine-1-carbonyl chloride (512 mg, 2.5 mmol, 1.25 eq.) in THF (3 mL) was added dropwise, and the reaction was stirred at 0° C. for 2 h. The volatiles were evaporated under reduced pressure and the resulting aqueous solution was neutralized at 0° C. with 2N HCl to pH 2, and extracted 3 times with ethyl acetate (50 mL each). The combined organic extracts were dried on Na₂SO₄, then filtered, and the solvent was evaporated under reduced pressure to generate (4-ethyl-2,3-dioxopiperazine-1-carbonyl)-L-alanine (380 mg), which was used in the next step without further purification.

Step 2. Synthesis of tert-Butyl 3-((2R)-2-((S)-2-(4-Ethyl-2,3-dioxopiperazine-1-carboxamido)-propanamido)-2-((3aS,4S,6S)-3a,5,5-trimethylhexahydro-4,6-methanobenzo[d][1,3,2]dioxaborol-2-yl)ethyl)-2-methoxybenzoate Step 2a A solution of tert-butyl 3-((2S)-2-chloro-2-((3aS,4S,6S)-3a,5,5-trimethylhexahydro-4,6-methanobenzo[d][1,3,2]dioxaborol-2-yl)ethyl)-2-methoxybenzoate (450 mg, 1.0 mmol) in THF (5 mL), stirred at −40° C. under an atmosphere of argon, was treated dropwise with a 1M solution of lithium bis(trimethylsilyl)amide (LHMDS) in THF (1 mL, 1 mmol, 1 eq.). After 5 min the reaction was allowed to warm to room temperature and was stirred for 1 h.

Step 2b

In a separate flask, (4-ethyl-2,3-dioxopiperazine-1-carbonyl)-L-alanine (283 mg, 1.1 mmol, 1.1 eq.), prepared as described in Step 1, in N,N-dimethylacetamide (DMA) (3 mL) was treated with 1-[bis(dimethylamino)methylene]-1H-1,2,3-triazolo[4,5-b]pyridinium 3-oxid hexafluorophosphate (HATU; 456.5 mg, 1.2 mmol, 1.2 eq) and 4-methylmorpholine (NMM; 0.15 mL, 1.3 mmol, 1.3 eq). The reaction mixture generated in Step 2(a) was added and stirring was continued for 12 h. The reaction mixture was diluted with water (20 mL) and extracted three times with diethyl ether (30 ml each). The combined organic extracts were dried on $Na_2SO_4$, then filtered, and the solvent was evaporated under reduced pressure. The product was isolated by flash-chromatography (Silica gel, ethyl acetate-hexanes, 0-100%): tert-butyl 3-((2R)-2-((S)-2-(4-ethyl-2,3-dioxopiperazine-1-carboxamido)propanamido)-2-((3aS,4S,6S)-3a,5,5-trimethylhexahydro-4,6-methanobenzo[d][1,3,2]dioxaborol-2-yl)ethyl)-2-methoxybenzoate (322 mg).

Step 3. (R)-3-((S)-2-(4-Ethyl-2,3-dioxopiperazine-1-carboxamido)propanamido)-2-hydroxy-3,4-dihydro-2H-benzo[e][1,2]oxaborinine-8-carboxylic acid To a stirred solution of tert-butyl 3-((2R)-2-((S)-2-(4-ethyl-2,3-dioxopiperazine-1-carboxamido)propanamido)-2-((3aS,4S,6S)-3a,5-trimethylhexahydro-4,6-methanobenzo[d][1,3,2]dioxaborol-2-yl)ethyl)-2-methoxybenzoate (321 mg, 0.5 mmol) in dichloromethane (5 mL) was added dropwise a 1 M solution of boron trichloride (2.5 mL, 2.5 mmol, 5 eq.) at −78° C. The reaction mixture was allowed to warm to 0° C. and was stirred at this temperature for 1 h. The reaction was quenched by addition of water (1.5 mL) and the resulting mixture was stirred for another 20 min. Dicholoromethane was evaporated under reduced pressure. The remaining aqueous residue was washed with diethyl ether, then homogenized by addition of acetonitrile and submitted to preparative reverse phase high performance liquid chromatography (Gilson, C18 stationary phase, acetonitrile/water 0-60% mobile phase modified with 0.1% TFA). Fractions containing the desired product were combined and freeze-dried to afford the title compound (38 mg). ESI-MS m/z 447.2 $(M+H)^+$.

Example 32: (R)-3-((S)-2-(4-Ethyl-2,3-dioxopiperazine-1-carboxamido)-3-hydroxy-propanamido)-2-hydroxy-3,4-dihydro-2H-benzo[e][1,2]oxaborinine-8-carboxylic acid

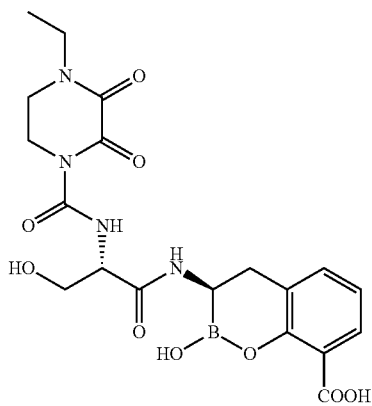

The title compound was prepared from L-serine and 3-((2S)-2-chloro-2-((3aS,4S,6S)-3a,5,5-trimethylhexahydro-4,6-methanobenzo[d][1,3,2]dioxaborol-2-yl)ethyl)-2-methoxybenzoate, by a procedure similar to Example 31. ESI-MS m/z 463.2 $(M+H)^+$.

Example 33: (3S)-3-(2-(2-aminothiazol-4-yl)-2-(4-ethyl-2,3-dioxopiperazine-1-carboxamido)acetamido)-2-hydroxy-3,4-dihydro-2H-benzo[e][1,2]oxaborinine-8-carboxylic acid

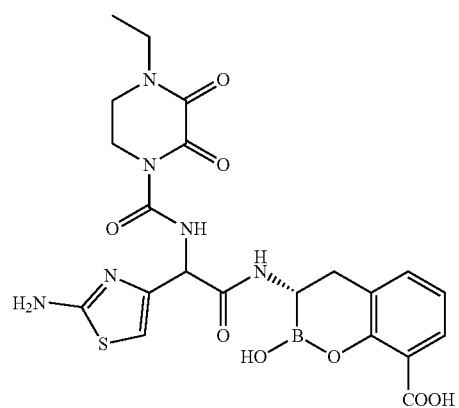 [SMILES: CCN1CCN(C(=O)NC(C(=O)N[C@@H]2Cc3cccc(C(=O)O)c3OB2O)c2csc(N)n2)C(=O)C1=O]

In a similar manner to the synthesis of Example 12, the title compound was prepared using the (R)-chloride intermediate, which was prepared as previously reported (WO2014/089365). ESI-MS m/z 531 $(MH)^+$.

Example 34: (R)-3-((R)-2-(4-Ethyl-2,3-dioxopiperazine-1-carboxamido)propanamido)-2-hydroxy-3,4-dihydro-2H-benzo[e][1,2]oxaborinine-8-carboxylic acid

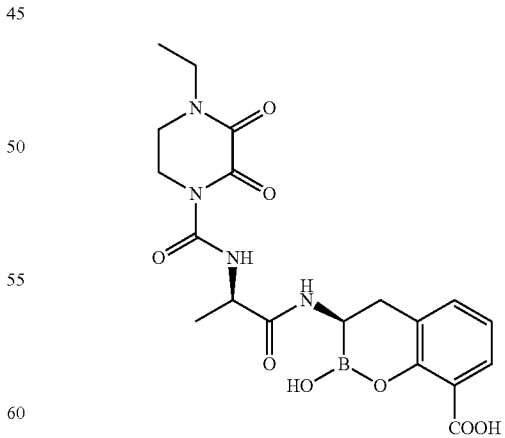

The title compound was prepared from D-alanine and 3-((2S)-2-chloro-2-((3aS,4S,6S)-3a,5,5-trimethylhexahydro-4,6-methanobenzo[d][1,3,2]dioxaborol-2-yl)ethyl)-2-methoxybenzoate, by a procedure similar to Example 31. ESI-MS m/z 447.2 $(M+H)^+$.

Example 35: (R)-3-((R)-2-(4-Ethyl-2,3-dioxopiperazine-1-carboxamido)-3-hydroxy-propanamido)-2-hydroxy-3,4-dihydro-2H-benzo[e][1,2]oxaborinine-8-carboxylic acid

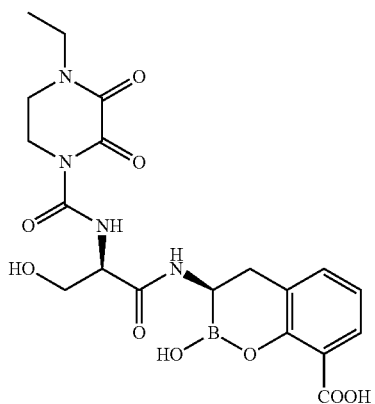

The title compound was prepared from D-serine and 3-((2S)-2-chloro-2-((3aS,4S,6S)-3a,5,5-trimethylhexahydro-4,6-methanobenzo[d][1,3,2]dioxaborol-2-yl)ethyl)-2-methoxybenzoate, by a procedure similar to Example 31. ESI-MS m/z 463.2 (M+H)$^+$.

Example 38: (3R)-3-(2-(2-aminothiazol-4-yl)-2-(4-ethyl-2,3-dioxopiperazine-1-carboxamido)acetamido)-2-hydroxy-6-methoxy-3,4-dihydro-2H-benzo[e][1,2]oxaborinine-8-carboxylic acid

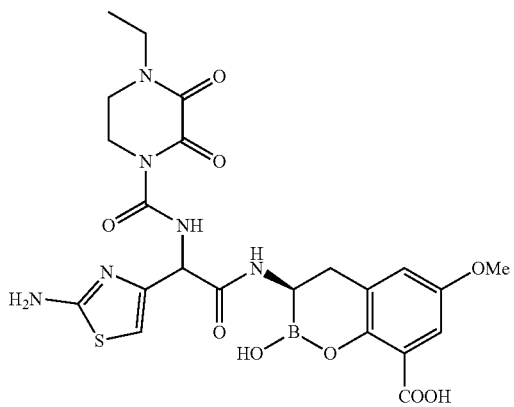 [SMILES: CCN1CCN(C(=O)NC(C(=O)N[C@H]2Cc3cc(OC)cc(C(=O)O)c3OB2O)c2csc(N)n2)C(=O)C1=O]

Step 1. Synthesis of tert-butyl 3-bromo-2,5-dimethoxybenzoate

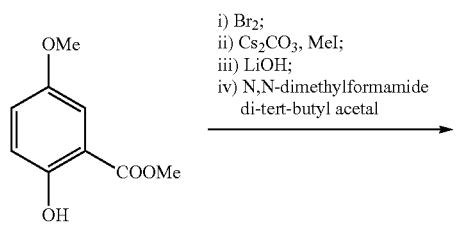

i) Br$_2$;
ii) Cs$_2$CO$_3$, MeI;
iii) LiOH;
iv) N,N-dimethylformamide di-tert-butyl acetal

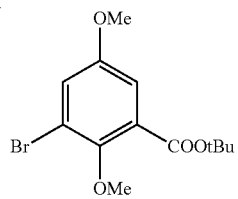

Step 1a. Bromination

To methyl 5-methoxysalicylate (5.46 g, 30 mmol) in chloroform (80 mL) at RT was added bromine (1.73 mL, 33.6 mmol), the reaction mixture was stirred at RT overnight, then concentrated in vacuo to give the brominated product, which was used for the next step without further purification. ESI-MS m/z 261/263 (MH/MH+2)$^+$.

Step 1b. Methyl Ether Preparation

The above crude product was dissolved in DMF (90 mL), Cs$_2$CO$_3$ (23.2 g, 71.2 mmol) was added. After 10 min, methyl iodide (5 mL, 80.3 mmol) was added, the reaction mixture was stirred at RT overnight, diluted with diethyl ether, washed with water, brine, dried over Na$_2$SO$_4$, and concentrated to give the crude product, which was used for the next step without further purification. ESI-MS m/z 275/277 (MH/MH+2)$^+$.

Step 1c. Hydrolysis of Methyl Ester

The above crude product was dissolved in THF (150 mL) and water (150 mL), treated with LiOH.H$_2$O (3.78 g, 90 mmol) at RT for 80 min, evaporated, acidified with 1 N HCl to pH~1-2, extracted with DCM. The organic extracts were dried over Na$_2$SO$_4$, and concentrated to give the acid, which was used for the next step without further purification. ESI-MS m/z 261/263 (MH/MH+2)$^+$. MS m/z 275/277 (MH/MH+2)$^+$.

Step 1d. Synthesis of Tert-Butyl Ester

To a reflux solution of the above crude product (30 mmol) in THF (60 mL) was added N,N-dimethylformamide di-tert-butyl acetal (total 22.5 mL, 62.8 mmol) in three periods. In each period ⅓ of the total amount was added over 15 min followed by 15 min stirring after each addition. After the third addition was completed, the mixture remained refluxed for 3.5 h, cooled to RT, dissolved in DCM, and washed with H$_2$O. Aqueous layer was extracted with DCM. The Organic layers were combined, washed with H$_2$O and brine, dried over Na$_2$SO$_4$, concentrated, and purified by flash chromatography on silica gel (hexane-EtOAc, 40:1-8:1) to give the title compound, 7.21 g. ESI-MS m/z 339/341 (M+Na/M+Na+2)$^+$.

Step 2. Synthesis of tert-butyl 2,5-dimethoxy-3-((3aS,4S,6S)-3a,5,5-trimethylhexahydro-4,6-methanobenzo[d][1,3,2]dioxaborol-2-yl)benzoate

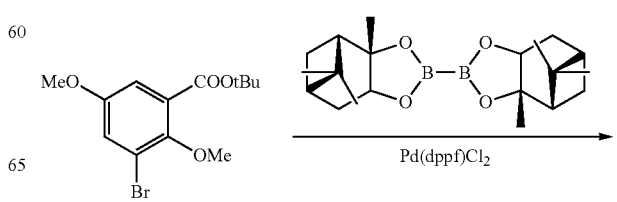

-continued

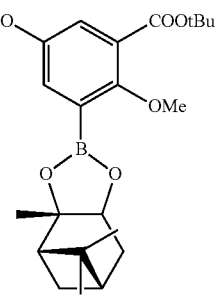

To the above product (1.9 g, 6 mmol) in dry DMF (20 mL) was added bis[(+)-pinanediolato]diboron (3.3 g, 9.2 mmol), KOAc (1.8 g, 18.4 mmol) and Pd(dppf)Cl$_2$.DCM (251 mg, 0.3 mmol). The reaction mixture was stirred at 90-100° C. overnight, added water, and extracted with diethyl ether. The ether extracts were washed with water, brine, dried over Na$_2$SO$_4$, and concentrated. The crude product was purified by flash chromatography on silica gel (hexane-DCM, 10:11:10, then hexane-DCM-diethyl ether, 4:1:1) to afford the title compound, 2.25 g. ESI-MS m/z 855 (2M+Na)$^+$.

Step 3. Synthesis of (3R)-3-(2-(2-aminothiazol-4-yl)-2-(4-ethyl-2,3-dioxopiperazine-1-carboxamido)acetamido)-2-hydroxy-6-methoxy-3,4-dihydro-2H-benzo[e][1,2]oxaborinine-8-carboxylic acid

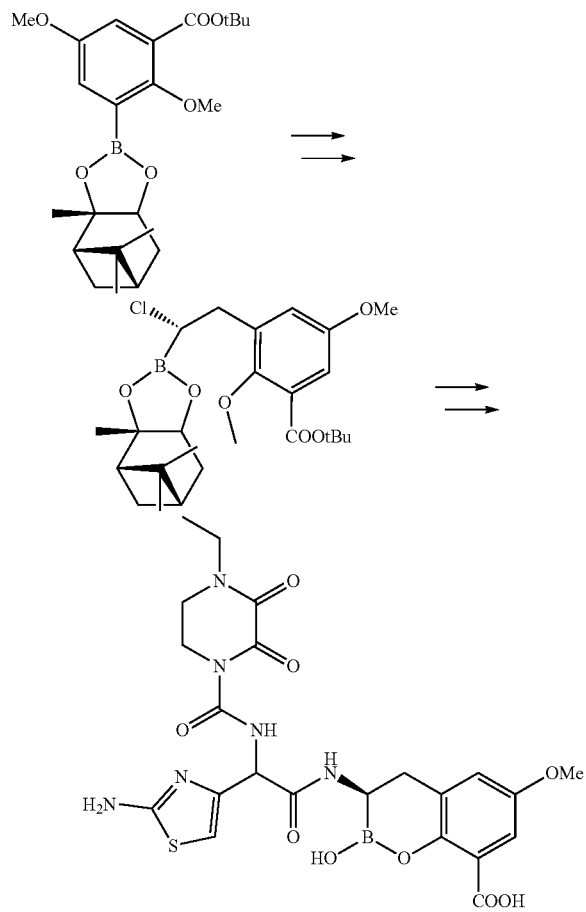

The title compound was prepared from above product by following the experimental procedures as described previously (WO 2014/089365). ESI-MS m/z 561 (MH)$^+$.

Example 39: (3R)-3-(2-(2-aminothiazol-4-yl)-2-(4-ethyl-2,3-dioxopiperazine-1-carboxamido)acetamido)-2,6-dihydroxy-3,4-dihydro-2H-benzo[e][1,2]oxaborinine-8-carboxylic acid

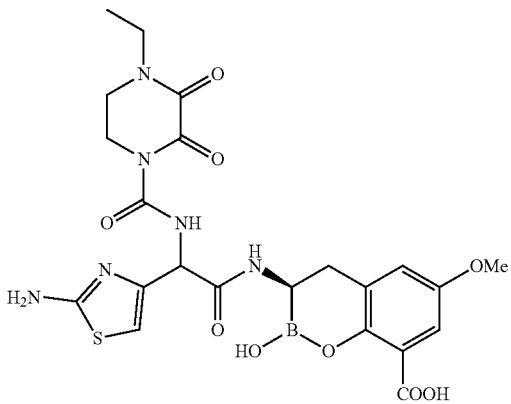 [SMILES: CCN1CCN(C(=O)NC(C(=O)N[C@H]2Cc3cc(OC)cc(C(=O)O)c3OB2O)c2csc(N)n2)C(=O)C1=O]

In a similar manner to the synthesis of Example 38, and using BBr$_3$ instead of BCl$_3$ for the last deprotection step, the title compound was prepared. ESI-MS m/z 547 (MH)$^+$.

Example 40: (R)-3-((R)-2-(4-ethyl-2,3-dioxopiperazine-1-carboxamido)-3-(1H-imidazol-4-yl)propanamido)-2-hydroxy-3,4-dihydro-2H-benzo[e][1,2]oxaborinine-8-carboxylic acid

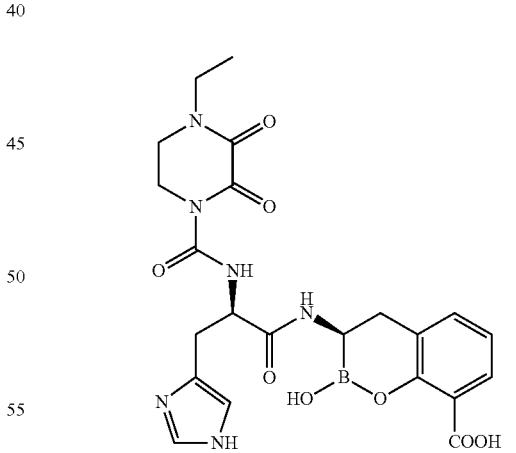

The title compound was prepared from N$^τ$-trityl-D-histidine and 3-((2S)-2-chloro-2-((3aS,4S,6S)-3a,5,5-trimethylhexahydro-4,6-methanobenzo[d][1,3,2]dioxaborol-2-yl)ethyl)-2-methoxybenzoate, by a procedure similar to Example 31, with the exception that in Step 3, prior to quenching with water, the reaction was further treated with 0.3 mL trifluoroacetic acid (TFA) for 1 h at room temperature. ESI-MS m/z 513.2 (M+H)$^+$.

Example 41: (3R)-3-(2-(2-aminothiazol-4-yl)-2-(2-methoxyisonicotinamido)acetamido)-2-hydroxy-3,4-dihydro-2H-benzo[e][1,2]oxaborinine-8-carboxylic acid

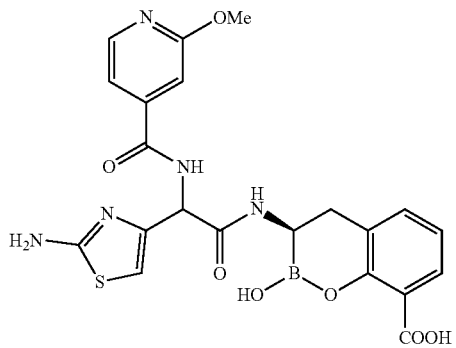 [SMILES: COc1cc(C(=O)NC(C(=O)N[C@H]2Cc3cccc(C(=O)O)c3OB2O)c2csc(N)n2)ccn1]

Step 1. Synthesis of tert-butyl 3-((2R)-2-(2-(((benzyloxy)carbonyl)amino)thiazol-4-yl)-2-(2-methoxyisonicotinamido)acetamido)-2-((3aS,4S,6R)-3a,5,5-trimethylhexahydro-4,6-methanobenzo[d][1,3,2]dioxaborol-2-yl)ethyl)-2-methoxybenzoate

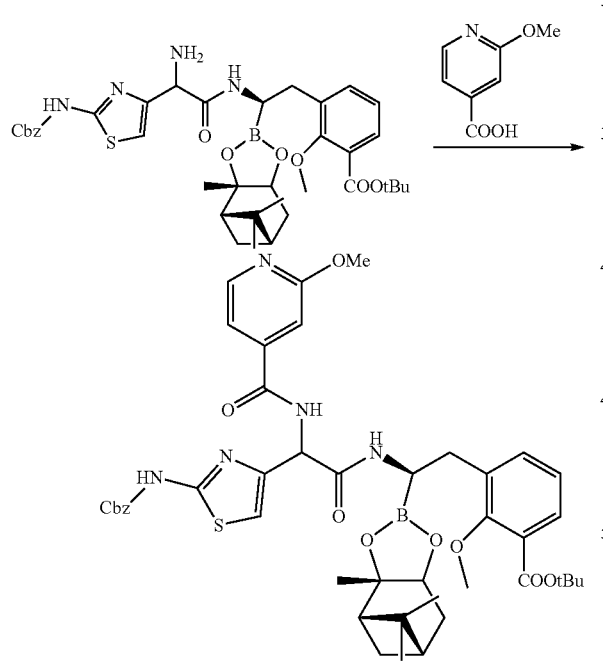

To the amine intermediate (product from step 2 of Example 25) (604 mg, 0.8 mmol) in DCM (15 mL) at 0° C. was added diisopropylethylamine (0.69 mL, 4 mmol) followed by 2-methoxyisonicotinic acid (153 mg, 1 mmol) and the Mukaiyama reagent (2-chloro-1-methylpyridinium iodide) (300 mg, 1.18 mmol). The reaction mixture was stirred at RT for 2 h, washed with aqueous saturated NaHCO$_3$, dried over Na$_2$SO$_4$, concentrated, and purified by flash chromatography on silica gel (hexane-acetone, 10:1-1:1) to afford the product, 290 mg. ESI-MS m/z 854 (MH)$^+$.

Step 2. Synthesis of (3R)-3-(2-(2-aminothiazol-4-yl)-2-(2-methoxyisonicotinamido)acetamido)-2-hydroxy-3,4-dihydro-2H-benzo[e][1,2]oxaborinine-8-carboxylic acid

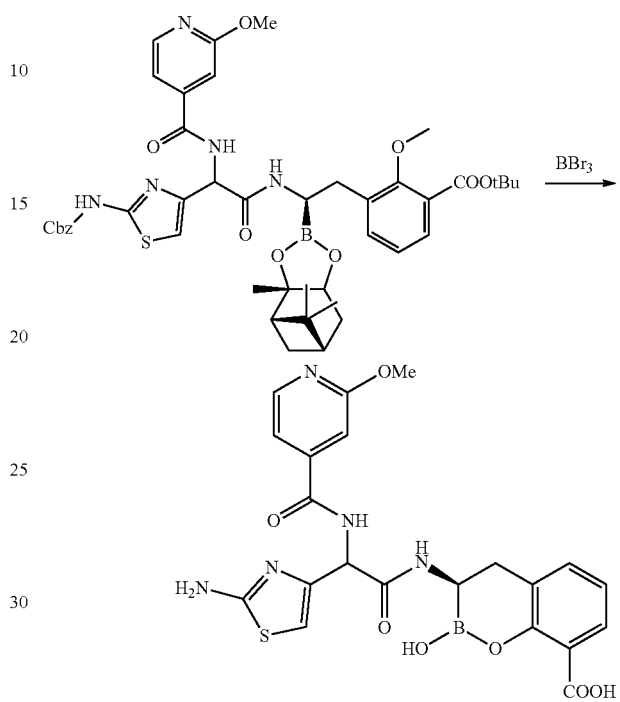

By following the General Method A, the above product was treated with BBr$_3$ to afford the title compound. ESI-MS m/z 498 (MH)$^+$.

Example 42: (3R)-3-(2-(2-aminothiazol-4-yl)-2-(1-methyl-2-oxo-1,2-dihydropyridine-4-carboxamido)acetamido)-2-hydroxy-3,4-dihydro-2H-benzo[e][1,2]oxaborinine-8-carboxylic acid

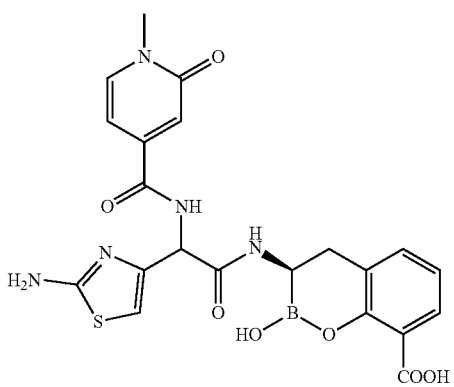 [SMILES: Cn1ccc(C(=O)NC(C(=O)N[C@H]2Cc3cccc(C(=O)O)c3OB2O)c2csc(N)n2)cc1=O]

In a similar manner to the synthesis of Example 41, utilizing 1-methyl-2-oxo-1,2-dihydropyridine-4-carboxylic acid in place of 2-methoxyisonicotinic acid in Step 1, the title compound was prepared. ESI-MS m/z 498 (MH)$^+$.

Example 43: (3R)-3-(2-(2-aminothiazol-4-yl)-2-(4-methyl-2,3-dioxopiperazine-1-carboxamido)acetamido)-2-hydroxy-3,4-dihydro-2H-benzo[e][1,2]oxaborinine-8-carboxylic acid

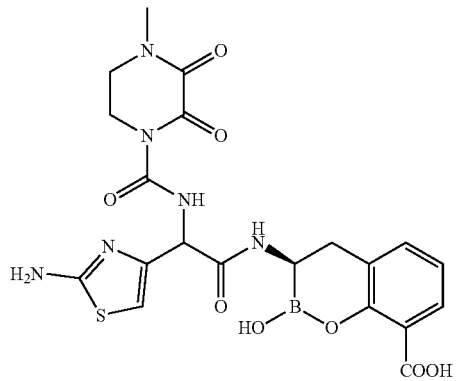 [SMILES: CN1CCN(C(=O)NC(C(=O)N[C@H]2Cc3cccc(C(=O)O)c3OB2O)c2csc(N)n2)C(=O)C1=O]

Step 1. Synthesis of 1-methylpiperazine-2,3-dione

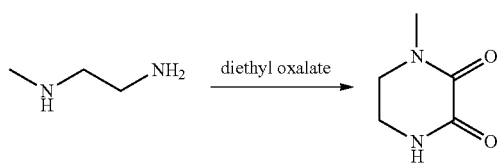

To N-methylethylenediamine 1 g, 13.5 mmol) in EtOH (4 mL) was added diethyl oxalate 1.83 mL (13.5 mmol), stirred at reflux for 18 h and cooled at RT. The white precipitate was filtered and dried under high vacuum to give the desired compound, 0.66 g. ESI-MS m/z 129 (MH)⁺.

Step 2. Synthesis of 4-methyl-2,3-dioxopiperazine-1-carbonyl chloride

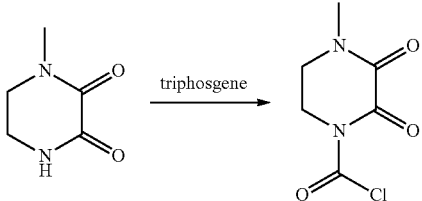

To 1-methylpiperazine-2,3-dione 0.66 g (5.19 mmol) in THF (3.5 mL) at −15° C. was added chlorotrimethylsilane 0.7 mL (5.45 mmol), triethylamine 0.86 mL (6.23 mmol), followed by triphosgene 0.62 g (2.08 mmol) in THF (3 mL). After addition was complete, the reaction was warmed at RT for 30 min and the solids were filtered off and washed with THF. The filtrate was concentrated, triturated with diethyl ether, filtered and dried under high vacuum to give the desired compound, 0.69 g. ESI-MS m/z 191 (MH)⁺.

Step 3. Synthesis of (3R)-3-(2-(2-aminothiazol-4-yl)-2-(4-methyl-2,3-dioxopiperazine-1-carboxamido)acetamido)-2-hydroxy-3,4-dihydro-2H-benzo[e][1,2]oxaborinine-8-carboxylic acid

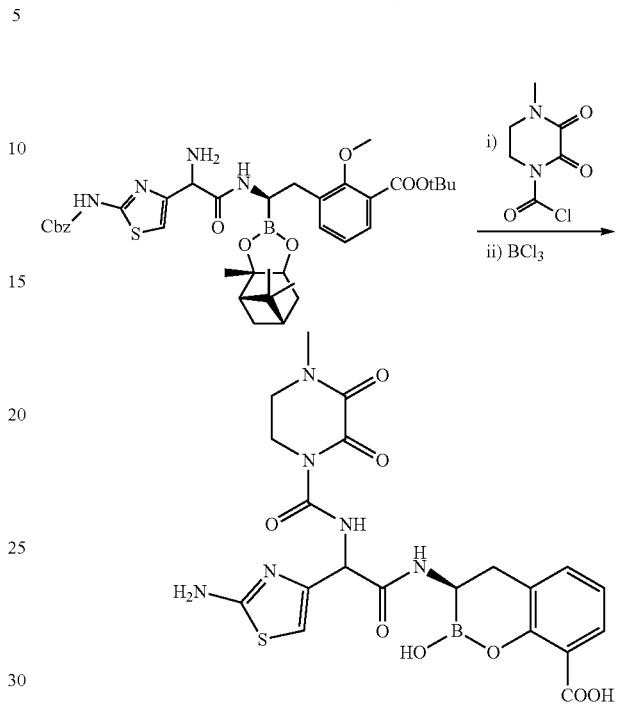

In a similar manner to the synthesis of Example 27, utilizing the above acyl chloride, 4-methyl-2,3-dioxopiperazine-1-carbonyl chloride in place of pyridine-3-sulfonyl chloride, the title compound was prepared. ESI-MS m/z 517 (MH)⁺.

Example 44: (3R)-3-(2-(2-aminothiazol-4-yl)-2-(4-cyclopropyl-2,3-dioxopiperazine-1-carboxamido)acetamido)-2-hydroxy-3,4-dihydro-2H-benzo[e][1,2]oxaborinine-8-carboxylic acid

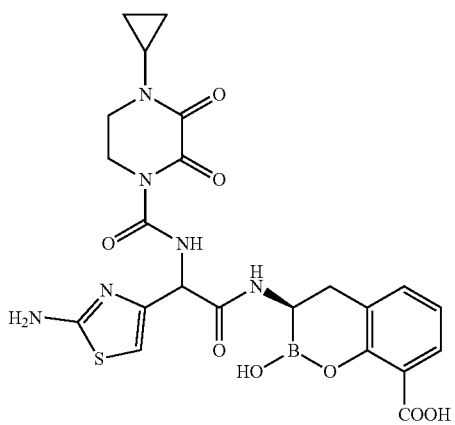 [SMILES: Nc1nc(C(NC(=O)N2CCN(C3CC3)C(=O)C2=O)C(=O)N[C@H]2Cc3cccc(C(=O)O)c3OB2O)cs1]

The title compound was prepared according to the method of Example 43, utilizing 4-cyclopropyl-2,3-dioxopiperazine-1-carbonyl chloride in place of 4-methyl-2,3-dioxopiperazine-1-carbonyl chloride. ESI-MS m/z 543 (MH)⁺.

Example 45: (3R)-3-(2-(2-aminothiazol-4-yl)-2-(2-(4-ethyl-2,3-dioxopiperazin-1-yl)acetamido)acetamido)-2-hydroxy-3,4-dihydro-2H-benzo[e][1,2]oxaborinine-8-carboxylic acid

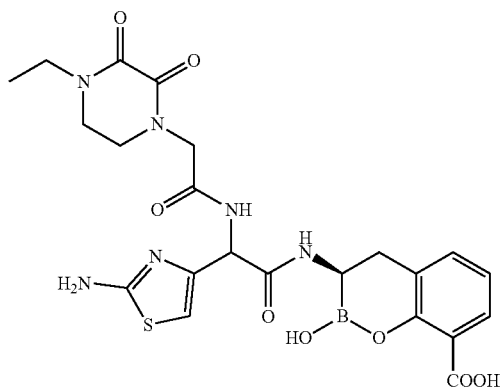 [SMILES: CCN1CCN(CC(=O)NC(C(=O)N[C@H]2Cc3cccc(C(=O)O)c3OB2O)c2csc(N)n2)C(=O)C1=O]

Step 1. Synthesis of tert-butyl 2-(4-ethyl-2,3-dioxopiperazin-1-yl)acetate

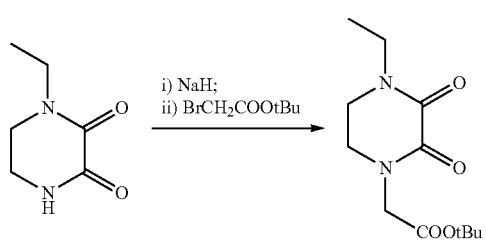

To N-ethyl-2,3-dioxopiperazine (2.84 g, 20 mmol) in DMF (25 mL) at RT under Argon atmosphere was added NaH (60%, 1.07 g, 26.6 mmol) in 3 portions. The reaction mixture was stirred at RT for 30 min, then tert-butyl bromoacetate (4.14 mL, 28 mmol) was added dropwise. The reaction mixture was stirred at RT for 3 h, quenched with aqueous saturated $NH_4Cl$, extracted with EtOAc. The organic extracts were combined, washed with water and brine, dried over $Na_2SO_4$, concentrated, and purified by flash chromatography on silica gel (hexane-acetone, 4:1-0:100) to afford the product, 940 mg. ESI-MS m/z 257 $(MH)^+$.

Step 2. Synthesis of 2-(4-ethyl-2,3-dioxopiperazin-1-yl)acetic acid

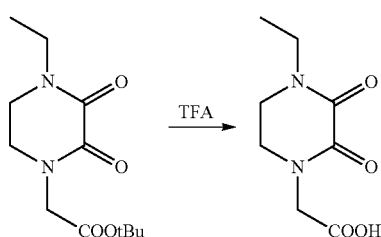

To a solution of above product (940 mg, 3.67 mmol) in DCM (12 mL) was added TFA (12 mL). The reaction mixture was stirred at RT for 1.5 h, then concentrated in vacuo to yield the title compound, 670 mg. ESI-MS m/z 201 $(MH)^+$.

Step 3. Synthesis of (3R)-3-(2-(2-aminothiazol-4-yl)-2-(2-(4-ethyl-2,3-dioxopiperazin-1-yl)acetamido)acetamido)-2-hydroxy-3,4-dihydro-2H-benzo[e][1,2]oxaborinine-8-carboxylic acid

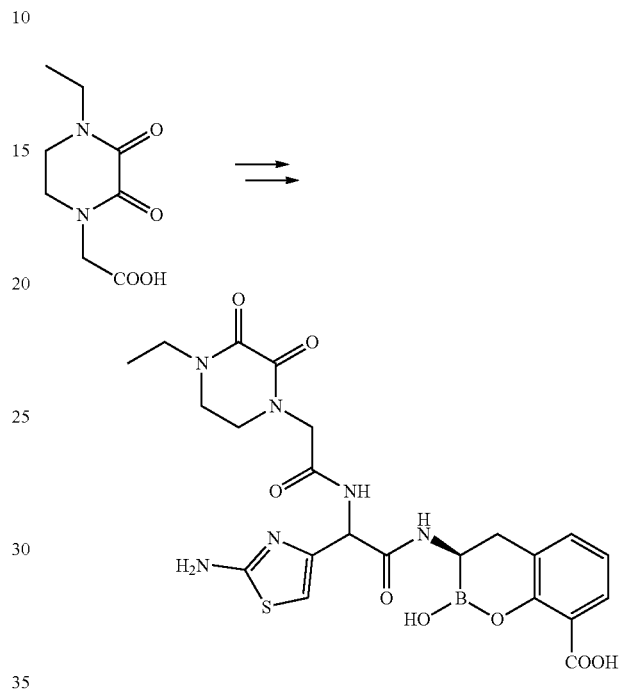

In a similar manner to the synthesis of Example 41, utilizing the above carboxylic acid in place of 2-methoxyisonicotinic acid in Step 1, and using $BCl_3$ instead of $BBr_3$ for the last deprotection step, the title compound was prepared. ESI-MS m/z 545 $(MH)^+$.

Example 46: (3R)-3-(2-(2-aminothiazol-4-yl)-2-(6-methoxy-2-oxo-1,2-dihydropyridine-3-carboxamido)acetamido)-2-hydroxy-3,4-dihydro-2H-benzo[e][1,2]oxaborinine-8-carboxylic acid

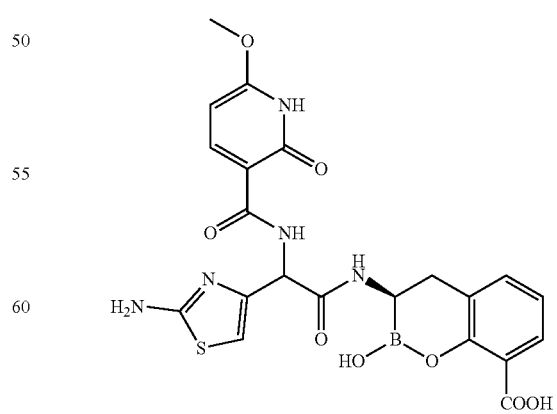

In a similar manner to the synthesis of Example 41, utilizing 2,6-dimethoxypyridine-3-carboxylic acid in place of 2-methoxyisonicotinic acid in Step 1, the title compound was prepared. ESI-MS m/z 514 (MH)+.

Example 47: (R)-3-((2R,3S)-2-(4-Ethyl-2,3-dioxopiperazine-1-carboxamido)-3-hydroxy-butanamido)-2-hydroxy-3,4-dihydro-2H-benzo[e][1,2]oxaborinine-8-carboxylic acid

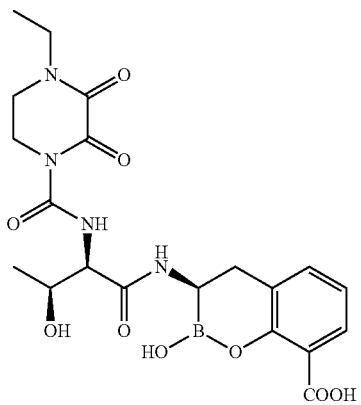 [SMILES: CCN1CCN(C(=O)N[C@@H](C(=O)N[C@H]2Cc3cccc(C(=O)O)c3OB2O)[C@H](C)O)C(=O)C1=O]

The title compound was prepared from D-threonine and 3-((2S)-2-chloro-2-((3aS,4S,6S)-3a,5,5-trimethylhexahydro-4,6-methanobenzo[d][1,3,2]dioxaborol-2-yl)ethyl)-2-methoxybenzoate, by a procedure similar to Example 31. ESI-MS m/z 477.2 (M+H)+.

Example 48: (R)-3-((2R,3R)-2-(4-Ethyl-2,3-dioxopiperazine-1-carboxamido)-3-hydroxy-butanamido)-2-hydroxy-3,4-dihydro-2H-benzo[e][1,2]oxaborinine-8-carboxylic acid

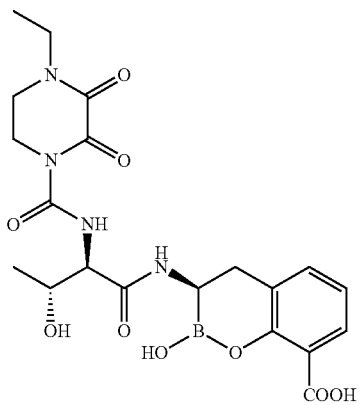 [SMILES: CCN1CCN(C(=O)N[C@@H](C(=O)N[C@H]2Cc3cccc(C(=O)O)c3OB2O)[C@@H](C)O)C(=O)C1=O]

The title compound was prepared from D-allothreonine and 3-((2S)-2-chloro-2-((3aS,4S,6S)-3a,5,5-trimethylhexahydro-4,6-methanobenzo[d][1,3,2]dioxaborol-2-yl)ethyl)-2-methoxybenzoate, by a procedure similar to Example 31. ESI-MS m/z 477.2 (M+H)+.

Example 49: (3R)-3-(2-(2-aminothiazol-4-yl)-2-(4-benzyl-2,3-dioxopiperazine-1-carboxamido)acetamido)-2-hydroxy-3,4-dihydro-2H-benzo[e][1,2]oxaborinine-8-carboxylic acid

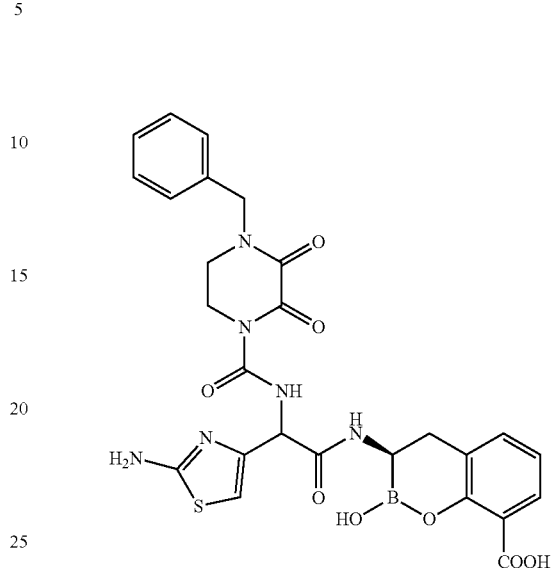

The title compound was prepared according to the method of Example 43, utilizing 4-benzyl-2,3-dioxopiperazine-1-carbonyl chloride in place of 4-methyl-2,3-dioxopiperazine-1-carbonyl chloride. ESI-MS m/z 593 (MH)+.

Example 50: (R)-3-((R)-5-amino-2-(4-ethyl-2,3-dioxopiperazine-1-carboxamido)-5-oxopentanamide)-2-hydroxy-3,4-dihydro-2H-benzo[e][1,2]oxaborinine-8-carboxylic acid

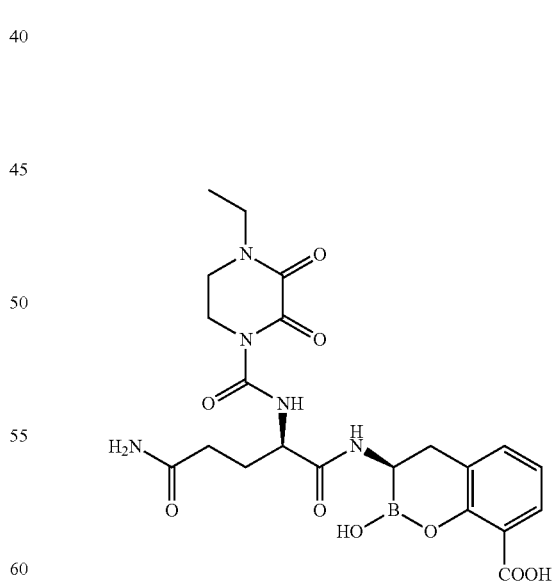

The title compound was prepared from D-glutamine and 3-((2S)-2-chloro-2-((3aS,4S,6S)-3a,5,5-trimethylhexahydro-4,6-methanobenzo[d][1,3,2]dioxaborol-2-yl)ethyl)-2-methoxybenzoate, by a procedure similar to Example 31. ESI-MS m/z 504.2 (M+H)+.

Example 51: (3R)-3-(2-(2-aminothiazol-4-yl)-2-(2,3-dioxo-4-propylpiperazine-1-carboxamido)acetamido)-2-hydroxy-3,4-dihydro-2H-benzo[e][1,2]oxaborinine-8-carboxylic acid

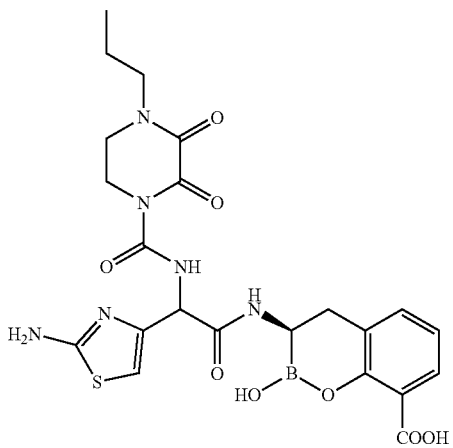 [SMILES: CCCN1CCN(C(=O)NC(C(=O)N[C@H]2Cc3cccc(C(=O)O)c3OB2O)c2csc(N)n2)C(=O)C1=O]

Step 1. Synthesis of 1-propylpiperazine-2,3-dione

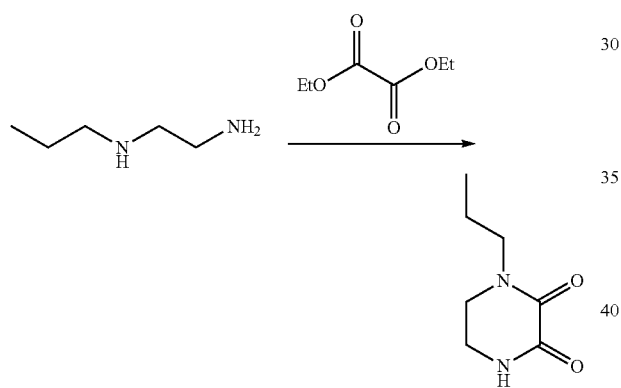

To N-propylethylenediamine (1.95 g, 19 mmol) in EtOH (35 mL) was added diethyl oxalate (2.8 mL, 20.6 mmol). The reaction mixture was stirred at reflux for 18 h, then concentrated in vacuo, the residue was purified by flash chromatography on silica gel (DCM-MeOH, 30:1-6:1) to afford the product, 2.32 g. ESI-MS m/z 157 (MH)$^+$.

Step 2. Synthesis of 2,3-dioxo-4-propylpiperazine-1-carbonyl Chloride

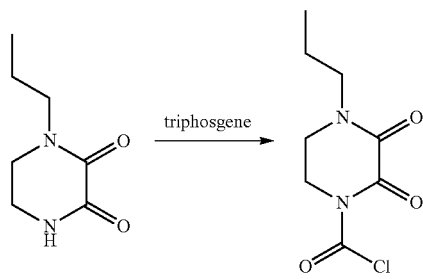

To the above product (2.3 g, 14.7 mmol) in THF (15 mL) and DCM (5 mL) at −15° C. was added chlorotrimethylsilane (2.06 mL, 16.2 mmol), followed by triethylamine (2.46 mL, 17.7 mmol). The reaction mixture was stirred between −15° C.-0° C. for 1 h, then triphosgene (1.77 g, 5.9 mmol) in THF (8 mL) was added dropwise to the reaction mixture. After addition was complete, the reaction mixture was warmed up to RT over 30 min, stirred for an additional 1 h, and the solid was filtered off and washed with THF. The filtrate was concentrated, triturated with diethyl ether. The solid was collected by filtration, dried in vacuo to give the title compound, 3 g.

Step 3. Synthesis of (3R)-3-(2-(2-aminothiazol-4-yl)-2-(2,3-dioxo-4-propylpiperazine-1-carboxamido)acetamido)-2-hydroxy-3,4-dihydro-2H-benzo[e][1,2]oxaborinine-8-carboxylic acid

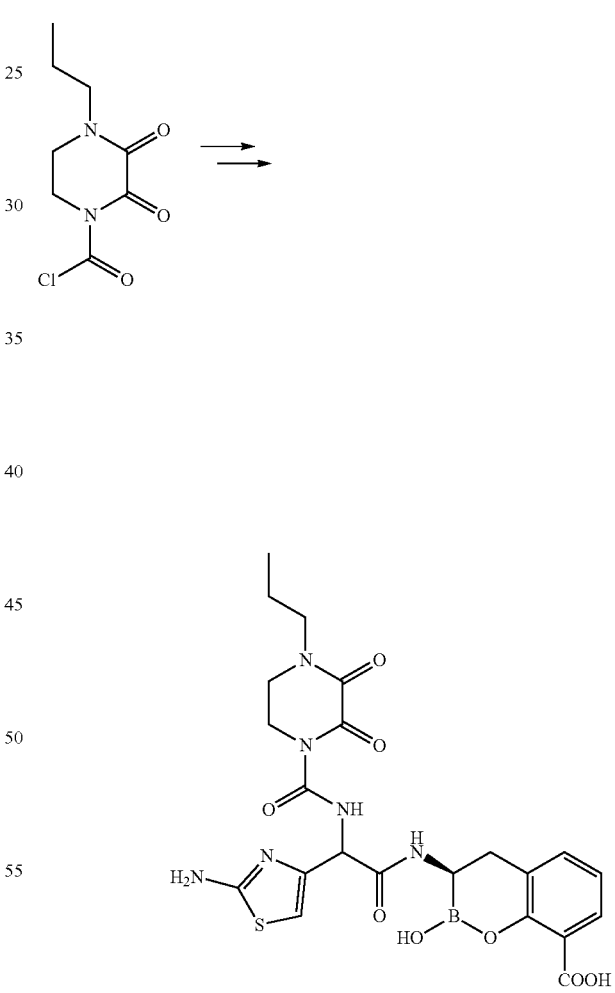

In a similar manner to the synthesis of Example 43, utilizing the above carbonyl chloride, 2,3-dioxo-4-propylpiperazine-1-carbonyl chloride in place of 4-methyl-2,3-dioxopiperazine-1-carbonyl chloride, the title compound was prepared. ESI-MS m/z 545 (MH)$^+$.

Example 52: (3R)-3-(2-(2-aminothiazol-4-yl)-2-(4-(2-fluoroethyl)-2,3-dioxopiperazine-1-carboxamido)acetamido)-2-hydroxy-3,4-dihydro-2H-benzo[e][1,2]oxaborinine-8-carboxylic acid

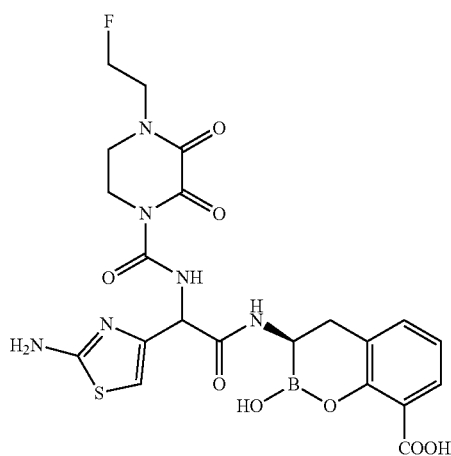 [SMILES: Nc1nc(C(NC(=O)N2CCN(CCF)C(=O)C2=O)C(=O)N[C@H]2Cc3cccc(C(=O)O)c3OB2O)cs1]

Step 1. Synthesis of N-(2-fluoroethyl)ethane-1,2-diamine

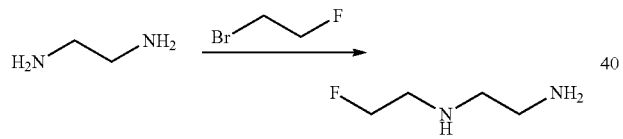

To ethylenediamine (22.5 g, 25 mL, 375 mmol) was added 1-bromo-2-fluoroethane (6.86 g, 54 mmol) in portions over 20 min. The reaction mixture was stirred at RT for an addition 3.5 h, then extracted with diethyl ether (2×40 mL). The ether extracts were combined, concentrated in vacuo to yield the title compound, 3 g, which was used directly for the next step without further purification.

Step 2. Synthesis of (3R)-3-(2-(2-aminothiazol-4-yl)-2-(4-(2-fluoroethyl)-2,3-dioxopiperazine-1-carboxamido)acetamido)-2-hydroxy-3,4-dihydro-2H-benzo[e][1,2]oxaborinine-8-carboxylic acid

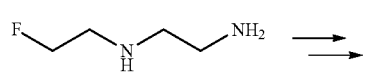

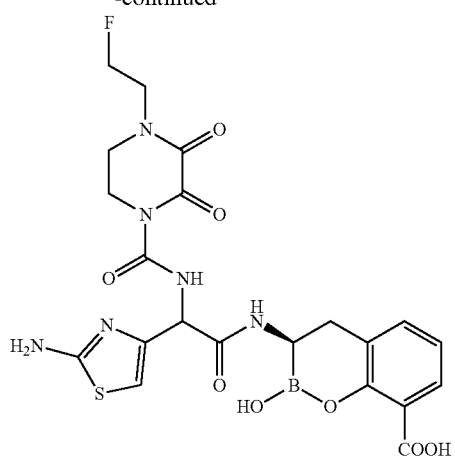

In a similar manner to the synthesis of Example 51, utilizing the above product in place of N-propylethylenediamine in Step 1, the title compound was prepared. ESI-MS m/z 549 (MH)+.

Example 53: (3R)-3-(2-(2-aminothiazol-4-yl)-2-(4-butyl-2,3-dioxopiperazine-1-carboxamido)acetamido)-2-hydroxy-3,4-dihydro-2H-benzo[e][1,2]oxaborinine-8-carboxylic acid

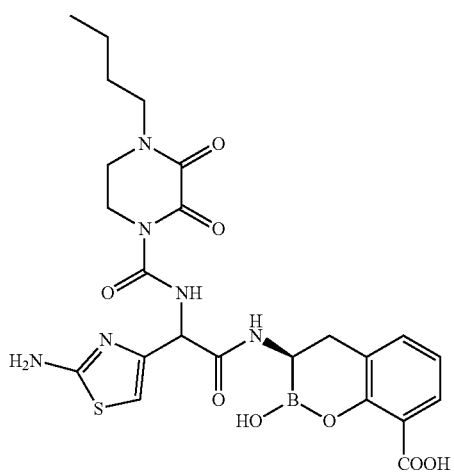 [SMILES: CCCCN1CCN(C(=O)NC(C(=O)N[C@H]2Cc3cccc(C(=O)O)c3OB2O)c2csc(N)n2)C(=O)C1=O]

The title compound was prepared according to the method of Example 43, utilizing 4-butyl-2,3-dioxopiperazine-1-carbonyl chloride in place of 4-methyl-2,3-dioxopiperazine-1-carbonyl chloride. ESI-MS m/z 559 (MH)+.

Example 54: (3R)-3-(2-(2-aminothiazol-4-yl)-2-(4-(3-fluoropropyl)-2,3-dioxopiperazine-1-carboxamido)acetamido)-2-hydroxy-3,4-dihydro-2H-benzo[e][1,2]oxaborinine-8-carboxylic acid

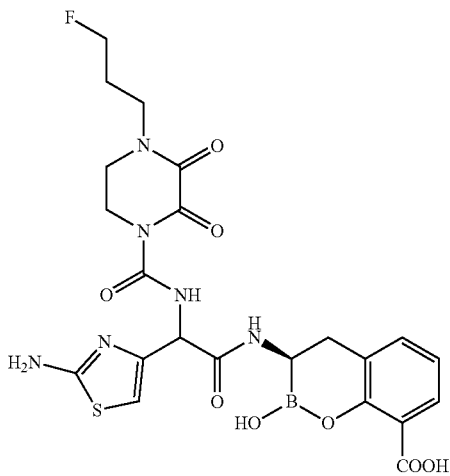 [SMILES: Nc1nc(C(NC(=O)N2CCN(CCCF)C(=O)C2=O)C(=O)N[C@H]2Cc3cccc(C(=O)O)c3OB2O)cs1]

In a similar manner to the synthesis of Example 52, utilizing 1-bromo-3-fluoropropane in place of 1-bromo-2-fluoroethane in Step 1, the title compound was prepared. ESI-MS m/z 563 (MH)$^+$.

Example 55: (3R)-3-(2-(2-aminothiazol-4-yl)-2-(4-isopropyl-2,3-dioxopiperazine-1-carboxamido)acetamido)-2-hydroxy-3,4-dihydro-2H-benzo[e][1,2]oxaborinine-8-carboxylic acid

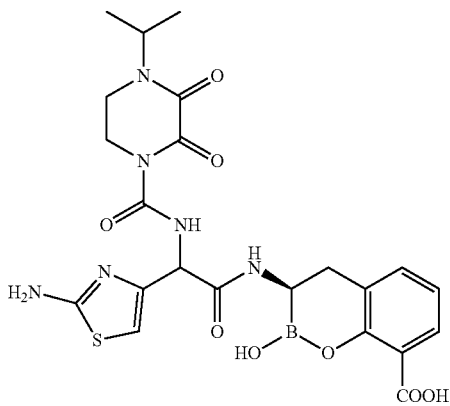 [SMILES: CC(C)N1CCN(C(=O)NC(C(=O)N[C@H]2Cc3cccc(C(=O)O)c3OB2O)c2csc(N)n2)C(=O)C1=O]

The title compound was prepared according to the method of Example 43, utilizing 4-isopropyl-2,3-dioxopiperazine-1-carbonyl chloride in place of 4-methyl-2,3-dioxopiperazine-1-carbonyl chloride. ESI-MS m/z 545 (MH)$^+$.

Example 56: (3R)-3-(2-(2-(((benzyloxy)carbonyl)amino)thiazol-4-yl)-2-(2,3-dioxo-4-propylpiperazine-1-carboxamido)acetamido)-2-hydroxy-3,4-dihydro-2H-benzo[e][1,2]oxaborinine-8-carboxylic acid

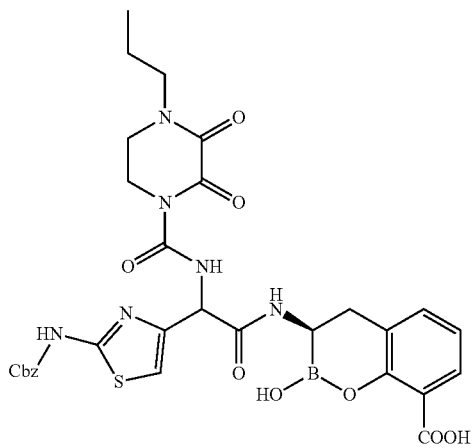 [SMILES: CCCN1CCN(C(=O)NC(C(=O)N[C@H]2Cc3cccc(C(=O)O)c3OB2O)c2csc(NC(=O)OCc3ccccc3)n2)C(=O)C1=O]

The fully protected precursor of Example 51 (198 mg, 0.22 mmol) in DCM (6 mL) was treated with TMSI (0.31 mL, 2.2 mmol) at RT for 1.5 h, more TMSI (0.31 mL, 2.2 mmol) was added, the reaction mixture was stirred at RT for an additional 5 h, quenched with methanol and water, evaporated. The residue was dissolved in EtOAc, washed with aqueous $Na_2S_2O_3$, brine, dried over $Na_2SO_4$, and concentrated in vacuo to afford the crude product, 150 mg, which was purified by reverse phase HPLC to afford the pure title compound. ESI-MS m/z 679 (MH)$^+$.

Example 57: (3R)-3-(2-(2-amino-5-chlorothiazol-4-yl)-2-(4-(2-fluoroethyl)-2,3-dioxopiperazine-1-carboxamido)acetamido)-2-hydroxy-3,4-dihydro-2H-benzo[e][1,2]oxaborinine-8-carboxylic acid

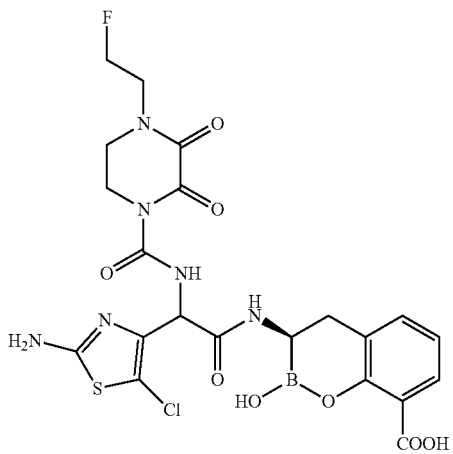 [SMILES: Nc1nc(C(NC(=O)N2CCN(CCF)C(=O)C2=O)C(=O)N[C@H]2Cc3cccc(C(=O)O)c3OB2O)c(Cl)s1]

137

Step 1. Synthesis of tert-butyl 3-((2R)-2-(2-(2-(((benzyloxy)carbonyl)amino)-5-chlorothiazol-4-yl)-2-(4-(2-fluoroethyl)-2,3-dioxopiperazine-1-carboxamido)acetamido)-2-((3aS,4S,6S,7aR)-3a,5,5-trimethylhexahydro-4,6-methanobenzo[d][1,3,2]dioxaborol-2-yl)ethyl)-2-methoxybenzoate

138

Step 2. Synthesis of (3R)-3-(2-(2-amino-5-chlorothiazol-4-yl)-2-(4-(2-fluoroethyl)-2,3-dioxopiperazine-1-carboxamido)acetamido)-2-hydroxy-3,4-dihydro-2H-benzo[e][1,2]oxaborinine-8-carboxylic acid

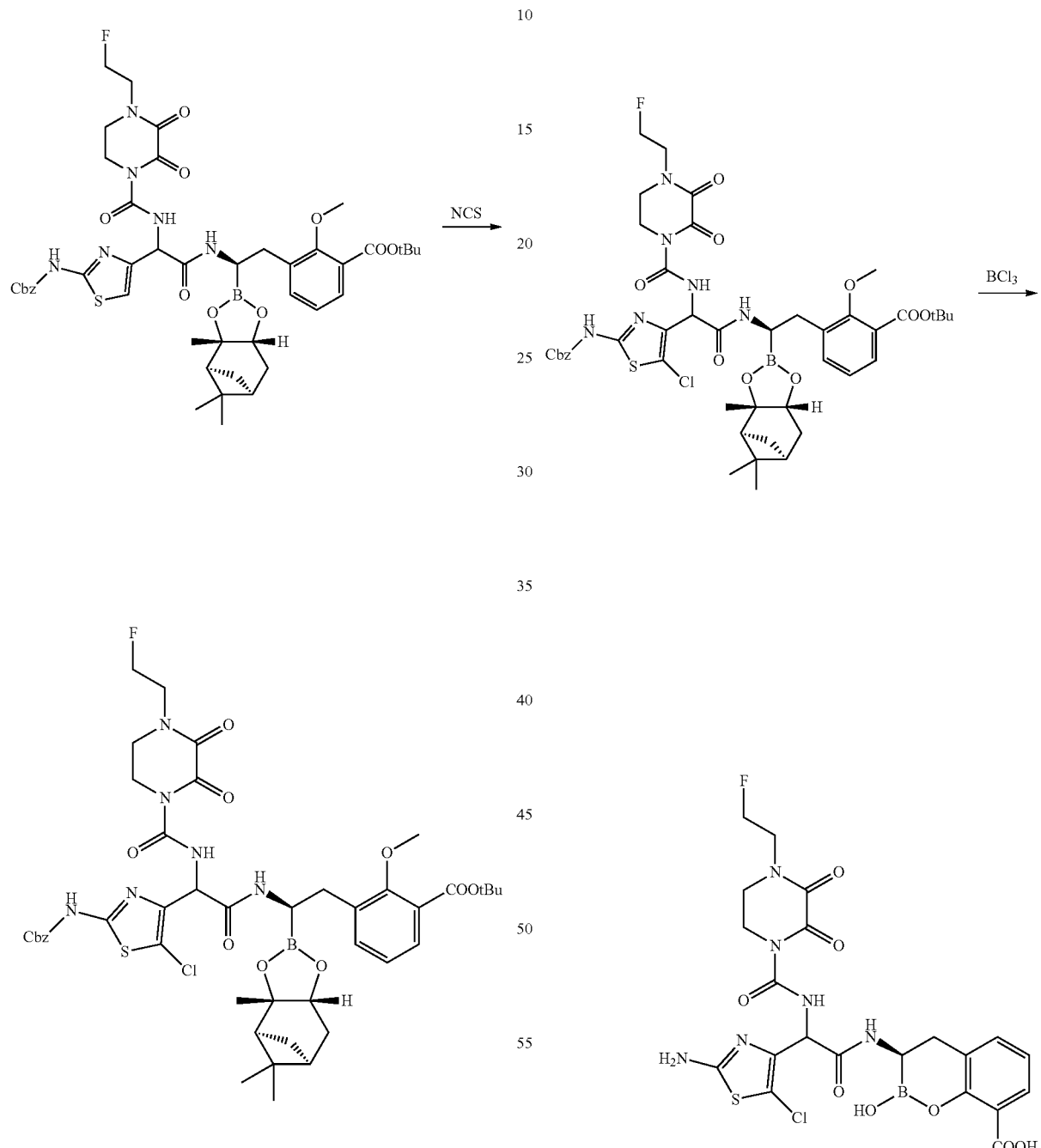

The fully protected precursor of Example 52 (460 mg, 0.51 mmol) in DMF (3 mL) was treated with NCS (88 mg, 0.66 mmol) at RT for 2 h, diluted with EtOAc, washed with water, brine, dried over $Na_2SO_4$, concentrated, and purified by flash chromatography on silica gel (hexane-acetone, 4:1-1:1) to afford the title compound, 330 mg. ESI-MS m/z 939/941 (MH/MH+2)$^+$.

The title compound was prepared by treatment of the above product with $BCl_3$ by following General Method A. ESI-MS m/z 583/585 (MH/MH+2)$^+$.

Example 58: (3R)-3-(2-(4-(2-aminoethyl)-2,3-dioxopiperazine-1-carboxamido)-2-(2-aminothiazol-4-yl)acetamido)-2-hydroxy-3,4-dihydro-2H-benzo[e][1,2]oxaborinine-8-carboxylic acid

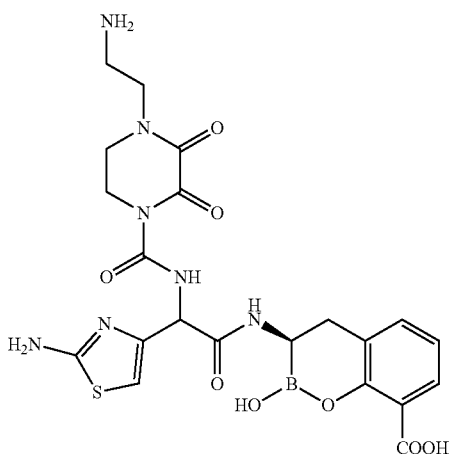 [SMILES: NCCN1CCN(C(=O)NC(C(=O)N[C@H]2Cc3cccc(C(=O)O)c3OB2O)c2csc(N)n2)C(=O)C1=O]

In a similar manner to the synthesis of Example 52, utilizing 2-(Boc-amino)ethyl bromide in place of 1-bromo-2-fluoroethane in Step 1, the title compound was prepared. ESI-MS m/z 546 (MH)$^+$.

Example 59: (R)-3-((R)-2-(4-ethyl-2,3-dioxopiperazine-1-carboxamido)-4-hydroxybutanamido)-2-hydroxy-3,4-dihydro-2H-benzo[e][1,2]oxaborinine-8-carboxylic acid

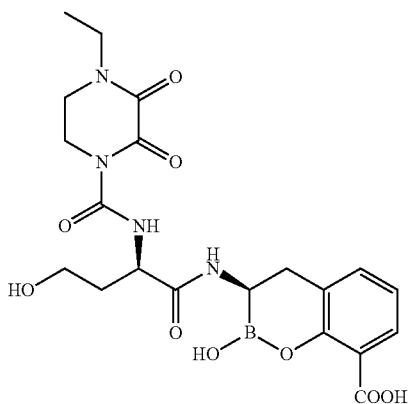 [SMILES: CCN1CCN(C(=O)N[C@H](CCO)C(=O)N[C@H]2Cc3cccc(C(=O)O)c3OB2O)C(=O)C1=O]

Step 1. Synthesis of O-(tert-butyldimethylsilyl)-D-homoserine

D-homoserine (2 g, 16.8 mmol) in acetonitrile (20 mL) was treated with 1,8-diazabicyclo[5.4.0]undec-7-ene (2.64 mL, 1.05 eq) and tert-butyldimethylsilyl chloride (2.66 g, 1.05 eq) at 0° C., and the reaction mixture was next allowed to warm to room temperature and stirred overnight. The reaction mixture was filtered and the collected precipitate was washed with acetonitrile and dried under high vacuum, to afford O-(tert-butyldimethy-lsilyl)-D-homoserine as a white solid, which was used in the next step without further purification.

Step 2. Synthesis of N-(4-ethyl-2,3-dioxopiperazine-1-carbonyl)-D-homoserine triethyl amine salt O-(tert-butyldimethylsilyl)-D-homoserine (1.65 g, 7 mmol) in dichloromethane (50 mL) was treated with triethylamine (2.2 mL, 2 eq) at 0° C., followed by a solution of 4-ethyl-2,3-dioxopiperazine-1-carbonyl chloride (1.8 g, 9 mmol, 1.25 eq.) in dichloromethane (10 mL). The reaction mixture was allowed to warm to room temperature and stirred overnight. The resulting mixture was partitioned between brine and additional dichloromethane (50 mL), and the aqueous phase was extracted once more with dichloromethane. The combined organic extracts were dried on $Na_2SO_4$, then filtered, and the volatiles were evaporated under reduced pressure. The desired product, N-(4-ethyl-2,3-dioxopiperazine-1-carbonyl)-D-homoserine was isolated by flash-chromatography (silicagel, methanol in dichloromethane, 0 to 15% gradient) as the triethyl amine salt.

Step 3. Synthesis of (R)-3-((R)-2-(4-ethyl-2,3-dioxopiperazine-1-carboxamido)-4-hydroxybutanamido)-2-hydroxy-3,4-dihydro-2H-benzo[e][1,2]oxaborinine-8-carboxylic acid The title compound was prepared from O-(tert-butyldimethylsilyl)-N-(4-ethyl-2,3-dioxopiperazine-1-carbonyl)-D-homoserine triethyl amine salt and 3-((2S)-2-chloro-2-((3aS,4S,6S)-3a,5,5-trimethylhexahydro-4,6-methanobenzo-[d][1,3,2]dioxaborol-2-yl)ethyl)-2-methoxybenzoate, by a procedure similar to Example 31. ESI-MS m/z 477.2 (M+H)$^+$.

Example 60: (3R)-3-(2-(2-aminothiazol-4-yl)-2-(4-(2-hydroxyethyl)-2,3-dioxopiperazine-1-carboxamido)acetamido)-2-hydroxy-3,4-dihydro-2H-benzo[e][1,2]oxaborinine-8-carboxylic acid

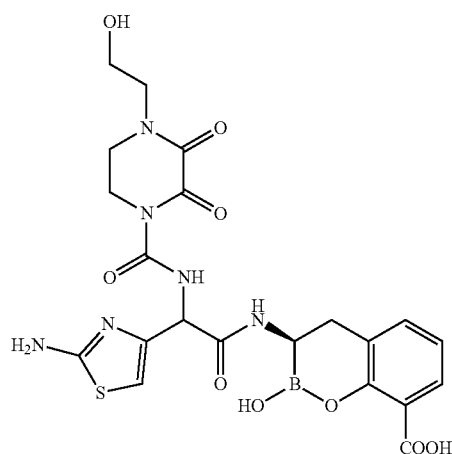 [SMILES: Nc1nc(C(NC(=O)N2CCN(CCO)C(=O)C2=O)C(=O)N[C@H]2Cc3cccc(C(=O)O)c3OB2O)cs1]

In a similar manner to the synthesis of Example 52, utilizing ((2-bromoethoxy)methyl)benzene in place of 1-bromo-2-fluoroethane in Step 1, the title compound was prepared. ESI-MS m/z 547 (MH)$^+$.

Example 61: (3R)-3-(2-(2-aminothiazol-4-yl)-2-(4-(2-methoxyethyl)-2,3-dioxopiperazine-1-carboxamido)acetamido)-2-hydroxy-3,4-dihydro-2H-benzo[e][1,2]oxaborinine-8-carboxylic acid

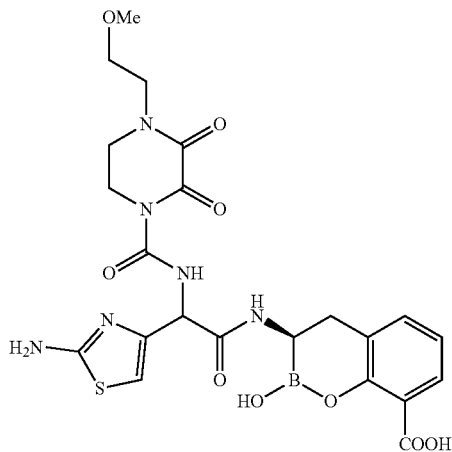 [SMILES: COCCN1CCN(C(=O)NC(C(=O)N[C@H]2Cc3cccc(C(=O)O)c3OB2O)c2csc(N)n2)C(=O)C1=O]

In a similar manner to the synthesis of Example 52, utilizing 1-bromo-2-methoxyethane in place of 1-bromo-2-fluoroethane in Step 1, the title compound was prepared. ESI-MS m/z 561 (MH)+.

Example 62: (3R)-3-(2-(2-aminothiazol-4-yl)-2-(4-ethyl-3-oxopiperazine-1-carboxamido)acetamido)-2-hydroxy-3,4-dihydro-2H-benzo[e][1,2]oxaborinine-8-carboxylic acid

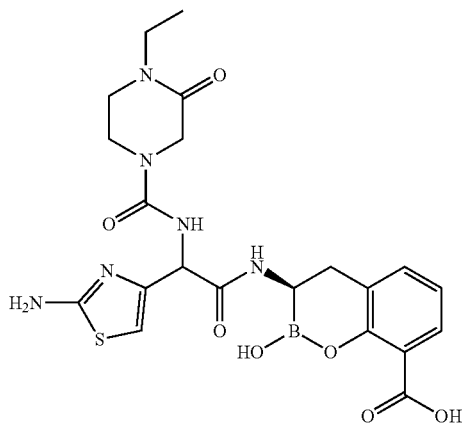 [SMILES: CCN1CCN(C(=O)NC(C(=O)N[C@H]2Cc3cccc(C(=O)O)c3OB2O)c2csc(N)n2)CC1=O]

Step 1. Synthesis of 4-ethyl-3-oxopiperazine-1-carboxylic acid

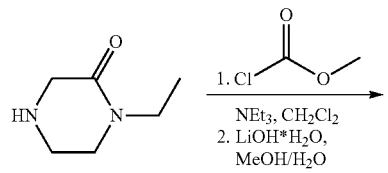

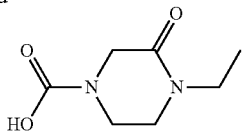

To a solution of 1-ethylpiperazin-2-one (1.08 g, 8.43 mmol) in DCM (38 mL) under Ar was added triethylamine (5.9 mL, 42.3 mmol) and methyl chloroformate (2.0 mL, 25.9 mmol). The reaction mixture was stirred at room temperature for 18 h. The reaction mixture was concentrated then redissolved in methanol (20 mL) and water (20 mL). Lithium hydroxide (1.33 g, 31.6 mmol) was added and the reaction was stirred at room temperature for 43 h. The reaction was concentrated and extracted one time with hexane. The aqueous layer was acidified to pH~2-3 with 1N HCl and extracted three times with ethyl acetate. Combined organic layers were dried over MgSO₄, filtered, and concentrated to afford the title compound (0.22 g, 15%).

Step 2. Synthesis of tert-butyl 3-((2R)-2-(2-(((benzyloxy)carbonyl)amino)thiazol-4-yl)-2-(4-ethyl-3-oxopiperazine-1-carboxamido)acetamido)-2-((3aS)-3a,5,5-trimethylhexahydro-4,6-methanobenzo[d][1,3,2]dioxaborol-2-yl)ethyl)-2-methoxybenzoate

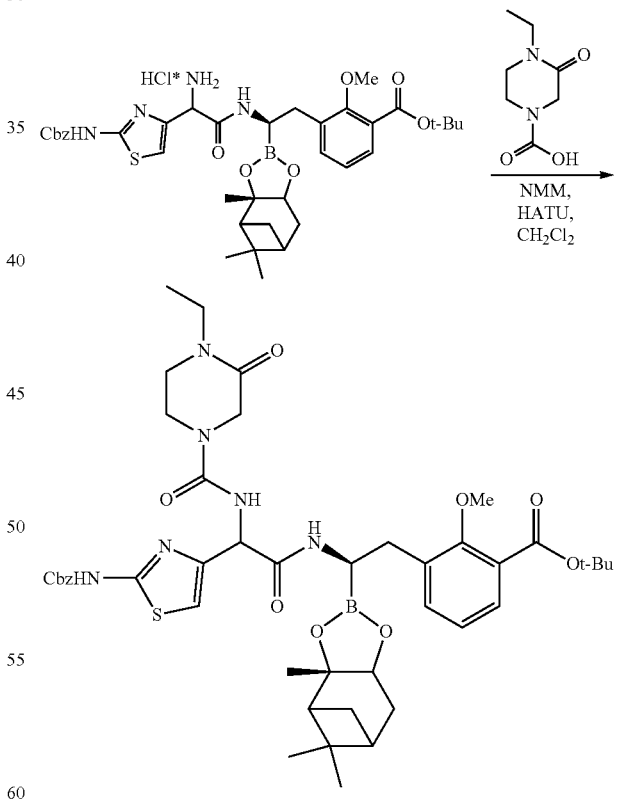

To a suspension of 4-ethyl-3-oxopiperazine-1-carboxylic acid (0.10 g, 0.60 mmol) in DCM (4 mL) under Ar was added HATU (0.25 g, 0.67 mmol) and N-Methylmorpholine (0.07 mL, 0.64 mmol) and the reaction mixture was stirred at room temperature for 75 min. A solution of tert-butyl 3-((2R)-2-(2-amino-2-(2-(((benzyloxy)carbonyl)amino)thiazol-4-yl)acetamido)-2-((3aS,4S,6R)-3a,5,5-trimethylhexahydro-4,6-methanobenzo[d][1,3,2]dioxaborol-2-yl)ethyl)-2-methoxybenzoate (Example 25, Steps 1-2) (0.20 g, 0.27 mmol), N-methylmorpholine (0.10 mL, 0.91 mmol), and DCM (2 mL) was added and the reaction stirred at room temperature for 21 h. The reaction was diluted with water and extracted three times with ethyl acetate. The combined organic layers were washed with brine, dried over MgSO$_4$, filtered, and concentrated. Column chromatography (5-100% Ethyl Acetate/Hexane) afforded the title compound (0.081 g, 35%). ESI-MS m/z 874 (MH)$^+$.

Step 3. Synthesis of (3R)-3-(2-(2-aminothiazol-4-yl)-2-(4-ethyl-3-oxopiperazine-1-carboxamido)acetamido)-2-hydroxy-3,4-dihydro-2H-benzo[e][1,2]oxaborinine-8-carboxylic acid tert-Butyl 3-((2R)-2-(2-(2-(((benzyloxy)carbonyl)amino)thiazol-4-yl)-2-(4-ethyl-3-oxopiperazine-1-carboxamido)acetamido)-2-((3aS)-3a,5,5-trimethylhexahydro-4,6-methanobenzo[d][1,3,2]dioxaborol-2-yl)ethyl)-2-methoxybenzoate (0.081 g, 0.093 mmol) was dissolved in hydrobromic acid (33% in acetic acid, 1.5 mL) under Ar and stirred at room temperature for 21 h. The reaction was diluted with water and purified by preparative HPLC followed by lyophilization to provide the title compound (0.030 g, 62%). ESI-MS m/z 517 (MH)$^+$.

Example 63: (3R)-3-(2-(2-((2-aminoethyl)amino)thiazol-4-yl)-2-(4-ethyl-2,3-dioxopiperazine-1-carboxamido)acetamido)-2-hydroxy-3,4-dihydro-2H-benzo[e][1,2]oxaborinine-8-carboxylic acid

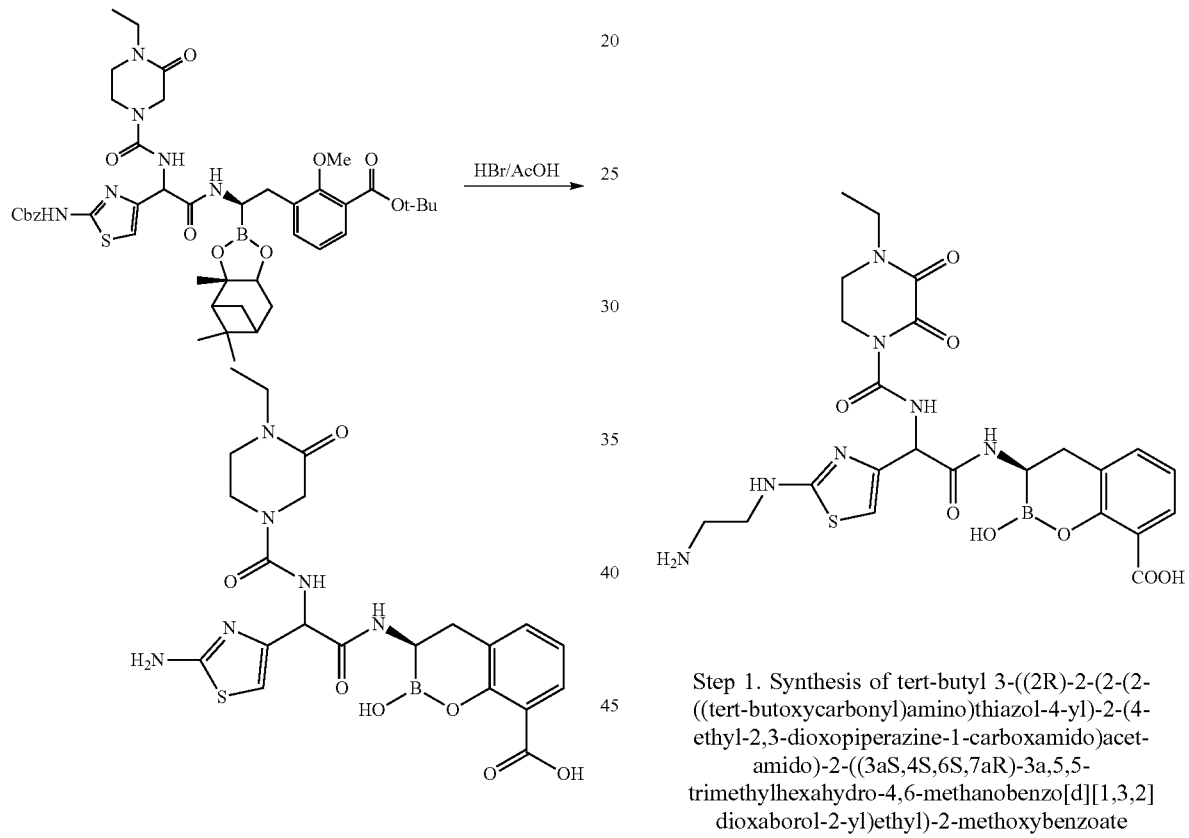

Step 1. Synthesis of tert-butyl 3-((2R)-2-(2-(2-((tert-butoxycarbonyl)amino)thiazol-4-yl)-2-(4-ethyl-2,3-dioxopiperazine-1-carboxamido)acetamido)-2-((3aS,4S,6S,7aR)-3a,5,5-trimethylhexahydro-4,6-methanobenzo[d][1,3,2]dioxaborol-2-yl)ethyl)-2-methoxybenzoate

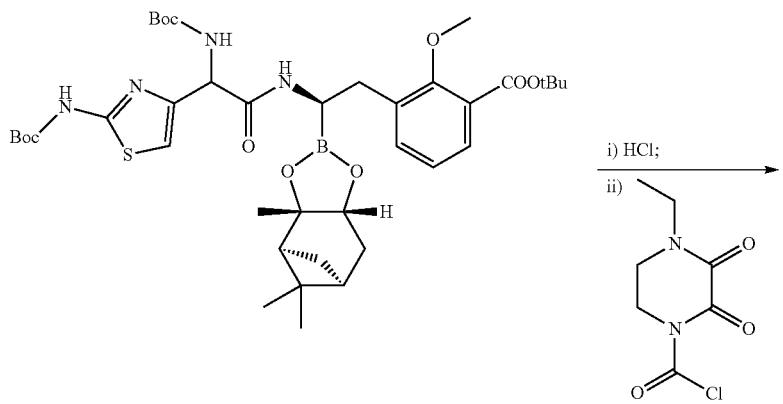

-continued

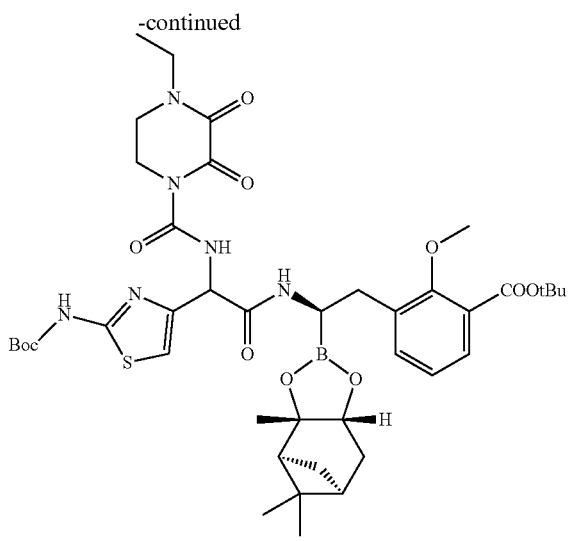

The fully protected precursor of Example 8, Example 9 (2.82 g, 3.6 mmol) was treated with 1.0 M HCl in diethyl ether (100 mL, 100 mmol) at RT overnight, then concentrated in vacuo. This crude product was dissolved in DCM (90 mL), treated with 4-ethyl-2,3-dioxopiperazine-1-carbonyl chloride (884 mg, 4.32 mmol) in the presence of iPr$_2$NEt (2.9 mL, 16.6 mmol) at RT for 1.5 h, washed with aqueous NaHCO$_3$, dried over Na$_2$SO$_4$, concentrated, and purified by flash chromatography on silica gel (hexane-acetone, 4:1-1:1) to afford the title compound, 610 mg. ESI-MS m/z 853 (MH)$^+$.

Step 2. Synthesis of 3-((2R)-2-(2-(2-((2-(((tert-butoxycarbonyl)amino)ethyl)amino)thiazol-4-yl)-2-(4-ethyl-2,3-dioxopiperazine-1-carboxamido)acetamido)-2-((3aS,4S,6S,7aR)-3a,5,5-trimethylhexahydro-4,6-methanobenzo[d][1,3,2]dioxaborol-2-yl)ethyl)-2-methoxybenzoic acid

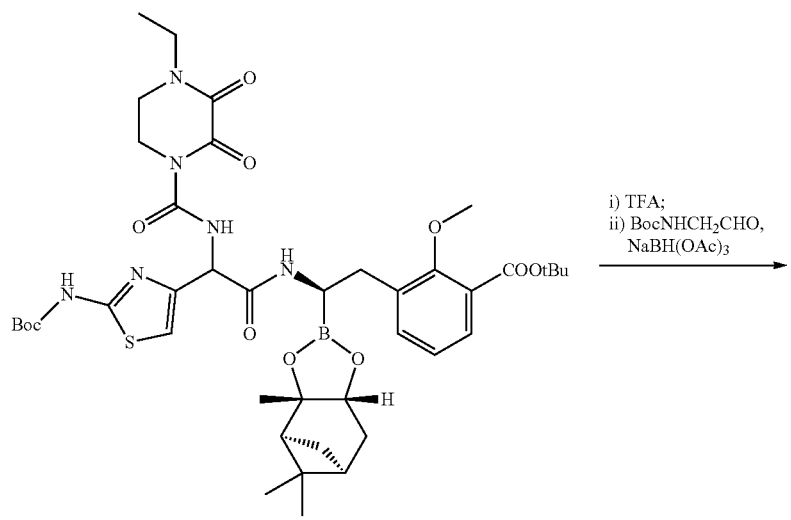

i) TFA;
ii) BocNHCH$_2$CHO, NaBH(OAc)$_3$

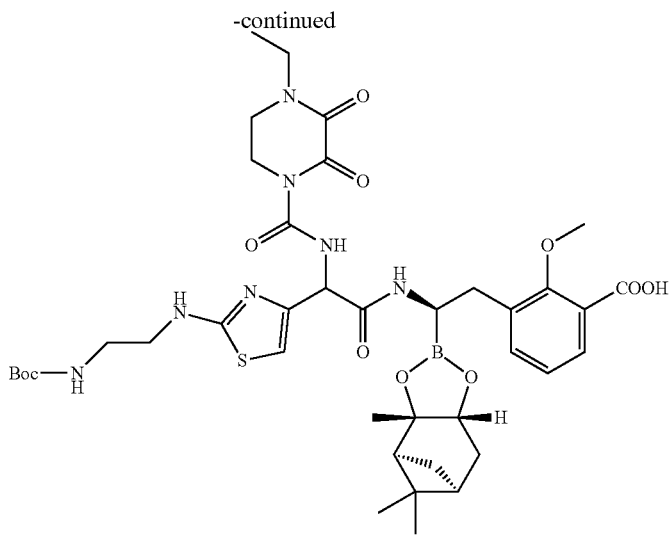

The above product (600 mg, 0.7 mmol) in DCM (6 mL) was treated with TFA (3 mL) at RT for 80 min, then concentrated in vacuo. This crude product was dissolved in DCE (9 mL), added N-Boc-2-aminoaectaldehyde (223 mg, 1.4 mmol), HOAc (0.24 mL, 4.2 mmol), and NaBH(OAc)$_3$ (340 mg, 1.6 mmol). The reaction mixture was stirred at RT for 4 h, added more N-Boc-2-aminoaectaldehyde (112 mg, 0.7 mmol) and NaBH(OAc)$_3$ (149 mg, 0.7 mmol). The reaction mixture was stirred at RT overnight, washed with water, brine, dried over Na$_2$SO$_4$, concentrated, and purified by flash chromatography on silica gel (DCM-MeOH, 20:1-4:1) to afford the title compound, 130 mg. ESI-MS m/z 840 (MH)$^+$.

Step 3. Synthesis of (3R)-3-(2-(2-((2-aminoethyl)amino)thiazol-4-yl)-2-(4-ethyl-2,3-dioxopiperazine-1-carboxamido)acetamido)-2-hydroxy-3,4-dihydro-2H-benzo[e][1,2]oxaborinine-8-carboxylic acid

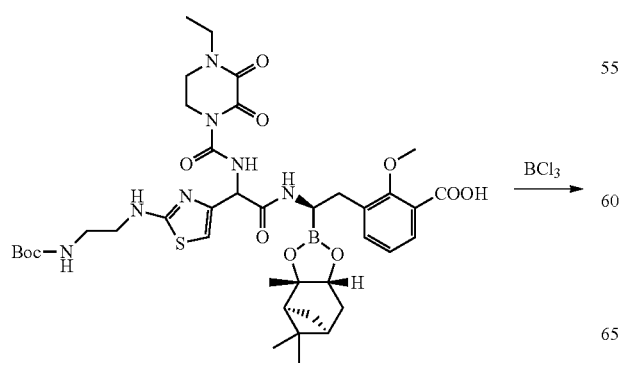

The title compound was prepared by treatment of the above product with BCl$_3$ by following General Method A. ESI-MS m/z 574 (MH)$^+$.

Example 64: (3R)-3-(2-(2-aminothiazol-4-yl)-2-(4-ethyl-3,5-dioxopiperazine-1-carboxamido)acetamido)-2-hydroxy-3,4-dihydro-2H-benzo[e][1,2]oxaborinine-8-carboxylic acid

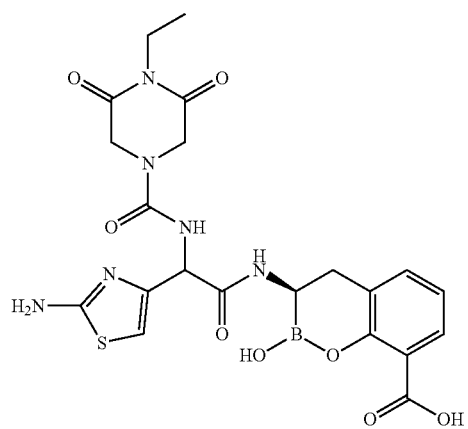 [SMILES: CCN1C(=O)CN(C(=O)NC(C(=O)N[C@H]2Cc3cccc(C(=O)O)c3OB2O)c2csc(N)n2)CC1=O]

Step 1. Synthesis of 4-ethyl-3,5-dioxopiperazine-1-carboxylic acid

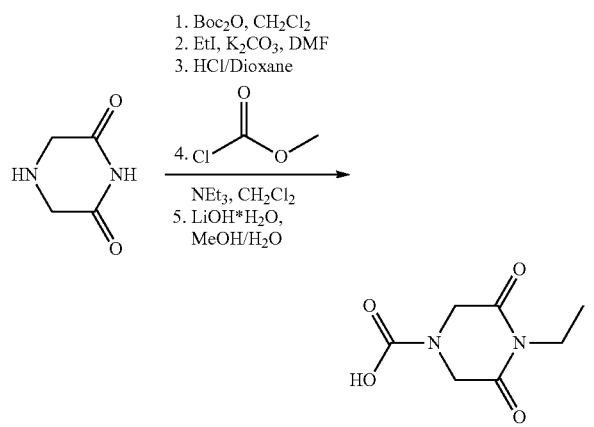

Di-tert-butyldicarbonate (5.78 g, 26.5 mmol) in DCM (5 mL) was added to a solution of piperazin-2,6-dione (2.01 g, 17.6 mmol) in DCM (75 mL) under Ar and the reaction was stirred at room temperature for 19 h. The reaction mixture was concentrated then redissolved in DMF (80 mL) under Ar. Potassium carbonate (4.87 g, 35.2 mmol) and iodoethane (2.8 mL, 34.8 mmol) were added and the reaction was heated to 90° C. and stirred for 15 h. The reaction was cooled, diluted with ethyl acetate, and washed with water, aqueous $Na_2S_2O_4$, and brine. The organic layer was dried over $MgSO_4$, filtered, and concentrated. Column chromatography (5-75% Ethyl Acetate/Hexane) afforded the desired product in a 71% yield. That product (3.03 g, 12.5 mmol) was dissolved in hydrochloric acid (4.0 M in 1,4-dioxane, 30 mL) and stirred under Ar at room temperature for 18 h. The reaction mixture was concentrated and azeotroped two times with toluene. The crude material was carried to the title compound following the procedure in Example 62, Step 1.

Step 2. Synthesis of tert-butyl 3-((2R)-2-(2-(2-(((benzyloxy)carbonyl)amino)thiazol-4-yl)-2-(4-ethyl-3,5-dioxopiperazine-1-carboxamido)acetamido)-2-((3aS)-3a,5,5-trimethylhexahydro-4,6-methanobenzo[d][1,3,2]dioxaborol-2-yl)ethyl)-2-methoxybenzoate

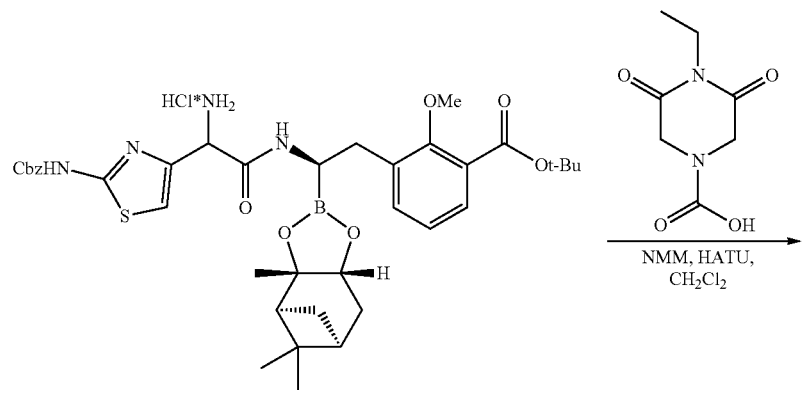

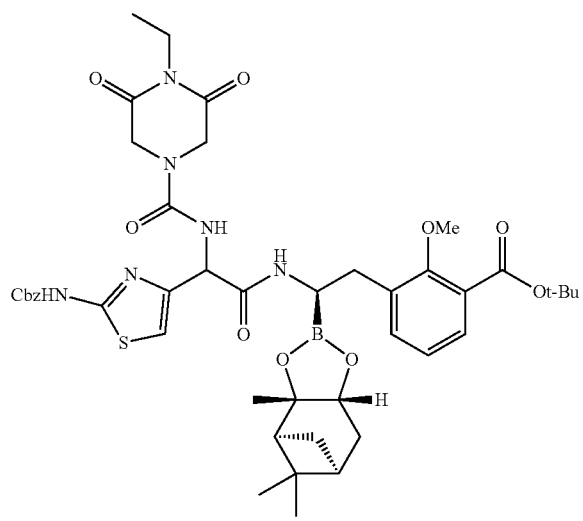

The title compound was prepared following the procedure in Example 62, Step 2. ESI-MS m/z 887 (MH)+.

Step 3. Synthesis of (3R)-3-(2-(2-aminothiazol-4-yl)-2-(4-ethyl-3,5-dioxopiperazine-1-carboxamido)acetamido)-2-hydroxy-3,4-dihydro-2H-benzo[e][1,2]oxaborinine-8-carboxylic acid

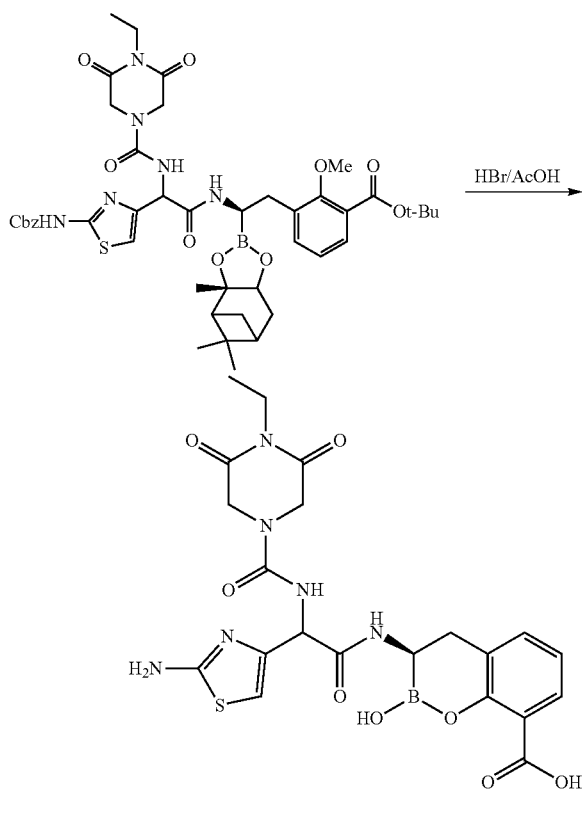

The title compound was prepared following the procedure in Example 62, Step 3. ESI-MS m/z 531 (MH)+.

Example 65: (3R)-3-(2-(2-aminothiazol-4-yl)-2-(1,1-dioxidothiomorpholine-4-carboxamido)acetamido)-2-hydroxy-3,4-dihydro-2H-benzo[e][1,2]oxaborinine-8-carboxylic acid

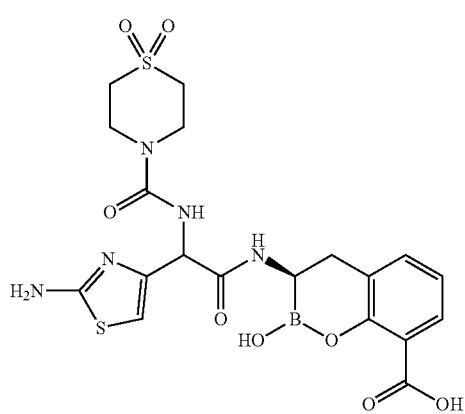 [SMILES: Nc1nc(C(NC(=O)N2CCS(=O)(=O)CC2)C(=O)N[C@H]2Cc3cccc(C(=O)O)c3OB2O)cs1]

Step 1. Synthesis of tert-butyl 3-((2R)-2-(2-(2-(((benzyloxy)carbonyl)amino)thiazol-4-yl)-2-(1,1-dioxidothiomorpholine-4-carboxamido)acetamido)-2-((3aS)-3a,5,5-trimethylhexahydro-4,6-methanobenzo[d][1,3,2]dioxaborol-2-yl)ethyl)-2-methoxybenzoate

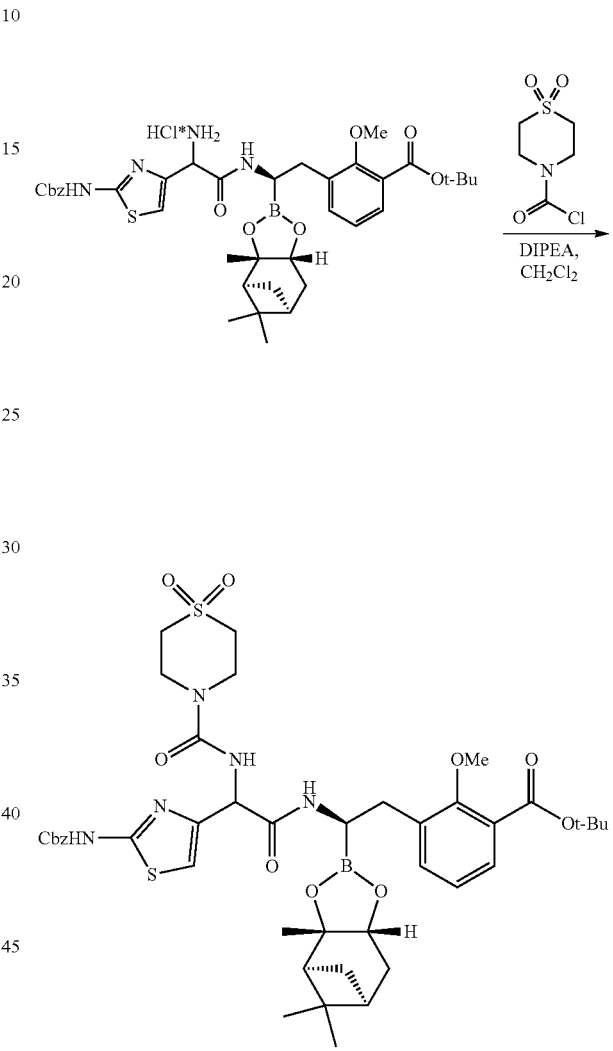

Diisopropylethylamine (0.23 mL, 1.32 mmol) was added to a solution of tert-butyl 3-((2R)-2-(2-amino-2-(2-(((benzyloxy)carbonyl)amino)thiazol-4-yl)acetamido)-2-((3aS,4S,6R)-3a,5,5-trimethylhexahydro-4,6-methanobenzo[d][1,3,2]dioxaborol-2-yl)ethyl)-2-methoxybenzoate (Example 25, Steps 1-2) (0.39 g, 0.52 mmol) in DCM (6 mL) under Ar and the reaction was cooled to 0° C. 1,1-Dioxothiomorpholino-4-carbonyl chloride (0.14 g, 0.72 mmol) was added in one portion and the reaction was stirred at 0° C. for 5 min then warmed to room temperature for 85 min. The reaction was quenched with water and extracted with DCM. The organic layer was dried over MgSO4, filtered, and concentrated. Column chromatography (5-100% Ethyl Acetate/Hexane) afforded the desired product (0.13 g, 28%). ESI-MS m/z 881 (MH)+.

Step 2. Synthesis of (3R)-3-(2-(2-aminothiazol-4-yl)-2-(1,1-dioxidothiomorpholine-4-carboxamido)acetamido)-2-hydroxy-3,4-dihydro-2H-benzo[e][1,2]oxaborinine-8-carboxylic acid

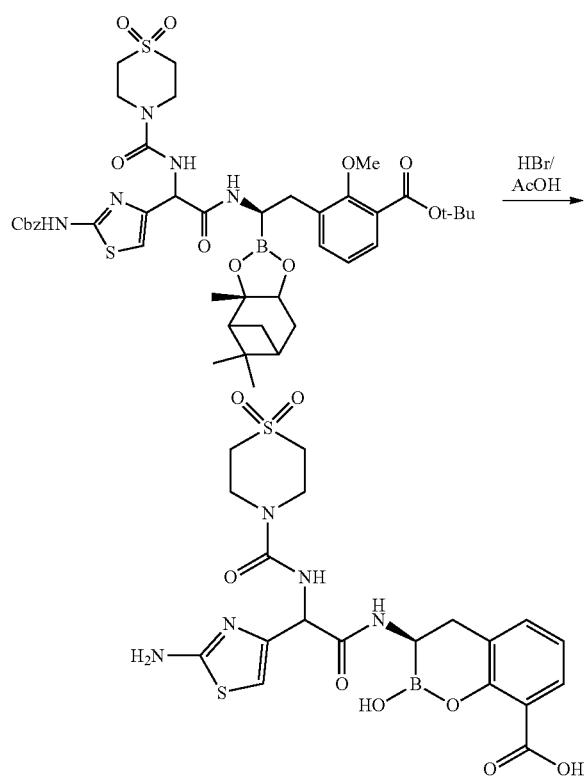

The title compound was prepared following the procedure in Example 62, Step 3. ESI-MS m/z 524 (MH)+.

Example 66: (3R)-3-(2-(2-aminothiazol-4-yl)-2-(4-isobutyl-2,3-dioxopiperazine-1-carboxamido)acetamido)-2-hydroxy-3,4-dihydro-2H-benzo[e][1,2]oxaborinine-8-carboxylic acid

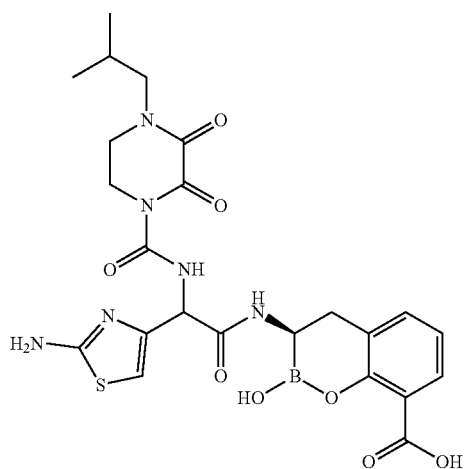 [SMILES: CC(C)CN1CCN(C(=O)NC(C(=O)N[C@H]2Cc3cccc(C(=O)O)c3OB2O)c2csc(N)n2)C(=O)C1=O]

The title compound was prepared according to the method of Example 43, utilizing 4-isobutyl-2,3-dioxopiperazine-1-carbonyl chloride in place of 4-methyl-2,3-dioxopiperazine-1-carbonyl chloride. ESI-MS m/z 559 (MH)+.

Example 67: (3R)-3-(2-(2-aminothiazol-4-yl)-2-(4-(cyclopropylmethyl)-2,3-dioxopiperazine-1-carboxamido)acetamido)-2-hydroxy-3,4-dihydro-2H-benzo[e][1,2]oxaborinine-8-carboxylic acid

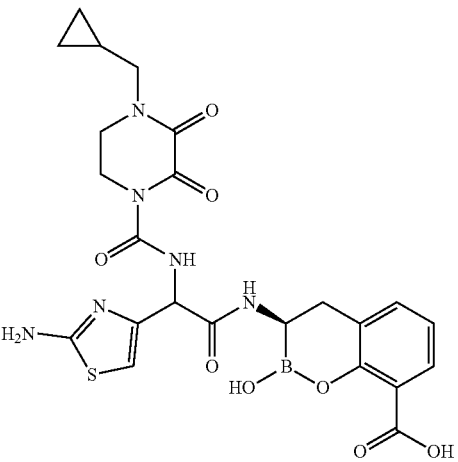 [SMILES: Nc1nc(C(NC(=O)N2CCN(CC3CC3)C(=O)C2=O)C(=O)N[C@H]2Cc3cccc(C(=O)O)c3OB2O)cs1]

The title compound was prepared according to the method of Example 43, utilizing 4-cyclopropylmethyl-2,3-dioxopiperazine-1-carbonyl chloride in place of 4-methyl-2,3-dioxopiperazine-1-carbonyl chloride. ESI-MS m/z 557 (MH)+.

Example 86: (3R)-3-(2-(2-aminothiazol-4-yl)-2-(6-oxopiperidine-2-carboxamido)acetamido)-2-hydroxy-3,4-dihydro-2H-benzo[e][1,2]oxaborinine-8-carboxylic acid

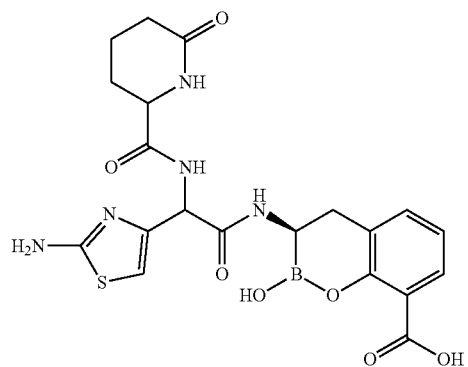 [SMILES: Nc1nc(C(NC(=O)C2CCCC(=O)N2)C(=O)N[C@H]2Cc3cccc(C(=O)O)c3OB2O)cs1]

Step 1. Synthesis of tert-butyl 3-((2R)-2-(2-(2-(((benzyloxy)carbonyl)amino)thiazol-4-yl)-2-(6-oxopiperidine-2-carboxamido)acetamido)-2-((3aS)-3a,5,5-trimethylhexahydro-4,6-methanobenzo[d][1,3,2]dioxaborol-2-yl)ethyl)-2-methoxybenzoate

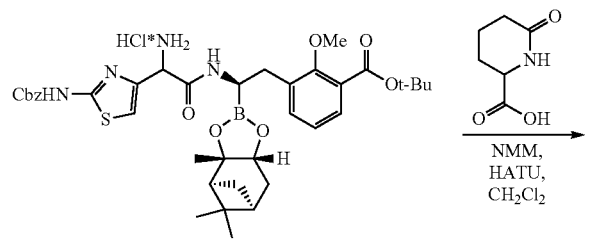
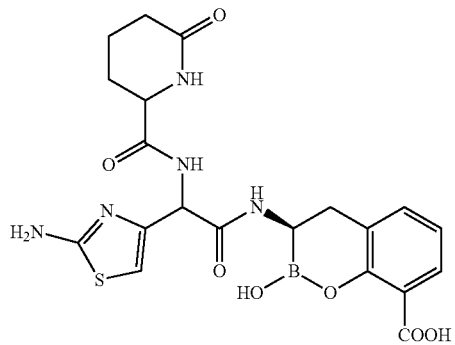

The title compound was prepared by treatment of the above product with BCl₃ by following General Method A. ESI-MS m/z 488 (MH)⁺.

Example 69: (3R)-3-(2-(2-aminothiazol-4-yl)-2-(4-(2,2-difluoroethyl)-2,3-dioxopiperazine-1-carboxamido)acetamido)-2-hydroxy-3,4-dihydro-2H-benzo[e][1,2]oxaborinine-8-carboxylic acid

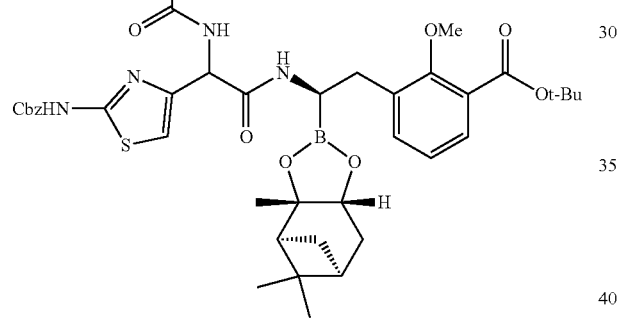

The title compound was prepared by following the procedure in Example 62, Step 2. ESI-MS m/z 844 (MH)⁺.

Step 2. Synthesis of (3R)-3-(2-(2-aminothiazol-4-yl)-2-(6-oxopiperidine-2-carboxamido)acetamido)-2-hydroxy-3,4-dihydro-2H-benzo[e][1,2]oxaborinine-8-carboxylic acid

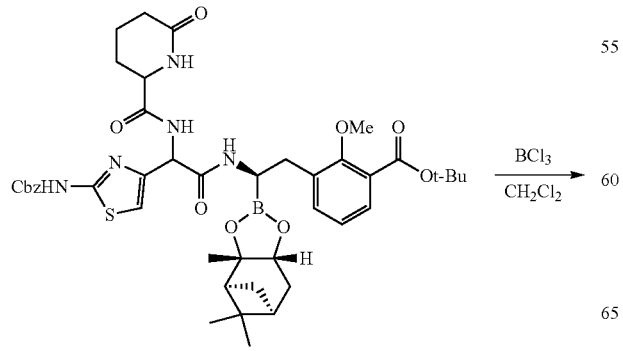
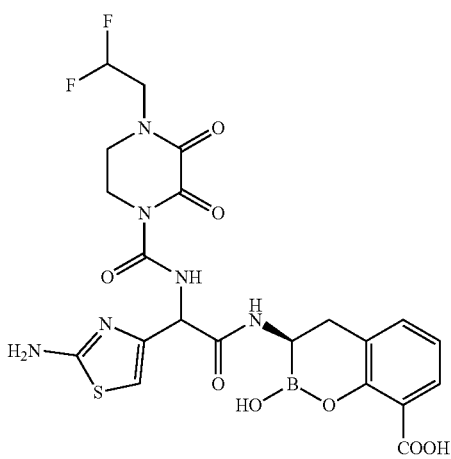 [SMILES: Nc1nc(C(NC(=O)N2CCN(CC(F)F)C(=O)C2=O)C(=O)N[C@H]2Cc3cccc(C(=O)O)c3OB2O)cs1]

In a similar manner to the synthesis of Example 52, utilizing 2-bromo-1,2-difluoroethane in place of 1-bromo-2-fluoroethane in Step 1, the title compound was prepared. ESI-MS m/z 567 (MH)⁺.

Example 70: (3R)-3-(2-(2-aminothiazol-4-yl)-2-(1-(methylsulfonyl)piperidine-4-carboxamido)acetamido)-2-hydroxy-3,4-dihydro-2H-benzo[e][1,2]oxaborinine-8-carboxylic acid

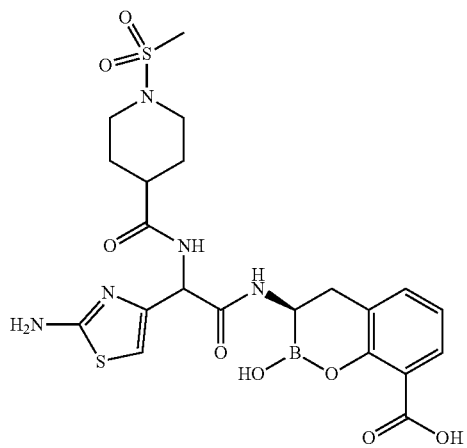 [SMILES: CS(=O)(=O)N1CCC(C(=O)NC(C(=O)N[C@H]2Cc3cccc(C(=O)O)c3OB2O)c2csc(N)n2)CC1]

Step 1. Synthesis of tert-butyl 3-((2R)-2-(2-(2-(((benzyloxy)carbonyl)amino)thiazol-4-yl)-2-(1-(methylsulfonyl)piperidine-4-carboxamido)acetamido)-2-((3aS)-3a,5,5-trimethylhexahydro-4,6-methanobenzo[d][1,3,2]dioxaborol-2-yl)ethyl)-2-methoxybenzoate

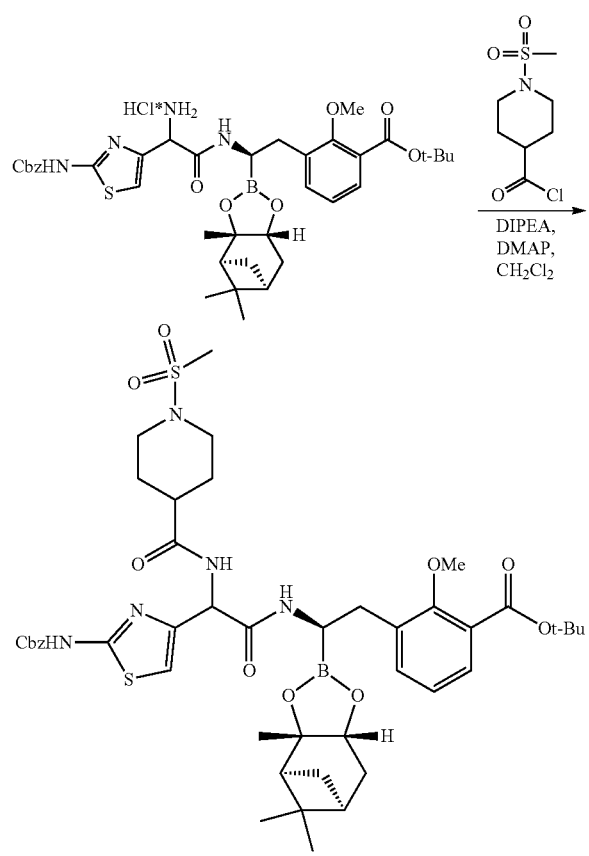

The title compound was prepared by following the procedure in Example 65, Step 1. ESI-MS m/z 909 (MH)+.

Step 2. Synthesis of (3R)-3-(2-(2-aminothiazol-4-yl)-2-(1-(methylsulfonyl)piperidine-4-carboxamido)acetamido)-2-hydroxy-3,4-dihydro-2H-benzo[e][1,2]oxaborinine-8-carboxylic acid

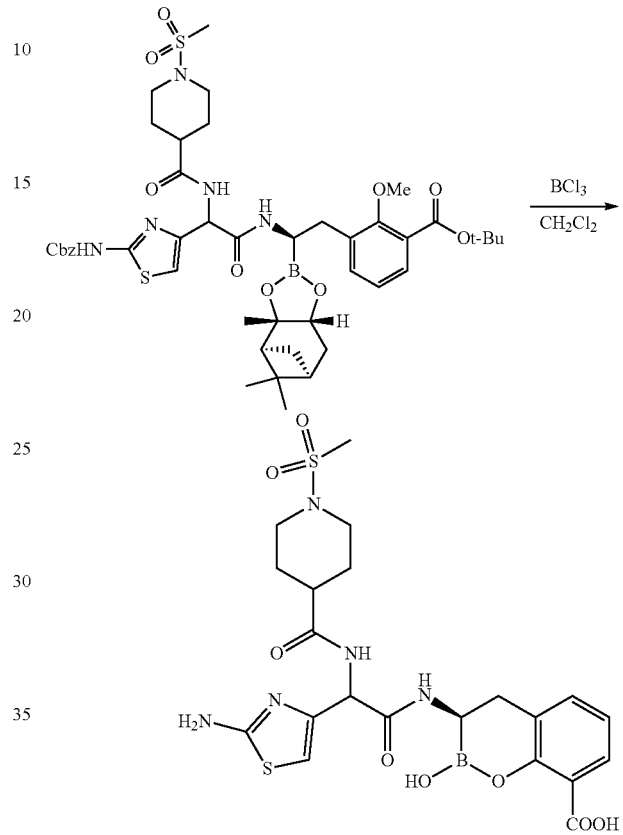

The title compound was prepared by treatment of the above product with BCl$_3$ by following General Method A. ESI-MS m/z 552 (MH)+.

Example 71: (3R)-3-(2-(3-acetyl-2-oxoimidazolidine-1-carboxamido)-2-(2-aminothiazol-4-yl)acetamido)-2-hydroxy-3,4-dihydro-2H-benzo[e][1,2]oxaborinine-8-carboxylic acid

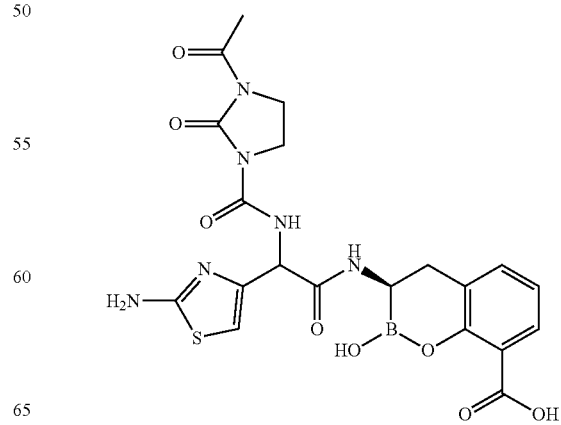

The title compound was prepared by following the procedures in Example 70. ESI-MS m/z 517 (MH)⁺.

Example 72: (3R)-3-(2-(2-aminothiazol-4-yl)-2-(4-hydroxy-2,3-dioxopiperazine-1-carboxamido)acetamido)-2-hydroxy-3,4-dihydro-2H-benzo[e][1,2]oxaborinine-8-carboxylic acid

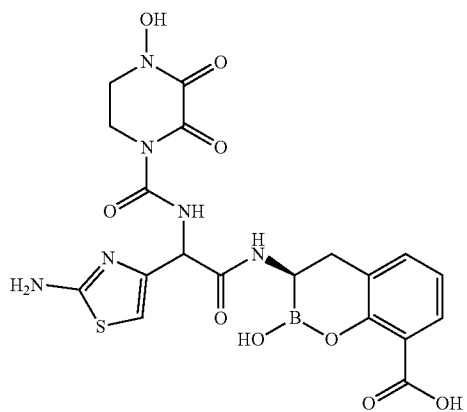 [SMILES: Nc1nc(C(NC(=O)N2CCN(O)C(=O)C2=O)C(=O)N[C@H]2Cc3cccc(C(=O)O)c3OB2O)cs1]

Step 1: Synthesis of tert-butyl 3-((2R)-2-((R)-2-(2-(((benzyloxy)carbonyl)amino)thiazol-4-yl)-2-(4-hydroxy-2,3-dioxopiperazine-1-carboxamido)acetamido)-2-((3aS,4S,6R)-3a,5,5-trimethylhexahydro-4,6-methanobenzo[d][1,3,2]dioxaborol-2-yl)ethyl)-2-methoxybenzoate

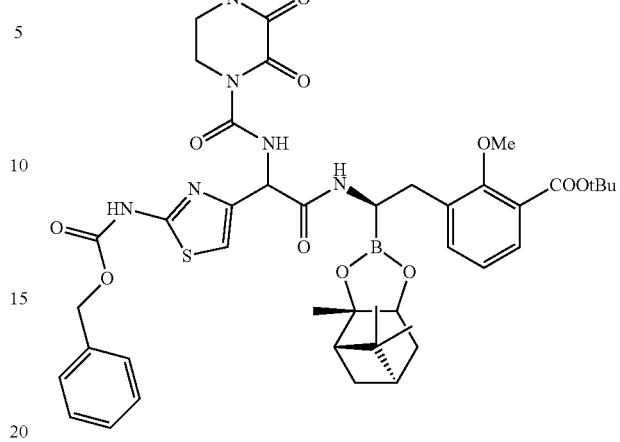

To tert-butyl 3-((2R)-2-((R)-2-(4-(benzyloxy)-2,3-dioxopiperazine-1-carboxamido)-2-(2-(((benzyloxy)carbonyl)amino)thiazol-4-yl)acetamido)-2-((3aS,4S,6R)-3a,5,5-trimethylhexahydro-4,6-methanobenzo[d][1,3,2]dioxaborol-2-yl)ethyl)-2-methoxybenzoate (prepared according to the method of Example 43, utilizing 4-benzyloxy-2,3-dioxopiperazine-1-carbonyl chloride in place of 4-methyl-2,3-dioxopiperazine-1-carbonyl chloride) 0.23 g (0.23 mmol) in methanol (5 mL) was added 10% palladium on carbon under an atmosphere of argon and the reaction was stirred under hydrogen at RT for 18 h. The mixture was filtered through celite, washed with methanol, concentrated and dried under high vacuum to give the desired compound, 0.18 g. ESI-MS m/z 875 (MH)⁺.

Step 2: Synthesis of (3R)-3-(2-(2-aminothiazol-4-yl)-2-(4-hydroxy-2,3-dioxopiperazine-1-carboxamido)acetamido)-2-hydroxy-3,4-dihydro-2H-benzo[e][1,2]oxaborinine-8-carboxylic acid

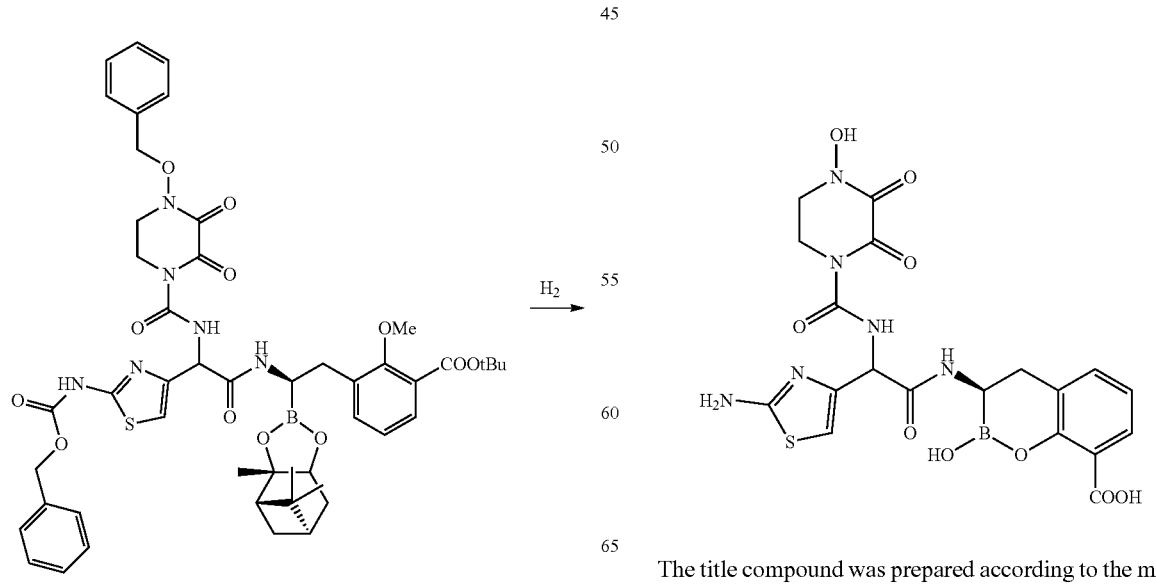

The title compound was prepared according to the method of Example 43. ESI-MS m/z 519 (MH)⁺.

Example 73: (R)-3-((2S,3S)-2-(4-ethyl-2,3-dioxopiperazine-1-carboxamido)-3,4-dihydroxybutanamido)-2-hydroxy-3,4-dihydro-2H-benzo[e][1,2]oxaborinine-8-carboxylic acid

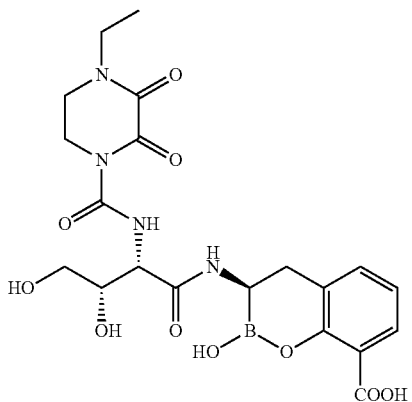 [SMILES: CCN1CCN(C(=O)N[C@H](C(=O)N[C@H]2Cc3cccc(C(=O)O)c3OB2O)[C@H](O)CO)C(=O)C1=O]

Step 1. Synthesis of (3S)-3,4-bis(benzyloxy)-2-(4-ethyl-2,3-dioxopiperazine-1-carboxamido)butanoic acid

Step 1a. Synthesis of (3S)-2-amino-3,4-bis(benzyloxy)butanenitrile

A solution of (R)-2,3-bis(benzyloxy)propanal (3 g, 11.1 mmol) in ethanol (50 mL) was treated with ammonium acetate (9.4 g, 111 mmol, 10 eq), and the reaction mixture was stirred at room temperature for 2 h. Neat trimethylsilyl cyanide (4 mL) was added dropwise and the reaction mixture was stirred at room temperature overnight. The reaction was quenched with a saturated sodium bicarbonate aqueous solution and extracted with ethyl acetate. The organic extract was washed with water and brine, dried on sodium sulfate and then filtered. The volatiles were evaporated under reduced pressure and the product was further purified by flash chromatography (Silicagel, ethyl acetate/hexanes) to provide (3S)-2-amino-3,4-bis(benzyloxy)butanenitrile as an oil (mixture of epimers in ~3:1 ratio).

Step 1b. Synthesis of methyl (3S)-2-amino-3,4-bis(benzyloxy)butanoate (3S)-2-amino-3,4-bis(benzyloxy)butanenitrile (2.2 g, 7.4 mmol) in a saturated methanolic solution of anhydrous hydrochloric acid (30 mL) was stirred at 60° C. overnight. Most of the volatiles were evaporated under reduced pressure, and the residue was suspended in ethyl acetate at 0° C. and basified with saturated aqueous sodium bicarbonate to pH 8. The aqueous phase was extracted once again with ethyl acetate and the combined organic extracts were dried on sodium sulfate and filtered. The solvent was evaporated under reduced pressure and the residue was subjected to flash chromatography (Silica gel, ethyl acetate/hexanes) to provide methyl (3S)-2-amino-3,4-bis(benzyloxy)butanoate.

Step 1c. Synthesis of (3S)-3,4-bis(benzyloxy)-2-(4-ethyl-2,3-dioxopiperazine-1-carboxamido)butanoic acid Methyl (3S)-2-amino-3,4-bis(benzyloxy)butanoate (356 mg, 1.1. mmol) in a 1:1 (v/v) mixture of tetrahydrofuran/water (10 mL) was treated with lithium hydroxide (39 mg, 1.6 mmol) at 0° C., then allowed to warm to room temperature and stirred for 4 hours. The reaction mixture was cooled back to 0° C. and the pH was adjusted first to 4 by addition of aqueous 2N HCl, then to 8.5 by addition of saturated aqueous sodium bicarbonate. To the resulting mixture was added dropwise a solution of 4-ethyl-2,3-dioxopiperazine-1-carbonyl chloride (275 mg, 1.25 eq) in tetrahydrofuran (5 mL) and the reaction mixture was stirred for 1 h at 0° C. The volatiles were evaporated under reduced pressure and the remaining aqueous residue was cooled back to 0° C., acidified to pH 2 with aqueous 2N HCl and extracted with ethyl acetate. The combined organic extracts were dried on sodium sulfate and then filtered. The solvent was evaporated under reduced pressure to provide (3S)-3,4-bis(benzyloxy)-2-(4-ethyl-2,3-dioxopiperazine-1-carboxamido)butanoic acid, which was used in the next step without further purification.

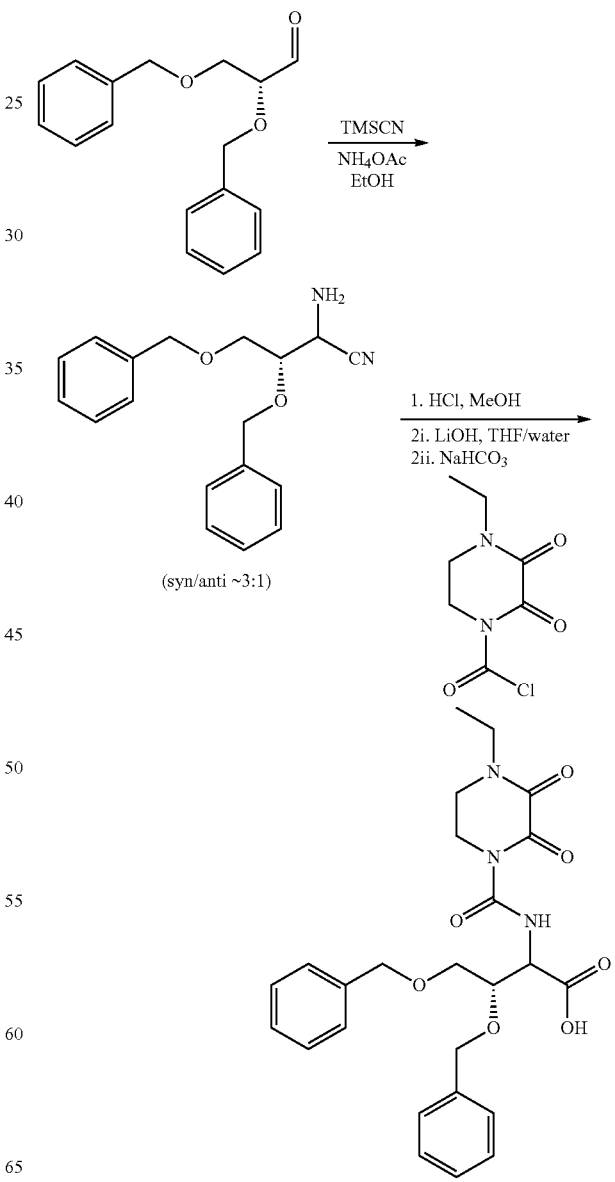

Step 2. Synthesis of (R)-3-((2S,3S)-2-(4-ethyl-2,3-dioxopiperazine-1-carboxamido)-3,4-dihydroxybutanamido)-2-hydroxy-3,4-dihydro-2H-benzo[e][1,2]oxaborinine-8-carboxylic acid The title compound was prepared from (3S)-3,4-bis(benzyloxy)-2-(4-ethyl-2,3-dioxopiperazine-1-carboxamido)butanoic acid and 3-((2S)-2-chloro-2-((3aS,4S,6S)-3a,5,5-trimethylhexahydro-4,6-methanobenzo[d][1,3,2]dioxaborol-2-yl)ethyl)-2-methoxybenzoate, by a procedure similar to Example 31. ESI-MS m/z 493.2 (M+H)⁺.

Example 74: (R)-3-((2R,3S)-2-(4-ethyl-2,3-dioxopiperazine-1-carboxamido)-3,4-dihydroxybutanamido)-2-hydroxy-3,4-dihydro-2H-benzo[e][1,2]oxaborinine-8-carboxylic acid The title compound was isolated by reverse phase hplc from the procedure described in Example 73, Step 2. ESI-MS m/z 493.2 (M+H)⁺.

Example 75: (3R)-3-(2-(4-(aminomethyl)piperidine-1-carboxamido)-2-(2-aminothiazol-4-yl)acetamido)-2-hydroxy-3,4-dihydro-2H-benzo[e][1,2]oxaborinine-8-carboxylic acid

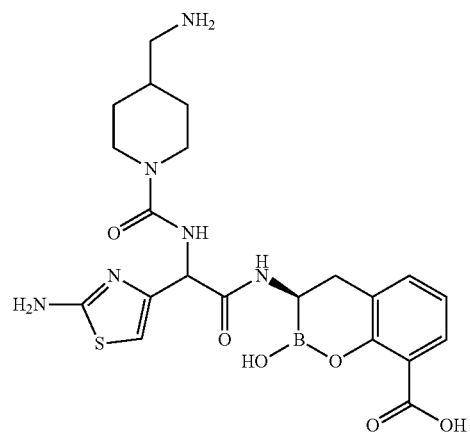

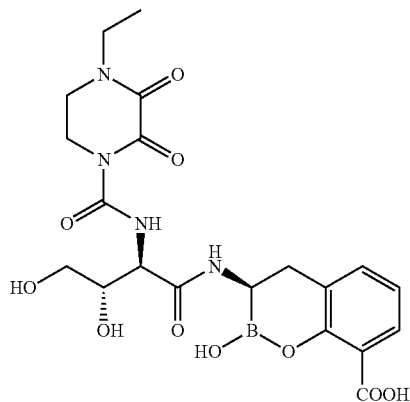 [SMILES: CCN1CCN(C(=O)N[C@@H](C(=O)N[C@H]2Cc3cccc(C(=O)O)c3OB2O)[C@H](O)CO)C(=O)C1=O]

Step 1. Synthesis of tert-butyl 3-((2R)-2-(2-(2-(((benzyloxy)carbonyl)amino)thiazol-4-yl)-2-(4-(((tert-butoxycarbonyl)amino)methyl)piperidine-1-carboxamido)acetamido)-2-((3aS)-3a,5,5-trimethylhexahydro-4,6-methanobenzo[d][1,3,2]dioxaborol-2-yl)ethyl)-2-methoxybenzoate

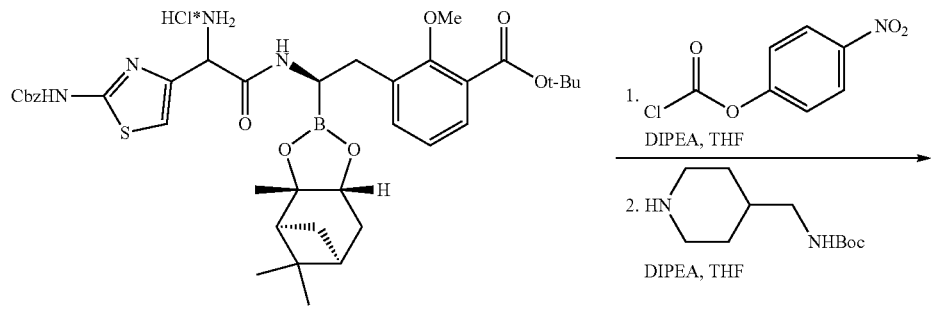

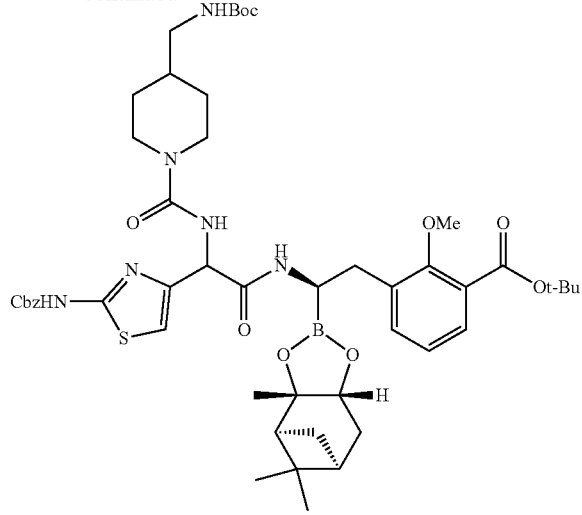

A solution of p-nitrophenyl chloroformate (0.09 g, 0.45 mmol) in THF (3.0 mL) under Ar was cooled to 0° C. A solution of tert-butyl 3-((2R)-2-(2-amino-2-(2-(((benzyloxy)carbonyl)amino)thiazol-4-yl)acetamido)-2-((3aS,4S,6R)-3a,5,5-trimethylhexahydro-4,6-methanobenzo[d][1,3,2]dioxaborol-2-yl)ethyl)-2-methoxybenzoate (Example 25, Steps 1-2) (0.31 g, 0.41 mmol) and diisopropylethylamine (0.17 mL, 1.25 mmol) in THF (2.5 mL) was added dropwise over 7 min. The reaction mixture was stirred at 0° C. for 75 min. A solution of 4-N-Boc-aminomethylpiperidine (0.22 g, 1.02 mmol) and diisopropylethylamine (0.14 mL, 1.03 mmol) in THF/DCM (1.5 mL/0.5 mL) was added and the reaction was stirred at 0° C. for an additional 5 min then warmed to room temperature for 18 h. The reaction was diluted with ethyl acetate and washed with 0.5 N NaOH, saturated NaHCO$_3$, and brine. The organic layer was dried over MgSO$_4$, filtered, concentrated. Column chromatography (5-100% Ethyl Acetate:Hexane) provided the title compound (0.038 g, 10%). ESI-MS m/z 960 (MH)$^+$.

Step 2. Synthesis of (3R)-3-(2-(4-(aminomethyl)piperidine-1-carboxamido)-2-(2-aminothiazol-4-yl)acetamido)-2-hydroxy-3,4-dihydro-2H-benzo[e][1,2]oxaborinine-8-carboxylic acid

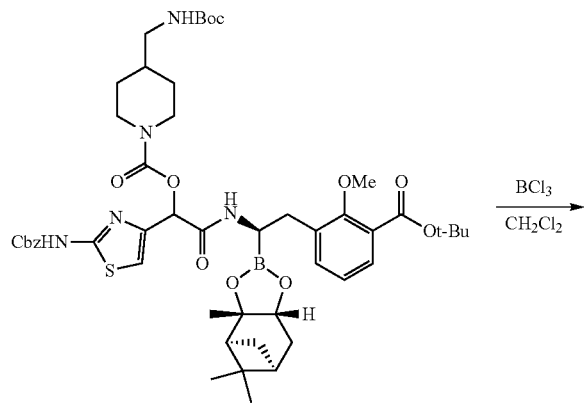

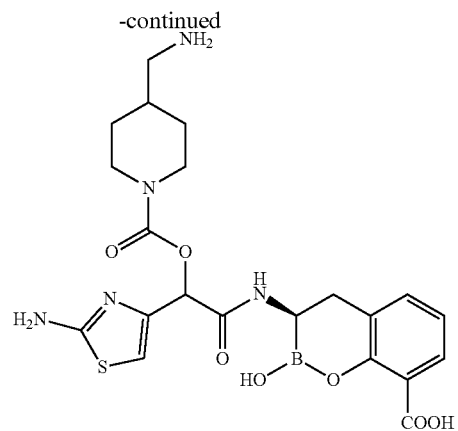

The title compound was prepared by treatment of the above product with BCl$_3$ by following General Method A. ESI-MS m/z 503 (MH)$^+$.

Example 76: (3R)-3-(2-(3-(aminomethyl)piperidine-1-carboxamido)-2-(2-aminothiazol-4-yl)acetamido)-2-hydroxy-3,4-dihydro-2H-benzo[e][1,2]oxaborinine-8-carboxylic acid

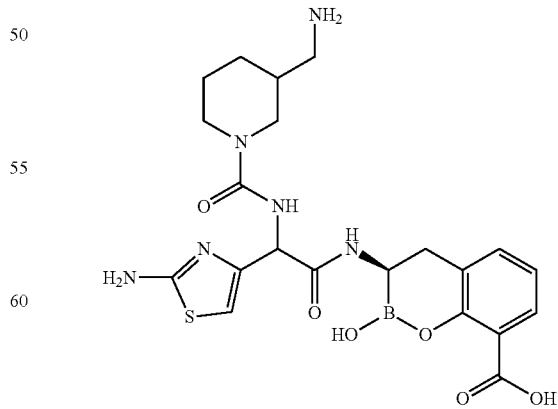

The title compound was prepared following the procedures in Example 75. ESI-MS m/z 503 (MH)$^+$.

Example 77: (3R)-3-(2-(2-aminothiazol-4-yl)-2-(6-hydroxy-1,1-dioxido-1,2,6-thiadiazinane-2-carboxamido)acetamido)-2-hydroxy-3,4-dihydro-2H-benzo[e][1,2]oxaborinine-8-carboxylic acid

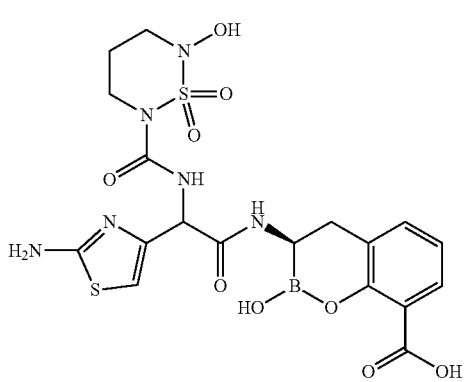 [SMILES: Nc1nc(C(NC(=O)N2CCCN(O)S2(=O)=O)C(=O)N[C@H]2Cc3cccc(C(=O)O)c3OB2O)cs1]

Step 1. Synthesis of tert-butyl (N-((tert-butyldimethylsilyl)oxy)sulfamoyl)carbamate

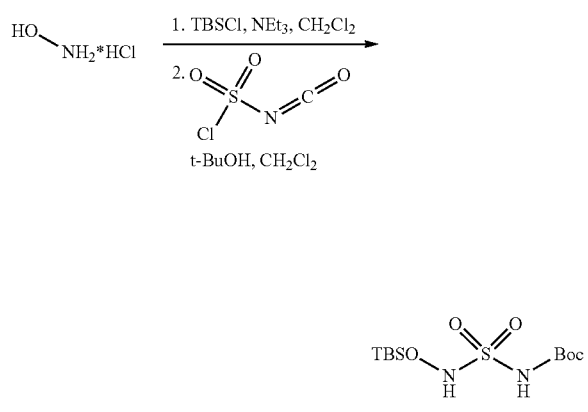

To a solution of hydroxylamine hydrochloride (2.52 g, 36.2 mmol) in DCM (60 mL) under Ar at 0° C. was added triethylamine (15 mL, 108 mmol) dropwise over 7 min. The reaction was warmed to room temperature for 2 h then cooled back down to 0° C. Tert-Butyldimethylsilyl chloride (5.47 g, 32.3 mmol) in DCM (30 mL) was added slowly and the reaction was allowed to warm to room temperature and stir for 21 h. The reaction mixture was cooled back down to 0° C. and additional triethylamine (15 mL, 108 mmol) was added. In a separate flask, t-butanol (3.5 mL, 36.8 mmol) was added dropwise to a cooled (0° C.) solution of chlorosulfonylisocyanate (3.2 mL, 36.8 mmol) in DCM (90 mL) under Ar and stirred at 0° C. for 45 min. The resulting sulfamoyl chloride solution was added to the original reaction mixture via syringe and the reaction mixture warmed to room temperature and stirred for 60 h. The reaction mixture was concentrated, diluted with ethyl acetate, and washed successively with water, 0.1 N HCl, saturated NaHCO₃, and brine. The organic layer was dried over MgSO₄, filtered, and concentrated to afford the title compound (10.1 g, 86%).

Step 2. Synthesis of tert-butyl 6-((tert-butyldimethylsilyl)oxy)-1,2,6-thiadiazinane-2-carboxylate 1,1-dioxide

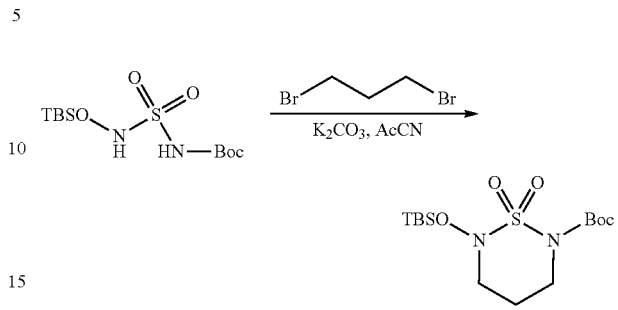

To a solution of tert-butyl (N-((tert-butyldimethylsilyl)oxy)sulfamoyl)carbamate (10.1 g, 30.9 mmol) in acetonitrile (300 mL) under Ar was added potassium carbonate (5.12 g, 37.0 mmol) and 1,3-dibromopropane (3.8 mL, 37.4 mmol). The reaction was heated at reflux for 17 h. The reaction mixture was cooled and concentrated. The residue was diluted with ethyl acetate, and washed successively with water (2×) and brine. The organic layer was dried over MgSO₄, filtered, and concentrated to afford the title compound (11.3 g, 98%).

Step 3. Synthesis of 6-((tert-butyldimethylsilyl)oxy)-1,2,6-thiadiazinane-2-carbonyl chloride 1,1-dioxide

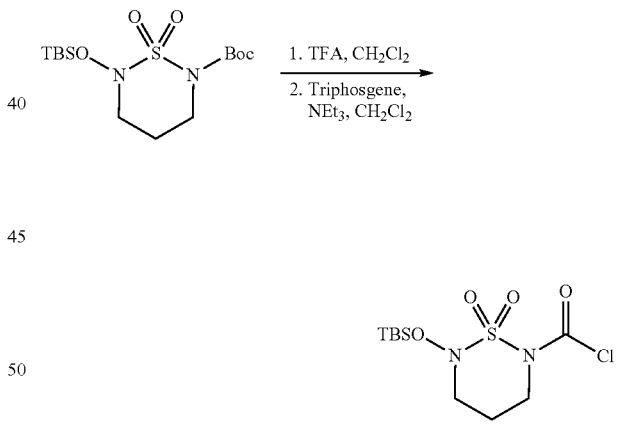

Trifluoroacetic acid (5.0 mL, 67.3 mmol) was added to a solution of tert-butyl 6-((tert-butyldimethylsilyl)oxy)-1,2,6-thiadiazinane-2-carboxylate 1,1-dioxide (5.55 g, 15.1 mmol) in DCM (200 mL) under Ar and the reaction was stirred at room temperature for 2 h. The reaction mixture was cooled and concentrated. To a solution of the crude product (1.74 g, 6.52 mmol) in DCM (20 mL) under Ar was added triethylamine (3.4 mL, 24.4 mmol) and the reaction was stirred at room temperature for 5 min. Triphosgene (1.93 g, 6.52 mmol) in DCM (5.0 mL) was added dropwise over 8 min and the reaction stirred at room temperature for 15 h. The reaction mixture was concentrated to afford the title compound.

Step 4. Synthesis of tert-butyl 3-((2R)-2-(2-(2-(((benzyloxy)carbonyl)amino)thiazol-4-yl)-2-(6-((tert-butyldimethylsilyl)oxy)-1,1-dioxido-1,2,6-thiadiazinane-2-carboxamido)acetamido)-2-((3aS)-3a,5,5-trimethylhexahydro-4,6-methanobenzo[d][1,3,2]dioxaborol-2-yl)ethyl)-2-methoxybenzoate

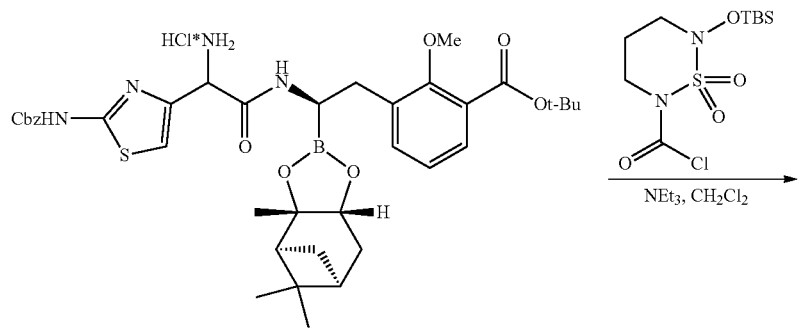

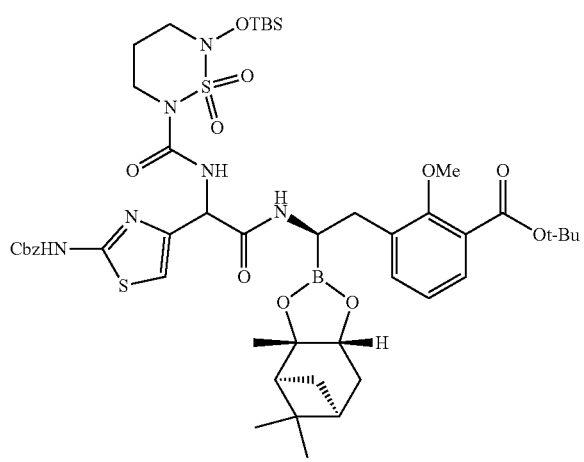

The title compound was prepared by following the procedure in Example 77, Step 1 but utilizing triethylamine as the base instead of diisopropylethylamine. ESI-MS m/z 1012 (MH)⁺.

Step 5. Synthesis of (3R)-3-(2-(2-aminothiazol-4-yl)-2-((6-((tert-butyldimethylsilyl)oxy)-1,1-dioxido-1,2,6-thiadiazinane-2-carbonyl)oxy)acetamido)-2-hydroxy-3,4-dihydro-2H-benzo[e][1,2]oxaborinine-8-carboxylic acid

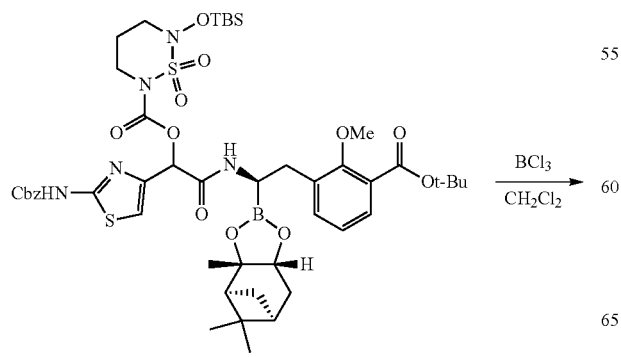

-continued

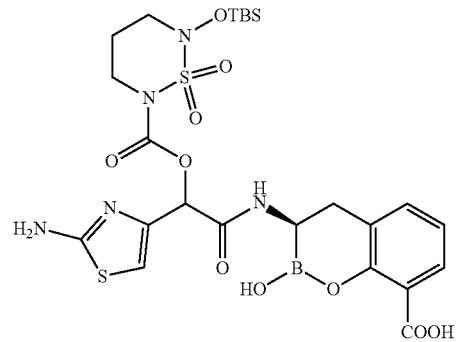

The title compound was prepared by treatment of the above product with BCl₃ by following General Method A. ESI-MS m/z 655 (MH)⁺.

Step 6. Synthesis of (3R)-3-(2-(2-aminothiazol-4-yl)-2-(6-hydroxy-1,1-dioxido-1,2,6-thiadiazinane-2-carboxamido)acetamido)-2-hydroxy-3,4-dihydro-2H-benzo[e][1,2]oxaborinine-8-carboxylic acid

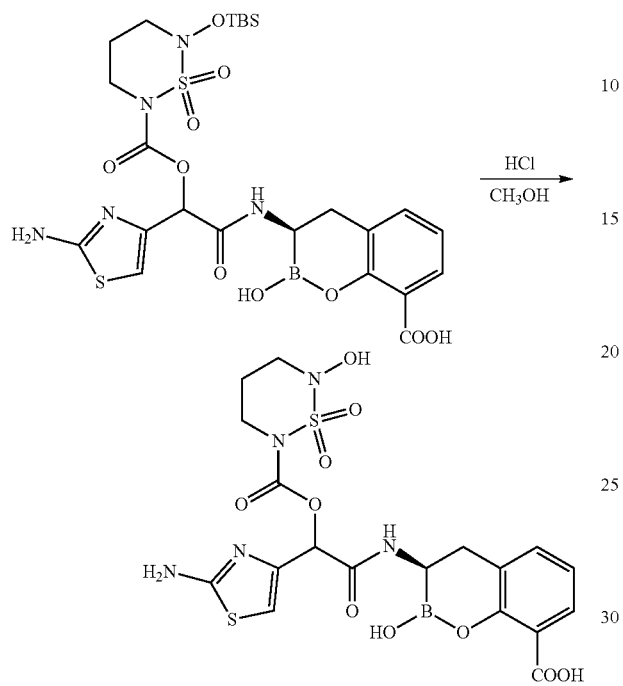

Hydrochloric acid (3N, 0.56 mL, 1.68 mmol) was added to a solution of (3R)-3-(2-(2-aminothiazol-4-yl)-2-((6-(((tert-butyldimethylsilyl)oxy)-1,1-dioxido-1,2,6-thiadiazinane-2-carbonyl)oxy)acetamido)-2-hydroxy-3,4-dihydro-2H-benzo[e][1,2]oxaborinine-8-carboxylic acid (0.035 g, 0.054 mmol) in methanol (1.4 mL) and stirred at room temperature for 48 h. The crude product was purified by reverse phase preparative HPLC and dried using lyophilization to yield the title compound (0.006 g, 21%). ESI-MS m/z 541 (MH)+.

Example 78: (R)-3-((R)-2-(4-ethyl-2,3-dioxopiperazine-1-carboxamido)-3-methylbutanamido)-2-hydroxy-3,4-dihydro-2H-benzo[e][1,2]oxaborinine-8-carboxylic acid

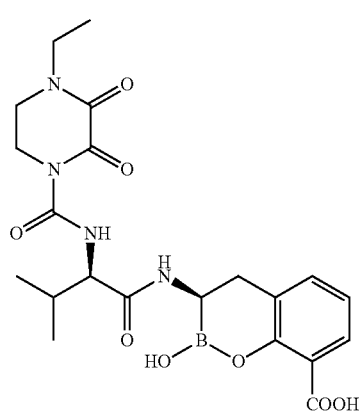 [SMILES: CCN1CCN(C(=O)N[C@@H](C(=O)N[C@H]2Cc3cccc(C(=O)O)c3OB2O)C(C)C)C(=O)C1=O]

The title compound was prepared from (D)-valine and 3-((2S)-2-chloro-2-((3aS,4S,6S)-3a,5,5-trimethylhexahydro-4,6-methanobenzo[d][1,3,2]dioxaborol-2-yl)ethyl)-2-methoxybenzoate, by a procedure similar to Example 31. ESI-MS m/z 475.2 (M+H)+.

Example 79: (3R)-3-(2-(4-ethyl-2,3-dioxopiperazine-1-carboxamido)-3-phenylpropanamido)-2-hydroxy-3,4-dihydro-2H-benzo[e][1,2]oxaborinine-8-carboxylic acid

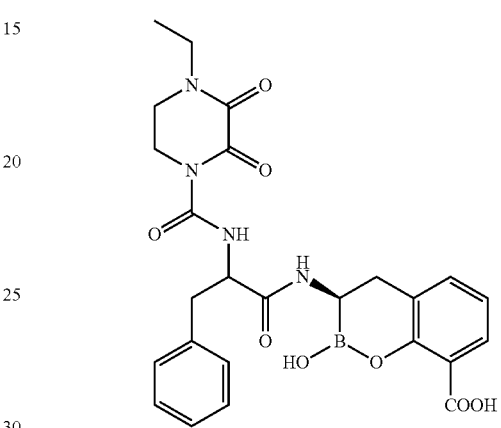

Step 1: Synthesis of (tert-butoxycarbonyl)phenylalanine

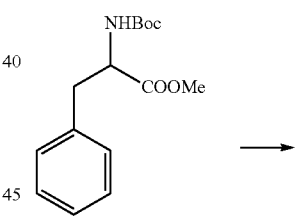

To methyl (tert-butoxycarbonyl)phenylalaninate 1.5 g (5.37 mmol) in tetrahydrofuran (18 mL)/water (18 mL) was added lithium hydroxide monohydrate 0.68 g (16.1 mmol, 3 eq) and the reaction was stirred at rt for 30 min. Acidified mixture drop wise with 2N hydrochloric acid to pH 2, extracted with dichloromethane, washed organic layer with water/brine, dried over sodium sulfate, and concentrated to give the desired compound. ESI-MS m/z 266 (MH)+.

Step 2: Synthesis of (3R)-3-(2-(4-ethyl-2,3-di-oxopiperazine-1-carboxamido)-2-(6-methoxypyri-din-3-yl)acetamido)-2-hydroxy-3,4-dihydro-2H-benzo[e][1,2]oxaborinine-8-carboxylic acid

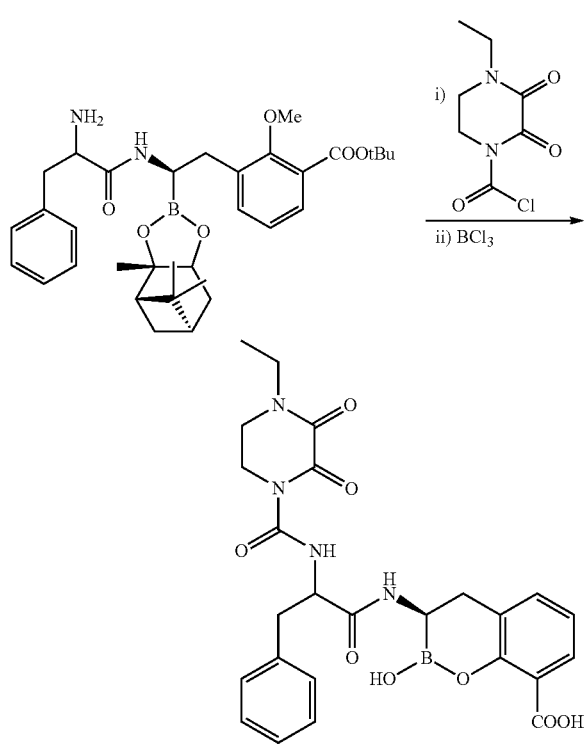

In a similar manner to the synthesis of Example 25 utilizing 4-ethyl-2,3-dioxopiperazine-1-carbonyl chloride in place of ethyl isocyanate, the title compound was prepared. ESI-MS m/z 523 (MH)+.

Example 80: (3R)-3-((2R)-2-(4-ethyl-2,3-dioxopip-erazine-1-carboxamido)-3-hydroxy-3-phenylpro-panamido)-2-hydroxy-3,4-dihydro-2H-benzo[e][1,2]oxaborinine-8-carboxylic acid

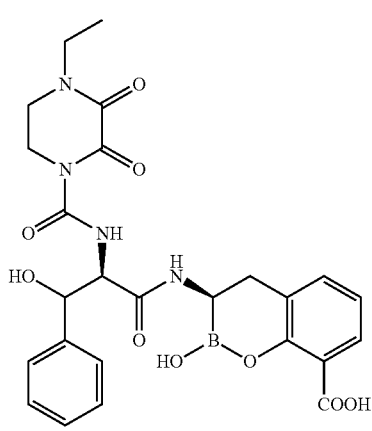 [SMILES: CCN1CCN(C(=O)N[C@@H](C(=O)N[C@H]2Cc3cccc(C(=O)O)c3OB2O)C(O)c2ccccc2)C(=O)C1=O]

The title compound was prepared, as the early eluting isomer in reverse phase hplc, from D,L-phenylserine and 3-((2S)-2-chloro-2-((3aS,4S,6S)-3a,5,5-trimethylhexa-hydro-4,6-methanobenzo[d][1,3,2]dioxaborol-2-yl)ethyl)-2-methoxybenzoate, by a procedure similar to Example 31. ESI-MS m/z 539.2 (M+H)+.

Example 81: (3R)-3-((2S)-2-(4-ethyl-2,3-dioxopip-erazine-1-carboxamido)-3-hydroxy-3-phenylpro-panamido)-2-hydroxy-3,4-dihydro-2H-benzo[e][1,2]oxaborinine-8-carboxylic acid

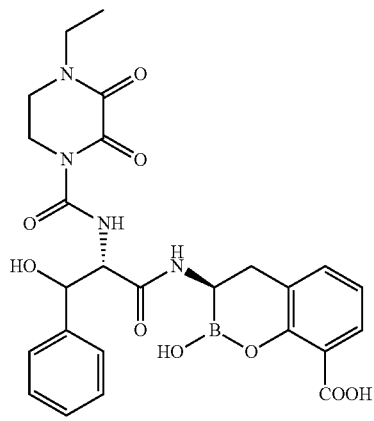 [SMILES: CCN1CCN(C(=O)N[C@H](C(=O)N[C@H]2Cc3cccc(C(=O)O)c3OB2O)C(O)c2ccccc2)C(=O)C1=O]

The title compound was prepared, as the late eluting isomer in reverse phase hplc, from D,L-phenylserine and 3-((2S)-2-chloro-2-((3aS,4S,6S)-3a,5,5-trimethylhexa-hydro-4,6-methanobenzo[d][1,3,2]dioxaborol-2-yl)ethyl)-2-methoxybenzoate, by a procedure similar to Example 31. ESI-MS m/z 539.2 (M+H)+.

Example 82: (3R)-3-((2R)-2-(4-ethyl-2,3-dioxopip-erazine-1-carboxamido)-3-hydroxypentanamido)-2-hydroxy-3,4-dihydro-2H-benzo[e][1,2]oxaborinine-8-carboxylic acid

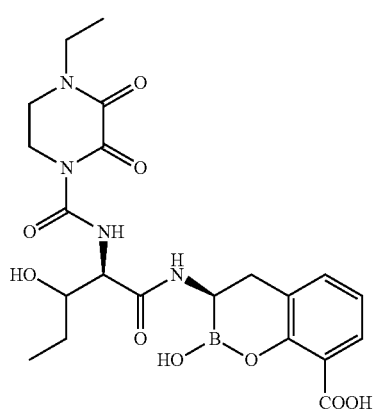 [SMILES: CCC(O)[C@@H](NC(=O)N1CCN(CC)C(=O)C1=O)C(=O)N[C@H]1Cc2cccc(C(=O)O)c2OB1O]

The title compound was prepared, as the early eluting isomer in reverse phase hplc, from DL-3-hydroxynorvaline and 3-((2S)-2-chloro-2-((3aS,4S,6S)-3a,5,5-trimethylhexa-hydro-4,6-methanobenzo-[d][1,3,2]dioxaborol-2-yl)ethyl)-2-methoxybenzoate, by a procedure similar to Example 31. ESI-MS m/z 491.2 (M+H)+.

Example 83: (3R)-3-((2S)-2-(4-ethyl-2,3-dioxopiperazine-1-carboxamido)-3-hydroxypentanamido)-2-hydroxy-3,4-dihydro-2H-benzo[e][1,2]oxaborinine-8-carboxylic acid

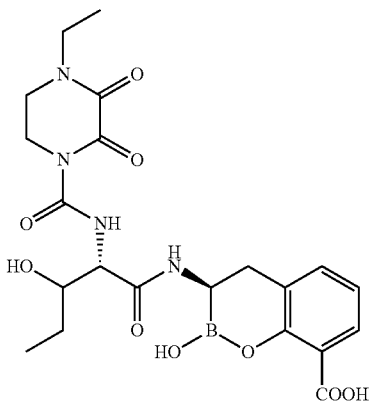

The title compound was prepared, as the late eluting isomer in reverse phase hplc, from DL-3-hydroxynorvaline and 3-((2S)-2-chloro-2-((3aS,4S,6S)-3a,5,5-trimethylhexahydro-4,6-methanobenzo-[d][1,3,2]dioxaborol-2-yl)ethyl)-2-methoxybenzoate, by a procedure similar to Example 31. ESI-MS m/z 491.2 (M+H)⁺.

Example 84: (3R)-3-(2-(4-ethyl-2,3-dioxopiperazine-1-carboxamido)-3-phenylbutanamido)-2-hydroxy-3,4-dihydro-2H-benzo[e][1,2]oxaborinine-8-carboxylic acid

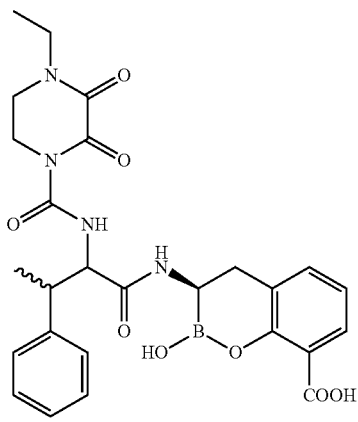 [SMILES: CCN1CCN(C(=O)NC(C(=O)N[C@H]2Cc3cccc(C(=O)O)c3OB2O)C(C)c2ccccc2)C(=O)C1=O]

The title compound was prepared according to the method of Example 79 utilizing 2-((tert-butoxycarbonyl)amino)-3-phenylbutanoic acid in place of (tert-butoxycarbonyl)phenylalanine. ESI-MS m/z 537 (MH)⁺.

Example 85: (R)-3-((R)-2-(4-ethyl-2,3-dioxopiperazine-1-carboxamido)-3,3-dimethylbutanamido)-2-hydroxy-3,4-dihydro-2H-benzo[e][1,2]oxaborinine-8-carboxylic acid

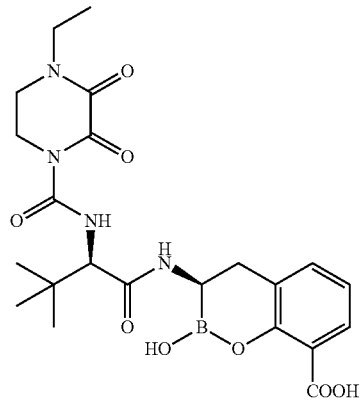

The title compound was prepared from (R)-2-amino-3,3-dimethylbutanamide and 3-((2S)-2-chloro-2-((3aS,4S,6S)-3a, 5,5-trimethylhexahydro-4,6-methanobenzo[d][1,3,2]dioxaborol-2-yl)ethyl)-2-methoxybenzoate, by a procedure similar to Example 31. ESI-MS m/z 489.2 (M+H)⁺.

Example 86: (R)-3-((R)-2-(4-ethyl-2,3-dioxopiperazine-1-carboxamido)-3-hydroxy-3-methylbutanamido)-2-hydroxy-3,4-dihydro-2H-benzo[e][1,2]oxaborinine-8-carboxylic acid

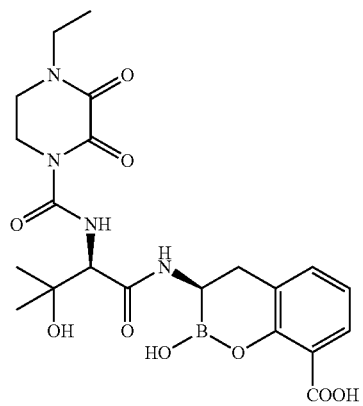 [SMILES: CCN1CCN(C(=O)N[C@@H](C(=O)N[C@H]2Cc3cccc(C(=O)O)c3OB2O)C(C)(C)O)C(=O)C1=O]

The title compound was prepared from (R)-2-amino-3-hydroxy-3-methylbutanamide and 3-((2S)-2-chloro-2-((3aS,4S,6S)-3a,5,5-trimethylhexahydro-4,6-methanobenzo[d][1,3,2]dioxaborol-2-yl)ethyl)-2-methoxybenzoate, by a procedure similar to Example 31. ESI-MS m/z 491.2 (M+H)⁺.

Example 87: (3R)-3-(2-(2-aminothiazol-4-yl)-2-(3-(2-carboxyethyl)ureido)acetamido)-2-hydroxy-3,4-dihydro-2H-benzo[e][1,2]oxaborinine-8-carboxylic acid

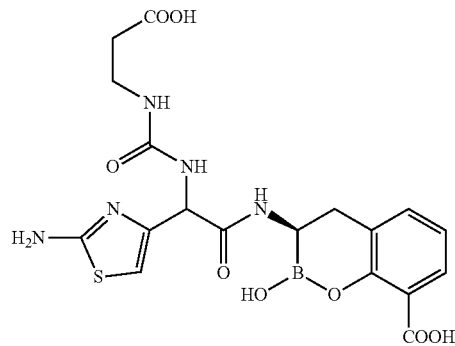 [SMILES: Nc1nc(C(NC(=O)NCCC(=O)O)C(=O)N[C@H]2Cc3cccc(C(=O)O)c3OB2O)cs1]

See Example 88.

Example 88: (3R)-3-(2-(2-aminothiazol-4-yl)-2-(3-(3-methoxy-3-oxopropyl)ureido)acetamido)-2-hydroxy-3,4-dihydro-2H-benzo[e][1,2]oxaborinine-8-carboxylic acid

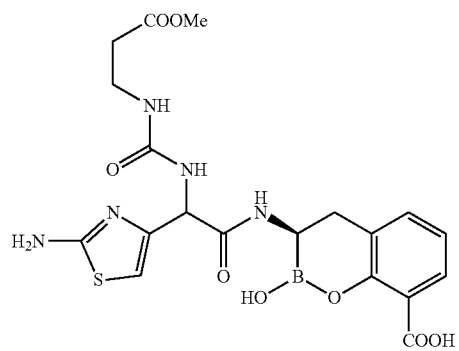

In a similar manner to the synthesis of Example 25, utilizing tert-butyl 3-isocyanatopropanoate in place of ethyl isocyanate in Step 3, and utilizing BBr$_3$ in place of BCl$_3$ in Step 4, Example 87 was prepared, and also the corresponding methyl ester, Example 88 was isolated during the purification of the crude BBr$_3$ reaction mixture of Example 87 by reverse phase HPLC. Example 87: ESI-MS m/z 478 (MH)$^+$; Example 88: ESI-MS m/z 482 (MH)$^+$.

Example 89: (3R)-3-(2-(2-aminothiazol-4-yl)-2-(3-boronopropanamido)acetamido)-2-hydroxy-3,4-dihydro-2H-benzo[e][1,2]oxaborinine-8-carboxylic acid

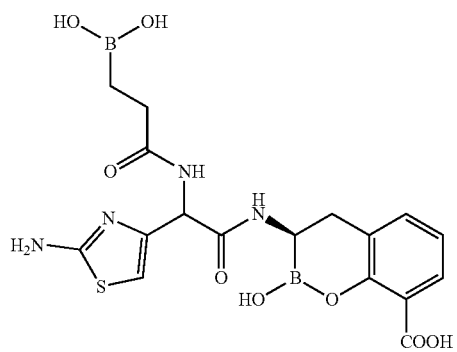 [SMILES: Nc1nc(C(NC(=O)CCB(O)O)C(=O)N[C@H]2Cc3cccc(C(=O)O)c3OB2O)cs1]

In a similar manner to the synthesis of Example 41, utilizing 3-(4,4,5,5-tetramethyl-1,3,2-dioxaborolan-2-yl)propanoic acid in place of 2-methoxyisonicotinic acid in Step 1, the title compound was prepared. ESI-MS m/z 445 (MH-H$_2$O)$^+$.

Example 90: (3R)-3-(2-(2-aminothiazol-4-yl)-2-(3-(carboxymethyl)ureido)acetamido)-2-hydroxy-3,4-dihydro-2H-benzo[e][1,2]oxaborinine-8-carboxylic acid

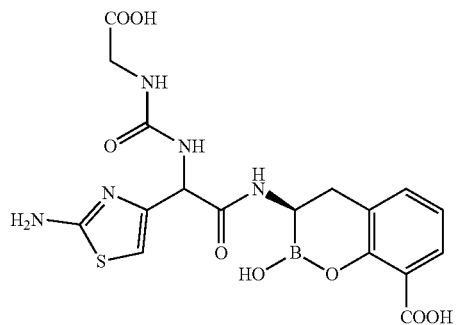 [SMILES: Nc1nc(C(NC(=O)NCC(=O)O)C(=O)N[C@H]2Cc3cccc(C(=O)O)c3OB2O)cs1]

In a similar manner to the synthesis of Example 25, utilizing tert-butyl 2-isocyanatoacetate in place of ethyl isocyanate in Step 3, and utilizing BBr$_3$ in place of BCl$_3$ in Step 4, Example 90 was prepared. ESI-MS m/z 464 (MH)$^+$.

Example 91: (R)-3-((2R,3R)-2-(4-(2-fluoroethyl)-2,3-dioxopiperazine-1-carboxamido)-3-hydroxybutanamido)-2-hydroxy-3,4-dihydro-2H-benzo[e][1,2]oxaborinine-8-carboxylic acid

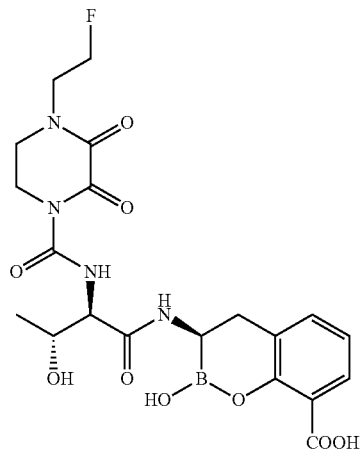 [SMILES: C[C@@H](O)[C@@H](NC(=O)N1CCN(CCF)C(=O)C1=O)C(=O)N[C@H]1Cc2cccc(C(=O)O)c2OB1O]

The title compound was prepared from D-allo-threonine, 4-(2-fluoroethyl)-2,3-dioxopiperazine-1-carbonyl chloride (prepared as described in Example 52), and 3-((2S)-2-chloro-2-((3aS,4S,6S)-3a,5,5-trimethylhexahydro-4,6-methanobenzo[d][1,3,2]dioxaborol-2-yl)ethyl)-2-methoxybenzoate, by a procedure similar to Example 31. ESI-MS m/z 495.2 (M+H)$^+$.

Example 92: (3R)-3-(2-(2-aminothiazol-4-yl)-2-(4-(2-(4-ethyl-2,3-dioxopiperazine-1-carboxamido)ethyl)-2,3-dioxopiperazine-1-carboxamido)acetamido)-2-hydroxy-3,4-dihydro-2H-benzo[e][1,2]oxaborinine-8-carboxylic acid

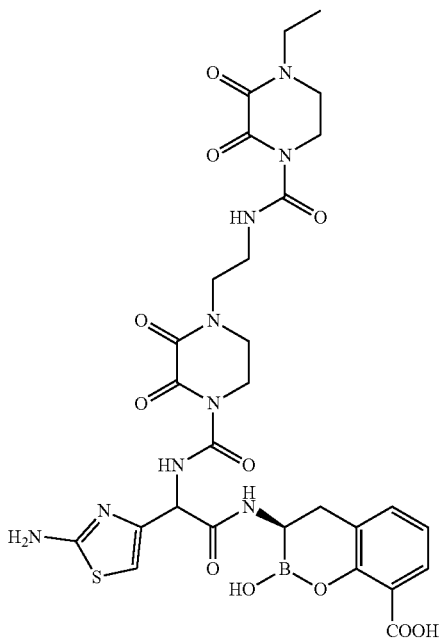 [SMILES: CCN1CCN(C(=O)NCCN2CCN(C(=O)NC(C(=O)N[C@H]3Cc4cccc(C(=O)O)c4OB3O)c3csc(N)n3)C(=O)C2=O)C(=O)C1=O]

The title compound was prepared from (3R)-3-(2-(4-(2-aminoethyl)-2,3-dioxopiperazine-1-carboxamido)-2-(2-aminothiazol-4-yl)acetamido)-2-hydroxy-3,4-dihydro-2H-benzo[e][1,2]oxaborinine-8-carboxylic acid (Example 58) and 4-ethyl-2,3-dioxopiperazine-1-carbonyl chloride, by a procedure similar to Example 13. ESI-MS m/z 714.2 (M+H)$^+$.

Example 93: (3R)-3-(2-(2-aminothiazol-4-yl)-2-(4-hexyl-2,3-dioxopiperazine-1-carboxamido)acetamido)-2-hydroxy-3,4-dihydro-2H-benzo[e][1,2]oxaborinine-8-carboxylic acid

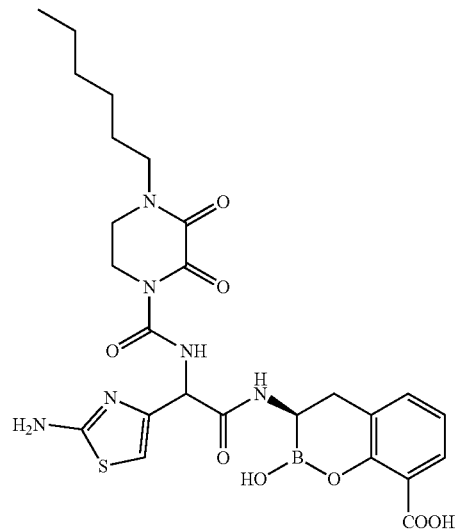 [SMILES: CCCCCCN1CCN(C(=O)NC(C(=O)N[C@H]2Cc3cccc(C(=O)O)c3OB2O)c2csc(N)n2)C(=O)C1=O]

The title compound was prepared according to the method of Example 52, utilizing 4-hexyl 2,3-dioxopiperazine-1-carbonyl chloride in place of 4-(2-fluoroethyl)-2,3-dioxopiperazine-1-carbonyl chloride. ESI-MS m/z 587 (MH)$^+$.

Example 94: (3R)-3-(2-(2-aminothiazol-4-yl)-2-(4-heptyl-2,3-dioxopiperazine-1-carboxamido)acetamido)-2-hydroxy-3,4-dihydro-2H-benzo[e][1,2]oxaborinine-8-carboxylic acid

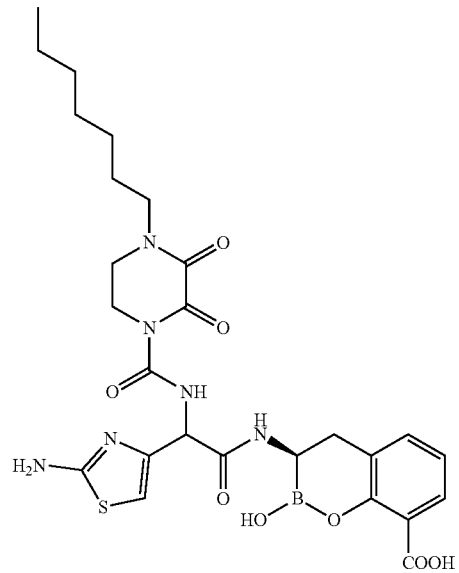 [SMILES: CCCCCCCN1CCN(C(=O)NC(C(=O)N[C@H]2Cc3cccc(C(=O)O)c3OB2O)c2csc(N)n2)C(=O)C1=O]

The title compound was prepared according to the method of Example 52, utilizing 4-heptyl-2,3-dioxopiperazine-1-carbonyl chloride in place of 4-(2-fluoroethyl)-2,3-dioxopiperazine-1-carbonyl chloride. ESI-MS m/z 601 (MH)$^+$.

Example 95: (3R)-3-(2-(2-aminothiazol-4-yl)-2-(4-(2-(3-(5,5-difluoro-7,9-dimethyl-5H-4l4,5l4-dipyrrolo[1,2-c:2',1'-f][1,3,2]diazaborinin-3-yl)propanamido)ethyl)-2,3-dioxopiperazine-1-carboxamido) acetamido)-2-hydroxy-3,4-dihydro-2H-benzo[e][1,2]oxaborinine-8-carboxylic acid

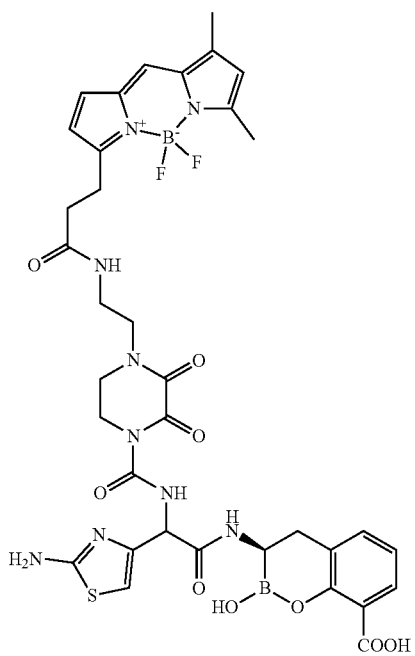 [SMILES: Cc1cc(C)n2c1C=C1C=CC(CCC(=O)NCCN3CCN(C(=O)NC(C(=O)N[C@H]4Cc5cccc(C(=O)O)c5OB4O)c4csc(N)n4)C(=O)C3=O)=[N+]1[B-]2(F)F]

The title compound was prepared from (3R)-3-(2-(4-(2-aminoethyl)-2,3-dioxopiperazine-1-carboxamido)-2-(2-aminothiazol-4-yl)acetamido)-2-hydroxy-3,4-dihydro-2H-benzo[e][1,2]oxaborinine-8-carboxylic acid (Example 58), by a procedure similar to Example 13. ESI-MS m/z 820.2 (M+H)$^+$.

Example 96: (R,Z)-3-(2-(2-aminothiazol-4-yl-2-$^{14}$C)-2-(hydroxyimino)acetamido)-2-hydroxy-3,4-dihydro-2H-benzo[e][1,2]oxaborinine-8-carboxylic acid

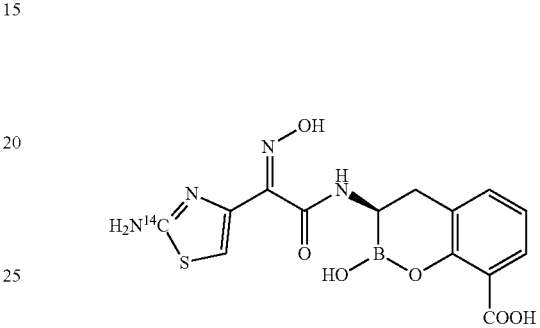

The title compound was prepared using the procedure of Example 1a, utilizing (Z)-2-((benzyloxy)imino)-2-(2-((tert-butoxycarbonyl)amino)thiazol-4-yl-2-$^{14}$C)acetic acid (prepared in analogy to the procedure described in Imanishi, M.; Tomimoto, M.; Watanabe, M.; Hayashi, N., *J Label Radiopharm.* 1986, 23, 951-956) in Step 3. The title compound was obtained as a solid following reverse-phase HPLC purification. Specific activity 53.7 mCi/mmol. The material was stored as a DMSO stock solution, 1.0 mCi/mL, 7.04 mg/mL. Radiochemical purity: 99.6%, as assessed by HPLC. ESI MS m/z 378.75 (M+H)$^+$.

TABLE 1

Example compounds

| Ex. | Structure | MW | ESI-MS (m/z) for [M + H]$^+$ |
|---|---|---|---|
| 1 | 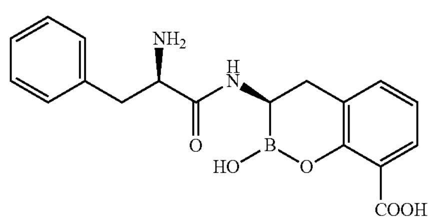 [SMILES: N[C@H](Cc1ccccc1)C(=O)N[C@H]1Cc2cccc(C(=O)O)c2OB1O] | 354.2 | 355 |
| 2 | 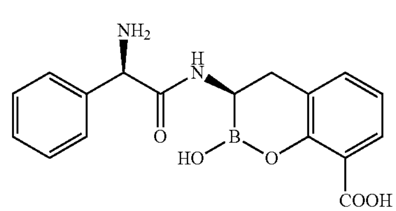 [SMILES: N[C@@H](C(=O)N[C@H]1Cc2cccc(C(=O)O)c2OB1O)c1ccccc1] | 340.1 | 341 |

TABLE 1-continued

Example compounds

| Ex. | Structure | MW | ESI-MS (m/z) for [M + H]+ |
|---|---|---|---|
| 3 | 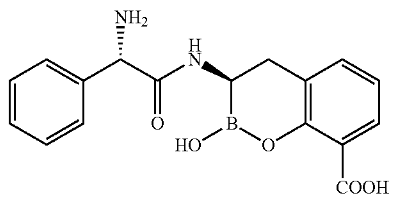 [SMILES: N[C@H](C(=O)N[C@H]1Cc2cccc(C(=O)O)c2OB1O)c1ccccc1] | 340.1 | 341 |
| 4 | 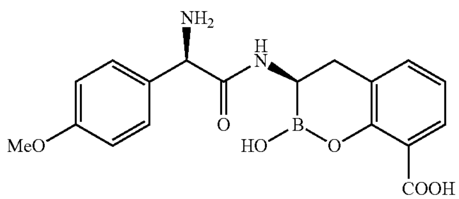 [SMILES: COc1ccc([C@@H](N)C(=O)N[C@H]2Cc3cccc(C(=O)O)c3OB2O)cc1] | 370.2 | 371 |
| 5 | 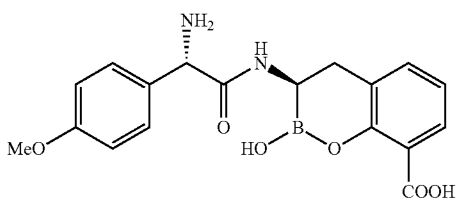 [SMILES: COc1ccc([C@H](N)C(=O)N[C@H]2Cc3cccc(C(=O)O)c3OB2O)cc1] | 370.2 | 371 |
| 6 | 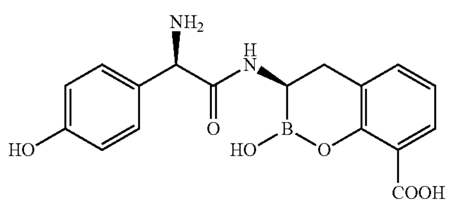 [SMILES: N[C@@H](C(=O)N[C@H]1Cc2cccc(C(=O)O)c2OB1O)c1ccc(O)cc1] | 356.1 | 357 |
| 7 | 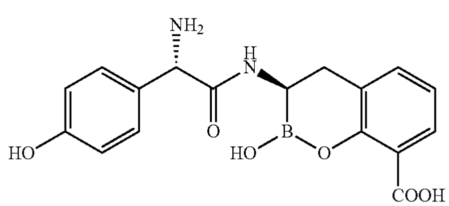 [SMILES: N[C@H](C(=O)N[C@H]1Cc2cccc(C(=O)O)c2OB1O)c1ccc(O)cc1] | 356.1 | 363 |
| 8 | 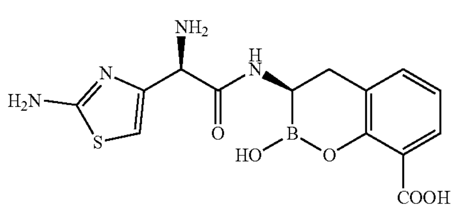 [SMILES: Nc1nc([C@@H](N)C(=O)N[C@H]2Cc3cccc(C(=O)O)c3OB2O)cs1] | 362.2 | 363 |
| 9 | 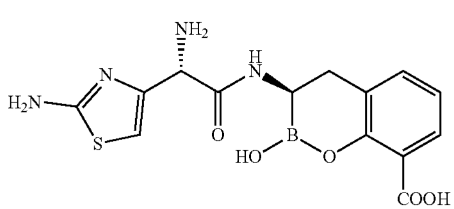 [SMILES: Nc1nc([C@H](N)C(=O)N[C@H]2Cc3cccc(C(=O)O)c3OB2O)cs1] | 362.2 | 363 |

TABLE 1-continued

Example compounds

| Ex. | Structure | MW | ESI-MS (m/z) for [M + H]+ |
|---|---|---|---|
| 10 | 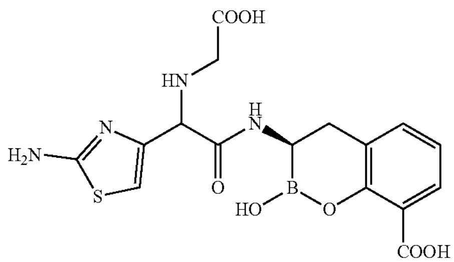 [SMILES: Nc1nc(C(NCC(=O)O)C(=O)N[C@H]2Cc3cccc(C(=O)O)c3OB2O)cs1] | 420.2 | 421 |
| 11 | 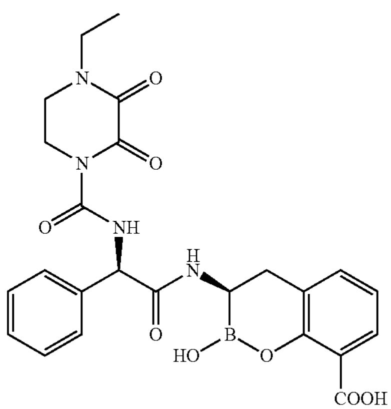 [SMILES: CCN1CCN(C(=O)N[C@@H](C(=O)N[C@H]2Cc3cccc(C(=O)O)c3OB2O)c2ccccc2)C(=O)C1=O] | 508.3 | 509 |
| 12 | 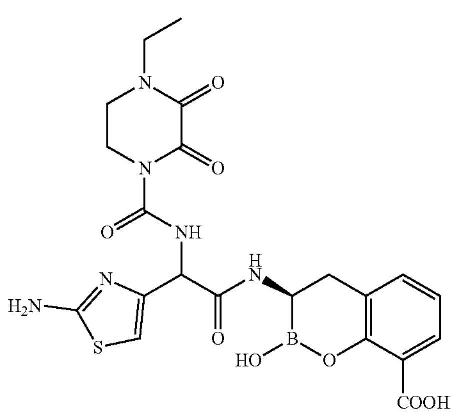 [SMILES: CCN1CCN(C(=O)NC(C(=O)N[C@H]2Cc3cccc(C(=O)O)c3OB2O)c2csc(N)n2)C(=O)C1=O] | 530.3 | 531 |

TABLE 1-continued

Example compounds

| Ex. | Structure | MW | ESI-MS (m/z) for [M + H]+ |
|---|---|---|---|
| 13 | 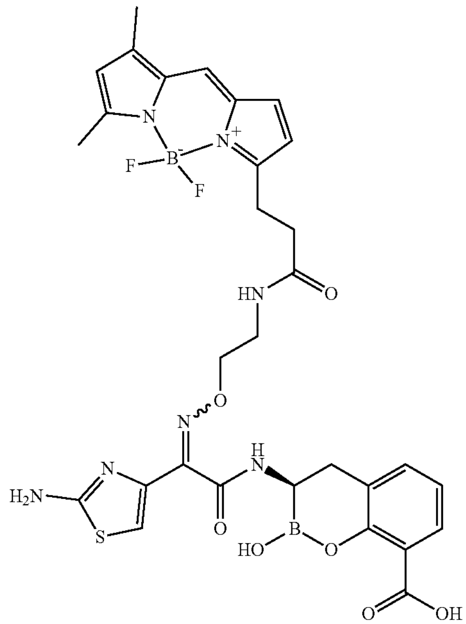 | 693.3 | 694 |
| 14 | 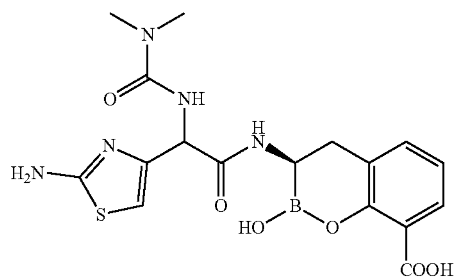 [SMILES: CN(C)C(=O)NC(C(=O)N[C@H]1Cc2cccc(C(=O)O)c2OB1O)c1csc(N)n1] | 433.2 | 434 |
| 15 | 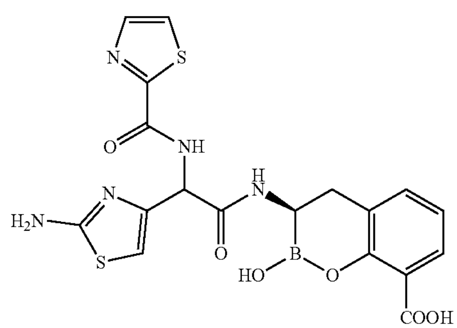 [SMILES: Nc1nc(C(NC(=O)c2nccs2)C(=O)N[C@H]2Cc3cccc(C(=O)O)c3OB2O)cs1] | 473.3 | 474 |
| 16 | 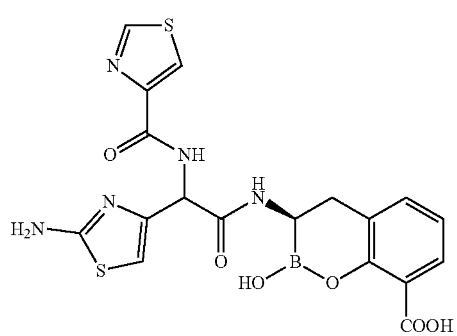 [SMILES: Nc1nc(C(NC(=O)c2cscn2)C(=O)N[C@H]2Cc3cccc(C(=O)O)c3OB2O)cs1] | 473.3 | 474 |

TABLE 1-continued

Example compounds

| Ex. | Structure | MW | ESI-MS (m/z) for [M + H]+ |
|---|---|---|---|
| 17 | 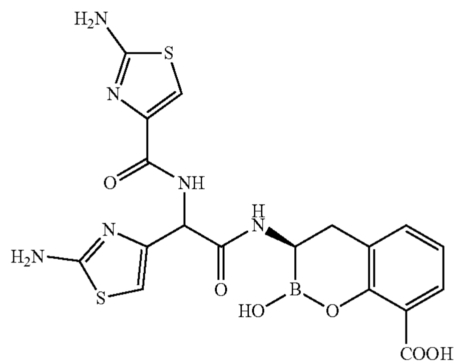 [SMILES: Nc1nc(C(=O)NC(C(=O)N[C@H]2Cc3cccc(C(=O)O)c3OB2O)c2csc(N)n2)cs1] | 488.3 | 489 |
| 18 | 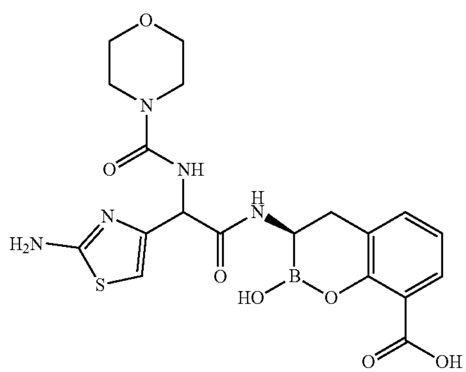 [SMILES: Nc1nc(C(NC(=O)N2CCOCC2)C(=O)N[C@H]2Cc3cccc(C(=O)O)c3OB2O)cs1] | 475.3 | 476 |
| 19 | 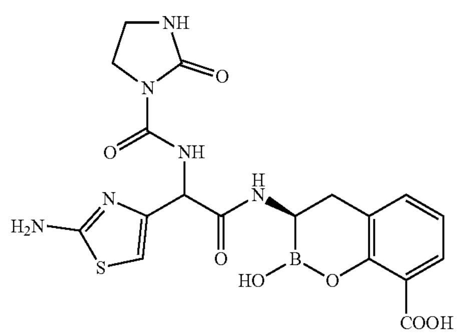 [SMILES: Nc1nc(C(NC(=O)N2CCNC2=O)C(=O)N[C@H]2Cc3cccc(C(=O)O)c3OB2O)cs1] | 474.4 | 475 |
| 20 | 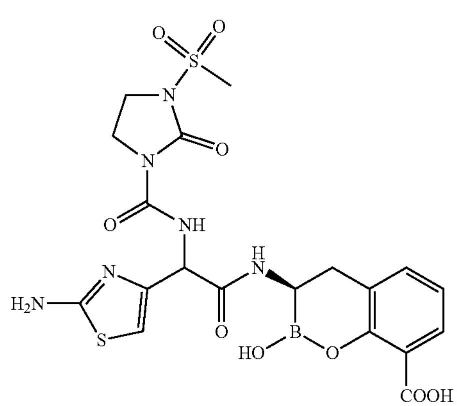 [SMILES: CS(=O)(=O)N1CCN(C(=O)NC(C(=O)N[C@H]2Cc3cccc(C(=O)O)c3OB2O)c2csc(N)n2)C1=O] | 552.3 | 553 |

TABLE 1-continued
Example compounds
| Ex. | Structure | MW | ESI-MS (m/z) for [M + H]+ |
|---|---|---|---|
| 21 | 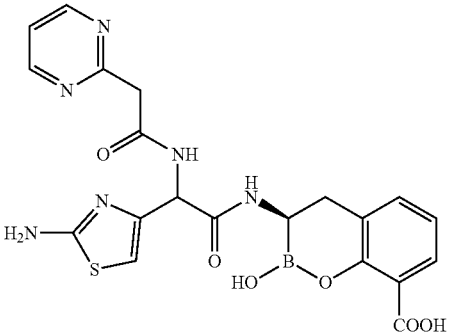 [SMILES: Nc1nc(C(NC(=O)Cc2ncccn2)C(=O)N[C@H]2Cc3cccc(C(=O)O)c3OB2O)cs1] | 482.3 | 483 |
| 22 | 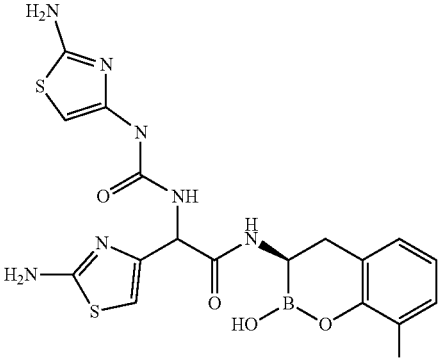 | 502.3 | 503 |
| 23 | 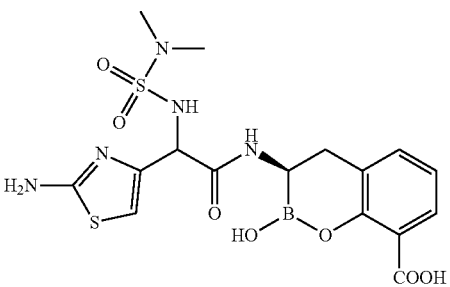 [SMILES: CN(C)S(=O)(=O)NC(C(=O)N[C@H]1Cc2cccc(C(=O)O)c2OB1O)c1csc(N)n1] | 469.3 | 470 |
| 24 | 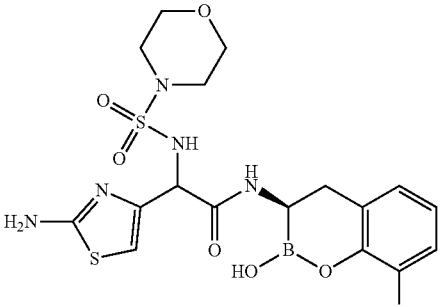 | 511.3 | 512 |

TABLE 1-continued

Example compounds

| Ex. | Structure | MW | ESI-MS (m/z) for [M + H]+ |
|---|---|---|---|
| 25 | 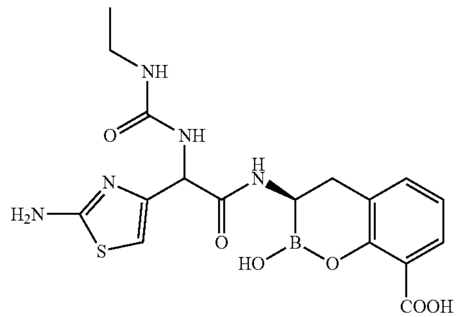 [SMILES: CCNC(=O)NC(C(=O)N[C@H]1Cc2cccc(C(=O)O)c2OB1O)c1csc(N)n1] | 433.2 | 434 |
| 26 | 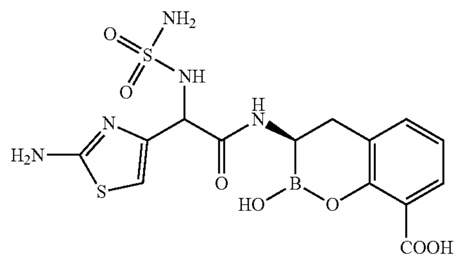 [SMILES: Nc1nc(C(NS(N)(=O)=O)C(=O)N[C@H]2Cc3cccc(C(=O)O)c3OB2O)cs1] | 441.2 | 442 |
| 27 | 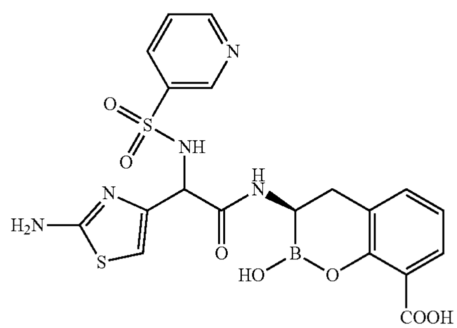 [SMILES: Nc1nc(C(NS(=O)(=O)c2cccnc2)C(=O)N[C@H]2Cc3cccc(C(=O)O)c3OB2O)cs1] | 503.3 | 504 |
| 28 | 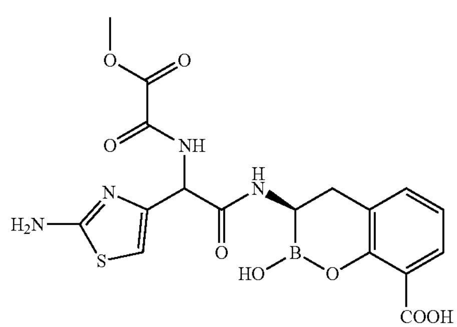 [SMILES: COC(=O)C(=O)NC(C(=O)N[C@H]1Cc2cccc(C(=O)O)c2OB1O)c1csc(N)n1] | 448.2 | 449 |
| 29 | 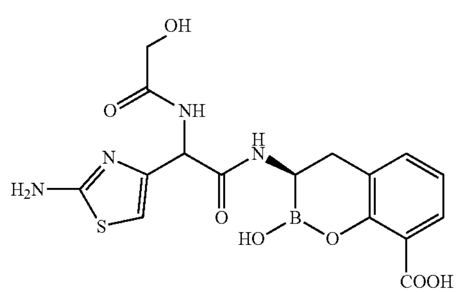 [SMILES: Nc1nc(C(NC(=O)CO)C(=O)N[C@H]2Cc3cccc(C(=O)O)c3OB2O)cs1] | 420.2 | 421 |

TABLE 1-continued

Example compounds

| Ex. | Structure | MW | ESI-MS (m/z) for [M + H]+ |
|---|---|---|---|
| 30 | 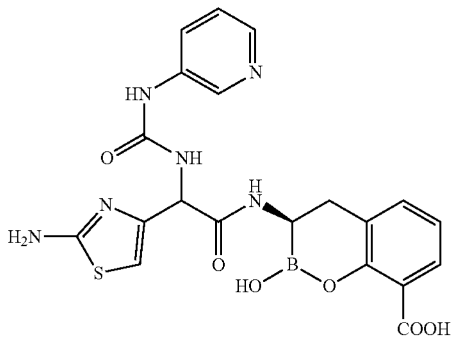 [SMILES: Nc1nc(C(NC(=O)Nc2cccnc2)C(=O)N[C@H]2Cc3cccc(C(=O)O)c3OB2O)cs1] | 482.3 | 483 |
| 31 | 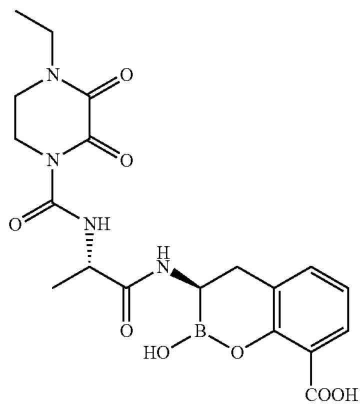 [SMILES: CCN1CCN(C(=O)N[C@@H](C)C(=O)N[C@H]2Cc3cccc(C(=O)O)c3OB2O)C(=O)C1=O] | 446.2 | 447 |
| 32 | 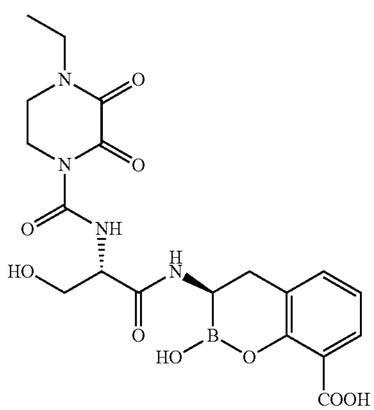 [SMILES: CCN1CCN(C(=O)N[C@@H](CO)C(=O)N[C@H]2Cc3cccc(C(=O)O)c3OB2O)C(=O)C1=O] | 462.2 | 463 |
| 33 | 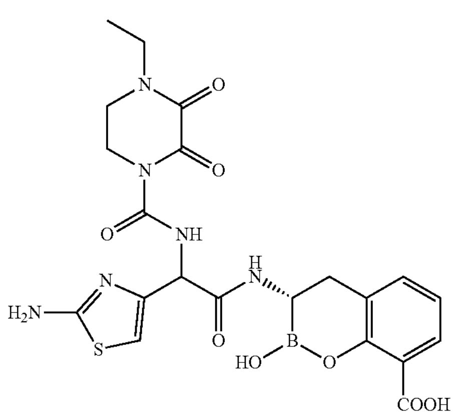 [SMILES: CCN1CCN(C(=O)NC(C(=O)N[C@@H]2Cc3cccc(C(=O)O)c3OB2O)c2csc(N)n2)C(=O)C1=O] | 530.3 | 531 |

TABLE 1-continued

Example compounds

| Ex. | Structure | MW | ESI-MS (m/z) for [M + H]+ |
|---|---|---|---|
| 34 | 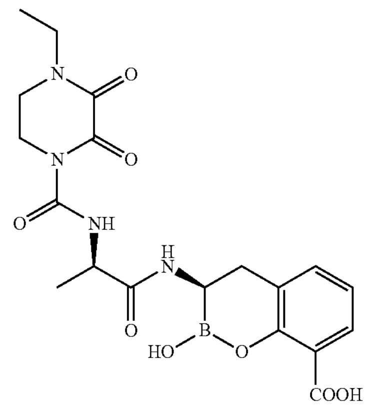 [SMILES: CCN1CCN(C(=O)N[C@H](C)C(=O)N[C@H]2Cc3cccc(C(=O)O)c3OB2O)C(=O)C1=O] | 446.2 | 447 |
| 35 | 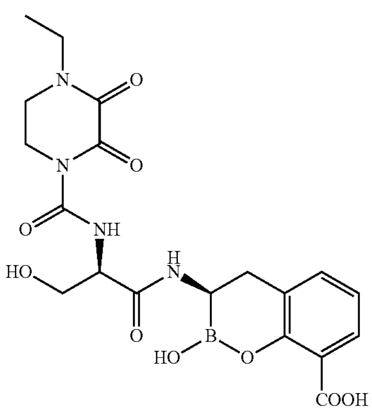 [SMILES: CCN1CCN(C(=O)N[C@H](CO)C(=O)N[C@H]2Cc3cccc(C(=O)O)c3OB2O)C(=O)C1=O] | 462.2 | 463 |
| 36 | 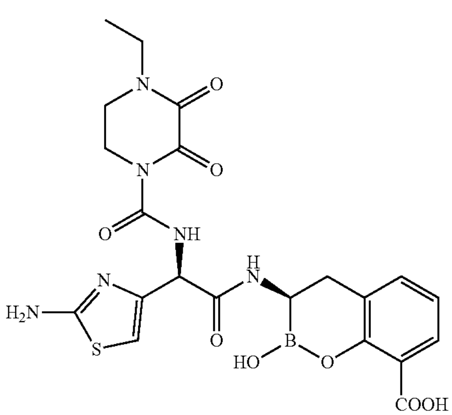 [SMILES: CCN1CCN(C(=O)N[C@@H](C(=O)N[C@H]2Cc3cccc(C(=O)O)c3OB2O)c2csc(N)n2)C(=O)C1=O] | 530.3 | 531 |

TABLE 1-continued

Example compounds

| Ex. | Structure | MW | ESI-MS (m/z) for [M + H]+ |
|---|---|---|---|
| 38 | 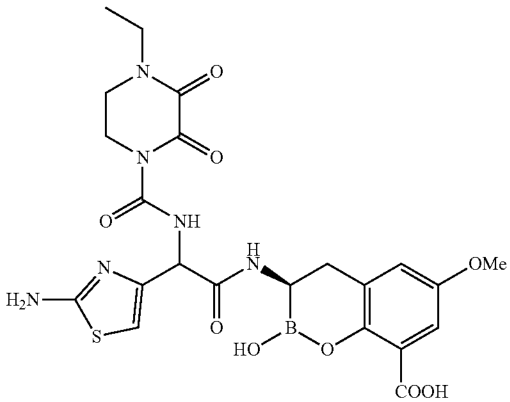 [SMILES: CCN1CCN(C(=O)NC(C(=O)N[C@H]2Cc3cc(OC)cc(C(=O)O)c3OB2O)c2csc(N)n2)C(=O)C1=O] | 560.3 | 561 |
| 39 | 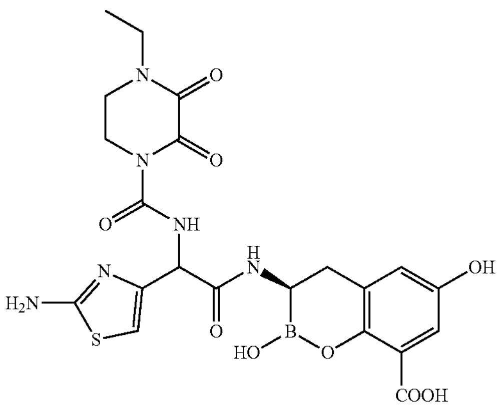 [SMILES: CCN1CCN(C(=O)NC(C(=O)N[C@H]2Cc3cc(O)cc(C(=O)O)c3OB2O)c2csc(N)n2)C(=O)C1=O] | 546.3 | 547 |
| 40 | 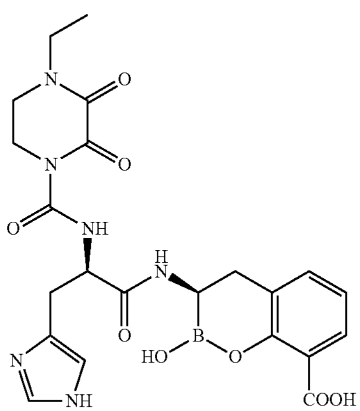 [SMILES: CCN1CCN(C(=O)N[C@H](Cc2c[nH]cn2)C(=O)N[C@H]2Cc3cccc(C(=O)O)c3OB2O)C(=O)C1=O] | 512.3 | 513 |
| 41 | 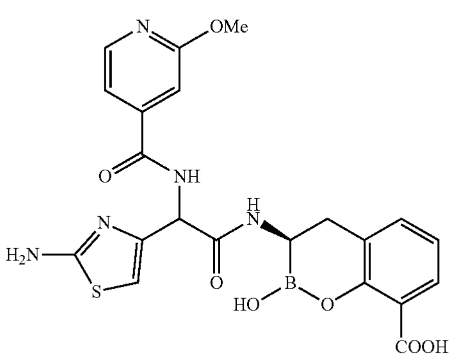 [SMILES: COc1cc(C(=O)NC(C(=O)N[C@H]2Cc3cccc(C(=O)O)c3OB2O)c2csc(N)n2)ccn1] | 497.3 | 498 |

TABLE 1-continued

Example compounds

| Ex. | Structure | MW | ESI-MS (m/z) for [M + H]+ |
|---|---|---|---|
| 42 | 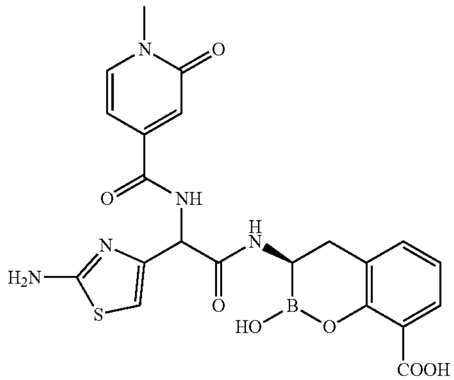 [SMILES: Cn1ccc(C(=O)NC(C(=O)N[C@H]2Cc3cccc(C(=O)O)c3OB2O)c2csc(N)n2)cc1=O] | 497.3 | 498 |
| 43 | 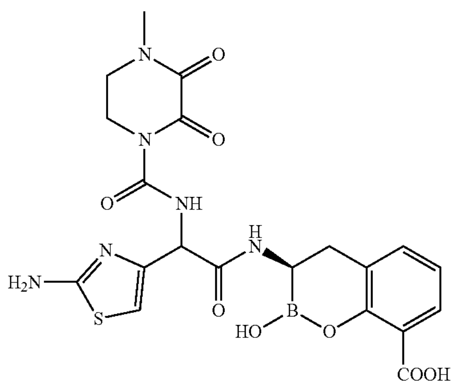 [SMILES: CN1CCN(C(=O)NC(C(=O)N[C@H]2Cc3cccc(C(=O)O)c3OB2O)c2csc(N)n2)C(=O)C1=O] | 516.3 | 517 |
| 44 | 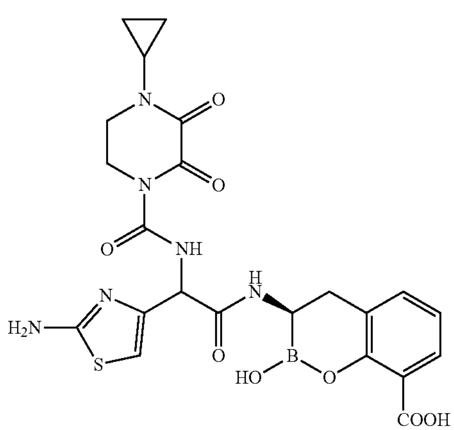 [SMILES: Nc1nc(C(NC(=O)N2CCN(C3CC3)C(=O)C2=O)C(=O)N[C@H]2Cc3cccc(C(=O)O)c3OB2O)cs1] | 542.3 | 543 |

TABLE 1-continued

| | Example compounds | | |
|---|---|---|---|
| Ex. | Structure | MW | ESI-MS (m/z) for [M + H]+ |
| 45 | | 544.3 | 545 |
| 46 | | 513.3 | 514 |
| 47 | | 476.2 | 477 |

TABLE 1-continued

Example compounds

| Ex. | Structure | MW | ESI-MS (m/z) for [M + H]+ |
|---|---|---|---|
| 48 | 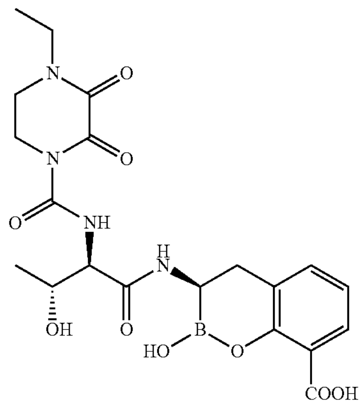 [SMILES: CCN1CCN(C(=O)N[C@@H](C(=O)N[C@H]2Cc3cccc(C(=O)O)c3OB2O)[C@@H](C)O)C(=O)C1=O] | 476.2 | 477 |
| 49 | 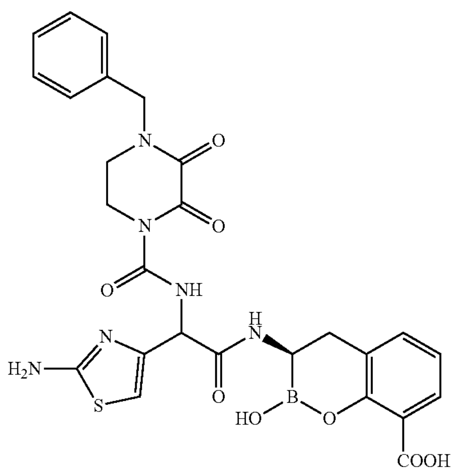 [SMILES: Nc1nc(C(NC(=O)N2CCN(Cc3ccccc3)C(=O)C2=O)C(=O)N[C@H]2Cc3cccc(C(=O)O)c3OB2O)cs1] | 592.4 | 593 |
| 50 | 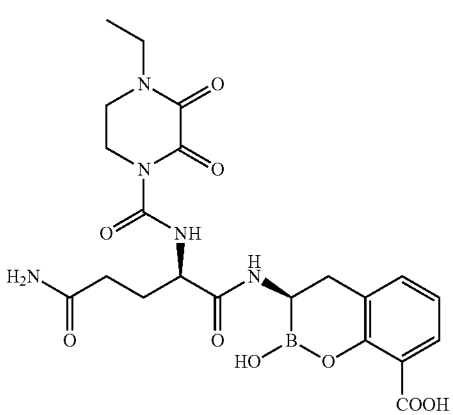 [SMILES: CCN1CCN(C(=O)N[C@H](CCC(N)=O)C(=O)N[C@H]2Cc3cccc(C(=O)O)c3OB2O)C(=O)C1=O] | 503.3 | 504.2 |

TABLE 1-continued
Example compounds
| Ex. | Structure | MW | ESI-MS (m/z) for [M + H]+ |
|---|---|---|---|
| 51 | 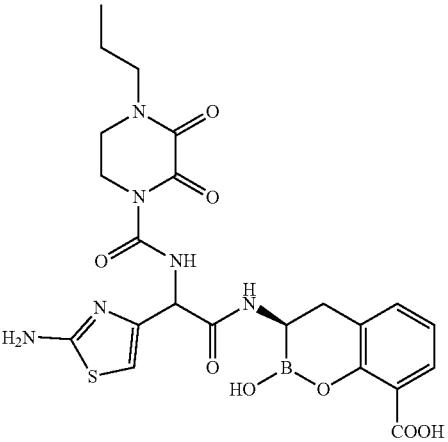 [SMILES: CCCN1CCN(C(=O)NC(C(=O)N[C@H]2Cc3cccc(C(=O)O)c3OB2O)c2csc(N)n2)C(=O)C1=O] | 544.3 | 545 |
| 52 | 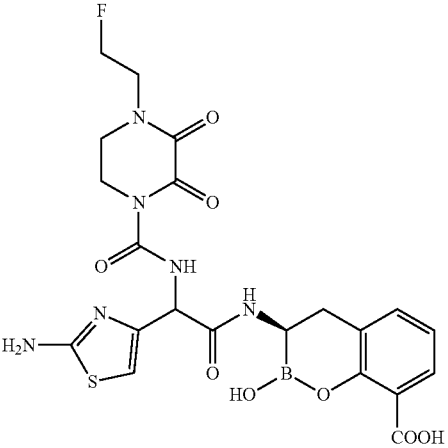 [SMILES: Nc1nc(C(NC(=O)N2CCN(CCF)C(=O)C2=O)C(=O)N[C@H]2Cc3cccc(C(=O)O)c3OB2O)cs1] | 548.3 | 549 |
| 53 | 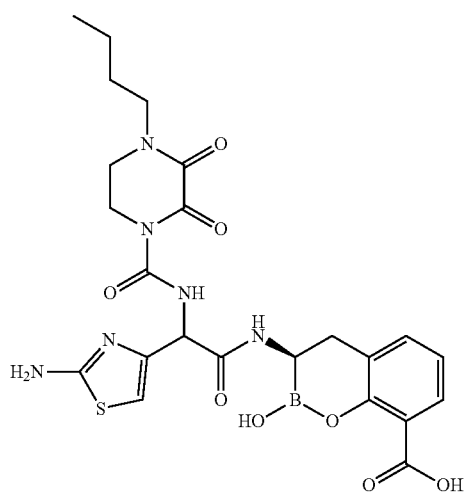 [SMILES: CCCCN1CCN(C(=O)NC(C(=O)N[C@H]2Cc3cccc(C(=O)O)c3OB2O)c2csc(N)n2)C(=O)C1=O] | 558.4 | 559 |

TABLE 1-continued
Example compounds
| Ex. | Structure | MW | ESI-MS (m/z) for [M + H]+ |
|---|---|---|---|
| 54 | 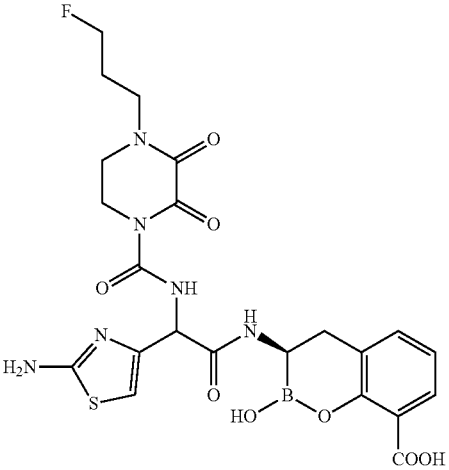 [SMILES: Nc1nc(C(NC(=O)N2CCN(CCCF)C(=O)C2=O)C(=O)N[C@H]2Cc3cccc(C(=O)O)c3OB2O)cs1] | 562.3 | 563 |
| 55 | 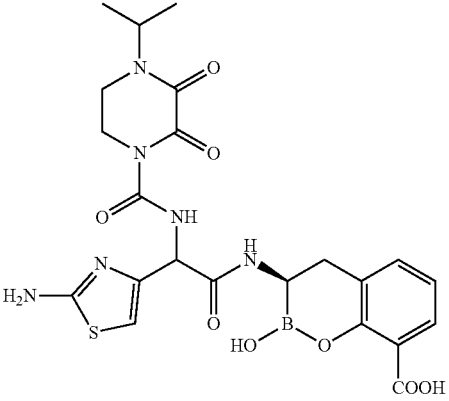 [SMILES: CC(C)N1CCN(C(=O)NC(C(=O)N[C@H]2Cc3cccc(C(=O)O)c3OB2O)c2csc(N)n2)C(=O)C1=O] | 544.3 | 545 |
| 56 | 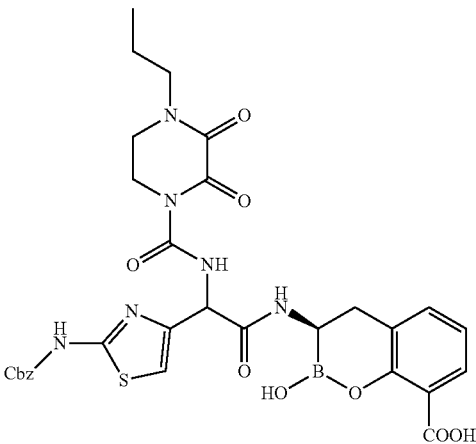 [SMILES: CCCN1CCN(C(=O)NC(C(=O)N[C@H]2Cc3cccc(C(=O)O)c3OB2O)c2csc(NC(=O)OCc3ccccc3)n2)C(=O)C1=O] | 678.5 | 679 |

TABLE 1-continued

Example compounds

| Ex. | Structure | MW | ESI-MS (m/z) for [M + H]+ |
|---|---|---|---|
| 57 | 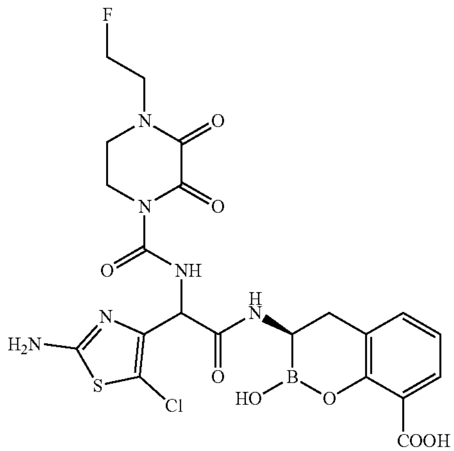 [SMILES: Nc1nc(C(NC(=O)N2CCN(CCF)C(=O)C2=O)C(=O)N[C@H]2Cc3cccc(C(=O)O)c3OB2O)c(Cl)s1] | 582.7 | 583 |
| 58 | 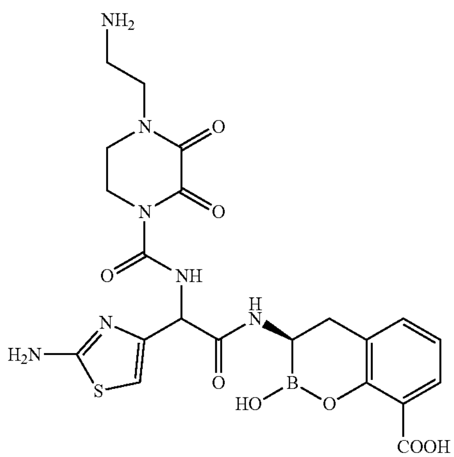 [SMILES: NCCN1CCN(C(=O)NC(C(=O)N[C@H]2Cc3cccc(C(=O)O)c3OB2O)c2csc(N)n2)C(=O)C1=O] | 545.3 | 546 |
| 59 | 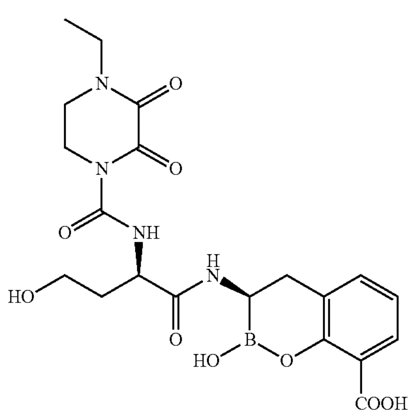 [SMILES: CCN1CCN(C(=O)N[C@H](CCO)C(=O)N[C@H]2Cc3cccc(C(=O)O)c3OB2O)C(=O)C1=O] | 476.3 | 477 |

TABLE 1-continued

Example compounds

| Ex. | Structure | MW | ESI-MS (m/z) for [M + H]+ |
|---|---|---|---|
| 60 | 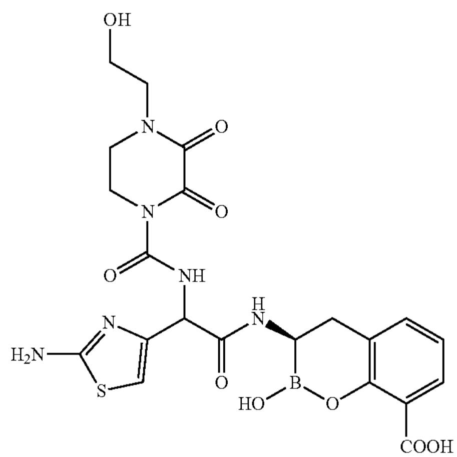 [SMILES: Nc1nc(C(NC(=O)N2CCN(CCO)C(=O)C2=O)C(=O)N[C@H]2Cc3cccc(C(=O)O)c3OB2O)cs1] | 546.3 | 547 |
| 61 | 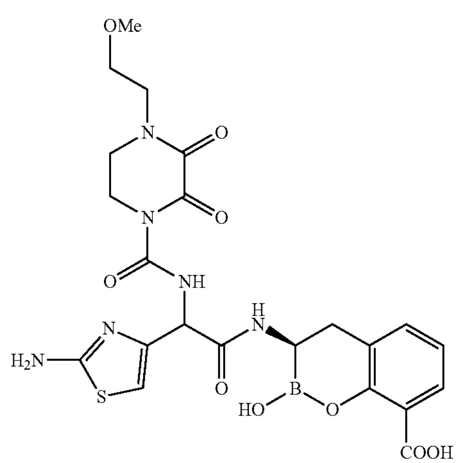 [SMILES: COCCN1CCN(C(=O)NC(C(=O)N[C@H]2Cc3cccc(C(=O)O)c3OB2O)c2csc(N)n2)C(=O)C1=O] | 560.3 | 561 |
| 62 | 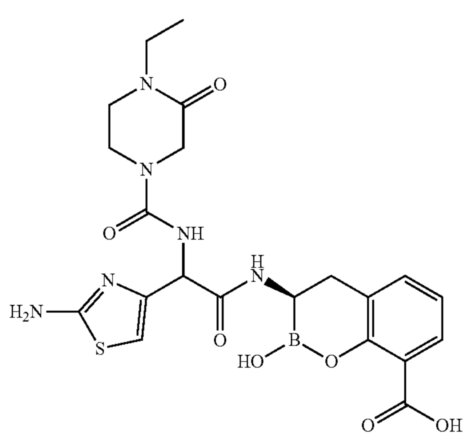 [SMILES: CCN1CCN(C(=O)NC(C(=O)N[C@H]2Cc3cccc(C(=O)O)c3OB2O)c2csc(N)n2)CC1=O] | 516.3 | 517 |

TABLE 1-continued
Example compounds
| Ex. | Structure | MW | ESI-MS (m/z) for [M + H]+ |
|---|---|---|---|
| 63 | 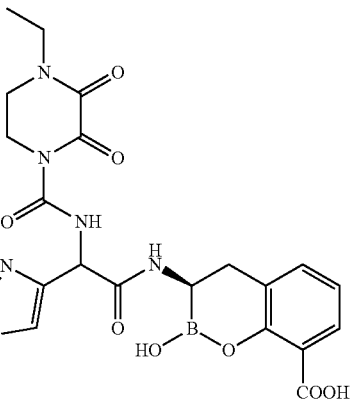 | 573.4 | 574 |
| 64 | 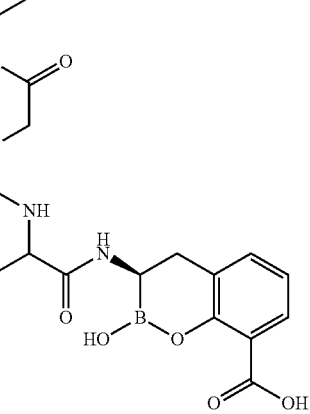 | 530.3 | 531 |
| 65 | 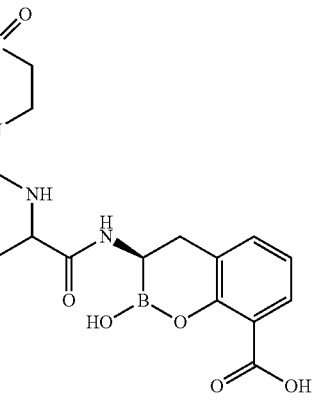 | 523.3 | 524 |

TABLE 1-continued

Example compounds

| Ex. | Structure | MW | ESI-MS (m/z) for [M + H]+ |
|---|---|---|---|
| 66 | 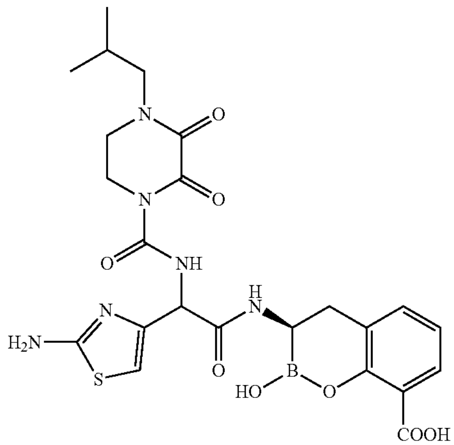 [SMILES: CC(C)CN1CCN(C(=O)NC(C(=O)N[C@H]2Cc3cccc(C(=O)O)c3OB2O)c2csc(N)n2)C(=O)C1=O] | 558.4 | 559.2 |
| 67 | 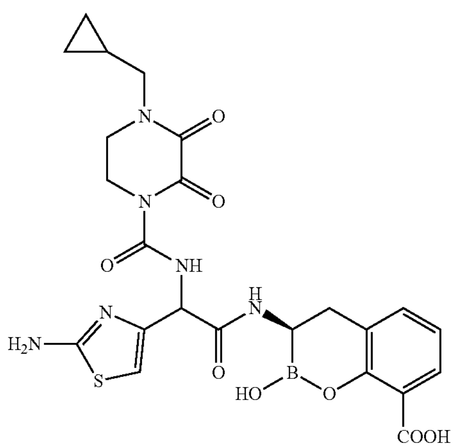 [SMILES: Nc1nc(C(NC(=O)N2CCN(CC3CC3)C(=O)C2=O)C(=O)N[C@H]2Cc3cccc(C(=O)O)c3OB2O)cs1] | 556.4 | 557.2 |
| 68 | 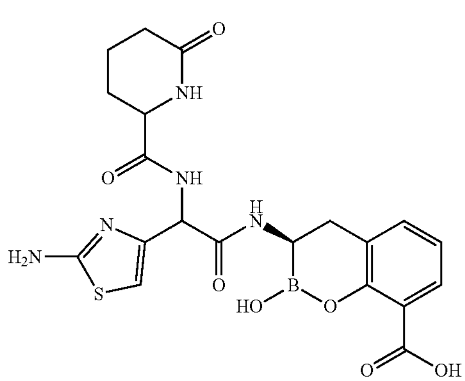 [SMILES: Nc1nc(C(NC(=O)C2CCCC(=O)N2)C(=O)N[C@H]2Cc3cccc(C(=O)O)c3OB2O)cs1] | 487.3 | 488 |

TABLE 1-continued

Example compounds

| Ex. | Structure | MW | ESI-MS (m/z) for [M + H]+ |
|---|---|---|---|
| 69 | 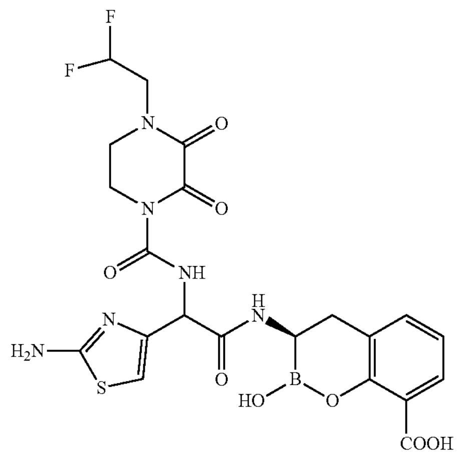 [SMILES: Nc1nc(C(NC(=O)N2CCN(CC(F)F)C(=O)C2=O)C(=O)N[C@H]2Cc3cccc(C(=O)O)c3OB2O)cs1] | 566.3 | 567 |
| 70 | 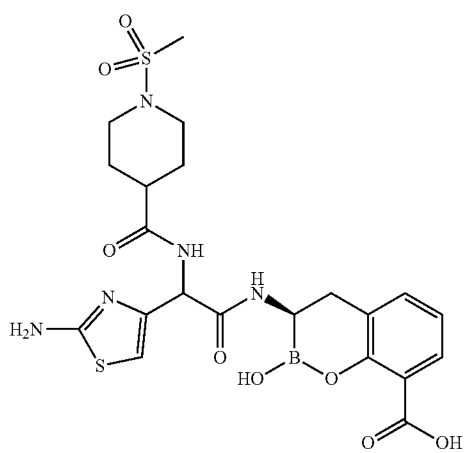 [SMILES: CS(=O)(=O)N1CCC(C(=O)NC(C(=O)N[C@H]2Cc3cccc(C(=O)O)c3OB2O)c2csc(N)n2)CC1] | 551.4 | 552 |
| 71 | 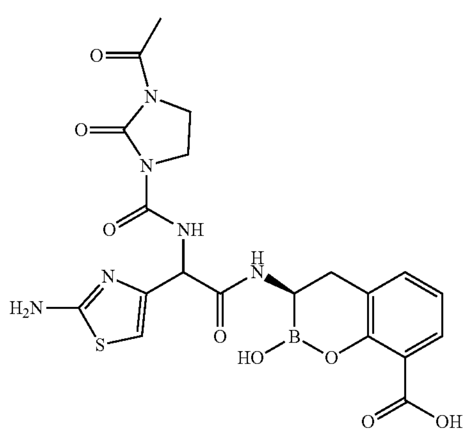 [SMILES: CC(=O)N1CCN(C(=O)NC(C(=O)N[C@H]2Cc3cccc(C(=O)O)c3OB2O)c2csc(N)n2)C1=O] | 516.3 | 517 |

TABLE 1-continued
Example compounds
| Ex. | Structure | MW | ESI-MS (m/z) for [M + H]+ |
|---|---|---|---|
| 72 | 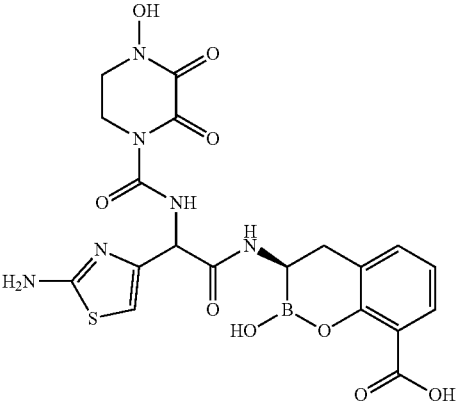 [SMILES: Nc1nc(C(NC(=O)N2CCN(O)C(=O)C2=O)C(=O)N[C@H]2Cc3cccc(C(=O)O)c3OB2O)cs1] | 518.3 | 519.1 |
| 73 | 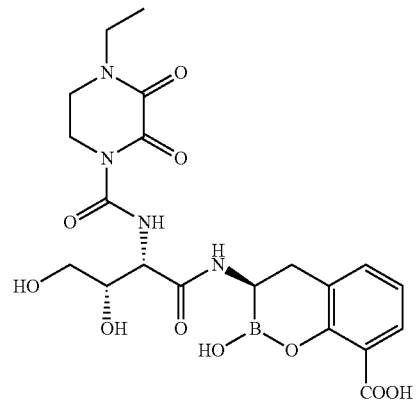 [SMILES: CCN1CCN(C(=O)N[C@H](C(=O)N[C@H]2Cc3cccc(C(=O)O)c3OB2O)[C@H](O)CO)C(=O)C1=O] | 492.3 | 493 |
| 74 | 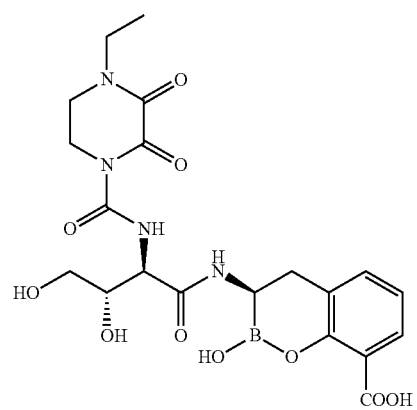 [SMILES: CCN1CCN(C(=O)N[C@@H](C(=O)N[C@H]2Cc3cccc(C(=O)O)c3OB2O)[C@H](O)CO)C(=O)C1=O] | 492.3 | 493 |

TABLE 1-continued

Example compounds

| Ex. | Structure | MW | ESI-MS (m/z) for [M + H]+ |
|---|---|---|---|
| 75 | 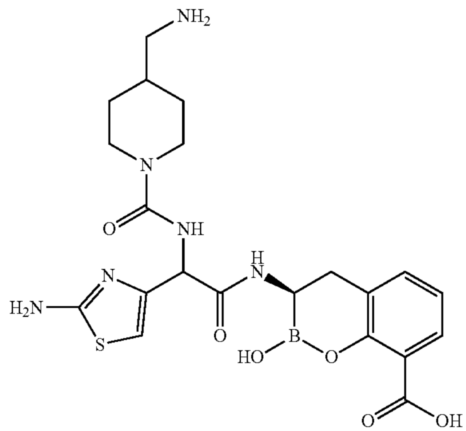 [SMILES: NCC1CCN(C(=O)NC(C(=O)N[C@H]2Cc3cccc(C(=O)O)c3OB2O)c2csc(N)n2)CC1] | 502.4 | 503 |
| 76 | 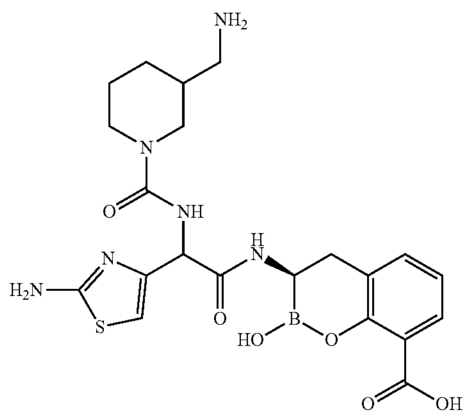 [SMILES: NCC1CCCN(C(=O)NC(C(=O)N[C@H]2Cc3cccc(C(=O)O)c3OB2O)c2csc(N)n2)C1] | 502.4 | 503 |
| 77 | 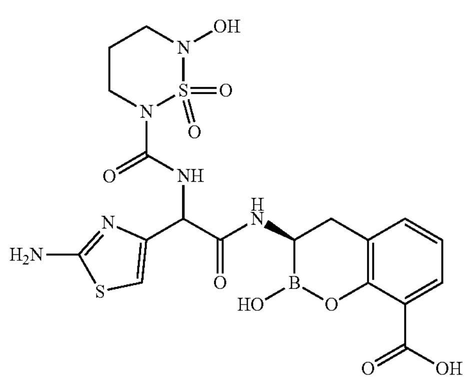 [SMILES: Nc1nc(C(NC(=O)N2CCCN(O)S2(=O)=O)C(=O)N[C@H]2Cc3cccc(C(=O)O)c3OB2O)cs1] | 540.3 | 541 |

TABLE 1-continued

Example compounds

| Ex. | Structure | MW | ESI-MS (m/z) for [M + H]+ |
|---|---|---|---|
| 78 | 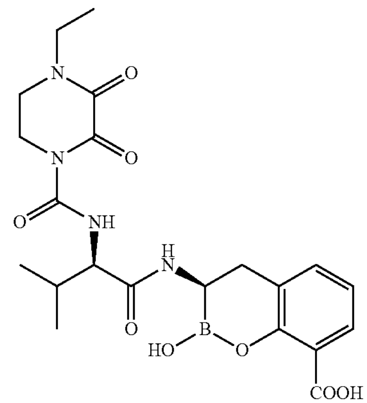 [SMILES: CCN1CCN(C(=O)N[C@@H](C(=O)N[C@H]2Cc3cccc(C(=O)O)c3OB2O)C(C)C)C(=O)C1=O] | 474.3 | 475 |
| 79 | 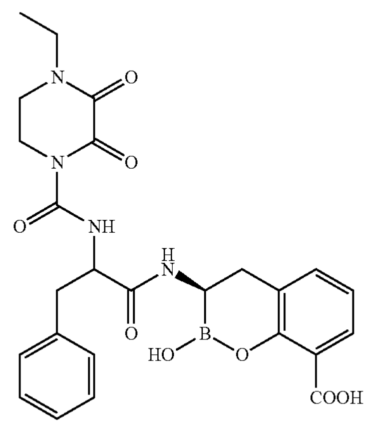 [SMILES: CCN1CCN(C(=O)NC(Cc2ccccc2)C(=O)N[C@H]2Cc3cccc(C(=O)O)c3OB2O)C(=O)C1=O] | 522.2 | 523.2 |
| 80 | 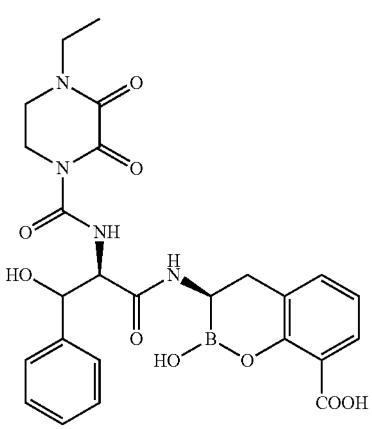 [SMILES: CCN1CCN(C(=O)N[C@@H](C(=O)N[C@H]2Cc3cccc(C(=O)O)c3OB2O)C(O)c2ccccc2)C(=O)C1=O] | 538.3 | 539 |

TABLE 1-continued

Example compounds

| Ex. | Structure | MW | ESI-MS (m/z) for [M + H]+ |
|---|---|---|---|
| 81 | 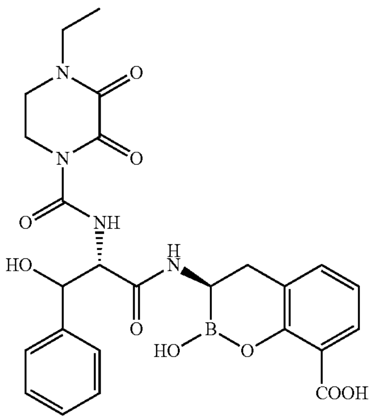 [SMILES: CCN1CCN(C(=O)N[C@H](C(=O)N[C@H]2Cc3cccc(C(=O)O)c3OB2O)C(O)c2ccccc2)C(=O)C1=O] | 538.3 | 539 |
| 82 | 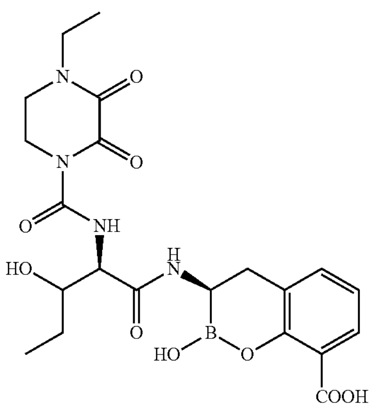 [SMILES: CCC(O)[C@@H](NC(=O)N1CCN(CC)C(=O)C1=O)C(=O)N[C@H]1Cc2cccc(C(=O)O)c2OB1O] | 490.3 | 491 |
| 83 | 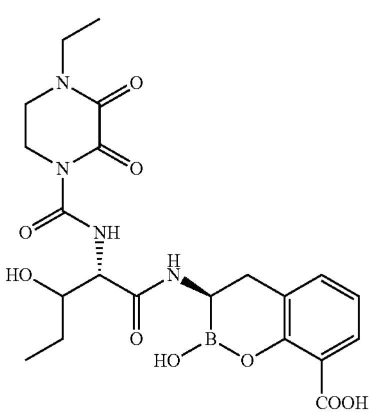 [SMILES: CCC(O)[C@H](NC(=O)N1CCN(CC)C(=O)C1=O)C(=O)N[C@H]1Cc2cccc(C(=O)O)c2OB1O] | 490.3 | 491 |

TABLE 1-continued

Example compounds

| Ex. | Structure | MW | ESI-MS (m/z) for [M + H]+ |
|---|---|---|---|
| 84 | 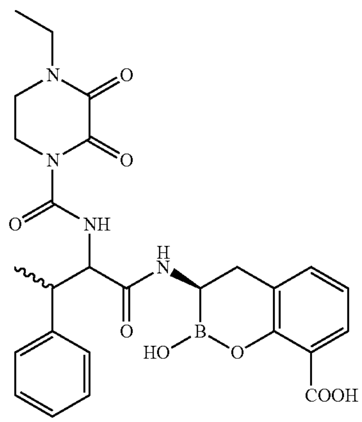 [SMILES: CCN1CCN(C(=O)NC(C(=O)N[C@H]2Cc3cccc(C(=O)O)c3OB2O)C(C)c2ccccc2)C(=O)C1=O] | 536.2 | 537.2 |
| 85 | 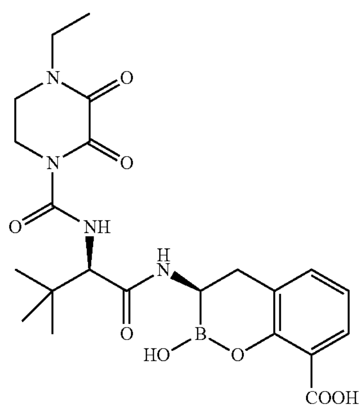 [SMILES: CCN1CCN(C(=O)N[C@@H](C(=O)N[C@H]2Cc3cccc(C(=O)O)c3OB2O)C(C)(C)C)C(=O)C1=O] | 488.3 | 489.2 |
| 86 | 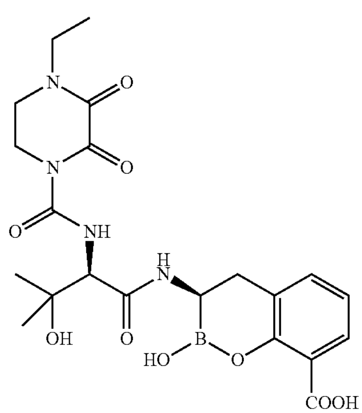 [SMILES: CCN1CCN(C(=O)N[C@@H](C(=O)N[C@H]2Cc3cccc(C(=O)O)c3OB2O)C(C)(C)O)C(=O)C1=O] | 490.2 | 491.2 |

TABLE 1-continued

Example compounds

| Ex. | Structure | MW | ESI-MS (m/z) for [M + H]+ |
|---|---|---|---|
| 87 | 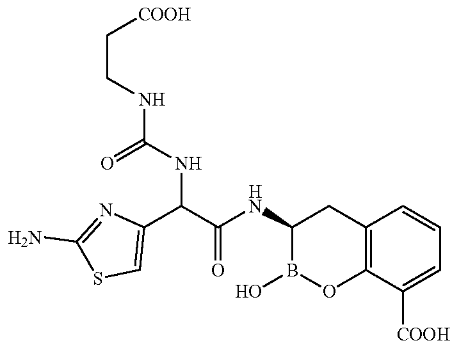 [SMILES: Nc1nc(C(NC(=O)NCCC(=O)O)C(=O)N[C@H]2Cc3cccc(C(=O)O)c3OB2O)cs1] | 477.3 | 478 |
| 88 | 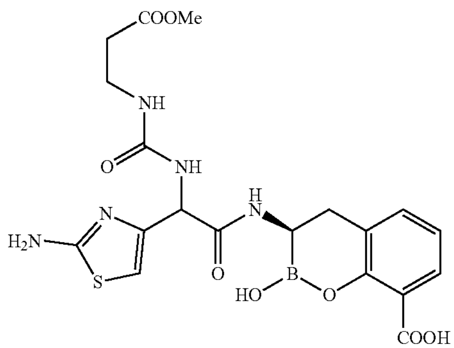 [SMILES: COC(=O)CCNC(=O)NC(C(=O)N[C@H]1Cc2cccc(C(=O)O)c2OB1O)c1csc(N)n1] | 491.3 | 492 |
| 89 | 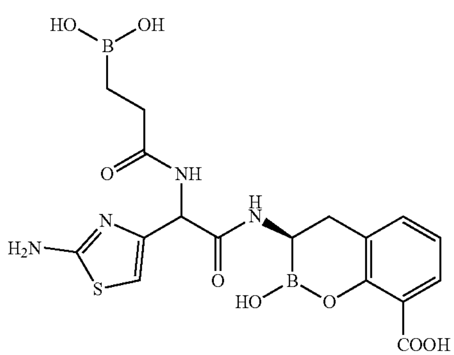 [SMILES: Nc1nc(C(NC(=O)CCB(O)O)C(=O)N[C@H]2Cc3cccc(C(=O)O)c3OB2O)cs1] | 462.0 | 445 (MH − H$_2$O)+ |
| 90 | 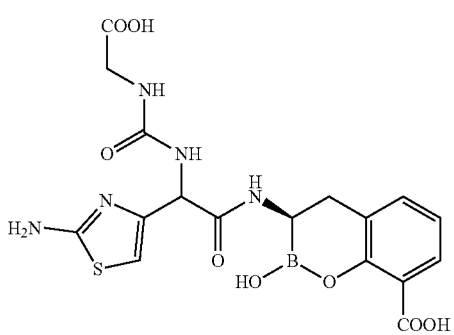 [SMILES: Nc1nc(C(NC(=O)NCC(=O)O)C(=O)N[C@H]2Cc3cccc(C(=O)O)c3OB2O)cs1] | 463.2 | 464 |

TABLE 1-continued
Example compounds
| Ex. | Structure | MW | ESI-MS (m/z) for [M + H]+ |
|---|---|---|---|
| 91 | 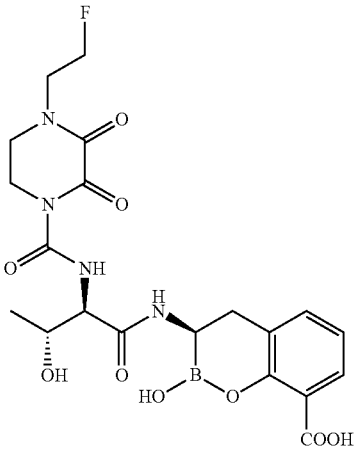 [SMILES: C[C@@H](O)[C@@H](NC(=O)N1CCN(CCF)C(=O)C1=O)C(=O)N[C@H]1Cc2cccc(C(=O)O)c2OB1O] | 494.2 | 495.2 |
| 92 | 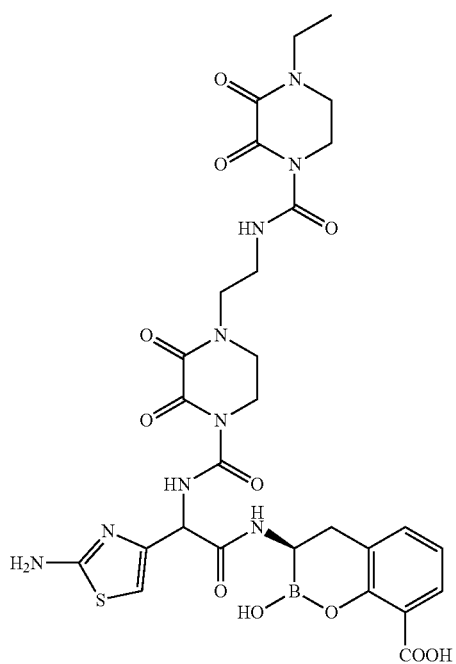 [SMILES: CCN1CCN(C(=O)NCCN2CCN(C(=O)NC(C(=O)N[C@H]3Cc4cccc(C(=O)O)c4OB3O)c3csc(N)n3)C(=O)C2=O)C(=O)C1=O] | 713.5 | 714.2 |

TABLE 1-continued
| | Example compounds | | |
|---|---|---|---|
| Ex. | Structure | MW | ESI-MS (m/z) for [M + H]$^+$ |
| 93 | | 586.4 | 587 |
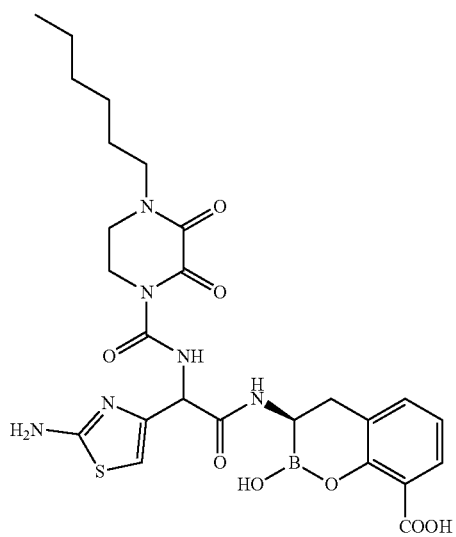 [SMILES: CCCCCCN1CCN(C(=O)NC(C(=O)N[C@H]2Cc3cccc(C(=O)O)c3OB2O)c2csc(N)n2)C(=O)C1=O]
| 94 | | 600.5 | 601 |
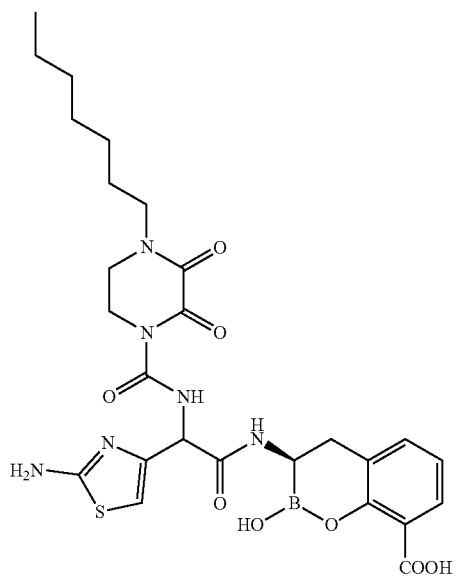 [SMILES: CCCCCCCN1CCN(C(=O)NC(C(=O)N[C@H]2Cc3cccc(C(=O)O)c3OB2O)c2csc(N)n2)C(=O)C1=O]

TABLE 1-continued

Example compounds

| Ex. | Structure | MW | ESI-MS (m/z) for [M + H]+ |
|---|---|---|---|
| 95 | 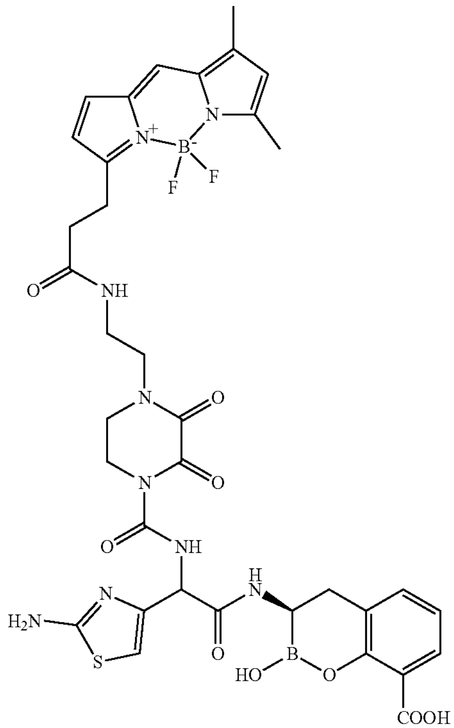 | 819.4 | 820.2 |

Example A1: Parenteral Composition of a Compounds of Formula (Ia), (Va)-(VIIa), (VIIa-1), (Ib), (Vb)-(VIIb), or (VIIb-1)

To prepare a parenteral pharmaceutical composition suitable for administration by injection, 100 mg of a compound of Formula (Ia), (Va)-(VIIa), (VIIa-1), (Ib), (Vb)-(VIIb), or (VIIb-1), or a water soluble pharmaceutically acceptable salt thereof, is dissolved in DMSO and then mixed with 10 ml of 0.9% sterile saline solution. The mixture is incorporated into a dosage unit suitable for administration by injection.

Example A2: Oral Composition of a Compounds of Formula (Ia), (Va)-(VIIa), (VIIa-1), (Ib), (Vb)-(VIIb), or (VIIb-1)

To prepare a pharmaceutical composition for oral delivery, 400 mg of compound of Formula (Ia), (Va)-(VIIa), (VIIa-1), (Ib), (Vb)-(VIIb), or (VIIb-1) and the following ingredients are mixed intimately and pressed into single scored tablets.

| Tablet Formulation | |
|---|---|
| Ingredient | Quantity per tablet (mg) |
| compound | 400 |
| cornstarch | 50 |
| croscarmellose sodium | 25 |

-continued

| Tablet Formulation | |
|---|---|
| Ingredient | Quantity per tablet (mg) |
| lactose | 120 |
| magnesium stearate | 5 |

The following ingredients are mixed intimately and loaded into a hard-shell gelatin capsule.

| Capsule Formulation | |
|---|---|
| Ingredient | Quantity per capsule (mg) |
| compound | 200 |
| lactose spray dried | 148 |
| magnesium stearate | 2 |

BIOLOGICAL EXAMPLES

Example I: Experimental Method to Assess Binding to Penicillin-Binding Proteins: Bocillin FL Competition Binding Assay To determine the ability of test compounds to bind Penicillin Binding Proteins (PBPs), a competition binding assay using Bocillin FL (fluorescent derivative of penicillin V) was adapted from the classical method used to assess PBP potency of beta-lactams.

Penicillin binding proteins were isolated from *Escherichia coli* K12 by growth of *Escherichia coli* K12 from a single colony in 4 L of Luria-Bertani (LB) broth at 35° C. and 250 rpm to an $OD_{600\ nm}$ of 0.5. The cells were harvested by centrifugation at 7,000×g for 10 min. at 4° C. Cells were resuspended and washed in 50 mM potassium phosphate pH 7.5. The cells were re-suspended in sonication buffer [50 mM Tris-HCl pH 7.5, 1 mM $MgCl_2$, 1 mM beta-mercaptoethanol, and 5 μg/mL DNAse I] and sonicated by 4 passes of 30 seconds at 45 W on ice. The sample was clarified by centrifugation at 3,000×g to remove cell debris and unbroken cells and supernatant containing the membrane proteins was retained. The membrane proteins including the PBPs were further purified from soluble constituents by an ultracentrifugation step at 100,000×g for 30 min. at 4° C. The membrane proteins are washed twice with 10 mM sodium phosphate pH 7, resuspended in a volume of 5 mL, quantitated by BCA assay, adjusted to 10 μg/mL and frozen at −80° C. until use.

The adapted Bocillin FL competition binding assay described herein incorporates a 15 min. pre-incubation of test compound with isolated PBPs to attempt to balance the difference in mechanism of inhibition between beta-lactams (largely irreversible covalent bond to active site Serine) and the boron-containing PBP inhibitor test compounds (reversible covalent bond to active site Serine). Briefly, 50 μL reactions consisted of 100 μg's of total membrane protein extracts containing PBPs incubated with a dilution series of test compound ranging from 0.005 μg/mL to 2,480 μg/mL in 10 mM sodium phosphate pH7 containing 350 mM NaCl. Thirty minute reactions at 35° C. were initiated by addition of 10 mM Bocillin FL, quenched by addition of SDS-PAGE loading buffer containing sodium dodecyl sulfate (SDS) and heated for 15 minutes at 95° C. to denature proteins in preparation for SDS-polyacrylamide gel electrophoresis. The Bocillin FL labeled PBPs are then separated by SDS-PAGE in Novex NuPage 10% Bis-Tris pre-cast gels (Invitrogen). The SDS-PAGE gel, post-electrophoresis, is then washed in water to remove excess SDS for 10 minutes at room temperature and placed on the scanning bed of a GE Healthcare/Amersham Biosciences Storm 860 fluorescence scanner. The excitation wavelength is in the blue spectrum at 450 nm and the emission at 520 nm is captured by the instrument. Effective PBP inhibitors are detected by a reduction in Bocillin FL labeling of the particular PBP over the dose range of test compound in a dose-responsive manner. High molecular weight PBP 1a/1b are not resolved by these gels, thus we report HMW PBP binding results in g/mL for PBPs 1a/1b combined as well as for PBP2 and PBP3.

Representative results are shown in Table 2, where A represents a potency of >1000 μg/mL, B represents a potency between 64 and 1000 μg/mL inclusive, and C represents a potency of <64 μg/mL.

TABLE 2

Inhibition of Penicillin-Binding Proteins by Exemplary Compounds

| Ex. | *E. coli* K12 PBP1a Potency | *E. coli* PBP1b Potency | *E. coli* PBP3 Potency |
|---|---|---|---|
| 3 | B | A | A |
| 12 | B | C | A |

Example II: Experimental Method for *E. coli* Penicillin-Binding Protein-3 Binding Assay with Bocillin-FL Via Fluorescence Polarization To determine the ability of boronic acid-based test PBP inhibitors to bind Penicillin Binding Proteins (PBPs), Bocillin-FL (fluorescently-labeled penicillin V; ThermoFisher Scientific) was used in a fluorescence polarization (FP) competition binding assay to assess boronic acid PBP inhibitor binding to PBP3 from *Escherichia coli*. PBP3 from *Escherichia coli* was cloned and purified as described previously (King, D. T, et al., *ACS Infectious Diseases* 2015, 1, 175-184). To establish assay conditions for competition binding, an enzyme titration/saturation binding experiment was performed. Bocillin-FL was prepared at 0.2 g M in a buffer comprised of 50 mM Hepes (pH 8.0), 300 mM NaCl and 5% (v/v) glycerol. Saturation binding was performed by mixing 40 g l of PBP3 ranging in concentrations from κ-12 μM with 40 μl of the 0.2 μM Bocillin-FL solution, in individual wells of a black 384-well microplate. FP was measured immediately upon addition of PBP3 (Ex, Em), using a Cytation3 (BioTek) microplate reader and measured continuously for 60 minutes. The FP response became stable after 30 minutes, and showed a dose dependence on PBP3 concentration, with FP approaching saturation with 1.5 μM PBP3 (final concentration). The competition binding assay was validated using the beta-lactam ampicillin, with Bocillin-FL at a final concentration of 0.1 μM, PBP3 at a final concentration of 1.5 μM and concentrations of ampicillin from 0-1000 μM. PBP3 was incubated with ampicillin at different concentrations in a black 384-well microplate (Corning) for 30 minutes, then Bocillin-FL added and the FP immediately measured for 60 minutes. The potency of ampicillin, reported as the concentration of ampicillin required to reduce binding of Bocillin-FL ($EC_{50}$) by 50% was determined to be 1.4 μM. Binding assays for boronic acid PBP inhibitors were performed in an identical fashion. Representative results are shown in Table 3, where A represents a potency of >500 μM, B represents a potency between 30 μM and 500 μM inclusive, and C represents a potency of <30 μM. NT=Not Tested.

TABLE 3

Binding affinity to *E. coli* PBP3 by Exemplary Compounds in fluorescence polarization competition binding assay using Bocillin-FL.

| Ex. | *E. coli* K12 PBP3 Potency | Ex. | *E. coli* K12 PBP3 Potency |
|---|---|---|---|
| 11 | C | 58 | B |
| 12 | C | 59 | A |
| 17 | B | 60 | B |
| 19 | B | 61 | C |
| 20 | B | 62 | B |
| 26 | B | 63 | B |
| 32 | A | 65 | B |
| 34 | B | 66 | B |
| 38 | A | 67 | B |
| 39 | B | 72 | B |
| 43 | B | 73 | A |
| 44 | B | 78 | C |
| 45 | B | 79 | B |
| 47 | A | 82 | B |
| 48 | B | 85 | C |
| 49 | C | 86 | B |
| 50 | A | 91 | A |
| 52 | B | 92 | B |
| 53 | C | 93 | C |
| 55 | B | 94 | C |
| 57 | B | | |

Example III: Experimental Method for Penicillin-Binding Protein Binding Assay with Example 95 (Bodipy FL-Labeled Boronic Acid PBP Inhibitor/Probe)

The method described in Example II was adapted to use a Bodipy-labeled boronic acid PBP inhibitor (Example 13 or Example 95) to assess PBP3 potency of boronic acid PBP inhibitors. The method is identical to that described in Example II for the Bocillin-FL competition binding assay, with the following exceptions: PBP3 from *Escherichia coli* is used at a final concentration of 3 µM. Representative results are shown in Table 4, where A represents a potency of >100 µM, B represents a potency between 10 µM and 100 µM inclusive, and C represents a potency of <10 µM.

TABLE 4

Binding affinity to *E. coli* PBP3 by Exemplary Compounds in competition binding assay using Bodipy-FL boronic acid probe (Example 95).

| Ex. | *E. coli* K12 PBP3 Potency |
|---|---|
| 12 | C |
| Ampicillin | C |

Example III: Experimental Method to Assess Binding to Penicillin-Binding Proteins: Radioligand Competition Binding Assay To determine the ability of boronic acid-based test PBP inhibitors to bind Penicillin Binding Proteins (PBPs), a radio-labelled boronic acid PBP inhibitor (Example 96) was used in competition binding assays to determine boronic acid PBP inhibitor binding to PBP1a or PBP1b from *Escherichia coli*. PBP1a and PBP1b were purified as described previously (Bertsche, U.; et al., *J. Biol. Chem.* 2005, 280 (45), 38096-38101; Born, P.; et al., *J Biol. Chem.* 2006. 281 (37), 26985-26993). To establish assay conditions for competition binding, an enzyme titration/saturation binding experiment was performed. Saturation binding was performed in a buffer comprised of 20 mM Tris (pH 7.5), 500 mM NaCl and 0.1% (v/v) TritonX-100, with PBP1a/PBP1b at a final concentration of 0.1 µM and 96 at final concentrations ranging from 0-100 µM. Mixtures were incubated for 60 minutes, then applied to Zeba Spin Desalting columns or plates (ThermoFisher Scientific) and centrifuged at 1000-1500×g for 2 minutes. The flow through, containing PBP bound with 96, was recovered and 100 µL mixed with 5 mL of UltimaGold liquid scintillation cocktail (Perkin Elmer), and the radioactivity counted using a Beckman Coulter LS 6500 Multipurpose scintillation counter. PBP binding of 96 approached saturation at 20 µM of $^{14}$C-labeled probe. The competition binding assay was validated using the beta-lactam ampicillin, with 96 at a final concentration of 20 µM, PBP1a/PBP1b at a final concentration of 0.1 µM. PBP1a/PBP1b was incubated with ampicillin in a 96-well microplate for 60 minutes, then 96 was added and the mixtures incubated for an additional 60 minutes. The mixtures were then applied to Zeba Spin desalting plates and centrifuged at 1000×g for 2 minutes. The flow through was recovered and 100 µl mixed with 5 ml of UltimaGold liquid scintillation cocktail and the radioactivity counted. Ampicillin inhibited binding of 96 with an $EC_{50}$ (the concentration of inhibitor required to reduce binding of 96 by 50%) of less than 0.5 µM. Binding assays with boronic acid PBP inhibitors were performed in an identical fashion. The potency of boronic acid PBP inhibitors was reported as the $EC_{50}$ value.

Representative results are shown in Table 5, where A represents a potency of >100 µM, B represents a potency between 10 µM and 100 µM inclusive, and C represents a potency of <10 µM. NT=Not Tested.

TABLE 5

Binding affinity to *E. coli* PBP1a and PBP1b by Exemplary Compounds in competition binding assay using $^{14}$C-labeled boronic acid probe.

| Ex. | *E. coli* K12 PBP1a $EC_{50}$ | *E. coli* K12 PBP1b $EC_{50}$ |
|---|---|---|
| 12 | C | C |
| 17 | A | NT |
| 19 | C | NT |
| 20 | C | NT |
| 26 | C | B |
| 34 | B | C |
| 38 | C | NT |
| 39 | B | NT |
| 43 | A | NT |
| 44 | C | NT |
| 45 | C | NT |
| 47 | C | NT |
| 48 | C | NT |
| 65 | C | NT |
| 67 | NT | C |
| 73 | NT | A |
| 78 | NT | C |
| 79 | NT | C |
| 82 | C | NT |
| 85 | C | NT |
| 91 | NT | C |
| Ampicillin | C | C |

Example IV: In Vitro Antibacterial Assays

To determine the ability of test compounds to potentiate the inhibition of the growth of bacterial strains, classic cell based broth microdilution MIC assays were employed. MIC assays are performed according to CLSI methods except where otherwise noted (CLSI, 2011 and CLSI, 2009). The reference strain *S. aureus* ATCC 29213 and the hyper-permeable *E. coli* 901C were used to determine the ability of the PBP compounds to inhibit bacterial growth. Briefly, cryo-preserved bacterial cultures of clinical strains are streaked for isolation on appropriate agar medium, in this case Mueller Hinton II agar. Following incubation to allow formation of colonies these plates are sealed with parafilm and stored refrigerated for up to two weeks. For preparation of assay inocula and to ensure low variability, at least 5 colonies are picked from the agar plates with an inoculating loop and aseptically transferred to a culture tube containing 3 mL of Mueller-Hinton Broth (supplemented with divalent cations to required levels based on Manufacturers' certification). The broth culture is grown for 3-5 hours at 37° C. with shaking at 200 rpm. Meanwhile, 2-fold serial dilutions of test compounds are conducted in a 96 well plate with a final volume of 75 µL per well at 2-fold the final desired concentration. After the dilution plates are set up the growing cultures are then diluted in a cuvette containing MH II broth and the optical density is measured at 600 nm. Inocula are diluted such that 75 µL of this culture in Mueller-Hinton Broth results in a starting bacterial concentration of 5×10$^5$ CFU/mL when added to the dilution plates. The plates are incubated 16-20 hours at 37° C. The MIC is read visually as the lowest concentration well with no bacterial growth.

Representative results are shown in Table 6 where A represents an MIC>128 µg/mL, B represents an MIC between 64 and 128 µg/mL inclusive, and C represents an MIC of <64 µg/mL. NT=Not Tested.

TABLE 6

Inhibition of bacterial growth. Minimum Inhibitory Concentrations of Exemplary Compounds.

| Ex. | S. aureus 29213 MIC (µg/mL) | E. coli 901C MIC (µg/mL) | Ex. | S. aureus 29213 MIC (µg/mL) | E. coli 901C MIC (µg/mL) |
|---|---|---|---|---|---|
| 1 | A | A | 49 | B | C |
| 2 | A | A | 50 | A | C |
| 3 | A | B | 51 | B | C |
| 4 | A | A | 52 | B | C |
| 5 | B | A | 53 | B | C |
| 6 | A | A | 54 | B | C |
| 7 | B | A | 55 | B | C |
| 8 | A | A | 56 | B | C |
| 9 | A | A | 57 | A | C |
| 10 | A | NT | 58 | A | C |
| 11 | B | C | 59 | A | C |
| 12 | B | C | 60 | B | C |
| 13 | A | A | 61 | B | C |
| 14 | A | C | 62 | A | C |
| 15 | C | C | 63 | B | C |
| 16 | B | C | 64 | A | C |
| 17 | C | C | 65 | B | C |
| 18 | A | C | 66 | B | C |
| 19 | B | C | 67 | B | C |
| 20 | B | C | 68 | A | C |
| 21 | B | B | 69 | B | C |
| 22 | B | C | 70 | A | C |
| 23 | A | C | 71 | B | C |
| 24 | A | C | 72 | B | C |
| 25 | A | C | 73 | A | A |
| 26 | A | C | 74 | A | C |
| 27 | A | C | 75 | A | C |
| 28 | A | C | 76 | A | B |
| 29 | A | C | 77 | A | C |
| 30 | B | B | 78 | B | C |
| 31 | A | A | 79 | C | C |
| 32 | A | A | 80 | B | C |
| 33 | A | C | 81 | A | A |
| 34 | A | C | 82 | A | C |
| 35 | A | C | 83 | A | B |
| 38 | B | C | 84 | B | C |
| 39 | A | C | 85 | A | C |
| 40 | A | B | 86 | A | C |
| 41 | B | C | 87 | A | B |
| 42 | B | C | 88 | A | C |
| 43 | B | C | 89 | A | A |
| 44 | B | C | 90 | A | C |
| 45 | A | C | 91 | A | C |
| 46 | A | C | 92 | A | C |
| 47 | A | C | 93 | B | C |
| 48 | A | C | 94 | B | C |

Example VI: Boronate Penicillin-Binding Protein (PBP) Inhibitors are not Impacted by CTX-M15 β-lactamase To determine if test compounds were affected by CTX-M15, the most abundant extended spectrum β-lactamase in clinical settings worldwide, the inhibition of the growth of an engineered strain of Escherichia coli harboring CTX-M15 was tested. This strain was constructed by cloning the gene encoding CTX-M15 into the NdeI and BamHI restriction endonuclease sites of plasmid pLBII, placing the gene(s) under the control of the Lac promoter. The constructed expression plasmid for CTX-M15 was used to transform competent E. coli DH5a cells to make the engineered strain, including an empty pLBII vector control strain. The classic cell based broth microdilution MIC assay was employed as described above with the addition of control antibiotics, known to be degraded by β-lactamases (Ceftazidime, piperacillin and piperacillin+tazobactam). Examples 1 through 128 display for the most part the same MIC values in both strains regardless of the presence of CTX-M15 β-lactamase, whereas β-lactams antibiotics, ceftazidime and piperacillin have weaker MICs in the CTX-M15 producer, and the protected piperacillin+tazobactam shows similar activity between the CTX-M15 producer and the parent strain with the empty pLBII plasmid.

Representative results are shown in Table 7, where A represents an MIC>512 µg/mL, B represents an MIC of 128 to 256 µg/mL, C represents an MIC from 32 to 64 µg/mL, D represents an MIC from 8 to 16 µg/mL, E represents an MIC from 2 to 4 µg/mL, and F represents an MIC<1 µg/mL. NT=Not Tested.

TABLE 7

Inhibition of growth of engineered Escherichia coli producing CTX-M15. Minimum Inhibitory Concentrations of exemplary compounds as compared to β-lactams antibiotics.

| | Microbiological Activity (MIC in mg/L) | |
|---|---|---|
| Compound | E. coli DH5α/pLBII | E. coli DH5α/pLBII-CTX-M15 |
| 1 | A | A |
| 2 | A | A |
| 3 | B | B |
| 4 | A | A |
| 5 | A | A |
| 6 | A | A |
| 7 | B | B |
| 8 | A | A |
| 9 | B | B |
| 11 | C | C |
| 12 | D | D |
| 13 | A | A |
| 14 | B | B |
| 15 | B | B |
| 16 | B | B |
| 17 | C | C |
| 18 | B | B |
| 19 | C | C |
| 20 | C | C |
| 21 | A | A |
| 22 | B | B |
| 23 | B | B |
| 24 | B | B |
| 25 | C | C |
| 26 | C | C |
| 27 | B | B |
| 28 | C | C |
| 29 | C | C |
| 30 | B | B |
| 31 | A | A |
| 32 | A | A |
| 33 | B | B |
| 34 | B | B |
| 35 | C | C |
| 38 | C | C |
| 39 | C | C |
| 40 | B | B |
| 41 | A | A |
| 42 | C | C |
| 43 | C | C |
| 44 | C | C |
| 45 | C | C |
| 46 | B | B |
| 47 | D | D |
| 48 | D | D |
| 49 | B | B |
| 50 | C | C |
| 51 | D | D |
| 52 | D | D |
| 53 | C | C |
| 54 | D | D |
| 55 | D | D |
| 56 | A | A |
| 57 | D | D |
| 58 | C | C |
| 59 | C | C |

TABLE 7-continued

Inhibition of growth of engineered *Escherichia coli* producing CTX-M15. Minimum Inhibitory Concentrations of exemplary compounds as compared to β-lactams antibiotics.

| | Microbiological Activity (MIC in mg/L) | |
|---|---|---|
| Compound | *E. coli* DH5α/pLBII | *E. coli* DH5α/pLBII-CTX-M15 |
| 60 | D | D |
| 61 | C | C |
| 62 | B | B |
| 64 | B | B |
| 65 | C | C |
| 66 | C | C |
| 67 | C | C |
| 68 | B | B |
| 69 | D | D |
| 72 | B | B |
| 73 | A | A |
| 74 | C | C |
| 77 | C | C |
| 78 | C | C |
| 82 | C | C |
| 83 | B | B |
| 84 | NT | B |
| 85 | NT | B |
| 86 | NT | C |
| 87 | NT | B |
| 88 | NT | B |
| 89 | NT | B |
| 90 | NT | B |
| 91 | NT | D |
| 92 | NT | B |
| 93 | NT | B |
| 94 | NT | B |
| Ceftazidime | F | D |
| Piperacillin | F | B |
| Piperacillin + Tazobactam | F | F |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

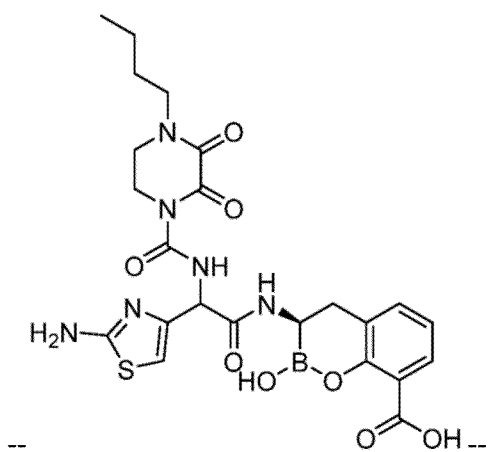

What is claimed is:

1. A compound of Formula (VIa) or (VIb), or a pharmaceutically acceptable salt, solvate, stereoisomer, tautomer, N-oxide, dimer, or trimer thereof:

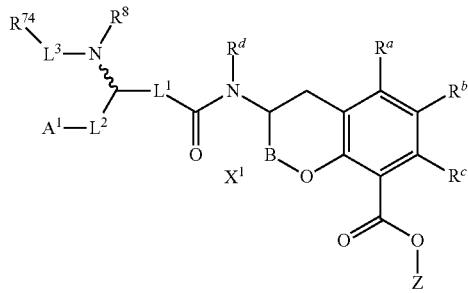

Formula (VIa)

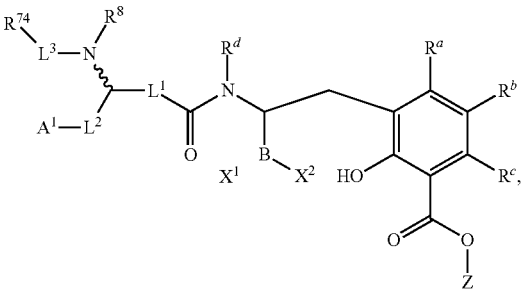

Formula (VIb)

wherein:
L$^1$ is —(CR$^1$R$^2$)$_n$—;
L$^2$ is —(CR$^1$R$^2$)$_m$—;
L$^3$ is —C(=O)—, —S(=O)—, or —S(=O)$_2$—;
A$^1$ is

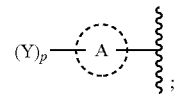

Ring A is thiazole;
each R$^1$ and R$^2$ are independently hydrogen, halogen, optionally substituted alkyl, —OH, —OR$^{34}$, —SR$^{35}$, —NR$^{32}$R$^{33}$, —NR$^{32}$C(=O)R$^{34}$, —C(=O)NR$^{32}$R$^{33}$, —NR$^{32}$S(=O)$_2$R$^{34}$, —C(=O)OH, —C(=O)OR$^{34}$, optionally substituted cycloalkyl, optionally substituted heterocycloalkyl, optionally substituted aryl, or optionally substituted heteroaryl; or
R$^1$ and R$^2$ are taken together with the carbon to which they are attached to form an optionally substituted cycloalkyl;
R$^8$ is hydrogen, optionally substituted alkyl, optionally substituted cycloalkyl, optionally substituted heterocycloalkyl, optionally substituted aryl, or optionally substituted heteroaryl;
each R$^{20}$ and R$^{21}$ are independently hydrogen, halogen, or optionally substituted alkyl;
R$^{22}$ and R$^{23}$ are independently hydrogen or optionally substituted alkyl; or
R$^{22}$ and R$^{23}$ are taken together with the nitrogen to which they are attached to form an optionally substituted heterocycloalkyl;
R$^{24}$ is optionally substituted alkyl, optionally substituted cycloalkyl, optionally substituted heterocycloalkyl, optionally substituted aryl, or optionally substituted heteroaryl;
R$^{25}$ is hydrogen, optionally substituted alkyl, optionally substituted cycloalkyl, optionally substituted heterocycloalkyl, optionally substituted aryl, optionally substituted heteroaryl;
each R$^{30}$, R$^{31}$, R$^{50}$, and R$^{51}$ are independently hydrogen, halogen, optionally substituted alkyl, optionally substituted cycloalkyl, optionally substituted heterocycloalkyl, optionally substituted aryl, optionally substituted heteroaryl, —OH, —OR$^{24}$, —SR$^{25}$, —NR$^{22}$R$^{23}$, —NR$^{22}$C(=O)R$^{24}$, —C(=O)NR$^{22}$R$^{23}$, —NR$^{22}$S(=O)$_2$R$^{24}$, —C(=O)OH, or —C(=O)OR$^{24}$; or
R$^{30}$ and R$^{31}$, or R$^{50}$ and R$^{51}$ are taken together with the carbon atom to which they are attached form an optionally substituted cycloalkyl; or two $R^{30}$ or two $R^{50}$ on adjacent carbons are taken together to form an alkenyl; or two $R^{30}$ and two $R^{31}$, or two $R^{50}$ and two $R^{51}$ on adjacent carbons are taken together to form an alkynyl;

$R^{32}$, $R^{33}$, $R^{52}$, $R^{53}$, $R^{82}$, and $R^{83}$ are independently hydrogen, optionally substituted alkyl, optionally substituted cycloalkyl, optionally substituted heterocycloalkyl, optionally substituted aryl, optionally substituted heteroaryl, (poly-ethylene-glycol)-ethyl, optionally substituted saccharide, —CN, —OH, —S(=O)$_2$R$^{24}$, —S(=O)$_2$NR$^{22}$R$^{23}$, or —C(=O)R$^{24}$; or $R^{32}$ and $R^{33}$, or $R^{52}$ and $R^{53}$, or $R^{82}$ and $R^{83}$ are taken together with the nitrogen to which they are attached to form an optionally substituted heterocycloalkyl;

$R^{34}$, $R^{54}$, and $R^{84}$ are independently optionally substituted alkyl, optionally substituted cycloalkyl, optionally substituted heterocycloalkyl, optionally substituted aryl, or optionally substituted heteroaryl;

$R^{35}$ and $R^{55}$ are independently hydrogen, optionally substituted alkyl, optionally substituted cycloalkyl, optionally substituted heterocycloalkyl, optionally substituted aryl, optionally substituted heteroaryl;

$R^{36}$ and $R^{56}$ are independently hydrogen, —OH, —OR$^{24}$, —CN, —NO$_2$, —NR$^{22}$R$^{23}$, or optionally substituted alkyl;

Z is hydrogen, $R^{61}$, —(R$^{60}$)$_q$OR$^{61}$, —(R$^{60}$)$_q$O(R$^{60}$)$_q$OR$^{61}$, —R$^{60}$OC(=O)R$^{61}$, —R$^{60}$OC(=O)OR$^{61}$, —R$^{60}$OC(=O)NHR$^{61}$, —R$^{60}$OC(=O)N(R$^{61}$)$_2$, optionally substituted alkyloxyalkyl, optionally substituted acyloxyalkyl, optionally substituted alkyloxycarbonyloxyalkyl, optionally substituted cycloalkyloxycarbonyloxyalkyl, optionally substituted aryloxycarbonyloxyalkyl, or optionally substituted alkyl-[1,3]dioxol-2-one;

each $R^{60}$ is independently —CH$_2$—, —CH(CH$_3$)—, —C(CH$_3$)$_2$—, or optionally substituted 1,1'-cyclopropylene;

each $R^{61}$ is independently optionally substituted alkyl, optionally substituted cycloalkyl, optionally substituted heterocycloalkyl, optionally substituted aryl, or optionally substituted heteroaryl; or two $R^{61}$ are taken together with the nitrogen to which they are attached to form an optionally substituted heterocycloalkyl;

$R^{74}$ is optionally substituted alkyl, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, —OH, —OR$^{84}$, —NR$^{82}$R$^{83}$, —C(=O)OH, or —C(=O)OR$^{84}$;

$R^a$, $R^b$, and $R^c$ are independently hydrogen, halogen, cyano, optionally substituted alkyl, optionally substituted cycloalkyl, optionally substituted heterocycloalkyl, optionally substituted aryl, optionally substituted heteroaryl, —OH, —OR$^{54}$, —O(CR$^{50}$R$^{51}$)$_w$NR$^{52}$R$^{53}$, —O(CR$^{50}$R$^{51}$)$_w$OH, —O(CR$^{50}$R$^{51}$)$_w$OR$^{54}$, —O(CR$^{50}$R$^{51}$)$_v$C(=O)OH, —O(CR$^{50}$R$^{51}$)$_v$C(=O)OR$^{54}$, —O(CR$^{50}$R$^{51}$)$_v$C(=O)NR$^{52}$R$^{53}$, —NR$^{52}$R$^{53}$, —NR$^{52}$(CR$^{50}$R$^{51}$)$_w$NR$^{52}$R$^{53}$, —NR$^{52}$(CR$^{50}$R$^{51}$)C(=O)OH, —NR$^{52}$(CR$^{50}$R$^{51}$)$_v$C(=O)OR$^{54}$, —NR$^{52}$(CR$^{50}$R$^{51}$)C(=O)NR$^{52}$R$^{53}$, —NR$^{52}$S(=O)$_{1,2}$R$^{54}$, —S(=O)$_{1,2}$R$^{54}$, —SR$^{55}$, —S(CR$^{50}$R$^{51}$)$_w$NR$^{52}$C(=NR$^{56}$)NR$^{52}$R$^{53}$, —S(CR$^{50}$R$^{51}$)$_v$C(=NR$^{56}$)NR$^{52}$R$^{53}$, —S(CR$^{50}$R$^{51}$)$_w$OH, —S(CR$^{50}$R$^{51}$)$_w$OR$^{54}$, —S(CR$^{50}$R$^{51}$)$_w$NR$^{52}$R$^{53}$, —S(CR$^{50}$R$^{51}$)$_v$C(=O)OH, —S(CR$^{50}$R$^{51}$)C(=O)OR$^{54}$, —S(CR$^{50}$R$^{51}$)C(=O)NR$^{52}$R$^{53}$, —C(=O)H, —C(=O)R$^{54}$, —C(=O)OH, —C(=O)OR$^{54}$, —C(=O)NR$^{52}$R$^{53}$, —(CR$^{50}$R$^{51}$)N(R$^{52}$)(CR$^{50}$R$^{51}$)$_v$C(=O)OH, —(CR$^{50}$R$^{51}$)$_w$OH, —(CR$^{50}$R$^{51}$)OR$^{54}$, —(CR$^{50}$R$^{51}$)$_v$C(=O)OH, —(CR$^{50}$R$^{51}$)$_v$C(=O)OR$^{54}$, —(CR$^{50}$R$^{51}$)$_v$C(=O)NR$^{52}$R$^{53}$, —(CR$^{50}$R$^{51}$)$_v$OC(=O)R$^{54}$, —(CR$^{50}$R$^{51}$)$_v$SR$^{55}$, —(CR$^{50}$R$^{51}$)$_v$NR$^{52}$C(=NR$^{56}$), —(CR$^{50}$R$^{51}$)$_v$NR$^{52}$R$^{53}$, —(CR$^{50}$R$^{51}$)$_v$C(=NR$^{56}$)NR$^{52}$R$^{53}$, —(CR$^{50}$R$^{51}$)$_v$C(=O)NR$^{52}$R$^{53}$, —(CR$^{50}$R$^{51}$)$_v$heterocycloalkyl, or —(CR$^{50}$R$^{51}$)heteroaryl;

$R^d$ is hydrogen, —CN, —OH, —S(=O)$_2$R$^{24}$, —S(=O)$_2$NR$^{22}$R$^{23}$, —(CR$^{20}$R$^{21}$)$_v$C(=O)OH, —C(=O)R$^{24}$, optionally substituted alkyl, optionally substituted cycloalkyl, optionally substituted heterocycloalkyl, optionally substituted aryl, optionally substituted heteroaryl, (poly-ethylene-glycol)-ethyl, an optionally substituted saccharide;

$R^X$ is optionally substituted alkyl or optionally substituted cycloalkyl;

$X^1$ and $X^2$ are independently —OH, —OR$^X$, or F; or $X^1$ and $X^2$ are taken together with the boron atom to which there are attached to form a cyclic boronate ester;

each Y is independently halogen, optionally substituted alkyl, optionally substituted cycloalkyl, optionally substituted heterocycloalkyl, optionally substituted aryl, optionally substituted heteroaryl, -heteroaryl-NR$^{32}$R$^{33}$, -heterocycloalkyl-NR$^{32}$R$^{33}$, -heteroaryl-N(R$^{32}$)C(=NR$^{32}$)NR$^{32}$R$^{33}$, -heterocycloalkyl-N(R$^{32}$)C(=NR$^{32}$)NR$^{32}$R$^{33}$, —OH, —OR$^{34}$, —O(CR$^{30}$R$^{31}$)$_w$OH, —O(CR$^{30}$R$^{31}$)$_w$OR$^{34}$, —O(CR$^{30}$R$^{31}$)$_w$NR$^{32}$R$^{33}$, —O(CR$^{30}$R$^{31}$)$_w$NR$^{32}$C(=O)R$^{34}$, —O(CR$^{30}$R$^{31}$)$_w$NR$^{32}$C(=O)OR$^{34}$, —O(CR$^{30}$R$^{31}$)$_w$NR$^{32}$C(=O)NR$^{32}$R$^{33}$, —O(CR$^{30}$R$^{31}$)$_v$C(=O)NR$^{32}$R$^{33}$, —O(CR$^{30}$R$^{31}$)$_w$NR$^{32}$S(=O)$_{0,1,2}$R$^{34}$, —O(CR$^{30}$R$^{31}$)$_w$NR$^{32}$S(=O)$_{0,1,2}$NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —O(CR$^{30}$R$^{31}$)$_v$C(=NR$^{36}$)NR$^{32}$R$^{33}$, —O(CR$^{30}$R$^{31}$)$_w$N(R$^{32}$)C(=NR$^{36}$)R$^{34}$, —O(CR$^{30}$R$^{31}$)$_v$C(=NR$^{36}$)NR$^{32}$C(=NR$^{36}$)NR$^{32}$R$^{33}$, —O(CR$^{30}$R$^{31}$)$_w$N(R$^{32}$)C(=NR$^{36}$)NR$^{32}$R$^{33}$, —O(CR$^{30}$R$^{31}$)$_w$S(=O)$_{0,1,2}$R$^{34}$, —O(CR$^{30}$R$^{31}$)$_w$S(=O)$_{0,1,2}$NR$^{32}$R$^{33}$, —OC(=O)R$^{34}$, —OC(=O)(CR$^{30}$R$^{31}$)$_v$NR$^{32}$R$^{33}$, —OC(=O)NR$^{32}$R$^{33}$, —OC(=O)OR$^{34}$, —OC(=O)NR$^{32}$(CR$^{30}$R$^{31}$)$_w$NR$^{32}$R$^{33}$, —O-heteroaryl, —O-heterocycloalkyl, —O(CR$^{30}$R$^{31}$)$_v$heteroaryl, —O(CR$^{30}$R$^{31}$)$_v$heterocycloalkyl, —O(CR$^{30}$R$^{31}$)$_w$NR$^{32}$-heteroaryl, —O(CR$^{30}$R$^{31}$)$_w$NR$^{32}$-heterocycloalkyl, —O(CR$^{30}$R$^{31}$)$_w$O-heterocycloalkyl, —NR$^{32}$R$^{33}$, —NR$^{32}$(CR$^{30}$R$^{31}$)$_w$NR$^{32}$R$^{33}$, —NR$^{32}$(CR$^{30}$R$^{31}$)$_w$O, —NR$^{32}$(CR$^{30}$R$^{31}$)$_w$OR$^{34}$, —NR$^{32}$C(=O)R$^{34}$, —NR$^{32}$C(=O)OR$^{34}$, —N(R$^{32}$)C(=O)(CR$^{30}$R$^{31}$)$_v$NR$^{32}$R$^{33}$, —NR$^{32}$C(=O)NR$^{32}$R$^{33}$, —NR$^{32}$C(=O)NR$^{32}$(CR$^{30}$R$^{31}$)$_w$NR$^{32}$R$^{33}$, —NR$^{32}$(CR$^{30}$R$^{31}$)$_w$S(=O)$_{0,1,2}$R$^{34}$, —NR$^{32}$(CR$^{30}$R$^{31}$)$_w$S(=O)$_{0,1,2}$NR$^{32}$R$^{33}$, —NR$^{32}$(CR$^{30}$R$^{31}$)$_w$NR$^{32}$R$^{33}$S(=O)$_{0,1,2}$R$^{34}$, —NR$^{32}$(CR$^{30}$R$^{31}$)$_w$NR$^{32}$S(=O)$_{0,1,2}$NR$^{32}$R$^{33}$, —NR$^{32}$C(=NR$^{36}$)NR$^{32}$R$^{33}$, —N(R$^{32}$)C(=NR$^{36}$)R$^{34}$, —NR$^{32}$(CR$^{30}$R$^{31}$)$_w$N(R$^{32}$)C(=NR$^{36}$)R$^{34}$, —NR$^{32}$(CR$^{30}$R$^{31}$)$_v$C(=NR$^{36}$)NR$^{32}$R$^{33}$, —NR$^{32}$(CR$^{30}$R$^{31}$)$_w$N(R$^{32}$)C(=NR$^{36}$)NR$^{32}$R$^{33}$, —NR$^{32}$(CR$^{30}$R$^{31}$)$_w$NR$^{32}$C(=O)NR$^{32}$R$^{33}$, —NR$^{32}$(CR$^{30}$R$^{31}$)$_w$NR$^{32}$C(=O)OR$^{34}$, —NR$^{32}$S(=O)$_{0,1,2}$R$^{34}$, —NR$^{32}$(CR$^{30}$R$^{31}$)CO$_2$H, —NR$^{32}$(CR$^{30}$R$^{31}$)CO$_2$R$^{34}$, —NR$^{32}$(CR$^{30}$R$^{31}$)C(=O)NR$^{32}$R$^{33}$, —N(R$^{32}$)-heteroaryl-NR$^{32}$R$^{33}$, —N(R$^{32}$)-heterocycloalkyl-NR$^{32}$R$^{33}$, —NR$^{32}$(CR$^{30}$R$^{31}$)$_v$heteroaryl, —NR³²(CR³⁰R³¹)ᵥheterocycloalkyl, —NR³² (CR³⁰R³¹)ᵥNR³²-heteroaryl, —NR³²(CR³⁰R³¹)ᵥ NR³²heterocycloalkyl, —CN, —(CR³⁰R³¹)ᵥCN, —(CR³⁰R³¹)ᵥNR³²R³³, —(CR³⁰R³¹)ᵥOH, —(CR³⁰R³¹)ᵥOR³⁴, —(CR³⁰R³¹)OC(=O)R³⁴, —(CR³⁰R³¹)ᵥOC(=O)NR³²R³³, —(CR³⁰R³¹)ᵥO (CR³⁰R³¹)ᵥOR³⁴, —(CR³⁰R³¹)ᵥO(CR³⁰R³¹)ᵥOH, —(CR³⁰R³¹)ᵥO(CR³⁰R³¹)ᵥNR³²R³³, —(CR³⁰R³¹)ᵥ NR³²(CR³⁰R³¹)ᵥOH, —(CR³⁰R³¹)ᵥNR³²(CR³⁰R³¹)ᵥ OR³⁴, —(CR³⁰R³¹)ᵥC(=O)NR³²R³³, —(CR³⁰R³¹)ᵥ C(=O)NR³²(CR³⁰R³¹)ᵥNR³²R³³, —(CR³⁰R³¹)ᵥC (=O)NR³²(CR³⁰R³¹)ᵥOR³⁴, —(CR³⁰R³¹)ᵥN(R³²)C (=O)R³⁴, —(CR³⁰R³¹)N(R³²)C(=O)OR³⁴, —(CR³⁰R³¹)ᵥN(R¹²)C(=O)NR³²R³³, —(CR³⁰R³¹)ᵥN (R³²)C(=O) (CR³⁰R³¹)ᵥNR³²R³³, —(CR³⁰R³¹)ᵥN (R³²)S(=O)₀,₁,₂R³⁴, —(CR³⁰R³¹)ᵥN(R³²)S(=O)₀,₁,₂ NR³²R³³, —(CR³⁰R³¹)ᵥS(=O)₀,₁,₂NR³²R³³, —(CR³⁰R³¹)ᵥNR³²(CR³⁰R³¹)ᵥNR³²R³³, —(CR³⁰R³¹)ᵥ N(R³²)CH(=NR³⁶), —(CR³⁰R³¹)ᵥN (R³²)C(=NR³⁶)R³⁴, —(CR³⁰R³¹)ᵥC(=NR³⁶) NR³²R³³, —(CR³⁰R³¹)ᵥ N(R³²)C(=NR³⁶)NR³²R³³, —(CR³⁰R³¹)ᵥC(=NR³⁶)NR³²C(=NR³⁶)NR³²R³³, —(CR³⁰R³¹)ᵥheterocycloalkyl-NR³²R³³, —(CR³⁰R³¹)ᵥheteroaryl-NR³²R³³, —(CR³⁰R³¹)ᵥheteroaryl-N (R³²)C(=NR³⁶)NR³²R³³, —(CR³⁰R³¹)ᵥheterocycloalkyl-N(R³²)C(=NR³⁶)NR³²R³³, —(CR³⁰R³¹)ᵥ heteroaryl, —(CR³⁰R³¹)ᵥheterocycloalkyl, —C(=O) OH, —C(=O)OR³⁴, —C(=O)NR³²R³³, —C(=O) NR³²(CR³⁰R³¹)ᵥ NR³²R³³, —C(=O)NR³² (CR³⁰R³¹)ᵥ OH, —C(=O)NR³²(CR³⁰R³¹)ᵥOR³⁴, —C(=NR³⁶)NR³²R³³, —C(=NR³⁶)NR³²C(=O)R³⁴, —S(=O)₁,₂ R³⁴, —SR³⁵, —S(=O)₀,₁,₂(CR³⁰R³¹)ᵥ NR³²R³³, —S(=O)₀,₁,₂(CR³⁰R³¹)ᵥOH, —S(=O)₀,₁,₂ (CR³⁰R³¹)ᵥ OR³⁴, —S(=O)₀,₁,₂NR³²R³³, —S (=O)₀,₁,₂NR³²(CR³⁰R³¹)ᵥ NR³²R³³, —S(=O)₀,₁,₂ (CR³⁰R³¹)ᵥN(R³²)C(=NR³⁶)R³⁴, —S(=O)₀,₁,₂ (CR³⁰R³¹)C(=NR³⁶)NR³²R³³, —S(=O)₀,₁,₂ (CR³⁰R³¹)ᵥN(R³²)C(=NR³⁶)NR³²R³³, —S(=O)₀,₁,₂ (CR³⁰R³¹)ᵥC(=NR³⁶)NR³²C(=NR³⁶)NR³²R³³, —Si (R³⁴)₃, —NR³²R³³R³⁴⁺Q⁻, —(CR³⁰R³¹)ᵥ NR³²R³³R³⁴⁺Q⁻, —NR³²(CR³⁰R³¹)ᵥ NR³²R³³R³⁴⁺ Q⁻, —NR³²R³⁴⁺(CR³⁰R³¹)ᵥ NR³²R³³R³⁴⁺Q⁻₂, —(CR³⁰R³¹)(T)⁺Q⁻, or —O(CR³⁰R³¹)ᵥNR³²R³³R³⁴⁺ Q⁻;

or two Ys taken together with the atoms to which they are attached form an optionally substituted cycloalkyl or an optionally substituted heterocycloalkyl;

T is pyridin-1-yl, pyrimidin-1-yl, or thiazol-3-yl;
Q is a pharmaceutically acceptable counterion;
n is 0-3;
m is 0-3;
p is 0-3;
each q is independently 2-6;
each v is independently 1-5; and
each w is independently 2-5.

2. The compound of claim 1, wherein L³ is —C(=O)—.
3. The compound of claim 1, wherein R⁸ is hydrogen.
4. The compound of claim 1, wherein R⁷⁴ is:

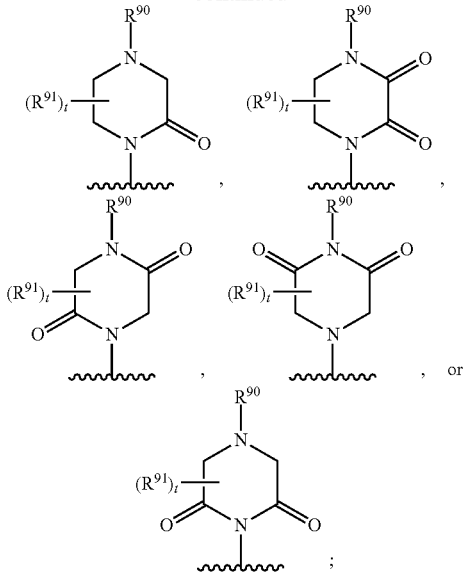

wherein
R⁹⁰ is hydrogen, —OH, optionally substituted alkyl, optionally substituted alkoxy, optionally substituted cycloalkyl, optionally substituted heterocycloalkyl, optionally substituted aryl, optionally substituted heteroaryl, optionally substituted cycloalkylalkyl, optionally substituted heterocycloalkylalkyl, optionally substituted aralkyl, optionally substituted heteroaralkyl, —S(=O)₂R²⁴, —S(=O)₂NR²²R²³, or —C(=O)R²⁴;

each R⁹¹ is independently hydrogen, halogen, —OH, —CN, NH₂, NO₂, optionally substituted alkyl, optionally substituted alkoxy, optionally substituted cycloalkyl, optionally substituted heterocycloalkyl, optionally substituted aryl, or optionally substituted heteroaryl; and t is 1-4.

5. The compound of claim 4, wherein R⁷⁴ is:

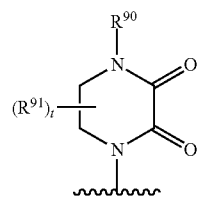

6. The compound of claim 1, wherein Rᵃ, Rᵇ, and Rᶜ are hydrogen.
7. The compound of claim 1, wherein X¹ is —OH and X² is —OH when present.
8. The compound of claim 1, wherein Rᵈ is alkyl or hydrogen.
9. The compound of claim 1, wherein each R¹ and R² are hydrogen.
10. The compound of claim 1, wherein Z is hydrogen.
11. The compound of claim 1, wherein each Y is independently halogen, optionally substituted heteroaryl, —NR³²R³³, —OH, —OR³⁴, —NR³²(CR³⁰R³¹)ᵥNR³²R³³, —NR³²C(=NR³⁶)NR³²R³³, —(CR³⁰R³¹)ᵥNR³²R³³, —SR³⁵, —NR³²(CR³¹R³¹)ᵥCO₂H, —NR³²(CR³⁰R³¹)ᵥC (=O)NR³²R³³, or —NR³²(CR³⁰R³¹)heteroaryl; or two Ys taken together with the atoms to which they are attached form an optionally substituted heterocycloalkyl.
12. The compound of claim 1, wherein each Y is independently halogen, —NR$^{32}$R$^{33}$, —OH, —OR$^{34}$, —NR$^{32}$(CR$^{30}$R$^{31}$)$_w$NR$^{32}$R$^{33}$, —C(=O)OH, or —C(=O)NR$^{32}$R$^{33}$.
13. The compound of claim 1 wherein p is 0-2.
14. The compound of claim 1 selected from the group consisting of:
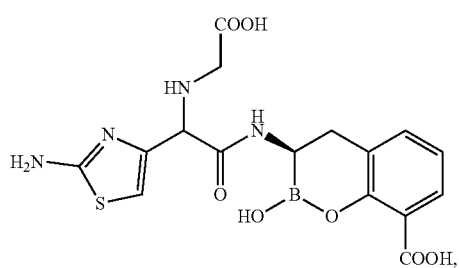
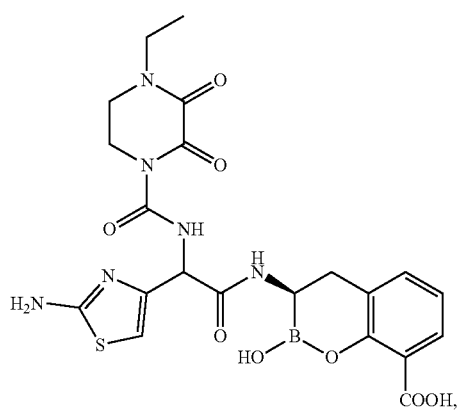
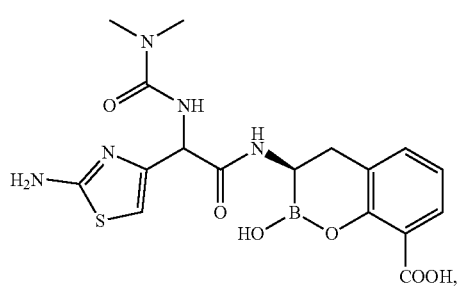
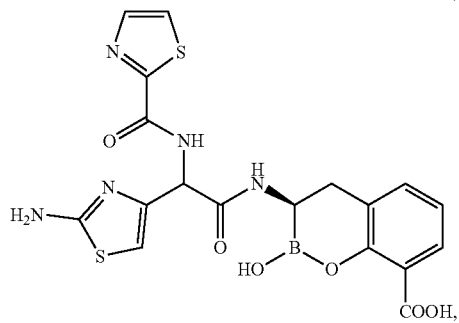
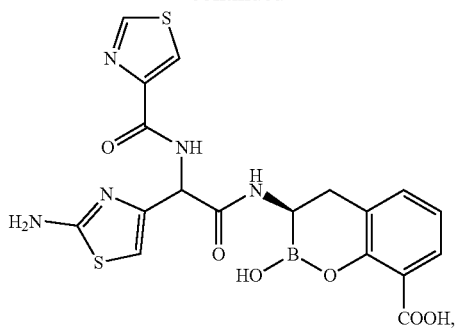
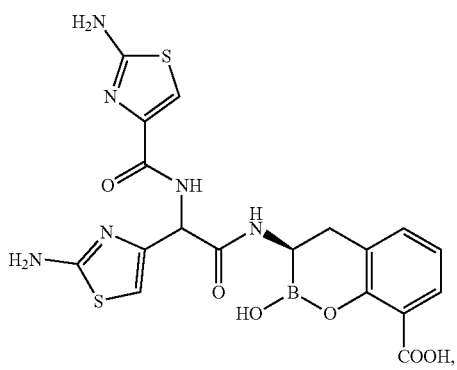
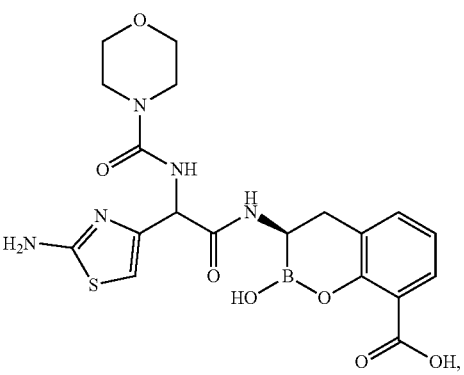
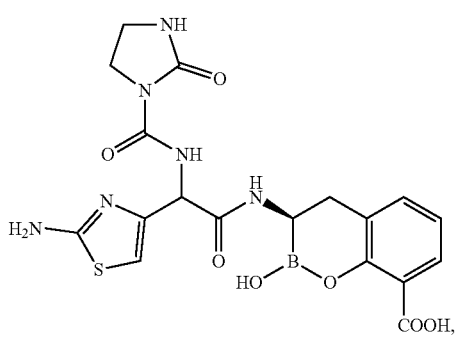

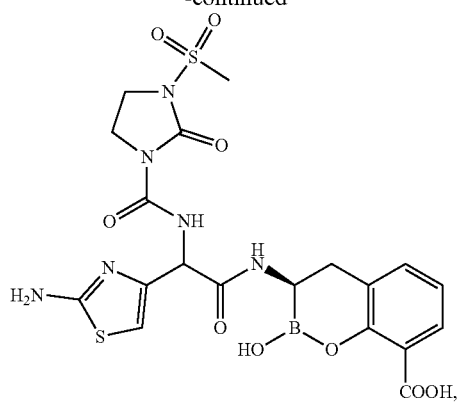
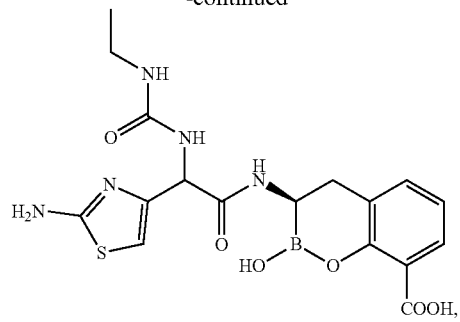
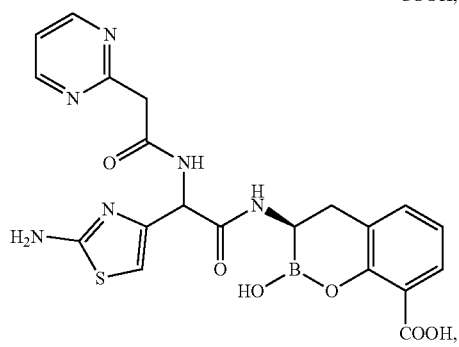
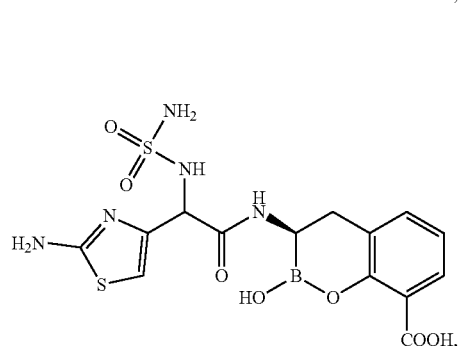
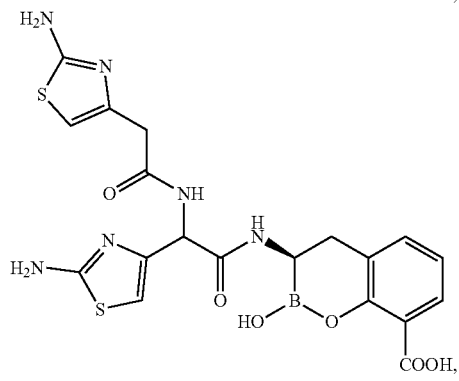
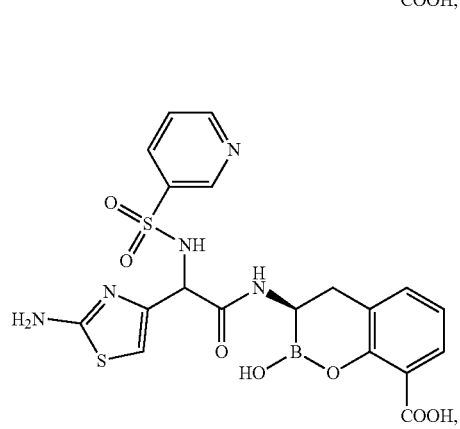
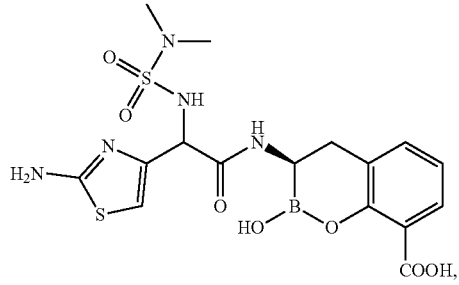
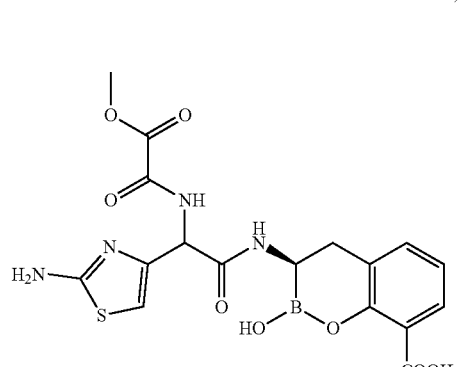
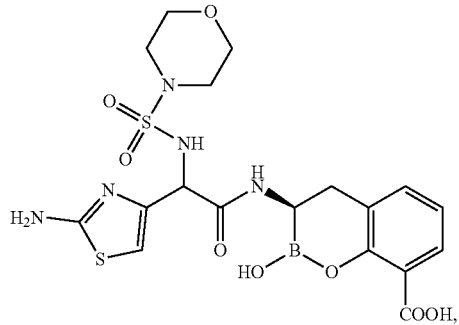
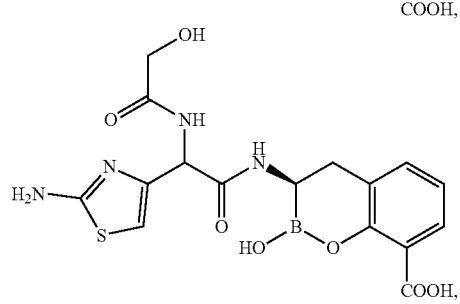

255
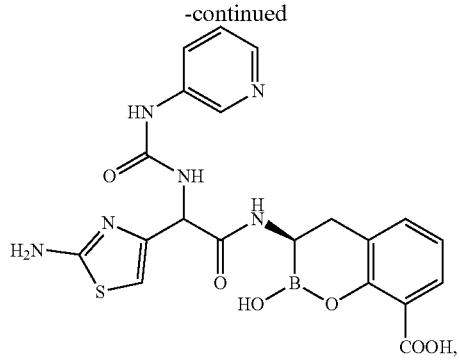
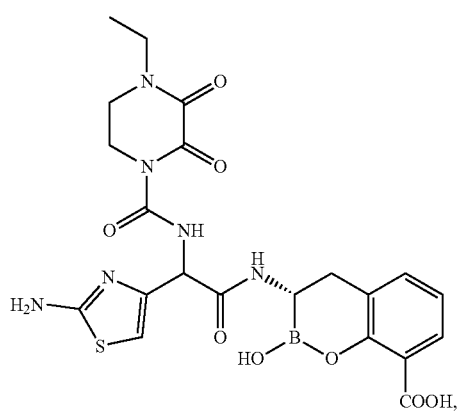
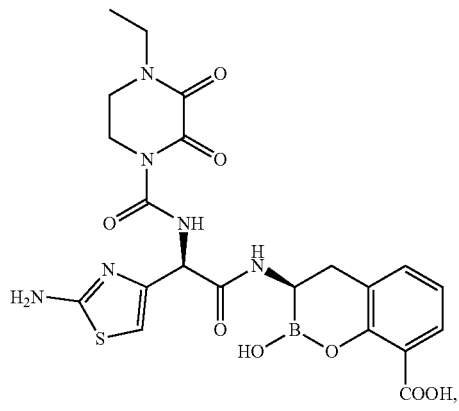
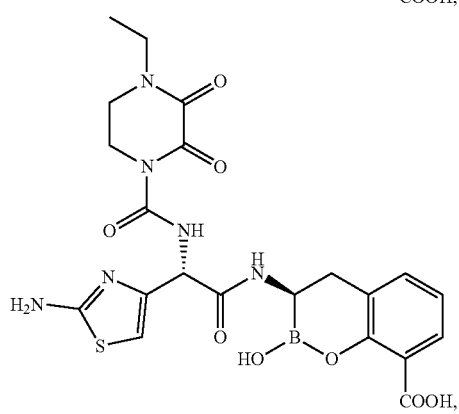
256
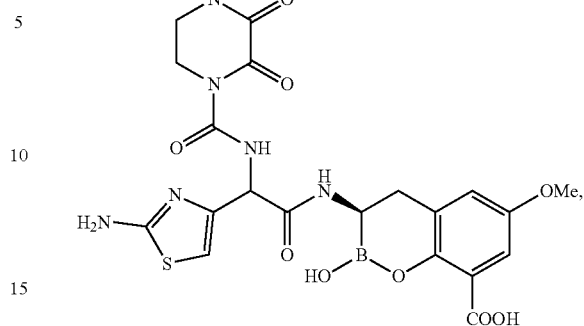
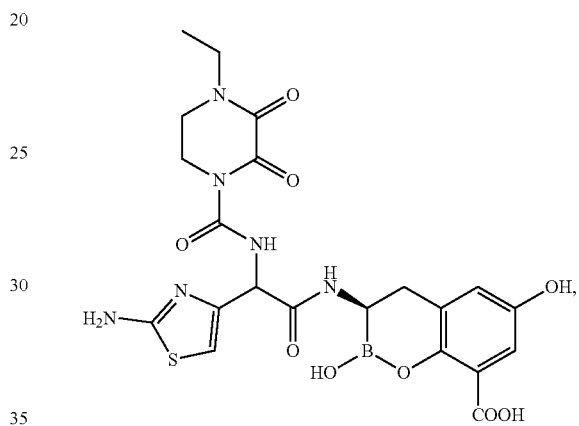
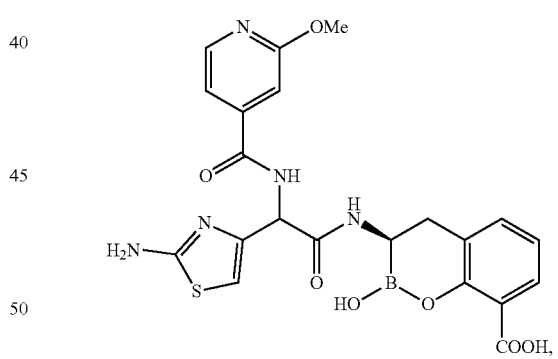
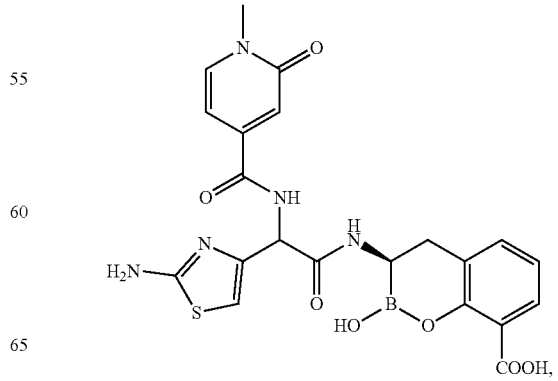

257
-continued
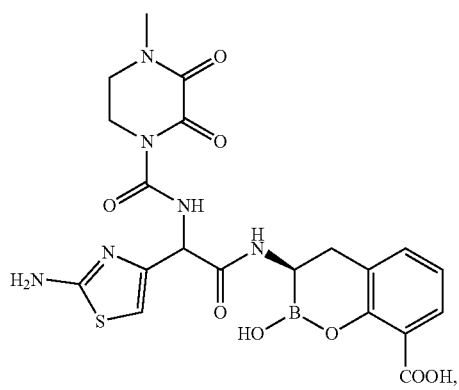
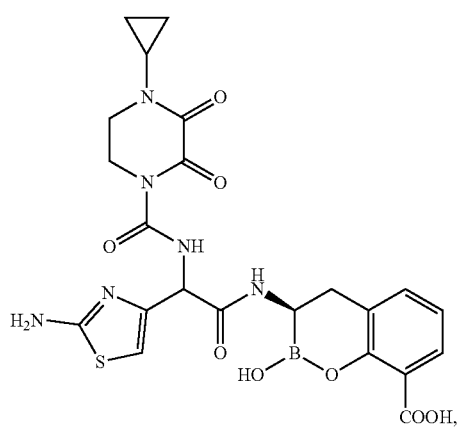
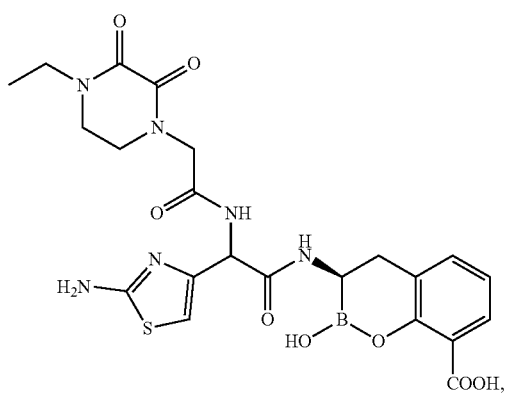
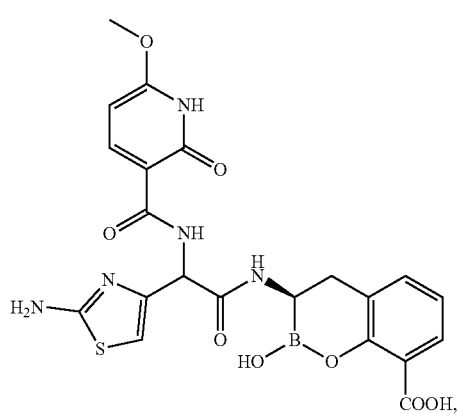
258
-continued
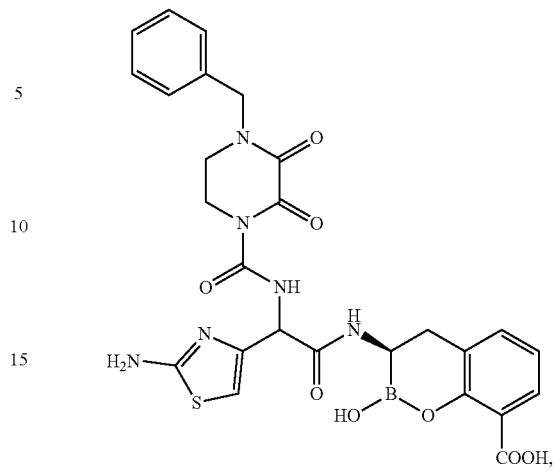
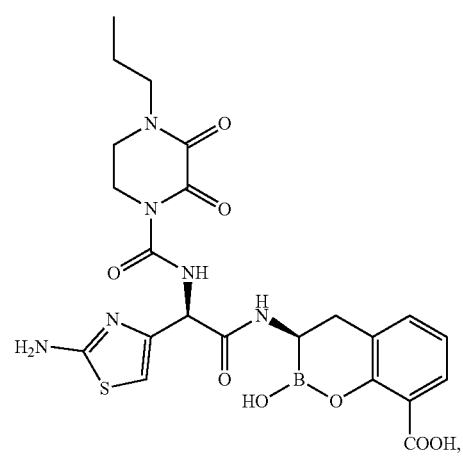
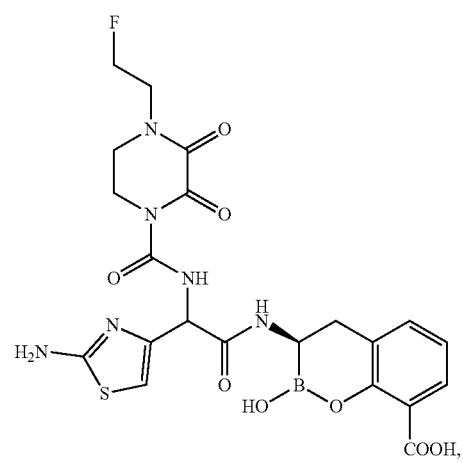

259
-continued
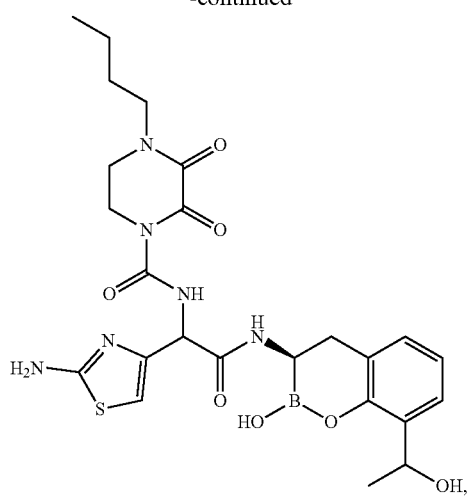
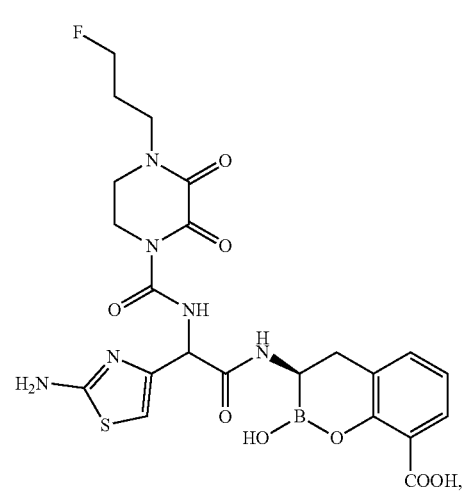
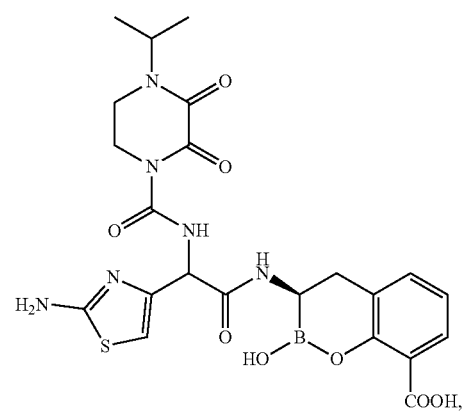
260
-continued
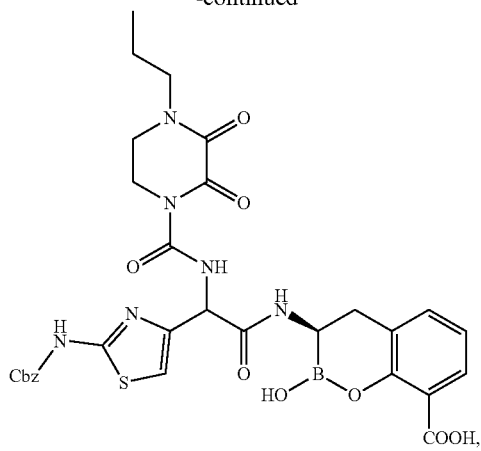
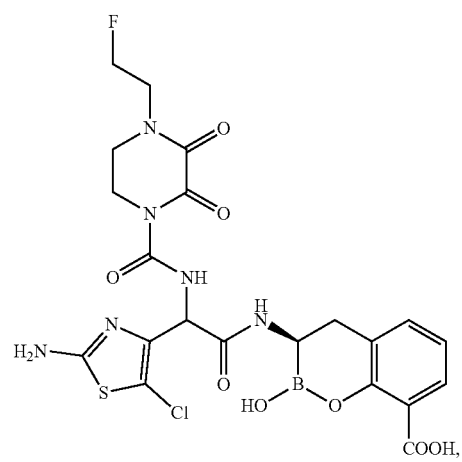
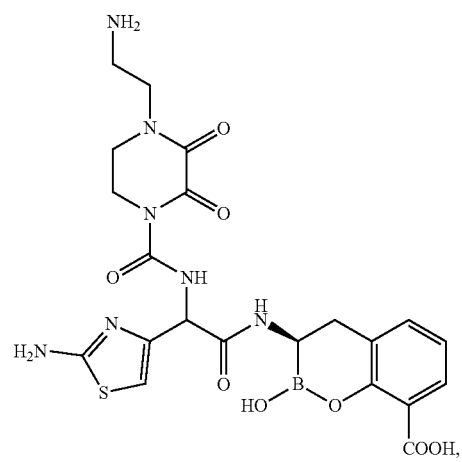

261
-continued
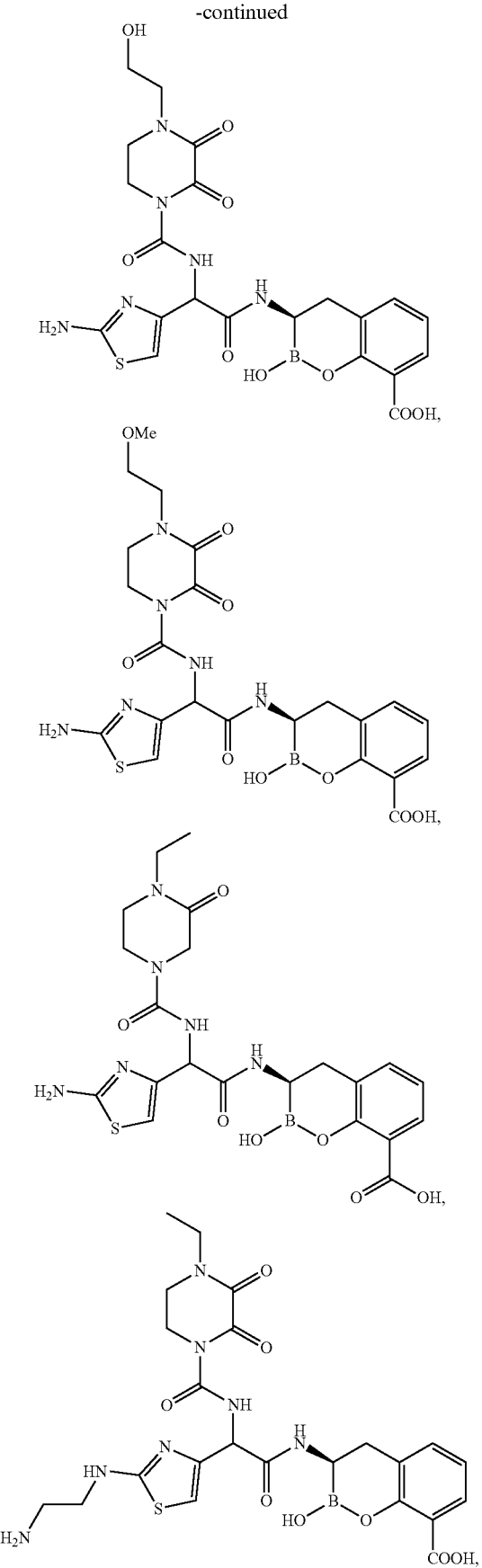
262
-continued
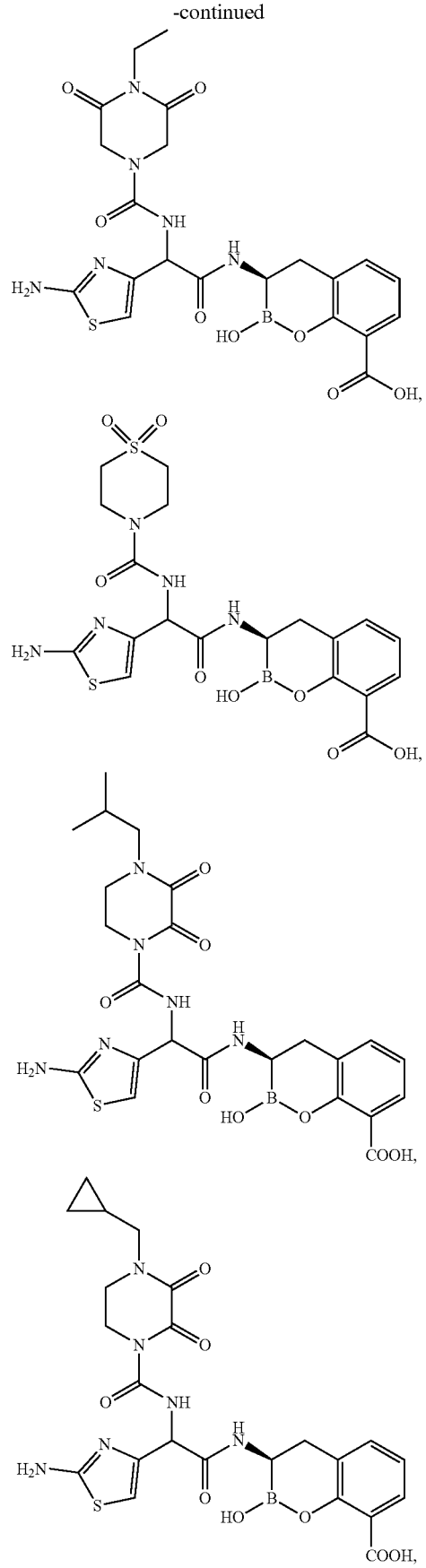

263
-continued
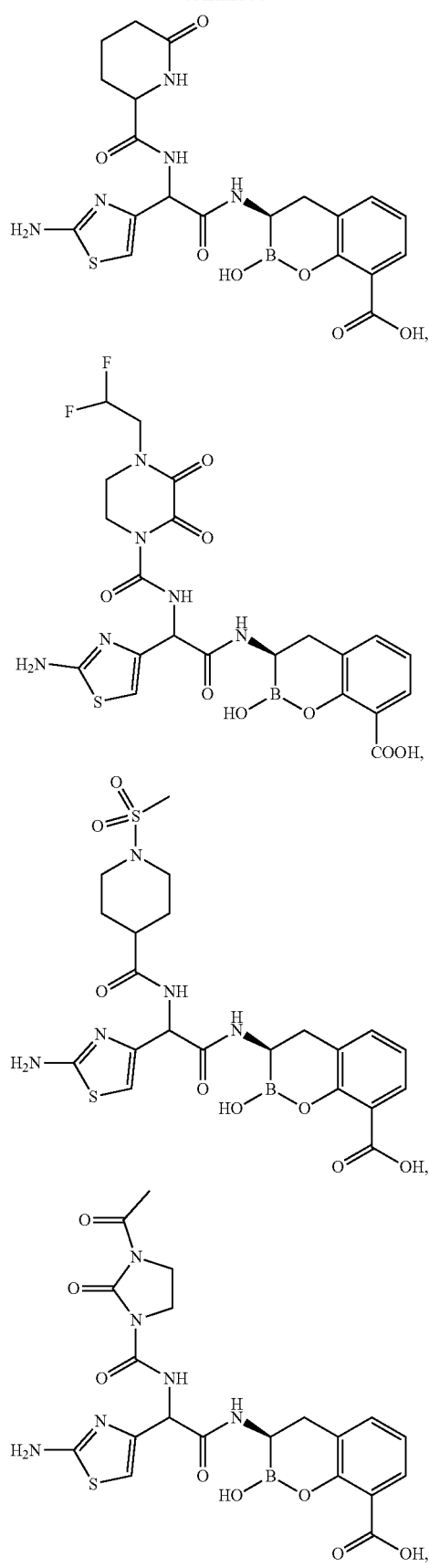
264
-continued
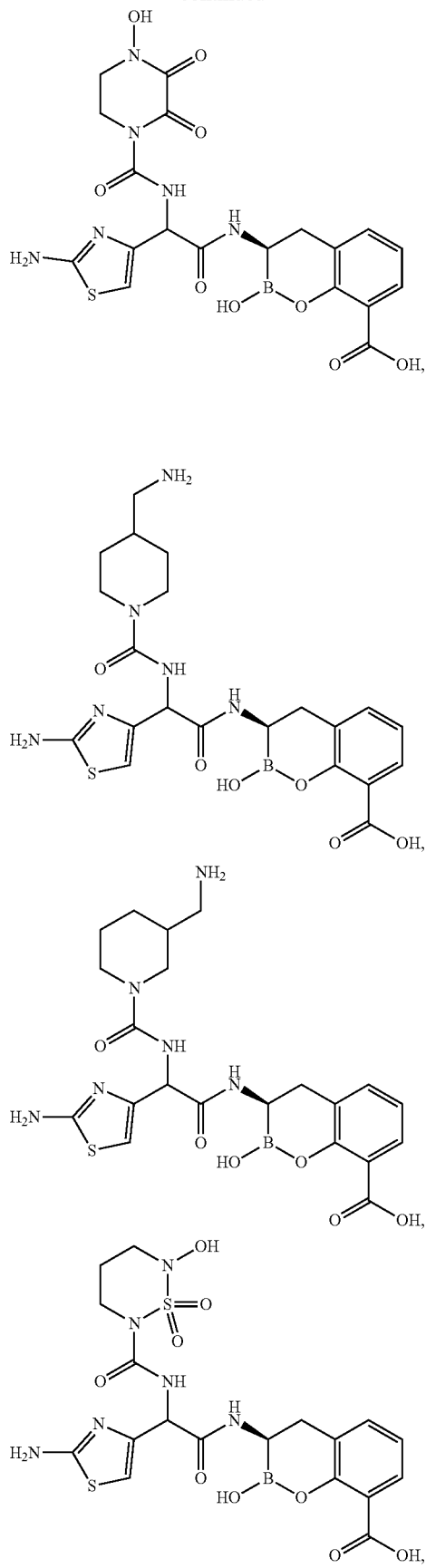

265
-continued
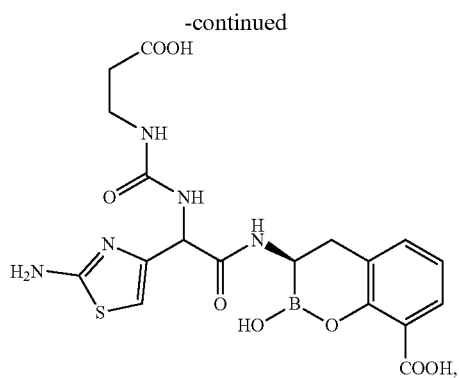
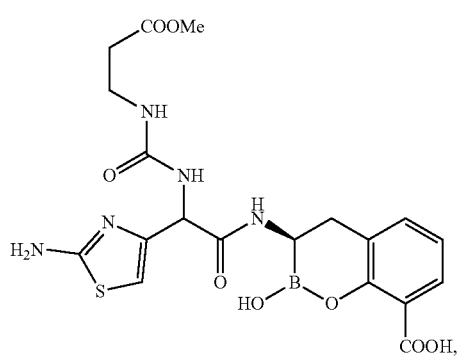
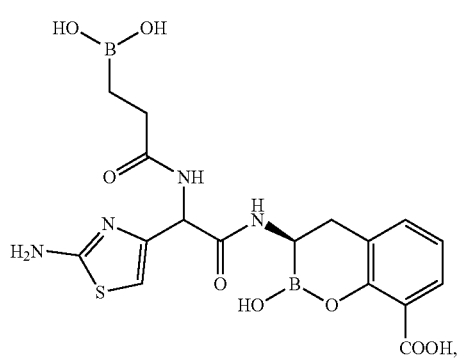
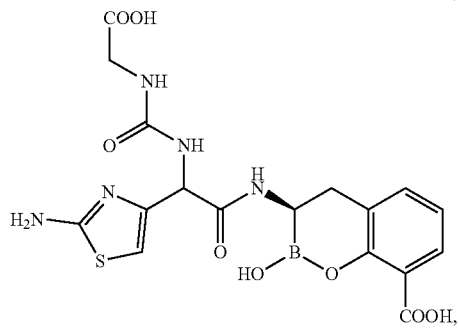
266
-continued
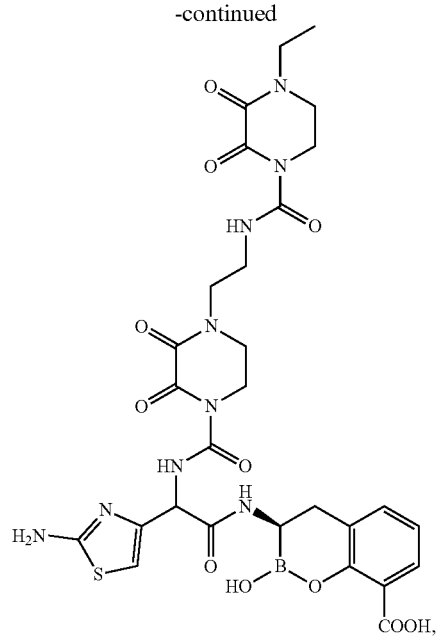
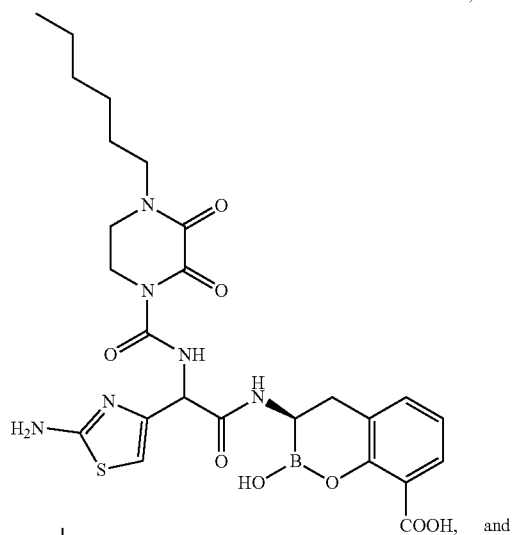
and
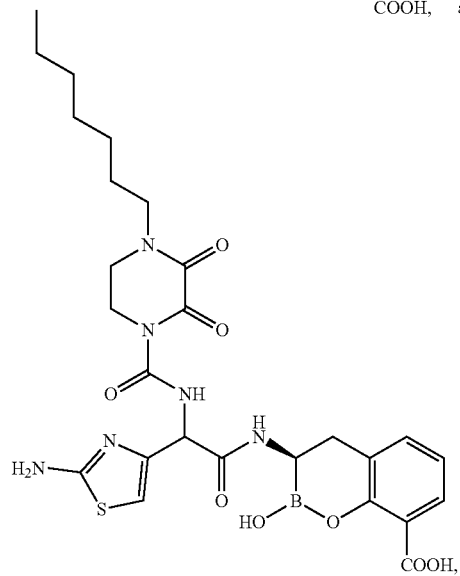

or a pharmaceutically acceptable salt, solvate, stereoisomer, tautomer, N-oxide, dimer, or trimer thereof.

15. A pharmaceutical composition comprising a compound of claim 1, or a pharmaceutically acceptable salt, solvate, stereoisomer, tautomer, N-oxide, dimer, or trimer thereof, and a pharmaceutically acceptable excipient.

16. A method of treating a bacterial infection in a subject, comprising administering to the subject an effective amount of a compound of claim 1, or a pharmaceutically acceptable salt, solvate, stereoisomer, tautomer, N-oxide, dimer, or trimer thereof.

* * * * *

UNITED STATES PATENT AND TRADEMARK OFFICE
CERTIFICATE OF CORRECTION

PATENT NO. : 11,332,485 B2
APPLICATION NO. : 16/616294
DATED : May 17, 2022
INVENTOR(S) : Burns et al.

It is certified that error appears in the above-identified patent and that said Letters Patent is hereby corrected as shown below:

In the Claims

Column 245, Lines 55-67:

In Claim 1, replace " 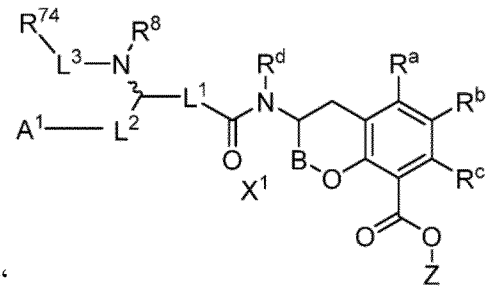 " with

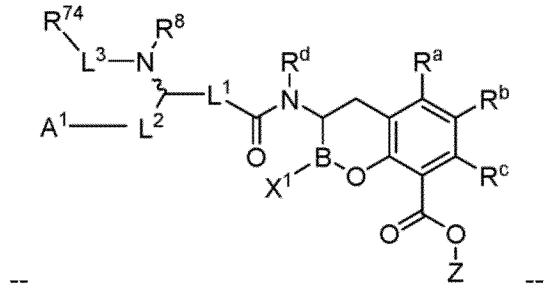

--

Column 246, Lines 1-14:

In Claim 1, replace " 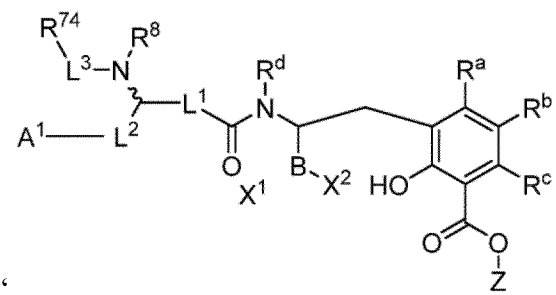 " with

Signed and Sealed this
Fifth Day of July, 2022

*Katherine Kelly Vidal*

Katherine Kelly Vidal
*Director of the United States Patent and Trademark Office*

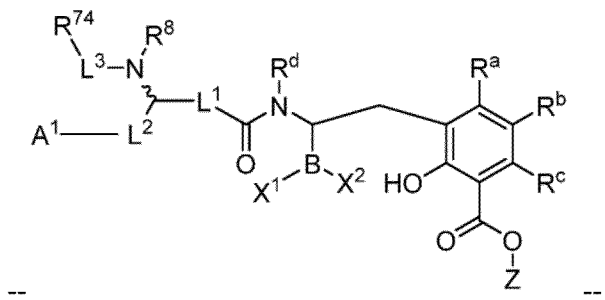

--                                                                                                              --

Column 247, Lines 61-62:
In Claim 1, replace "-NR$^{52}$(CR$^{50}$R$^{51}$)C(=O)OH" with -- -NR$^{52}$(CR$^{50}$R$^{51}$)$_v$C(=O)OH--

Column 247, Lines 62-63:
In Claim 1, replace "-NR$^{52}$(CR$^{50}$R$^{51}$)C(=O)NR$^{52}$R$^{53}$" with -- -NR$^{52}$(CR$^{50}$R$^{51}$)$_v$C(=O)NR$^{52}$R$^{53}$--

Column 248, Lines 2-3:
In Claim 1, replace "-S(CR$^{50}$R$^{51}$)C(=O)OR$^{54}$, -S(CR$^{50}$R$^{51}$)C(=O)NR$^{52}$R$^{53}$" with
-- -S(CR$^{50}$R$^{51}$)$_v$C(=O)OR$^{54}$, -S(CR$^{50}$R$^{51}$)$_v$C(=O)NR$^{52}$R$^{53}$--

Column 248, Line 6:
In Claim 1, replace "-(CR$^{50}$R$^{51}$)OR$^{54}$" with -- -(CR$^{50}$R$^{51}$)$_v$OR$^{54}$--

Column 248, Line 12:
In Claim 1, replace "-(CR$^{50}$R$^{51}$)heteroaryl" with -- -(CR$^{50}$R$^{51}$)$_v$heteroaryl--

Column 248, Lines 64-66:
In Claim 1, replace "-NR$^{32}$(CR$^{30}$R$^{31}$)CO$_2$H, -NR$^{32}$(CR$^{30}$R$^{31}$)CO$_2$R$^{34}$, -NR$^{32}$(CR$^{30}$R$^{31}$)C(=O)NR$^{32}$R$^{33}$"
with -- -NR$^{32}$(CR$^{30}$R$^{31}$)$_v$CO$_2$H, -NR$^{32}$(CR$^{30}$R$^{31}$)$_v$CO$_2$R$^{34}$, -NR$^{32}$(CR$^{30}$R$^{31}$)$_v$C(=O)NR$^{32}$R$^{33}$--

Column 249, Line 5:
In Claim 1, replace "-(CR$^{30}$R$^{31}$)OC(=O)R$^{34}$" with -- -(CR$^{30}$R$^{31}$)$_v$OC(=O)R$^{34}$--

Column 249, Lines 35-36:
In Claim 1, replace "-S(=O)$_{0,1,2}$(CR$^{30}$R$^{31}$)C(=NR$^{36}$)NR$^{32}$R$^{33}$" with
-- -S(=O)$_{0,1,2}$(CR$^{30}$R$^{31}$)$_v$C(=NR$^{36}$)NR$^{32}$R$^{33}$--

Column 250, Line 62:
In Claim 11, replace "-NR$^{32}$(CR$^{30}$R$^{31}$)heteroaryl" with -- -NR$^{32}$(CR$^{30}$R$^{31}$)$_v$heteroaryl--

CERTIFICATE OF CORRECTION (continued)
U.S. Pat. No. 11,332,485 B2

Page 3 of 4

Column 258, Lines 25-40:

In Claim 14, replace " 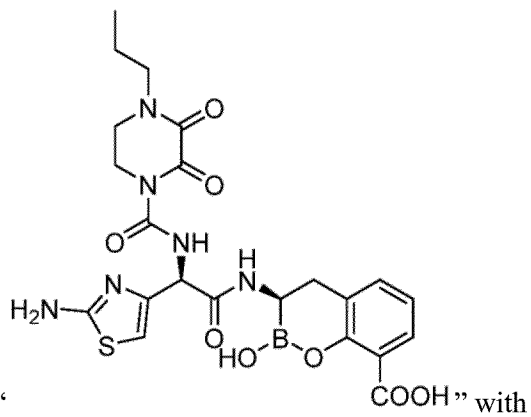 " with  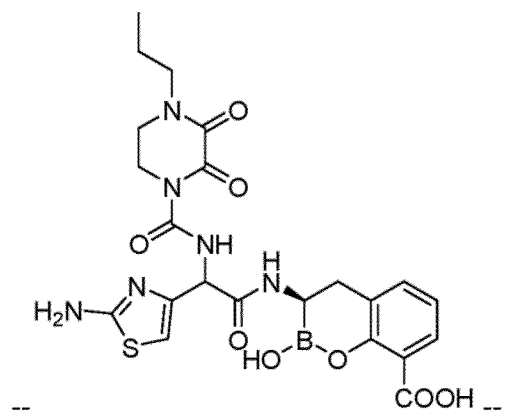 --

Column 259, Lines 1-20:

In Claim 14, replace " 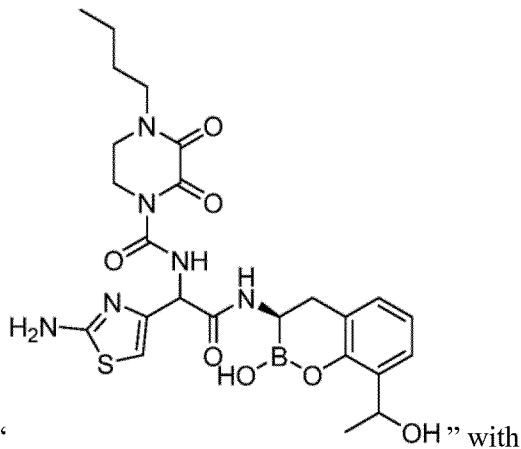 " with

CERTIFICATE OF CORRECTION (continued) Page 4 of 4
U.S. Pat. No. 11,332,485 B2